(12) United States Patent
Tremblay et al.

(10) Patent No.: US 10,323,073 B2
(45) Date of Patent: Jun. 18, 2019

(54) CRISPR-BASED METHODS AND PRODUCTS FOR INCREASING FRATAXIN LEVELS AND USES THEREOF

(71) Applicant: UNIVERSITÉ LAVAL, Québec (CA)

(72) Inventors: Jacques P. Tremblay, Stoneham et Tewkesbury (CA); Pierre Chapdelaine, Saint-Romuald (CA); Joël Rousseau, Québec (CA)

(73) Assignee: UNIVERSITÉ LAVAL, Quebec (CA)

( * ) Notice: Subject to any disclaimer, the term of this patent is extended or adjusted under 35 U.S.C. 154(b) by 0 days.

(21) Appl. No.: 15/127,087

(22) PCT Filed: Mar. 20, 2015

(86) PCT No.: PCT/CA2015/050213
§ 371 (c)(1),
(2) Date: Sep. 19, 2016

(87) PCT Pub. No.: WO2015/139139
PCT Pub. Date: Sep. 24, 2015

(65) Prior Publication Data
US 2018/0170985 A1 Jun. 21, 2018

Related U.S. Application Data

(60) Provisional application No. 61/955,882, filed on Mar. 20, 2014.

(51) Int. Cl.
| | |
|---|---|
| *C07K 14/47* | (2006.01) |
| *C12N 15/113* | (2010.01) |
| *C12N 15/10* | (2006.01) |
| *C12N 9/16* | (2006.01) |
| *C12N 15/90* | (2006.01) |
| *C12N 15/63* | (2006.01) |
| *C12N 9/22* | (2006.01) |
| *A61K 48/00* | (2006.01) |

(52) U.S. Cl.
CPC .......... *C07K 14/4705* (2013.01); *C07K 14/47* (2013.01); *C12N 9/16* (2013.01); *C12N 9/22* (2013.01); *C12N 15/102* (2013.01); *C12N 15/113* (2013.01); *C12N 15/63* (2013.01); *C12N 15/907* (2013.01); *A61K 48/005* (2013.01); *A61K 48/0066* (2013.01); *C07K 2319/80* (2013.01); *C12N 2310/10* (2013.01); *C12N 2310/20* (2017.05)

(58) Field of Classification Search
None
See application file for complete search history.

(56) References Cited

U.S. PATENT DOCUMENTS

| | | |
|---|---|---|
| 2014/0227787 A1 | 8/2014 | Zhang |
| 2014/0377868 A1 | 12/2014 | Young et al. |
| 2015/0044772 A1* | 2/2015 | Zhao ........................ C12N 9/22 435/462 |

FOREIGN PATENT DOCUMENTS

| | | |
|---|---|---|
| WO | 2013/071440 A1 | 5/2013 |
| WO | 2014/197568 | 12/2014 |
| WO | PCT/CA2015/050213 | 6/2015 |
| WO | PCT/CA2015/050213 | 9/2016 |

OTHER PUBLICATIONS

Li et al ("Synthetic construct Cas9 mediating guide RNA" Score result dated Nov. 3, 2013) (Year: 2013).*
Zhao (US2015/044772 with US priority to Aug. 9, 2013 Score result (Year: 2013).*
Sapranauskas, R., The *Streptococcus thermophilus* CRISPR/Cas system provides immunity in *Escherichia coli*. Nucleic Acids Res, 39, 9275-82, 2011.
Schoenfeld, R. A.,Frataxin deficiency alters heme pathway transcripts and decreases mitochondrial heme metabolites in mammalian cells. Hum Mol Genet, 14, 3787-99, 2005.
Sultan, M., A global view of gene activity and alternative splicing by deep sequencing of the human transcriptome. Science 321, 956-960, 2008.
Tanenbaum, A Protein-Tagging System for Signal Amplification in Gene Expression and Fluorescence Imaging, Cell, 159:3, 635-646, 2014.
Trehin, R., Cellular uptake but low permeation of human calcitonin-derived cell penetrating peptides and Tat(47-57) through well-differentiated epithelial models. Pharm Res, 21, 1248-56, 2004.
Virmouni, S. A., A novel GAA repeat expansion-based mouse model of Friedreich ataxia. Disease Models & Mechanisms, 8, 225-235, 2015.
Wang, Z., RNA-Seq: a revolutionary tool for transcriptomics. Nat Rev Genet 10, 57-63, 2009.
Zhang, P. , Immunodominant liver-specific expression suppresses transgene-directed immune responses in murine pompe disease. Hum Gene Ther 23, 460-472, 2012.
Zender, L., VP22-mediated intercellular transport of p53 in hepatoma cells in vitro and in vivo. Cancer Gene Ther, 9, 489-96, 2002.
Al-Mandawi, S., GAA repeat instability in Friedreich ataxia YAC transgenic mice. Genomics 84, 301-310, 2004.
Al-Mandawi, S., GAA repeat expansion mutation mouse models of Friedreich ataxia exhibit oxidative stress leading to progressive neuronal and cardiac pathology. Genomics 88, 580-590, 2006.
Altschul, S. F., Basic local alignment search tool. J Mol Biol, 215, 403-10, 1990.
Annoni, A., Immune responses in liver-directed lentiviral gene therapy. Translational research : the journal of laboratory and clinical medicine 161, 230-240, 2013.

(Continued)

*Primary Examiner* — Catherine S Hibbert
(74) *Attorney, Agent, or Firm* — S. Serge Shahinian

(57) ABSTRACT

Methods and products (e.g., gRNAs, recombinant fusion proteins, frataxin targeting systems, compositions and kits) are described for increasing frataxin expression/levels in a cell, as well as uses of such methods and products, for example for the treatment of Friedreich ataxia in a subject suffering therefrom.

17 Claims, 24 Drawing Sheets

Specification includes a Sequence Listing.

(56) References Cited

OTHER PUBLICATIONS

Bostick, B., AAV-9 transduction in mice is influenced by animal age but not by the route of administration. Gene Ther 14, 1605-1609, 2007.
Campuzano, V., Friedreich's ataxia: autosomal recessive disease caused by an intronic GAA triplet repeat expansion. Science, 271, 1423-7, 1996.
Chapdelaine P.A. et al., A Potential New Therapeutic Approach for Friedreich Ataxia: Induction of Frataxin Expression with TALE Proteins, Mol. Ther. Nucleic Acids, 2:9, 1-9, 2013.
Cho, S. W., Targeted genome engineering in human cells with the Cas9 RNA-guided endonuclease. Nat Biotechnol, 31, 230-2, 2013.
Cheng A.W., Multiplexed activation of endogenous genes by CRISPR-on an RNA-guided transcriptional activator system, Cell Research, 23, 1163-1171, 2013.
Cirulli, E. T. et al. Screening the human exome: a comparison of whole genome and whole transcriptome sequencing. Genome Biol 11, R57, 1-8, 2010.
Cong, L., Multiplex genome engineering using CRISPR/Cas systems. Science, 339, 819-23, 2013.
Coppola, G., Gene expression profiling in frataxin deficient mice: microarray evidence for significant expression changes without detectable neurodegeneration. Neurobiol Dis, 22, 302-11, 2006.
Coppola, G., Functional genomic analysis of frataxin deficiency reveals tissue-specific alterations and identifies the PPARgamma pathway as a therapeutic target in Friedreich's ataxia. Hum Mol Genet, 18, 2452-61, 2009.
Deltcheva, E., CRISPR RNA maturation by trans-encoded small RNA and host factor RNase III. Nature, 471, 602-7, 2011.
El-Sayed, A., Delivery of macromolecules using arginine-rich cell-penetrating peptides: ways to overcome endosomal entrapment. AAPS J, 11, 13-22, 2009.
Fominaya, J., A chimeric fusion protein containing transforming growth factor-alpha mediates gene transfer via binding to the EGF receptor. Gene Ther, 5, 521-30, 1998.
Fonfara et al., Phylogeny of Cas9 determines functional exchangeability of dual-RNA and Cas9 among orthologous, Nucleic Acids Res. 42:2577-2590, 2014.
Fu, Y., High-frequency off-target mutagenesis induced by CRISPR-Cas nucleases in human cells. Nat Biotechnol, 31, 822-6, 2013.
Gérard, C., An AAV9 coding for frataxin clearly improved the symptoms and prolonged the life of Friedreich ataxia mouse models. Molecular Therapy Methods and Clinical Development 1, 1-11, 2014.
Ghosh, A., D. Expanding adeno-associated viral vector capacity: a tale of two vectors. Biotechnology & genetic engineering reviews 24, 165-177, 2007.
Ghosh, A., Efficient transgene reconstitution with hybrid dual AAV vectors carrying the minimized bridging sequences. Hum Gene Ther 22, 77-83, 2011.
Ghosh, A., A hybrid vector system expands adeno-associated viral vector packaging capacity in a transgene-independent manner. Mol Ther 16, 124-130, 2008.
Hou, Z., Efficient genome engineering in human pluripotent stem cells using Cas9 from Neisseria meningitidis. Proc Natl Acad Sci U S A, 110, 15644-9, 2013.
Jiang, RNA-guided editing of bacterial genomes using CRISPR-Cas sytems, Nat. Biotechnol. 31:233-239, 2013.
Jinek, M., A programmable dual-RNA-guided DNA endonuclease in adaptive bacterial immunity. Science, 337, 816-21, 2012.
Jinek, Structures of Cas9 endonucleases reveal RNA-mediated conformational activation, Science 343:1247997-1247997, 2014.
Kakimoto, S., The conjugation of diphtheria toxin T domain to poly(ethylenimine) based vectors for enhanced endosomal escape during gene transfection. Biomaterials, 30, 402-8, 2009.
Kakudo, T., Transferrin-modified liposomes equipped with a pH-sensitive fusogenic peptide: an artificial viral-like delivery system. Biochemistry, 43, 5618-28, 2004.
Kichler, A., Histidine-rich amphipathic peptide antibiotics promote efficient delivery of DNA into mammalian cells. Proc Natl Acad Sci U S A, 100, 1564-8, 2003.
Konermann, S. , Genome-scale transcriptional activation by an engineered CRISPR-Cas9 complex. Nature 517, 583-588, doi:10.1038/nature14136, 2015.
Kwon, E., Application of an HIV gp41-derived peptide for enhanced intracellular trafficking of synthetic gene and siRNA delivery vehicles. Bioconjug Chem, 19, 920-7, 2008.
Li, K., Expression of human frataxin is regulated by transcription factors SRF and TFAP2. PLoS One, 5, e12286, 2010.
Lorieau, J. L., The complete influenza hemagglutinin fusion domain adopts a tight helical hairpin arrangement at the lipid:water interface. Proc Natl Acad Sci U S A, 107, 11341-6, 2010.
Lundberg, P., Delivery of short interfering RNA using endosomolytic cell-penetrating peptides. FASEB J, 21, 2664-71, 2007.
Maeder, ML, CRISPR RNA-guided gene activation of endogenous methods, Nat Methods, 10:10, 977-979, 2013.
Mali, P., CAS9 transcriptional activators for target specificity screening and paired nickases for cooperative genome engineering. Nat Biotechnol, 31, 833-8, 2013.
Mali, P., RNA-guided human genome engineering via Cas9. Science, 339, 823-6, 2013.
Markusic, D. M. Liver-Directed Adeno-Associated Viral Gene Therapy for Hemophilia. Journal of genetic syndrome & gene therapy 1, 1-9, 2012.
Matrai, J. Hepatocyte-targeted expression by integrase-defective lentiviral vectors induces antigen-specific tolerance in mice with low genotoxic risk. Hepatology 53, 1696-1707, 2011.
Midoux P. Membrane permeabilization and efficient gene transfer by a peptide containing several histidines. Bioconjug Chem, 9, 260-7, 1998.
Nietupski, J. B., Systemic administration of AAV8-alpha-galactosidase A induces humoral tolerance in nonhuman primates despite low hepatic expression. Mol Ther 19, 1999-2011, 2011.
Nishimasu, Crystal structure of Cas9 in complex with guide RNA and target DNA, Cell 156:935-494, 2014.
Noguchi, H., PDX-1 protein containing its own antennapedia-like protein transduction domain can transduce pancreatic duct and islet cells. Diabetes, 52, 1732-7, 2003.
Pandolfo, M., Friedreich ataxia. Handbook of Clinical Neurology, 103, 275-294, 2012.
Pearson, W. R., Improved tools for biological sequence comparison. Proc Natl Acad Sci U S A, 85, 2444-8, 1988.
Pepke, S., Computation for ChIP-seq and RNA-seq studies. Nat Methods 6, S22-32, 2009.
Perez-Pinera, P., RNA-guided gene activation by CRISPR-Cas9-based transcription factors. Nat Methods., 10:10, 973-976, 2013.
Pook, M. A., Rescue of the Friedreich's ataxia knockout mouse by human YAC transgenesis. Neurogenetics 3, 185-193, 2001.
Qi, L. S., Repurposing CRISPR as an RNA-guided platform for sequence-specific control of gene expression. Cell, 152, 1173-83, 2013.
Salomone, F., A novel chimeric cell-penetrating peptide with membrane-disruptive properties for efficient endosomal escape. J Control Release, 163, 293-303, 2012.
Kearns et al.,"Cas9 effector-mediated regulation of transcription and differentiation in human pluripotent stem cells", The Company of Biologists Ltd, Development (2014) 141 : 219-223.
Gilbert et al.,"CRISPR-Mediated Modular RNA-Guided Regulation of Transcription in Eukaryotes", Cell (2013) 154 : 442-451.
Bikard et al.,"Programmable repression and activation of bacterial gene expression using an engineered CRISPR-Cas system", Nucleic Acids Research (2013), vol. 41, No. 15 : 7429-7437.
Extended European Search Report of application No. EP 15764921.1.

* cited by examiner

```
3961 ggctcacatt tgacatcctc taaagcatat ataaaatgtg aagaaaactt tcacaatttg
4021 catccctttg taatatgtaa cagaaataaa attctctttt aaaatctatc aacaataggc
4081 aaggcacggt ggctcacgcc tgtcgtctca gcactttgtg aggcccaggc gggcagatcg
4141 tttgagccta gaagttcaag accaccctgg gcaacatagc gaaaccccct ttctacaaaa
4201 aatacaaaaa ctagctgggt gtggtggtgc acacctgtag tcccagctac ttggaaggct
4261 gaaatgggaa gactgcttga gcccgggagg gagaagttgc agtaagccag gaccacacca
4321 ctgcactcca gcctgggcaa cagagtgaga ctctgtctca aacaaacaaa taaatgaggc
4381 gggtggatca cgaggtcagt agatcgagac catcctggct aacacggtga aacccgtctc
4441 tactaaaaaa aaaaaaaaat acaaaaaatt agccaggcat ggtggcgggc gcctgtagtc
4501 ccagttactc gggaggctga ggcaggagaa tggcgtgaaa ccgggaggca gagcttgcag
4561 tgagccgaga tcgcaccact gccctccagc ctgggcgaca gagcggact ccgtctcaat
4621 caatcaatca atcaataaaa tctattaaca atatttattg tgcacttaac aggaacatgc
4681 cctgtccaaa aaaacttta cagggcttaa ctcattttat ccttaccaca atcctatgaa
4741 gtaggaactt ttataaaacg cattttataa acaaggcaca gagaggttaa ttaacttgcc
4801 ctctggtcac acagctagga agtgggcaga gtacagattt acacaaggca tccgtctcct
4861 ggcccacat acccaactgc tgtaaaccca taccggcggc caagcagcct caatttgtgc
4921 atgcacccac ttcccagcaa gacagcagct cccaagttcc tcctgtttag aattttagaa
4981 gcggcgggcc accaggctgc agtctccctt gggtcagggg tcctggttgc actccgtgct
5041 ttgcacaaag caggctctcc attttgtta aatgcacgaa tagtgctaag ctgggaagtt
5101 cttcctgagg tctaacctct agctgctccc ccacagaaga gtgcctgcgg ccagtggcca
5161 ccaggggtcg ccgcagcacc cagcgctgga gggcggagcg ggcggcagac ccggagcagc
5221 ATGtggactc tcgggcgccg cgcagtagcc ggcctcctgg cgtcacccag cccagcccag
5281 gcccagaccc tcacccgggt cccgcggccg gcagagttgg ccccactctg cggccgccgt
5341 ggcctgcgca ccgacatcga tgcgacctgc acgccccgcc gcgcagtaag tatccgcgcc
5401 gggaacagcc gcgggccgca cgccgcgggc cgcacgccgc acgcctgcgc agggaggcgc
```

Figure 2

MYPYDVPDYASPKKKRKVEASDKKYSIGLAIGTNSVGWAVITDEYKVPSKKFKVLGNTDR
HSIKKNLIGALLFDSGETAEATRLKRTARRRYTRRKNRICYLQEIFSNEMAKVDDSFFHR
LEESFLVEEDKKHERHPIFGNIVDEVAYHEKYPTIYHLRKKLVDSTDKADLRLIYLALAH
MIKFRGHFLIEGDLNPDNSDVDKLFIQLVQTYNQLFEENPINASGVDAKAILSARLSKSR
RLENLIAQLPGEKKNGLFGNLIALSLGLTPNFKSNFDLAEDAKLQLSKDTYDDDLDNLLA
QIGDQYADLFLAAKNLSDAILLSDILRVNTEITKAPLSASMIKRYDEHHQDLTLLKALVR
QQLPEKYKEIFFDQSKNGYAGYIDGGASQEEFYKFIKPILEKMDGTEELLVKLNREDLLR
KQRTFDNGSIPHQIHLGELHAILRRQEDFYPFLKDNREKIEKILTFRIPYYVGPLARGNS
RFAWMTRKSEETITPWNFEEVVDKGASAQSFIERMTNFDKNLPNEKVLPKHSLLYEYFTV
YNELTKVKYVTEGMRKPAFLSGEQKKAIVDLLFKTNRKVTVKQLKEDYFKKIECFDSVEI
SGVEDRFNASLGTYHDLLKIIKDKDFLDNEENEDILEDIVLTLTLFEDREMIEERLKTYA
HLFDDKVMKQLKRRRYTGWGRLSRKLINGIRDKQSGKTILDFLKSDGFANRNFMQLIHDD
SLTFKEDIQKAQVSGQGDSLHEHIANLAGSPAIKKGILQTVKVVDELVKVMGRHKPENIV
IEMARENQTTQKGQKNSRERMKRIEEGIKELGSQILKEHPVENTQLQNEKLYLYYLQNGR
DMYVDQELDINRLSDYDVDAIVPQSFLKDDSIDNKVLTRSDKNRGKSDNVPSEEVVKKMK
NYWRQLLNAKLITQRKFDNLTKAERGGLSELDKAGFIKRQLVETRQITKHVAQILDSRMN
TKYDENDKLIREVKVITLKSKLVSDFRKDFQFYKVREINNYHHAHDAYLNAVVGTALIKK
YPKLESEFVYGDYKVYDVRKMIAKSEQEIGKATAKYFFYSNIMNFFKTEITLANGEIRKR
PLIETNGETGEIVWDKGRDFATVRKVLSMPQVNIVKKTEVQTGGFSKESILPKRNSDKLI
ARKKDWDPKKYGGFDSPTVAYSVLVVAKVEKGKSKKLKSVKELLGITIMERSSFEKNPID
FLEAKGYKEVKKDLIIKLPKYSLFELENGRKRMLASAGELQKGNELALPSKYVNFLYLAS
HYEKLKGSPEDNEQKQLFVEQHKHYLDEIIEQISEFSKRVILADANLDKVLSAYNKHRDK
PIREQAENIIHLFTLTNLGAPAAFKYFDTTIDRKRYTSTKEVLDATLIHQSITGLYETRI
DLSQLGGDSPKKKRKVEASGPAGSGRADALDDFDLDMLGSDALDDFDLDMLGSDALDDFD
LDMLGSDALDDFDLDMLGSDALDDFDLDMLGSDALDDFDLDMLGSDALDDFDLDMLGSDA
LDDFDLDMLGSDALDDFDLDMLGSDALDDFDLDMLYID

Figure 3 gagggcctatttcccatgattccttcatatttgcatatacgatacaaggctgttagagagataattggaattaatt
tgactgtaaacacaaagatattagtacaaaatacgtgacgtagaaagtaataatttcttgggtagtttgcagtttt
aaaattatgttttaaaatggactatcatatgcttaccgtaacttgaaagtatttcgatttcttggctttatatatc
ttGTGGAAAGGACGAAACACCgAGCTGGGAAGTTCTTCCTGgttttagagctaGAAAtagcaagttaaaataaggc
tagtccgttatcaacttgaaaaagtggcaccgagtcggtgcTTTTTTgttttagagctagaaatagcaagttaaaa
taaggctagtccgtTTTTagcgcgtgcgccaattctgcagacaaatggctctagaggtacccgttacataacttac
ggtaaatggcccgcctggctgaccgcccaacgaccccgcccattgacgtcaatagtaacgccaatagggactttc
cattgacgtcaatgggtggagtatttacggtaaactgcccacttggcagtacatcaagtgtatcatatgccaagta
cgcccctattgacgtcaatgacggtaaatggcccgcctggcattGtgcccagtacatgaccttatgggactttcc
tacttggcagtacatctacgtattagtcatcgctattaccatggtcgaggtgagccccacgttctgcttcactctc
cccatctcccccccctcccaccccaatttgtatttatttattttttaattattttgtgcagcgatggggcgg
gggggggggggggcgcgcgccaggcggggcggggcggggcgaggggcggggcggggcgaggcggagaggtgcggc
ggcagccaatcagagcggcgcgctccgaaagtttccttttatggcgaggcggcggcggcggcccctataaaaag
cgaagcgcgcggcgggcgggagtcgctgcgacgctgccttcgcccgtgccccgctccgccgcgcctcgcgccgc
ccgccccggctctgactgaccgcgttactcccacaggtgagcgggcgggacggcccttctcctccgggctgtaatt
agctgagcaagaggtaagggtttaagggatggttggttggtggggtattaatgtttaattacctggagcacctgcc
tgaaatcacttttttttcaggttGGACCGGTgccaccATGTACCCATACGATGTTCCAGATTACGCTTCGCCGAAGA
AAAAGCGCAAGGTCGAAGCGTCCGACAAGAAGTACAGCATCGGCCTGGCCATCGGCACCAACTCTGTGGGCTGGGC
CGTGATCACCGACGAGTACAAGGTGCCCAGCAAGAAATTCAAGGTGCTGGGCAACACCGACCGGCACAGCATCAAG
AAGAACCTGATCGGAGCCCTGCTGTTCGACAGCGGCGAAACAGCCGAGGCCACCCGGCTGAAGAGAACCGCCAGAA
GAAGATACACCAGACGGAAGAACCGGATCTGCTATCTGCAAGAGATCTTCAGCAACGAGATGGCCAAGGTGGACGA
CAGCTTCTTCCACAGACTGGAAGAGTCCTTCCTGGTGGAAGAGGATAAGAAGCACGAGCGGCACCCCATCTTCGGC
AACATCGTGGACGAGGTGGCCTACCACGAGAAGTACCCCACCATCTACCACCTGAGAAAGAAACTGGTGGACAGCA
CCGACAAGGCCGACCTGCGGCTGATCTATCTGGCCCTGGCCCACATGATCAAGTTCCGGGGCCACTTCCTGATCGA
GGGCGACCTGAACCCCGACAACAGCGACGTGGACAAGCTGTTCATCCAGCTGGTGCAGACCTACAACCAGCTGTTC
GAGGAAAACCCCATCAACGCCAGCGGCGTGGACGCCAAGGCCATCCTGTCTGCCAGACTGAGCAAGAGCAGACGGC
TGGAAAATCTGATCGCCCAGCTGCCCGGCGAGAAGAAGAATGGCCTGTTCGGCAACCTGATTGCCCTGAGCCTGGG
CCTGACCCCCAACTTCAAGAGCAACTTCGACCTGGCCGAGGATGCCAAACTGCAGCTGAGCAAGGACACCTACGAC
GACGACCTGGACAACCTGCTGGCCCAGATCGGCGACCAGTACGCCGACCTGTTTCTGGCCGCCAAGAACCTGTCCG
ACGCCATCCTGCTGAGCGACATCCTGAGAGTGAACACCGAGATCACCAAGGCCCCCCTGAGCGCCTCTATGATCAA
GAGATACGACGAGCACCACCAGGACCTGACCCTGCTGAAAGCTCTCGTGCGGCAGCAGCTGCCTGAGAAGTACAAA
GAGATTTTCTTCGACCAGAGCAAGAACGGCTACGCCGGCTACATTGACGGCGGAGCCAGCCAGGAAGAGTTCTACA
AGTTCATCAAGCCCATCCTGGAAAAGATGGACGGCACCGAGGAACTGCTCGTGAAGCTGAACAGAGAGGACCTGCT
GCGGAAGCAGCCGGACCTTCGACAACGGCAGCATCCCCCACCAGATCCACCTGGGAGAGCTGCACGCCATTCTGCGG
CGGCAGGAAGATTTTTACCCATTCCTGAAGGACAACCGGGAAAAGATCGAGAAGATCCTGACCTTCCGCATCCCCT
ACTACGTGGGCCCTCTGGCCAGGGGAAACAGCAGATTCGCCTGGATGACCAGAAAGAGCGAGGAAACCATCACCCC
CTGGAACTTCGAGGAAGTGGTGGACAAGGGCGCTTCCGCCCAGAGCTTCATCGAGCGGATGACCAACTTCGATAAG
AACCTGCCCAACGAGAAGGTGCTGCCCAAGCACAGCCTGCTGTACGAGTACTTCACCGTGTATAACGAGCTGACCA
AAGTGAAATACGTGACCGAGGGAATGAGAAAGCCCGCCTTCCTGAGCGGCGAGCAGAAAAAGGCCATCGTGGACCT
GCTGTTCAAGACCAACCGGAAAGTGACCGTGAAGCAGCTGAAAGAGGACTACTTCAAGAAAATCGAGTGCTTCGAC
TCCGTGGAAATCTCCGGCGTGGAAGATCGGTTCAACGCCTCCCTGGGCACATACCACGATCTGCTGAAAATTATCA
AGGACAAGGACTTCCTGGACAATGAGGAAAACGAGGACATTCTGGAAGATATCGTGCTGACCCTGACACTGTTTGA
GGACAGAGAGATGATCGAGGAACGGCTGAAAACCTATGCCCACCTGTTCGACGACAAAGTGATGAAGCAGCTGAAG
CGGCGGAGATACACCGGCTGGGGCAGGCTGAGCCGGAAGCTGATCAACGGCATCCGGGACAAGCAGTCCGGCAAGA
CAATCCTGGATTTCCTGAAGTCCGACGGCTTCGCCAACAGAAACTTCATGCAGCTGATCCACGACGACAGCCTGAC
CTTTAAAGAGGACATCCAGAAAGCCCAGGTGTCCGGCCAGGGCGATAGCCTGCACGAGCACATTGCCAATCTGGCC
GGCAGCCCCGCCATTAAGAAGGGCATCCTGCAGACAGTGAAGGTGGTGGACGAGCTCGTGAAAGTGATGGGCCGGC
ACAAGCCCGAGAACATCGTGATCGAAATGGCCAGAGAGAACCAGACCACCCAGAAGGGACAGAAGAACAGCCGCGA
GAGAATGAAGCGGATCGAAGAGGGCATCAAAGAGCTGGGCAGCCAGATCCTGAAAGAACACCCCGTGGAAAACACC
CAGCTGCAGAACGAGAAGCTGTACCTGTACTACCTGCAGAATGGGCGGGATATGTACGTGGACCAGGAACTGGACA
TCAACCGGCTGTCCGA

Figure 4

```
CTACGATGTGGACGCCATCGTGCCTCAGAGCTTTCTGAAGGACGACTCCATCGACAACAAGGTGCTGACCAGAAGC
GACAAGAACCGGGGCAAGAGCGACAACGTGCCCTCCGAAGAGGTCGTGAAGAAGATGAAGAACTACTGGCGGCAGC
TGCTGAACGCCAAGCTGATTACCCAGAGAAAGTTCGACAATCTGACCAAGGCCGAGAGAGGCGGCCTGAGCGAACT
GGATAAGGCCGGCTTCATCAAGAGACAGCTGGTGGAAACCCGGCAGATCACAAAGCACGTGGCACAGATCCTGGAC
TCCCGGATGAACACTAAGTACGACGAGAATGACAAGCTGATCCGGGAAGTGAAAGTGATCACCCTGAAGTCCAAGC
TGGTGTCCGATTTCCGGAAGGATTTCCAGTTTTACAAAGTGCGCGAGATCAACAACTACCACCACGCCCACGACGC
CTACCTGAACGCCGTCGTGGGAACCGCCCTGATCAAAAAGTACCCTAAGCTGGAAAGCGAGTTCGTGTACGGCGAC
TACAAGGTGTACGACGTGCGGAAGATGATCGCCAAGAGCGAGCAGGAAATCGGCAAGGCTACCGCCAAGTACTTCT
TCTACAGCAACATCATGAACTTTTTCAAGACCGAGATTACCCTGGCCAACGGCGAGATCCGGAAGCGGCCTCTGAT
CGAGACAAACGGCGAAACCGGGGAGATCGTGTGGGATAAGGGCCGGGATTTTGCCACCGTGCGGAAAGTGCTGAGC
ATGCCCCAAGTGAATATCGTGAAAAAGACCGAGGTGCAGACAGGCGGCTTCAGCAAAGAGTCTATCCTGCCCAAGA
GGAACAGCGATAAGCTGATCGCCAGAAAGAAGGACTGGGACCCTAAGAAGTACGGCGGCTTCGACAGCCCCACCGT
GGCCTATTCTGTGCTGGTGGTGGCCAAAGTGGAAAAGGGCAAGTCCAAGAAACTGAAGAGTGTGAAAGAGCTGCTG
GGGATCACCATCATGGAAAGAAGCAGCTTCGAGAAGAATCCCATCGACTTTCTGGAAGCCAAGGGCTACAAAGAAG
TGAAAAAGGACCTGATCATCAAGCTGCCTAAGTACTCCCTGTTCGAGCTGGAAAACGGCCGGAAGAGAATGCTGGC
CTCTGCCGGCGAACTGCAGAAGGGAAACGAACTGGCCCTGCCCTCCAAATATGTGAACTTCCTGTACCTGGCCAGC
CACTATGAGAAGCTGAAGGGCTCCCCCGAGGATAATGAGCAGAAACAGCTGTTTGTGGAACAGCACAAGCACTACC
TGGACGAGATCATCGAGCAGATCAGCGAGTTCTCCAAGAGAGTGATCCTGGCCGACGCTAATCTGGACAAAGTGCT
GTCCGCCTACAACAAGCACCGGGATAAGCCCATCAGAGAGCAGGCCGAGAATATCATCCACCTGTTTACCCTGACC
AATCTGGGAGCCCCTGCCGCCTTCAAGTACTTTGACACCACCATCGACCGGAAGAGGTACACCAGCACCAAAGAGG
TGCTGGACGCCACCCTGATCCACCAGAGCATCACCGGCCTGTACGAGACACGGATCGACCTGTCTCAGCTGGGAGG
CGACAGCCCCAAGAAGAAGAGAAAGGTGGAGGCCAGCGggccggccGGATCCGGGCGCGCCGACGCGCTGGACGAT
TTCGATCTCGACATGCTGGGTTCTGATGCCCTCGATGACTTTGACCTGGATATGTTGGGAAGCGACGCATTGGATG
ACTTTGATCTGGACATGCTCGGCTCCGATGCTCTGGACGATTTCGATCTCGATATGTTAgggtcagacgcactgga
tgatttcgaccttgaTatgttgGGAAGCGATGCCCTTGATGATTTCGACCTGGACATGCTCggcagcgacgccctg
gacgatttcgatctggacatgctgGGGTCCGATGCCTTGGATGATTTTGACTTGGATATGCTGgggagtgatgccc
tggacgactttgacctggacatgctgGGCTCCGATGCGCTCGATGACTTCGATTTGGATATGTTGTATATCGATtg
aTTAATTAAGAATTCCTAGAGCTCGCTGATCAGCCTCGACTGTGCCTTCTAGTTGCCAGCCATCTGTTGTTTGCCC
CTCCCCCGTGCCTTCCTTGACCCTGGAAGGTGCCACTCCCACTGTCCTTTCCTAATAAAATGAGGAAATTGCATCG
CATTGTCTGAGTAGGTGTCATTCTATTCTGGGGGGTGGGGTGGGGCAGGACAGCAAGGGGGAGGATTGGGAAGAgA
ATAGCAGGCATGCTGGGGAgcggccgcaggaaccctagtgatggagttggccactccctctctgcgcgctcgctc
gctcactgaggccgggcgaccaaaggtcgcccgacgcccgggctttgcccgggcggcctcagtgagcgagcgagcg
cgcagctgcctgcaggggcgcctgatgcggtattttctccttacgcatctgtgcggtatttcacaccgcatacgtc
aaagcaaccatagtacgcgccctgtagcggcgcattaagcgcggcgggtgtggtggttacgcgcagcgtgaccgct
acacttgccagcgccctagcgcccgctcctttcgctttcttcccttcctttctcgccacgttcgccggctttcccc
gtcaagctctaaatcgggggctccctttagggttccgatttagtgctttacggcacctcgaccccaaaaaacttga
tttgggtgatggttcacgtagtgggccatcgccctgatagacggtttttcgccctttgacgttggagtccacgttc
tttaatagtggactcttgttccaaactggaacaacactcaaccctatctcgggctattcttttgatttataaggga
ttttgccgatttcggcctattggttaaaaaatgagctgatttaacaaaaatttaacgcgaattttaacaaaatatt
aacgtttacaattttatggtgcactctcagtacaatctgctctgatgccgcatagttaagccagccccgacacccg
ccaacacccgctgacgcgccctgacgggcttgtctgctcccggcatccgcttacagacaagctgtgaccgtctccg
ggagctgcatgtgtcagaggttttcaccgtcatcaccgaaacgcgcgagacgaaagggcctcgtgatacgcctatt
tttataggttaatgtcatgataataatggtttcttagacgtcaggtggcacttttcggggaaatgtgcgcggaacc
cctatttgtttatttttctaaatacattcaaatatgtatccgctcatgagacaataaccctgataaatgcttcaat
aatattgaaaaaggaagagtatgagtattcaacatttccgtgtcgcccttattccctttttgcggcattttgcct
tcctgttttgctcacccagaaacgctggtgaaagtaaaagatgctgaagatcagttgggtgcacgagtgggttac
atcgaactggatctcaacagcggtaagatccttgagagttttcgccccgaagaacgttttccaatgatgagcactt
ttaaagttctgctatgtggcgcggtattatcccgtattgacgccgggcaagagcaactcggtcgccgcatacacta
ttctcagaatgacttggttgagtactcaccagtcacagaaaagcatcttacggatggcatgacagtaagagaatta
tgcagtgctgccataaccatgagtgataacactgcggccaacttacttctgacaacgatcggaggaccgaaggagc
taaccgcttttttgcacaacatgggggatcatgtaactcgccttgatcgttgggaaccggagctgaatgaagccat
accaaacgacga
```

Figure 4 (continued)

```
gcgtgacaccacgatgcctgtagcaatggcaacaacgttgcgcaaactattaactggcgaactacttactctagct
tcccggcaacaattaatagactggatggaggcggataaagttgcaggaccacttctgcgctcggcccttccggctg
gctggtttattgctgataaatctggagccggtgagcgtggaagccgcggtatcattgcagcactggggccagatgg
taagccctcccgtatcgtagttatctacacgacggggagtcaggcaactatggatgaacgaaatagacagatcgct
gagataggtgcctcactgattaagcattggtaactgtcagaccaagtttactcatatatactttagattgatttaa
aacttcattttttaatttaaaaggatctaggtgaagatccttttgataatctcatgaccaaaatcccttaacgtga
gttttcgttccactgagcgtcagaccccgtagaaaagatcaaggatcttcttgagatcctttttttctgcgcgta
atctgctgcttgcaaacaaaaaaaccaccgctaccagcggtggtttgtttgccggatcaagagctaccaactcttt
ttccgaaggtaactggcttcagcagagcgcagataccaaatactgtccttctagtgtagccgtagttaggccacca
cttcaagaactctgtagcaccgcctacatacctcgctctgctaatcctgttaccagtggctgctgccagtggcgat
aagtcgtgtcttaccgggttggactcaagacgatagttaccggataaggcgcagcggtcgggctgaacggggggtt
cgtgcacacagcccagcttggagcgaacgacctacaccgaactgagatacctacagcgtgagctatgagaaagcgc
cacgcttcccgaagggagaaaggcggacaggtatccggtaagcggcagggtcggaacaggagagcgcacgagggag
cttccaggggaaacgcctggtatctttatagtcctgtcgggtttcgccacctctgacttgagcgtcgattttgt
gatgctcgtcagggggcggagcctatggaaaaacgccagcaacgcggccttttacggttcctggccttttgctg
gcctttgctcacatgt
```

Figure 4 (continued)

```
                                                                    BamH1
                                                              Fse1   |
                                                              Nae1 | |
              Pvu2                                            Eag1 | |
              BseY1                Ear1                       NgoM4 | | |
              |                    |                          | | | |
              AGCTGGGAGGCGACAGCCCCAAGAAGAAGAGAAAGGTGGAGGCCAGCGggccggccGGAT
       5401   ---------+---------+---------+---------+---------+---------+ 5460
              TCGACCCTCCGCTGTCGGGGTTCTTCTTCTCTTTCCACCTCCGGTCGCccggccggCCTA
orf 1      >  L  G  G  D  S  P  K  K  K  R  K  V  E  A  S  G  P  A  G  S BssH2
              Asc1                                 BseY1
              |                                    |
              CCGGGCGCGCCGACGCGCTGGACGATTTCGATCTCGACATGCTGGGTTCTGATGCCCTCG
       5461   ---------+---------+---------+---------+---------+---------+ 5520
              GGCCCGCGCGGCTGCGCGACCTGCTAAAGCTAGAGCTGTACGACCCAAGACTACGGGAGC
orf 1      >  G  R  A  D  A  L  D  D  F  D  L  D  M  L  G  S  D  A  L  D ATGACTTTGACCTGGATATGTTGGGAAGCGACGCATTGGATGACTTTGATCTGGACATGC
       5521   ---------+---------+---------+---------+---------+---------+ 5580
              TACTGAAACTGGACCTATACAACCCTTCGCTGCGTAACCTACTGAAACTAGACCTGTACG
orf 1      >  D  F  D  L  D  M  L  G  S  D  A  L  D  D  F  D  L  D  M  L TCGGCTCCGATGCTCTGGACGATTTCGATCTCGATATGTTAgggtcagacgcactggatg
       5581   ---------+---------+---------+---------+---------+---------+ 5640
              AGCCGAGGCTACGAGACCTGCTAAAGCTAGAGCTATACAATcccagtctgcgtgacctac
orf 1      >  G  S  D  A  L  D  D  F  D  L  D  M  L  G  S  D  A  L  D  D BtgZ1
                                                |
              atttcgaccttgaTatgttgGGAAGCGATGCCCTTGATGATTTCGACCTGGACATGCTCg
       5641   ---------+---------+---------+---------+---------+---------+ 5700
              taaagctggaactAtacaacCCTTCGCTACGGGAACTACTAAAGCTGGACCTGTACGAGc
orf 1      >  F  D  L  D  M  L  G  S  D  A  L  D  D  F  D  L  D  M  L  G BseY1
                                   |
              gcagcgacgccctggacgatttcgatctggacatgctgGGGTCCGATGCCTTGGATGATT
       5701   ---------+---------+---------+---------+---------+---------+ 5760
              cgtcgctgcgggacctgctaaagctagacctgtacgacCCCAGGCTACGGAACCTACTAA
orf 1      >  S  D  A  L  D  D  F  D  L  D  M  L  G  S  D  A  L  D  D  F BseY1                              BseY1
                        |                                  |
              TTGACTTGGATATGCTGgggagtgatgccctggacgactttgacctggacatgctgGGCT
       5761   ---------+---------+---------+---------+---------+---------+ 5820
              AACTGAACCTATACGACccctcactacgggacctgctgaaactggacctgtacgacCCGA
orf 1      >  D  L  D  M  L  G  S  D  A  L  D  D  F  D  L  D  M  L  G  S EcoR1
                                                          Pac1  |
                                              Cla1   Ase1  |  |
                                              |      |   |  |
              CCGATGCGCTCGATGACTTCGATTTGGATATGTTGTATATCGATtgaTTAATTAAGAATT
       5821   ---------+---------+---------+---------+---------+---------+ 5880
              GGCTACGCGAGCTACTGAAGCTAAACCTATACAACATATAGCTAactAATTAATTCTTAA
orf 1      >  D  A  L  D  D  F  D  L  D  M  L  Y  I  D  *

Sac1
              Ec12  |                              T7Ter
              |  |                                 |
              CCTAGAGCTCGCTGATCAGCCTCGACTGTGCCTTCTAGTTGCCAGCCATCTGTTGTTTGC
       5881   ---------+---------+---------+---------+---------+---------+ 5940
              GGATCTCGAGCGACTAGTCGGAGCTGACACGGAAGATCAACGGTCGGTAGACAACAAACG
```

MASNFTQFVLVDNGGTGDVTVAPSNFANGVAEWISSNSRSQAYKVTCSVRQSSAQKRKYT
IKVEVPKVATQTVGGVELPVAAWRSYLNMELTIPIFATNSDCELIVKAMQGLLKDGNPIP
SAIAANSGIYSAGGGGSGGGGSGGGGSGPKKKRKVAAAGSPSGQISNQALALAPSSAPVL
AQTMVPSSAMVPLAQPPAPAPVLTPGPPQSLSAPVPKSTQAGEGTLSEALLHLQFDADED
LGALLGNSTDPGVFTDLASVDNSEFQQLLNQGVSMSHSTAEPMLMEYPEAITRLVTGSQR
PPDPAPTPLGTSGLPNGLSGDEDFSSIADMDFSALLSQISSSGQGGGGSGFSVDTSALLD
LFSPSVTVPDMSLPDLDSSLASIQELLSPQEPPRPPEAENSSPDSGKQLVHYTAQPLFLL
DPGSVDTGSNDLPVLFELGEGSYFSEGDGFAEDPTISLLTGSEPPKAKDPTV

B

MASNFTQFVLVDNGGTGDVTVAPSNFANGVAEWISSNSRSQAYKVTCSVRQSSAQKRKYT
IKVEVPKVATQTVGGVELPVAAWRSYLNMELTIPIFATNSDCELIVKAMQGLLKDGNPIPSAIAAN
SGIY

C.

PSGQISNQALALAPSSAPVLAQTMVPSSAMVPLAQPPAPAPVLTPGPPQSLSAPVPKSTQAGEGTL
SEALLHLQFDADEDLGALLGNSTDPGVFTDLASVDNSEFQQLLNQGVSMSHSTAEPMLMEYPEAIT
RLVTGSQRPPDPAPTPLGTSGLPNGLSGDEDFSSIADMDFSALLSQISSSGQ

D.

GGGGSGFSVDTSALLDLFSPSVTVPDMSLPDLDSSLASIQELLSPQEPPRPPEAENSSPDSGKQLV
HYTAQPLFLLDPGSVDTGSNDLPVLFELGEGSYFSEGDGFAEDPTISLLTGSEPPKAKDPTV

Figure 15

MYPYDVPDYASPKKKRKVEASDKKYSIGLAIGTNSVGWAVITDEYKVPSKKFKVLGNTDR
HSIKKNLIGALLFDSGETAEATRLKRTARRRYTRRKNRICYLQEIFSNEMAKVDDSFFHR
LEESFLVEEDKKHERHPIFGNIVDEVAYHEKYPTIYHLRKKLVDSTDKADLRLIYLALAH
MIKFRGHFLIEGDLNPDNSDVDKLFIQLVQTYNQLFEENPINASGVDAKAILSARLSKSR
RLENLIAQLPGEKKNGLFGNLIALSLGLTPNFKSNFDLAEDAKLQLSKDTYDDDLDNLLA
QIGDQYADLFLAAKNLSDAILLSDILRVNTEITKAPLSASMIKRYDEHHQDLTLLKALVR
QQLPEKYKEIFFDQSKNGYAGYIDGGASQEEFYKFIKPILEKMDGTEELLVKLNREDLLR
KQRTFDNGSIPHQIHLGELHAILRRQEDFYPFLKDNREKIEKILTFRIPYYVGPLARGNS
RFAWMTRKSEETITPWNFEEVVDKGASAQSFIERMTNFDKNLPNEKVLPKHSLLYEYFTV
YNELTKVKYVTEGMRKPAFLSGEQKKAIVDLLFKTNRKVTVKQLKEDYFKKIECFDSVEI
SGVEDRFNASLGTYHDLLKIIKDKDFLDNEENEDILEDIVLTLTLFEDREMIEERLKTYA
HLFDDKVMKQLKRRRYTGWGRLSRKLINGIRDKQSGKTILDFLKSDGFANRNFMQLIHDD
SLTFKEDIQKAQVSGQGDSLHEHIANLAGSPAIKKGILQTVKVVDELVKVMGRHKPENIV
IEMARENQTTQKGQKNSRERMKRIEEGIKELGSQILKEHPVENTQLQNEKLYLYYLQNGR
DMYVDQELDINRLSDYDVDAIVPQSFLKDDSIDNKVLTRSDKNRGKSDNVPSEEVVKKMK
NYWRQLLNAKLITQRKFDNLTKAERGGLSELDKAGFIKRQLVETRQITKHVAQILDSRMN
TKYDENDKLIREVKVITLKSKLVSDFRKDFQFYKVREINNYHHAHDAYLNAVVGTALIKK
YPKLESEFVYGDYKVYDVRKMIAKSEQEIGKATAKYFFYSNIMNFFKTEITLANGEIRKR
PLIETNGETGEIVWDKGRDFATVRKVLSMPQVNIVKKTEVQTGGFSKESILPKRNSDKLI
ARKKDWDPKKYGGFDSPTVAYSVLVVAKVEKGKSKKLKSVKELLGITIMERSSFEKNPID
FLEAKGYKEVKKDLIIKLPKYSLFELENGRKRMLASAGELQKGNELALPSKYVNFLYLAS
HYEKLKGSPEDNEQKQLFVEQHKHYLDEIIEQISEFSKRVILADANLDKVLSAYNKHRDK
PIREQAENIIHLFTLTNLGAPAAFKYFDTTIDRKRYTSTKEVLDATLIHQSITGLYETRI
DLSQLGGDSPKKKRKVEASGPAGSGRADALDDFDLDMLGSDALDDFDLDMLGSDALDDFD
LDMLGSDALDDFDLDMLGSDALDDFDLDMLGSDALDDFDLDMLGSDALDDFDLDMLGSDA
LDDFDLDMLGSDALDDFDLDMLGSDALDDFDLDMLYID

EELLSKNYHLENEVARLKK

B.

PKKKRKV

C.

PKKKRKVEASGSGGLNGPTDAAEEELLSKNYHLENEVARLKKGSGSGEELLSKNYHLE
NEVARLKKGSGSGEELLSKNYHLENEVARLKKGSGSGEELLSKNYHLENEVARLKKGS
GSGEELLSKNYHLENEVARLKKGSGSGEELLSKNYHLENEVARLKKGSGSGEELLSKN
YHLENEVARLKKGSGSGEELLSKNYHLENEVARLKKGSGSGEELLSKNYHLENEVARL
KKGSGSGEELLSKNYHLENEVARLKKGSGSR-

Crisp A
AGCUGGGAAGUUCUUCCUGGUUUUAGAGCUAGAAAUAGCAAGUUAAAAUAAGGCUAG
UCCGUUAUCAACUUGAAAAGUGGCACCGAGUCGGUGCUUUUU Crisp B
UCCCUUGGGUCAGGGGUCCGUUUUAGAGCUAGAAAUAGCAAGUUAAAAUAAGGCUAG
UCCGUUAUCAACUUGAAAAGUGGCACCGAGUCGGUGCUUUUU Crisp C
ACACAAGGCAUCCGUCUCCGUUUUAGAGCUAGAAAUAGCAAGUUAAAAUAAGGCUAG
UCCGUUAUCAACUUGAAAAGUGGCACCGAGUCGGUGCUUUUU Crisp D
UAUUUAUUGUGCACUUAACGUUUUAGAGCUAGAAAUAGCAAGUUAAAAUAAGGCUAG
UCCGUUAUCAACUUGAAAAGUGGCACCGAGUCGGUGCUUUUU Crisp E
GCUACUUGGAAGGCUGAAAGUUUUAGAGCUAGAAAUAGCAAGUUAAAAUAAGGCUAG
UCCGUUAUCAACUUGAAAAGUGGCACCGAGUCGGUGCUUUUU

B.

MS2-Crisp A
AGCUGGGAAGUUCUUCCUGGUUUUAGAGCUAGGCC**AACAUGAGGAUCACCCAUGUC
UGCAGGGCCUAGCAAGUUAAAAUAAGGCUAGUCCGUUAUCAACUUGGCCAACAUGAG
GAUCACCCAUGUCUGCAG**GGCCAAGUGGCACCGAGUCGGUGCUUUUU MS2-Crisp B
UCCCUUGGGUCAGGGGUCCGUUUUAGAGCUAGGCCAACAUGAGGAUCACCCAUGUC
UGCAGGGCCUAGCAAGUUAAAAUAAGGCUAGUCCGUUAUCAACUUGGCCAACAUGAGG
AUCACCCAUGUCUGCAGGGCCAAGUGGCACCGAGUCGGUGCUUUUU MS2-Crisp C
ACACAAGGCAUCCGUCUCCGUUUUAGAGCUAGGCCAACAUGAGGAUCACCCAUGUCU
GCAGGGCCUAGCAAGUUAAAAUAAGGCUAGUCCGUUAUCAACUUGGCCAACAUGAGGA
UCACCCAUGUCUGCAGGGCCAAGUGGCACCGAGUCGGUGCUUUUU MS2-Crisp D
UAUUUAUUGUGCACUUAACGUUUUAGAGCUAGGCCAACAUGAGGAUCACCCAUGUCU
GCAGGGCCUAGCAAGUUAAAAUAAGGCUAGUCCGUUAUCAACUUGGCCAACAUGAGGA
UCACCCAUGUCUGCAGGGCCAAGUGGCACCGAGUCGGUGCUUUUU MS2-Crisp E
GCUACUUGGAAGGCUGAAGUUUUAGAGCUAGGCCAACAUGAGGAUCACCCAUGUCU
GCAGGGCCUAGCAAGUUAAAAUAAGGCUAGUCCGUUAUCAACUUGGCCAACAUGAGGA
UCACCCAUGUCUGCAGGGCCAAGUGGCACCGAGUCGGUGCUUUUU

Figure 18

```
MDKKYSIGLDIGTNSVGWAVITDEYKVPSKKFKVLGNTDRHSIKKNLIGALLFDSGETAEATR
LKRTARRRYTRRKNRICYLQEIFSNEMAKVDDSFFHRLEESFLVEEDKKHERHPIFGNIVDEV
AYHEKYPTIYHLRKKLVDSTDKADLRLIYLALAHMIKFRGHFLIEGDLNPDNSDVDKLFIQLV
QTYNQLFEENPINASGVDAKAILSARLSKSRRLENLIAQLPGEKKNGLFGNLIALSLGLTPNF
KSNFDLAEDAKLQLSKDTYDDDLDNLLAQIGDQYADLFLAAKNLSDAILLSDILRVNTEITKA
PLSASMIKRYDEHHQDLTLLKALVRQQLPEKYKEIFFDQSKNGYAGYIDGGASQEEFYKFIKP
ILEKMDGTEELLVKLNREDLLRKQRTFDNGSIPHQIHLGELHAILRRQEDFYPFLKDNREKIE
KILTFRIPYYVGPLARGNSRFAWMTRKSEETITPWNFEEVVDKGASAQSFIERMTNFDKNLPN
EKVLPKHSLLYEYFTVYNELTKVKYVTEGMRKPAFLSGEQKKAIVDLLFKTNRKVTVKQLKED
YFKKIECFDSVEISGVEDRFNASLGTYHDLLKIIKDKDFLDNEENEDILEDIVLTLTLFEDRE
MIEERLKTYAHLFDDKVMKQLKRRRYTGWGRLSRKLINGIRDKQSGKTILDFLKSDGFANRNF
MQLIHDDSLTFKEDIQKAQVSGQGDSLHEHIANLAGSPAIKKGILQTVKVVDELVKVMGRHKP
ENIVIEMARENQTTQKGQKNSRERMKRIEEGIKELGSQILKEHPVENTQLQNEKLYLYYLQNG
RDMYVDQELDINRLSDYDVDHIVPQSFLKDDSIDNKVLTRSDKNRGKSDNVPSEEVVKKMKNY
WRQLLNAKLITQRKFDNLTKAERGGLSELDKAGFIKRQLVETRQITKHVAQILDSRMNTKYDE
NDKLIREVKVITLKSKLVSDFRKDFQFYKVREINNYHHAHDAYLNAVVGTALIKKYPKLESEF
VYGDYKVYDVRKMIAKSEQEIGKATAKYFFYSNIMNFFKTEITLANGEIRKRPLIETNGETGE
IVWDKGRDFATVRKVLSMPQVNIVKKTEVQTGGFSKESILPKRNSDKLIARKKDWDPKKYGGF
DSPTVAYSVLVVAKVEKGKSKKLKSVKELLGITIMERSSFEKNPIDFLEAKGYKEVKKDLIIK
LPKYSLFELENGRKRMLASAGELQKGNELALPSKYVNFLYLASHYEKLKGSPEDNEQKQLFVE
QHKHYLDEIIEQISEFSKRVILADANLDKVLSAYNKHRDKPIREQAENIIHLFTLTNLGAPAA
FKYFDTTIDRKRYTSTKEVLDATLIHQSITGLYETRIDLSQLGGD
```

Figure 19

| Feature Key | Position(s) | Length | Description | References |
|---|---|---|---|---|
| Mutagenesis | 10-10 | 1 | D → A: Target DNA noncomplementary to the crRNA is not cleaved; nickase activity. Processes guide RNAs. In vivo, loss of Cas9-mediated CRISPR interference in plasmid transformation. Able to bind guide RNAs and target DNA but not cleave DNA; when associated with A-840. | Jinek et al., 2012<br><br>Fonfara et al., 2014<br><br>Nishimasu et al., 2014 |
| Mutagenesis | 15-15 | 1 | S → A: Decreased DNA cleavage. | Nishimasu et al., 2014 |
| Mutagenesis | 66-66 | 1 | R → A: Significantly decreased DNA cleavage. | Nishimasu et al., 2014 |
| Mutagenesis | 70-70 | 1 | R → A: No DNA cleavage. | Nishimasu et al., 2014 |
| Mutagenesis | 74-74 | 1 | R → A: Significantly decreased DNA cleavage. | Nishimasu et al., 2014 |
| Mutagenesis | 78-78 | 1 | R → A: Moderately decreased DNA cleavage. | Nishimasu et al., 2014 |
| Mutagenesis | 97-150 | 54 | Missing : No nuclease activity. | Nishimasu et al., 2014 |
| Mutagenesis | 165-165 | 1 | R → A: Moderately decreased DNA cleavage. | Nishimasu et al., 2014 |
| Mutagenesis | 175-307 | 133 | Missing : About 50% nuclease activity. | Nishimasu et al., 2014 |
| Mutagenesis | 312-409 | 98 | Missing : No nuclease activity. | Nishimasu et al., 2014 |
| Mutagenesis | 475-477 | 3 | PWN → AAA: Slight decrease in target DNA cleavage and DNA-binding. Almost complete loss of DNA cleavage and binding; when associated with 1125-A--A-1127. | Jinek et al., 2014 |
| Mutagenesis | 762-762 | 1 | E → A: Only cleaves 1 DNA strand, probably the noncomplementary strand. Processes guide RNAs correctly. In vivo, loss of Cas9-mediated CRISPR interference in plasmid transformation. | Fonfara et al., 2014<br><br>Nishimasu et al., 2014 |

Figure 20

| Feature Key | Position(s) | Length | Description | References |
|---|---|---|---|---|
| Mutagenesis | 840-840 | 1 | H → A: Target DNA complementary to the crRNA is not cleaved; nickase activity. In vivo, loss of Cas9-mediated CRISPR interference in plasmid transformation. Able to process and bind guide RNAs and target DNA but not cleave DNA; when associated with A-10. | Jinek et al., 2012<br><br>Fonfara et al., 2014<br><br>Nishimasu et al., 2014 |
| Mutagenesis | 854-854 | 1 | N → A: Decreased DNA cleavage. Processes guide RNAs correctly. In vivo, retains Cas9-mediated CRISPR interference in plasmid transformation. | Fonfara et al., 20104<br><br>Nishimasu et al., 2014 |
| Mutagenesis | 863-863 | 1 | N → A: Only cleaves 1 DNA strand, probably the complementary strand. Processes guide RNAs correctly. In vivo, loss of Cas9-mediated CRISPR interference in plasmid transformation. | Fonfara et al., 2014<br><br>Nishimasu et al., 2014 |
| Mutagenesis | 982-983 | 2 | HH → AA: Processes guide RNAs correctly. | Fonfara et al., 2014 |
| Mutagenesis | 982-982 | 1 | H → A: Decreased DNA cleavage. In vivo, loss of Cas9-mediated CRISPR interference in plasmid transformation. | Nishimasu et al., 2014 |
| Mutagenesis | 983-983 | 1 | H → A: Only cleaves 1 DNA strand, probably the noncomplementary strand. | Nishimasu et al., 2014 |
| Mutagenesis | 986-986 | 1 | D → A: Only cleaves 1 DNA strand, probably the noncomplementary strand. Processes guide RNAs correctly. In vivo, loss of Cas9-mediated CRISPR interference in plasmid transformation. | Fonfara et al., 2014<br><br>Nishimasu et al., 2014 |

Figure 20 (continued)

| Feature Key | Position(s) | Length | Description | References |
|---|---|---|---|---|
| Mutagenesis | 1099-1368 | 270 | Missing : No nuclease activity. | Nishimasu et al., 2014 |
| Mutagenesis | 1125-1127 | 3 | DWD → AAA: No change in target DNA cleavage, slight decrease in DNA-binding. Almost complete loss of DNA cleavage and binding; when associated with 475-A--A-477. | Jinek et al., 2014 |
| Mutagenesis | 1132-1132 | 1 | G → C: Probably inactivates protein. | Jiang et al., 2013 |

Figure 20 (continued)

SEQUENCE LISTING

<160> NUMBER OF SEQ ID NOS: 117

<210> SEQ ID NO 1
<211> LENGTH: 210
<212> TYPE: PRT

<213> ORGANISM: Homosapiens

<400> SEQUENCE: 1

Met Trp Thr Leu Gly Arg Arg Ala Val Ala Gly Leu Leu Ala Ser Pro
1               5                   10                  15

Ser Pro Ala Gln Ala Gln Thr Leu Thr Arg Val Pro Arg Pro Ala Glu
            20                  25                  30

Leu Ala Pro Leu Cys Gly Arg Arg Gly Leu Arg Thr Asp Ile Asp Ala
        35                  40                  45

Thr Cys Thr Pro Arg Arg Ala Ser Ser Asn Gln Arg Gly Leu Asn Gln
    50                  55                  60

Ile Trp Asn Val Lys Lys Gln Ser Val Tyr Leu Met Asn Leu Arg Lys
65                  70                  75                  80

Ser Gly Thr Leu Gly His Pro Gly Ser Leu Asp Glu Thr Thr Tyr Glu
                85                  90                  95

Arg Leu Ala Glu Glu Thr Leu Asp Ser Leu Ala Glu Phe Phe Glu Asp
            100                 105                 110

Leu Ala Asp Lys Pro Tyr Thr Phe Glu Asp Tyr Asp Val Ser Phe Gly
        115                 120                 125

Ser Gly Val Leu Thr Val Lys Leu Gly Gly Asp Leu Gly Thr Tyr Val
    130                 135                 140

Ile Asn Lys Gln Thr Pro Asn Lys Gln Ile Trp Leu Ser Ser Pro Ser
145                 150                 155                 160

Ser Gly Pro Lys Arg Tyr Asp Trp Thr Gly Lys Asn Trp Val Tyr Ser
                165                 170                 175

His Asp Gly Val Ser Leu His Glu Leu Leu Ala Ala Glu Leu Thr Lys
            180                 185                 190

Ala Leu Lys Thr Lys Leu Asp Leu Ser Ser Leu Ala Tyr Ser Gly Lys
        195                 200                 205

Asp Ala
    210

<210> SEQ ID NO 2
<211> LENGTH: 196
<212> TYPE: PRT
<213> ORGANISM: Homosapiens

<400> SEQUENCE: 2

Met Trp Thr Leu Gly Arg Arg Ala Val Ala Gly Leu Leu Ala Ser Pro
1               5                   10                  15

Ser Pro Ala Gln Ala Gln Thr Leu Thr Arg Val Pro Arg Pro Ala Glu
            20                  25                  30

Leu Ala Pro Leu Cys Gly Arg Arg Gly Leu Arg Thr Asp Ile Asp Ala
        35                  40                  45

Thr Cys Thr Pro Arg Arg Ala Ser Ser Asn Gln Arg Gly Leu Asn Gln
    50                  55                  60

Ile Trp Asn Val Lys Lys Gln Ser Val Tyr Leu Met Asn Leu Arg Lys
65                  70                  75                  80

Ser Gly Thr Leu Gly His Pro Gly Ser Leu Asp Glu Thr Thr Tyr Glu
                85                  90                  95

Arg Leu Ala Glu Glu Thr Leu Asp Ser Leu Ala Glu Phe Phe Glu Asp
            100                 105                 110

Leu Ala Asp Lys Pro Tyr Thr Phe Glu Asp Tyr Asp Val Ser Phe Gly
        115                 120                 125

Ser Gly Val Leu Thr Val Lys Leu Gly Gly Asp Leu Gly Thr Tyr Val

```
                130                 135                 140
Ile Asn Lys Gln Thr Pro Asn Lys Gln Ile Trp Leu Ser Ser Pro Ser
145                 150                 155                 160

Arg Tyr Val Val Asp Leu Ser Val Met Thr Gly Leu Gly Lys Thr Gly
                165                 170                 175

Cys Thr Pro Thr Thr Ala Cys Pro Ser Met Ser Cys Trp Pro Gln Ser
                180                 185                 190

Ser Leu Lys Pro
        195

<210> SEQ ID NO 3
<211> LENGTH: 171
<212> TYPE: PRT
<213> ORGANISM: Homosapiens

<400> SEQUENCE: 3

Met Trp Thr Leu Gly Arg Arg Ala Val Ala Gly Leu Leu Ala Ser Pro
1               5                   10                  15

Ser Pro Ala Gln Ala Gln Thr Leu Thr Arg Val Pro Arg Pro Ala Glu
                20                  25                  30

Leu Ala Pro Leu Cys Gly Arg Arg Gly Leu Arg Thr Asp Ile Asp Ala
            35                  40                  45

Thr Cys Thr Pro Arg Arg Ala Ser Ser Asn Gln Arg Gly Leu Asn Gln
    50                  55                  60

Ile Trp Asn Val Lys Lys Gln Ser Val Tyr Leu Met Asn Leu Arg Lys
65                  70                  75                  80

Ser Gly Thr Leu Gly His Pro Gly Ser Leu Asp Glu Thr Thr Tyr Glu
                85                  90                  95

Arg Leu Ala Glu Glu Thr Leu Asp Ser Leu Ala Glu Phe Phe Glu Asp
            100                 105                 110

Leu Ala Asp Lys Pro Tyr Thr Phe Glu Asp Tyr Asp Val Ser Phe Gly
        115                 120                 125

Ser Gly Val Leu Thr Val Lys Leu Gly Gly Asp Leu Gly Thr Tyr Val
    130                 135                 140

Ile Asn Lys Gln Thr Pro Asn Lys Gln Ile Trp Leu Ser Ser Pro Ser
145                 150                 155                 160

Arg Leu Thr Trp Leu Leu Trp Leu Phe His Pro
                165                 170

<210> SEQ ID NO 4
<211> LENGTH: 19
<212> TYPE: PRT
<213> ORGANISM: Artificial sequence
<220> FEATURE:
<223> OTHER INFORMATION: Synthetic peptide

<400> SEQUENCE: 4

Glu Glu Leu Leu Ser Lys Asn Tyr His Leu Glu Asn Glu Val Ala Arg
1               5                   10                  15

Leu Lys Lys

<210> SEQ ID NO 5
<211> LENGTH: 240
<212> TYPE: PRT
<213> ORGANISM: Artificial sequence
<220> FEATURE:
<223> OTHER INFORMATION: Synthetic peptide

<400> SEQUENCE: 5
```

-continued

Glu Glu Leu Leu Ser Lys Asn Tyr His Leu Glu Asn Glu Val Ala Arg
1               5                   10                  15

Leu Lys Lys Gly Ser Gly Ser Gly Glu Glu Leu Leu Ser Lys Asn Tyr
            20                  25                  30

His Leu Glu Asn Glu Val Ala Arg Leu Lys Lys Gly Ser Gly Ser Gly
        35                  40                  45

Glu Glu Leu Leu Ser Lys Asn Tyr His Leu Glu Asn Glu Val Ala Arg
    50                  55                  60

Leu Lys Lys Gly Ser Gly Ser Gly Glu Glu Leu Leu Ser Lys Asn Tyr
65                  70                  75                  80

His Leu Glu Asn Glu Val Ala Arg Leu Lys Lys Gly Ser Gly Ser Gly
            85                  90                  95

Glu Glu Leu Leu Ser Lys Asn Tyr His Leu Glu Asn Glu Val Ala Arg
                100                 105                 110

Leu Lys Lys Gly Ser Gly Ser Gly Glu Glu Leu Leu Ser Lys Asn Tyr
            115                 120                 125

His Leu Glu Asn Glu Val Ala Arg Leu Lys Lys Gly Ser Gly Ser Gly
        130                 135                 140

Glu Glu Leu Leu Ser Lys Asn Tyr His Leu Glu Asn Glu Val Ala Arg
145                 150                 155                 160

Leu Lys Lys Gly Ser Gly Ser Gly Glu Glu Leu Leu Ser Lys Asn Tyr
                165                 170                 175

His Leu Glu Asn Glu Val Ala Arg Leu Lys Lys Gly Ser Gly Ser Gly
            180                 185                 190

Glu Glu Leu Leu Ser Lys Asn Tyr His Leu Glu Asn Glu Val Ala Arg
        195                 200                 205

Leu Lys Lys Gly Ser Gly Ser Gly Glu Glu Leu Leu Ser Lys Asn Tyr
    210                 215                 220

His Leu Glu Asn Glu Val Ala Arg Leu Lys Lys Gly Ser Gly Ser Arg
225                 230                 235                 240

<210> SEQ ID NO 6
<211> LENGTH: 256
<212> TYPE: PRT
<213> ORGANISM: Artificial sequence
<220> FEATURE:
<223> OTHER INFORMATION: Synthetic peptide

<400> SEQUENCE: 6

Glu Ala Ser Gly Ser Gly Gly Leu Asn Gly Pro Thr Asp Ala Ala Glu
1               5                   10                  15

Glu Glu Leu Leu Ser Lys Asn Tyr His Leu Glu Asn Glu Val Ala Arg
            20                  25                  30

Leu Lys Lys Gly Ser Gly Ser Gly Glu Glu Leu Leu Ser Lys Asn Tyr
        35                  40                  45

His Leu Glu Asn Glu Val Ala Arg Leu Lys Lys Gly Ser Gly Ser Gly
    50                  55                  60

Glu Glu Leu Leu Ser Lys Asn Tyr His Leu Glu Asn Glu Val Ala Arg
65                  70                  75                  80

Leu Lys Lys Gly Ser Gly Ser Gly Glu Glu Leu Leu Ser Lys Asn Tyr
                85                  90                  95

His Leu Glu Asn Glu Val Ala Arg Leu Lys Lys Gly Ser Gly Ser Gly
            100                 105                 110

Glu Glu Leu Leu Ser Lys Asn Tyr His Leu Glu Asn Glu Val Ala Arg
        115                 120                 125

```
Leu Lys Lys Gly Ser Gly Ser Gly Glu Glu Leu Leu Ser Lys Asn Tyr
    130                 135                 140

His Leu Glu Asn Glu Val Ala Arg Leu Lys Lys Gly Ser Gly Ser Gly
145                 150                 155                 160

Glu Glu Leu Leu Ser Lys Asn Tyr His Leu Glu Asn Glu Val Ala Arg
                165                 170                 175

Leu Lys Lys Gly Ser Gly Ser Gly Glu Glu Leu Leu Ser Lys Asn Tyr
            180                 185                 190

His Leu Glu Asn Glu Val Ala Arg Leu Lys Lys Gly Ser Gly Ser Gly
        195                 200                 205

Glu Glu Leu Leu Ser Lys Asn Tyr His Leu Glu Asn Glu Val Ala Arg
    210                 215                 220

Leu Lys Lys Gly Ser Gly Ser Gly Glu Glu Leu Leu Ser Lys Asn Tyr
225                 230                 235                 240

His Leu Glu Asn Glu Val Ala Arg Leu Lys Lys Gly Ser Gly Ser Arg
                245                 250                 255

<210> SEQ ID NO 7
<211> LENGTH: 130
<212> TYPE: PRT
<213> ORGANISM: Artificial sequence
<220> FEATURE:
<223> OTHER INFORMATION: Synthetic peptide

<400> SEQUENCE: 7

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
                20                  25                  30

Trp Ile Ser Ser Asn Ser Arg Ser Gln Ala Tyr Lys Val Thr Cys Ser
            35                  40                  45

Val Arg Gln Ser Ser Ala Gln Lys Arg Lys Tyr Thr Ile Lys Val Glu
        50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr
    130

<210> SEQ ID NO 8
<211> LENGTH: 184
<212> TYPE: PRT
<213> ORGANISM: Artificial sequence
<220> FEATURE:
<223> OTHER INFORMATION: Synthetic peptide

<400> SEQUENCE: 8

Pro Ser Gly Gln Ile Ser Asn Gln Ala Leu Ala Leu Ala Pro Ser Ser
1               5                   10                  15

Ala Pro Val Leu Ala Gln Thr Met Val Pro Ser Ser Ala Met Val Pro
                20                  25                  30

Leu Ala Gln Pro Pro Ala Pro Ala Pro Val Leu Thr Pro Gly Pro Pro
```

```
                35                  40                  45
Gln Ser Leu Ser Ala Pro Val Pro Lys Ser Thr Gln Ala Gly Glu Gly
        50                  55                  60

Thr Leu Ser Glu Ala Leu Leu His Leu Gln Phe Asp Ala Asp Glu Asp
65                  70                  75                  80

Leu Gly Ala Leu Leu Gly Asn Ser Thr Asp Pro Gly Val Phe Thr Asp
                85                  90                  95

Leu Ala Ser Val Asp Asn Ser Glu Phe Gln Gln Leu Leu Asn Gln Gly
            100                 105                 110

Val Ser Met Ser His Ser Thr Ala Glu Pro Met Leu Met Glu Tyr Pro
        115                 120                 125

Glu Ala Ile Thr Arg Leu Val Thr Gly Ser Gln Arg Pro Pro Asp Pro
    130                 135                 140

Ala Pro Thr Pro Leu Gly Thr Ser Gly Leu Pro Asn Gly Leu Ser Gly
145                 150                 155                 160

Asp Glu Asp Phe Ser Ser Ile Ala Asp Met Asp Phe Ser Ala Leu Leu
                165                 170                 175

Ser Gln Ile Ser Ser Ser Gly Gln
            180

<210> SEQ ID NO 9
<211> LENGTH: 128
<212> TYPE: PRT
<213> ORGANISM: Artificial sequence
<220> FEATURE:
<223> OTHER INFORMATION: Synthetic peptide

<400> SEQUENCE: 9

Gly Gly Gly Gly Ser Gly Phe Ser Val Asp Thr Ser Ala Leu Leu Asp
1               5                   10                  15

Leu Phe Ser Pro Ser Val Thr Val Pro Asp Met Ser Leu Pro Asp Leu
            20                  25                  30

Asp Ser Ser Leu Ala Ser Ile Gln Glu Leu Leu Ser Pro Gln Glu Pro
        35                  40                  45

Pro Arg Pro Pro Glu Ala Glu Asn Ser Ser Pro Asp Ser Gly Lys Gln
    50                  55                  60

Leu Val His Tyr Thr Ala Gln Pro Leu Phe Leu Leu Asp Pro Gly Ser
65                  70                  75                  80

Val Asp Thr Gly Ser Asn Asp Leu Pro Val Leu Phe Glu Leu Gly Glu
                85                  90                  95

Gly Ser Tyr Phe Ser Glu Gly Asp Gly Phe Ala Glu Asp Pro Thr Ile
            100                 105                 110

Ser Leu Leu Thr Gly Ser Glu Pro Pro Lys Ala Lys Asp Pro Thr Val
        115                 120                 125

<210> SEQ ID NO 10
<211> LENGTH: 472
<212> TYPE: PRT
<213> ORGANISM: Artificial sequence
<220> FEATURE:
<223> OTHER INFORMATION: Synthetic peptide

<400> SEQUENCE: 10

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30
```

-continued

Trp Ile Ser Ser Asn Ser Arg Ser Gln Ala Tyr Lys Val Thr Cys Ser
                35                  40                  45

Val Arg Gln Ser Ser Ala Gln Lys Arg Lys Tyr Thr Ile Lys Val Glu
 50                  55                  60

Val Pro Lys Val Ala Thr Gln Thr Val Gly Gly Val Glu Leu Pro Val
 65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr Ser Ala Gly Gly Gly Ser Gly Gly Gly Ser Gly Gly
        130                 135                 140

Gly Gly Ser Gly Pro Lys Lys Lys Arg Lys Val Ala Ala Ala Gly Ser
145                 150                 155                 160

Pro Ser Gly Gln Ile Ser Asn Gln Ala Leu Ala Leu Ala Pro Ser Ser
                165                 170                 175

Ala Pro Val Leu Ala Gln Thr Met Val Pro Ser Ser Ala Met Val Pro
            180                 185                 190

Leu Ala Gln Pro Pro Ala Pro Ala Pro Val Leu Thr Pro Gly Pro Pro
        195                 200                 205

Gln Ser Leu Ser Ala Pro Val Pro Lys Ser Thr Gln Ala Gly Glu Gly
    210                 215                 220

Thr Leu Ser Glu Ala Leu Leu His Leu Gln Phe Asp Ala Asp Glu Asp
225                 230                 235                 240

Leu Gly Ala Leu Leu Gly Asn Ser Thr Asp Pro Gly Val Phe Thr Asp
                245                 250                 255

Leu Ala Ser Val Asp Asn Ser Glu Phe Gln Gln Leu Leu Asn Gln Gly
            260                 265                 270

Val Ser Met Ser His Ser Thr Ala Glu Pro Met Leu Met Glu Tyr Pro
        275                 280                 285

Glu Ala Ile Thr Arg Leu Val Thr Gly Ser Gln Arg Pro Pro Asp Pro
    290                 295                 300

Ala Pro Thr Pro Leu Gly Thr Ser Gly Leu Pro Asn Gly Leu Ser Gly
305                 310                 315                 320

Asp Glu Asp Phe Ser Ser Ile Ala Asp Met Asp Phe Ser Ala Leu Leu
                325                 330                 335

Ser Gln Ile Ser Ser Ser Gly Gln Gly Gly Gly Ser Gly Phe Ser
            340                 345                 350

Val Asp Thr Ser Ala Leu Leu Asp Leu Phe Ser Pro Ser Val Thr Val
        355                 360                 365

Pro Asp Met Ser Leu Pro Asp Leu Asp Ser Ser Leu Ala Ser Ile Gln
    370                 375                 380

Glu Leu Leu Ser Pro Gln Glu Pro Pro Arg Pro Pro Glu Ala Glu Asn
385                 390                 395                 400

Ser Ser Pro Asp Ser Gly Lys Gln Leu Val His Tyr Thr Ala Gln Pro
                405                 410                 415

Leu Phe Leu Leu Asp Pro Gly Ser Val Asp Thr Gly Ser Asn Asp Leu
            420                 425                 430

Pro Val Leu Phe Glu Leu Gly Glu Gly Ser Tyr Phe Ser Glu Gly Asp
        435                 440                 445

Gly Phe Ala Glu Asp Pro Thr Ile Ser Leu Leu Thr Gly Ser Glu Pro

Pro Lys Ala Lys Asp Pro Thr Val
465                 470

<210> SEQ ID NO 11
<211> LENGTH: 1500
<212> TYPE: DNA
<213> ORGANISM: Homosapiens

<400> SEQUENCE: 11

| ggctcacatt | tgacatcctc | taaagcatat | ataaaatgtg | aagaaaactt | tcacaatttg | 60 |
| catcccttttg | taatatgtaa | cagaaataaa | attctctttt | aaaatctatc | aacaataggc | 120 |
| aaggcacggt | ggctcacgcc | tgtcgtctca | gcactttgtg | aggcccaggc | gggcagatcg | 180 |
| tttgagccta | gaagttcaag | accaccctgg | gcaacatagc | gaaaccccct | ttctacaaaa | 240 |
| aatacaaaaa | ctagctgggt | gtggtggtgc | acacctgtag | tcccagctac | ttggaaggct | 300 |
| gaaatgggaa | gactgcttga | gcccgggagg | gagaagttgc | agtaagccag | gaccacacca | 360 |
| ctgcactcca | gcctgggcaa | cagagtgaga | ctctgtctca | aacaaacaaa | taaatgaggc | 420 |
| gggtggatca | cgaggtcagt | agatcgagac | catcctggct | aacacggtga | aacccgtctc | 480 |
| tactaaaaaa | aaaaaaaaat | acaaaaaatt | agccaggcat | ggtggcgggc | gcctgtagtc | 540 |
| ccagttactc | gggaggctga | ggcaggagaa | tggcgtgaaa | ccgggaggca | gagcttgcag | 600 |
| tgagccgaga | tcgcaccact | gccctccagc | ctgggcgaca | gagcgagact | ccgtctcaat | 660 |
| caatcaatca | atcaataaaa | tctattaaca | atatttattg | tgcacttaac | aggaacatgc | 720 |
| cctgtccaaa | aaaactttta | cagggcttaa | ctcattttat | ccttaccaca | atcctatgaa | 780 |
| gtaggaactt | ttataaaacg | cattttataa | acaaggcaca | gagaggttaa | ttaacttgcc | 840 |
| ctctggtcac | acagctagga | agtgggcaga | gtacagattt | acacaaggca | tccgtctcct | 900 |
| ggccccacat | acccaactgc | tgtaaaccca | taccggcggc | caagcagcct | caatttgtgc | 960 |
| atgcacccac | ttcccagcaa | gacagcagct | cccaagttcc | tcctgtttag | aattttagaa | 1020 |
| gcggcgggcc | accaggctgc | agtctcccctt | gggtcagggg | tcctggttgc | actccgtgct | 1080 |
| ttgcacaaag | caggctctcc | atttttgtta | aatgcacgaa | tagtgctaag | ctgggaagtt | 1140 |
| cttcctgagg | tctaacctct | agctgctccc | ccacagaaga | gtgcctgcgg | ccagtggcca | 1200 |
| ccaggggtcg | ccgcagcacc | cagcgctgga | gggcggagcg | ggcggcagac | ccggagcagc | 1260 |
| atgtggactc | tcgggcgccg | cgcagtagcc | ggcctcctgg | cgtcacccag | cccagcccag | 1320 |
| gcccagaccc | tcacccgggt | cccgcggccg | gcagagttgg | ccccactctg | cggccgccgt | 1380 |
| ggcctgcgca | ccgacatcga | tgcgacctgc | acgccccgcc | gcgcagtaag | tatccgcgcc | 1440 |
| gggaacagcc | gcgggccgca | cgccgcgggc | cgcacgccgc | acgcctgcgc | agggaggcgc | 1500 |

<210> SEQ ID NO 12
<211> LENGTH: 7
<212> TYPE: PRT
<213> ORGANISM: Artificial sequence
<220> FEATURE:
<223> OTHER INFORMATION: Synthetic peptide

<400> SEQUENCE: 12

Pro Lys Lys Lys Arg Lys Val
1               5

<210> SEQ ID NO 13
<211> LENGTH: 16

```
<212> TYPE: PRT
<213> ORGANISM: Artificial sequence
<220> FEATURE:
<223> OTHER INFORMATION: Synthetic peptide

<400> SEQUENCE: 13

Lys Arg Pro Ala Ala Thr Lys Lys Ala Gly Gln Ala Lys Lys Lys
1               5                   10                  15

<210> SEQ ID NO 14
<211> LENGTH: 11
<212> TYPE: PRT
<213> ORGANISM: Artificial sequence
<220> FEATURE:
<223> OTHER INFORMATION: Synthetic peptide

<400> SEQUENCE: 14

Ser Pro Lys Lys Lys Arg Lys Val Glu Ala Ser
1               5                   10

<210> SEQ ID NO 15
<211> LENGTH: 6
<212> TYPE: PRT
<213> ORGANISM: Artificial sequence
<220> FEATURE:
<223> OTHER INFORMATION: Synthetic peptide

<400> SEQUENCE: 15

Lys Lys Lys Arg Lys Val
1               5

<210> SEQ ID NO 16
<211> LENGTH: 18
<212> TYPE: PRT
<213> ORGANISM: Artificial sequence
<220> FEATURE:
<223> OTHER INFORMATION: Synthetic peptide

<400> SEQUENCE: 16

Ser Pro Lys Lys Lys Arg Lys Val Glu Ala Ser Pro Lys Lys Lys Arg
1               5                   10                  15

Lys Val

<210> SEQ ID NO 17
<211> LENGTH: 11
<212> TYPE: PRT
<213> ORGANISM: Artificial sequence
<220> FEATURE:
<223> OTHER INFORMATION: Synthetic peptide

<400> SEQUENCE: 17

Asp Ala Leu Asp Asp Phe Asp Leu Asp Met Leu
1               5                   10

<210> SEQ ID NO 18
<211> LENGTH: 131
<212> TYPE: PRT
<213> ORGANISM: Artificial sequence
<220> FEATURE:
<223> OTHER INFORMATION: Synthetic peptide

<400> SEQUENCE: 18

Asp Ala Leu Asp Asp Phe Asp Leu Asp Met Leu Gly Ser Asp Ala Leu
1               5                   10                  15

Asp Asp Phe Asp Leu Asp Met Leu Gly Ser Asp Ala Leu Asp Asp Phe
                20                  25                  30
```

Asp Leu Asp Met Leu Gly Ser Asp Ala Leu Asp Asp Phe Asp Leu Asp
            35                  40                  45

Met Leu Gly Ser Asp Ala Leu Asp Asp Phe Asp Leu Asp Met Leu Gly
    50                  55                  60

Ser Asp Ala Leu Asp Asp Phe Asp Leu Asp Met Leu Gly Ser Asp Ala
65                  70                  75                  80

Leu Asp Asp Phe Asp Leu Asp Met Leu Gly Ser Asp Ala Leu Asp Asp
                85                  90                  95

Phe Asp Leu Asp Met Leu Gly Ser Asp Ala Leu Asp Asp Phe Asp Leu
            100                 105                 110

Asp Met Leu Gly Ser Asp Ala Leu Asp Asp Phe Asp Leu Asp Met Leu
            115                 120                 125

Tyr Ile Asp
    130

<210> SEQ ID NO 19
<211> LENGTH: 9
<212> TYPE: PRT
<213> ORGANISM: Artificial sequence
<220> FEATURE:
<223> OTHER INFORMATION: Synthetic peptide

<400> SEQUENCE: 19

Glu Thr Phe Ser Asp Leu Trp Lys Leu
1               5

<210> SEQ ID NO 20
<211> LENGTH: 9
<212> TYPE: PRT
<213> ORGANISM: Artificial sequence
<220> FEATURE:
<223> OTHER INFORMATION: Synthetic peptide

<400> SEQUENCE: 20

Asp Asp Ile Glu Gln Trp Phe Thr Glu
1               5

<210> SEQ ID NO 21
<211> LENGTH: 9
<212> TYPE: PRT
<213> ORGANISM: Artificial sequence
<220> FEATURE:
<223> OTHER INFORMATION: Synthetic peptide

<400> SEQUENCE: 21

Ser Asp Ile Met Asp Phe Val Leu Lys
1               5

<210> SEQ ID NO 22
<211> LENGTH: 9
<212> TYPE: PRT
<213> ORGANISM: Artificial sequence
<220> FEATURE:
<223> OTHER INFORMATION: Synthetic peptide

<400> SEQUENCE: 22

Asp Leu Leu Asp Phe Ser Met Met Phe
1               5

<210> SEQ ID NO 23
<211> LENGTH: 9
<212> TYPE: PRT
<213> ORGANISM: Artificial sequence

```
<220> FEATURE:
<223> OTHER INFORMATION: Synthetic peptide

<400> SEQUENCE: 23

Glu Thr Leu Asp Phe Ser Leu Val Thr
1               5

<210> SEQ ID NO 24
<211> LENGTH: 9
<212> TYPE: PRT
<213> ORGANISM: Artificial sequence
<220> FEATURE:
<223> OTHER INFORMATION: Synthetic peptide

<400> SEQUENCE: 24

Arg Lys Ile Leu Asn Asp Leu Ser Ser
1               5

<210> SEQ ID NO 25
<211> LENGTH: 9
<212> TYPE: PRT
<213> ORGANISM: Artificial sequence
<220> FEATURE:
<223> OTHER INFORMATION: Synthetic peptide

<400> SEQUENCE: 25

Glu Ala Ile Leu Ala Glu Leu Lys Lys
1               5

<210> SEQ ID NO 26
<211> LENGTH: 9
<212> TYPE: PRT
<213> ORGANISM: Artificial sequence
<220> FEATURE:
<223> OTHER INFORMATION: Synthetic peptide

<400> SEQUENCE: 26

Asp Asp Val Val Gln Tyr Leu Asn Ser
1               5

<210> SEQ ID NO 27
<211> LENGTH: 9
<212> TYPE: PRT
<213> ORGANISM: Artificial sequence
<220> FEATURE:
<223> OTHER INFORMATION: Synthetic peptide

<400> SEQUENCE: 27

Asp Asp Val Tyr Asn Tyr Leu Phe Asp
1               5

<210> SEQ ID NO 28
<211> LENGTH: 9
<212> TYPE: PRT
<213> ORGANISM: Artificial sequence
<220> FEATURE:
<223> OTHER INFORMATION: Synthetic peptide

<400> SEQUENCE: 28

Asp Leu Phe Asp Tyr Asp Phe Leu Val
1               5

<210> SEQ ID NO 29
<211> LENGTH: 9
<212> TYPE: PRT
<213> ORGANISM: Artificial sequence
<220> FEATURE:
```

<223> OTHER INFORMATION: Synthetic peptide

<400> SEQUENCE: 29

Asp Phe Phe Asp Tyr Asp Leu Leu Phe
1               5

<210> SEQ ID NO 30
<211> LENGTH: 9
<212> TYPE: PRT
<213> ORGANISM: Artificial sequence
<220> FEATURE:
<223> OTHER INFORMATION: Synthetic peptide

<400> SEQUENCE: 30

Glu Asp Leu Tyr Ser Ile Leu Trp Ser
1               5

<210> SEQ ID NO 31
<211> LENGTH: 9
<212> TYPE: PRT
<213> ORGANISM: Artificial sequence
<220> FEATURE:
<223> OTHER INFORMATION: Synthetic peptide

<400> SEQUENCE: 31

Thr Asp Leu Tyr His Thr Leu Trp Asn
1               5

<210> SEQ ID NO 32
<211> LENGTH: 1538
<212> TYPE: PRT
<213> ORGANISM: Artificial sequence
<220> FEATURE:
<223> OTHER INFORMATION: Synthetic peptide

<400> SEQUENCE: 32

Met Tyr Pro Tyr Asp Val Pro Asp Tyr Ala Ser Pro Lys Lys Lys Arg
1               5                   10                  15

Lys Val Glu Ala Ser Asp Lys Lys Tyr Ser Ile Gly Leu Ala Ile Gly
                20                  25                  30

Thr Asn Ser Val Gly Trp Ala Val Ile Thr Asp Glu Tyr Lys Val Pro
            35                  40                  45

Ser Lys Lys Phe Lys Val Leu Gly Asn Thr Asp Arg His Ser Ile Lys
        50                  55                  60

Lys Asn Leu Ile Gly Ala Leu Leu Phe Asp Ser Gly Glu Thr Ala Glu
65                  70                  75                  80

Ala Thr Arg Leu Lys Arg Thr Ala Arg Arg Arg Tyr Thr Arg Arg Lys
                85                  90                  95

Asn Arg Ile Cys Tyr Leu Gln Glu Ile Phe Ser Asn Glu Met Ala Lys
            100                 105                 110

Val Asp Asp Ser Phe Phe His Arg Leu Glu Glu Ser Phe Leu Val Glu
        115                 120                 125

Glu Asp Lys Lys His Glu Arg His Pro Ile Phe Gly Asn Ile Val Asp
    130                 135                 140

Glu Val Ala Tyr His Glu Lys Tyr Pro Thr Ile Tyr His Leu Arg Lys
145                 150                 155                 160

Lys Leu Val Asp Ser Thr Asp Lys Ala Asp Leu Arg Leu Ile Tyr Leu
                165                 170                 175

Ala Leu Ala His Met Ile Lys Phe Arg Gly His Phe Leu Ile Glu Gly
            180                 185                 190

```
Asp Leu Asn Pro Asp Asn Ser Asp Val Asp Lys Leu Phe Ile Gln Leu
            195                 200                 205

Val Gln Thr Tyr Asn Gln Leu Phe Glu Glu Asn Pro Ile Asn Ala Ser
    210                 215                 220

Gly Val Asp Ala Lys Ala Ile Leu Ser Ala Arg Leu Ser Lys Ser Arg
225                 230                 235                 240

Arg Leu Glu Asn Leu Ile Ala Gln Leu Pro Gly Glu Lys Lys Asn Gly
                245                 250                 255

Leu Phe Gly Asn Leu Ile Ala Leu Ser Leu Gly Leu Thr Pro Asn Phe
            260                 265                 270

Lys Ser Asn Phe Asp Leu Ala Glu Asp Ala Lys Leu Gln Leu Ser Lys
    275                 280                 285

Asp Thr Tyr Asp Asp Leu Asp Asn Leu Leu Ala Gln Ile Gly Asp
290                 295                 300

Gln Tyr Ala Asp Leu Phe Leu Ala Ala Lys Asn Leu Ser Asp Ala Ile
305                 310                 315                 320

Leu Leu Ser Asp Ile Leu Arg Val Asn Thr Glu Ile Thr Lys Ala Pro
                325                 330                 335

Leu Ser Ala Ser Met Ile Lys Arg Tyr Asp Glu His His Gln Asp Leu
            340                 345                 350

Thr Leu Leu Lys Ala Leu Val Arg Gln Gln Leu Pro Glu Lys Tyr Lys
    355                 360                 365

Glu Ile Phe Phe Asp Gln Ser Lys Asn Gly Tyr Ala Gly Tyr Ile Asp
    370                 375                 380

Gly Gly Ala Ser Gln Glu Glu Phe Tyr Lys Phe Ile Lys Pro Ile Leu
385                 390                 395                 400

Glu Lys Met Asp Gly Thr Glu Glu Leu Leu Val Lys Leu Asn Arg Glu
                405                 410                 415

Asp Leu Leu Arg Lys Gln Arg Thr Phe Asp Asn Gly Ser Ile Pro His
            420                 425                 430

Gln Ile His Leu Gly Glu Leu His Ala Ile Leu Arg Arg Gln Glu Asp
    435                 440                 445

Phe Tyr Pro Phe Leu Lys Asp Asn Arg Glu Lys Ile Glu Lys Ile Leu
    450                 455                 460

Thr Phe Arg Ile Pro Tyr Tyr Val Gly Pro Leu Ala Arg Gly Asn Ser
465                 470                 475                 480

Arg Phe Ala Trp Met Thr Arg Lys Ser Glu Glu Thr Ile Thr Pro Trp
                485                 490                 495

Asn Phe Glu Glu Val Val Asp Lys Gly Ala Ser Ala Gln Ser Phe Ile
            500                 505                 510

Glu Arg Met Thr Asn Phe Asp Lys Asn Leu Pro Asn Glu Lys Val Leu
    515                 520                 525

Pro Lys His Ser Leu Leu Tyr Glu Tyr Phe Thr Val Tyr Asn Glu Leu
    530                 535                 540

Thr Lys Val Lys Tyr Val Thr Glu Gly Met Arg Lys Pro Ala Phe Leu
545                 550                 555                 560

Ser Gly Glu Gln Lys Lys Ala Ile Val Asp Leu Leu Phe Lys Thr Asn
                565                 570                 575

Arg Lys Val Thr Val Lys Gln Leu Lys Glu Asp Tyr Phe Lys Lys Ile
            580                 585                 590

Glu Cys Phe Asp Ser Val Glu Ile Ser Gly Val Glu Asp Arg Phe Asn
    595                 600                 605

Ala Ser Leu Gly Thr Tyr His Asp Leu Leu Lys Ile Ile Lys Asp Lys
```

```
              610                 615                 620
Asp Phe Leu Asp Asn Glu Glu Asn Glu Asp Ile Leu Glu Asp Ile Val
625                 630                 635                 640

Leu Thr Leu Thr Leu Phe Glu Asp Arg Glu Met Ile Glu Glu Arg Leu
                645                 650                 655

Lys Thr Tyr Ala His Leu Phe Asp Asp Lys Val Met Lys Gln Leu Lys
                660                 665                 670

Arg Arg Arg Tyr Thr Gly Trp Gly Arg Leu Ser Arg Lys Leu Ile Asn
            675                 680                 685

Gly Ile Arg Asp Lys Gln Ser Gly Lys Thr Ile Leu Asp Phe Leu Lys
        690                 695                 700

Ser Asp Gly Phe Ala Asn Arg Asn Phe Met Gln Leu Ile His Asp Asp
705                 710                 715                 720

Ser Leu Thr Phe Lys Glu Asp Ile Gln Lys Ala Gln Val Ser Gly Gln
                725                 730                 735

Gly Asp Ser Leu His Glu His Ile Ala Asn Leu Ala Gly Ser Pro Ala
            740                 745                 750

Ile Lys Lys Gly Ile Leu Gln Thr Val Lys Val Val Asp Glu Leu Val
        755                 760                 765

Lys Val Met Gly Arg His Lys Pro Glu Asn Ile Val Ile Glu Met Ala
770                 775                 780

Arg Glu Asn Gln Thr Thr Gln Lys Gly Gln Lys Asn Ser Arg Glu Arg
785                 790                 795                 800

Met Lys Arg Ile Glu Glu Gly Ile Lys Glu Leu Gly Ser Gln Ile Leu
                805                 810                 815

Lys Glu His Pro Val Glu Asn Thr Gln Leu Gln Asn Glu Lys Leu Tyr
            820                 825                 830

Leu Tyr Tyr Leu Gln Asn Gly Arg Asp Met Tyr Val Asp Gln Glu Leu
        835                 840                 845

Asp Ile Asn Arg Leu Ser Asp Tyr Asp Val Asp Ala Ile Val Pro Gln
850                 855                 860

Ser Phe Leu Lys Asp Asp Ser Ile Asp Asn Lys Val Leu Thr Arg Ser
865                 870                 875                 880

Asp Lys Asn Arg Gly Lys Ser Asp Asn Val Pro Ser Glu Glu Val Val
                885                 890                 895

Lys Lys Met Lys Asn Tyr Trp Arg Gln Leu Leu Asn Ala Lys Leu Ile
            900                 905                 910

Thr Gln Arg Lys Phe Asp Asn Leu Thr Lys Ala Glu Arg Gly Gly Leu
        915                 920                 925

Ser Glu Leu Asp Lys Ala Gly Phe Ile Lys Arg Gln Leu Val Glu Thr
    930                 935                 940

Arg Gln Ile Thr Lys His Val Ala Gln Ile Leu Asp Ser Arg Met Asn
945                 950                 955                 960

Thr Lys Tyr Asp Glu Asn Asp Lys Leu Ile Arg Glu Val Lys Val Ile
                965                 970                 975

Thr Leu Lys Ser Lys Leu Val Ser Asp Phe Arg Lys Asp Phe Gln Phe
            980                 985                 990

Tyr Lys Val Arg Glu Ile Asn Asn Tyr His His Ala His Asp Ala Tyr
        995                 1000                1005

Leu Asn Ala Val Val Gly Thr Ala Leu Ile Lys Lys Tyr Pro Lys
        1010                1015                1020

Leu Glu Ser Glu Phe Val Tyr Gly Asp Tyr Lys Val Tyr Asp Val
        1025                1030                1035
```

```
Arg Lys Met Ile Ala Lys Ser Glu Gln Glu Ile Gly Lys Ala Thr
    1040                1045                1050
Ala Lys Tyr Phe Phe Tyr Ser Asn Ile Met Asn Phe Phe Lys Thr
    1055                1060                1065
Glu Ile Thr Leu Ala Asn Gly Glu Ile Arg Lys Arg Pro Leu Ile
    1070                1075                1080
Glu Thr Asn Gly Glu Thr Gly Glu Ile Val Trp Asp Lys Gly Arg
    1085                1090                1095
Asp Phe Ala Thr Val Arg Lys Val Leu Ser Met Pro Gln Val Asn
    1100                1105                1110
Ile Val Lys Lys Thr Glu Val Gln Thr Gly Gly Phe Ser Lys Glu
    1115                1120                1125
Ser Ile Leu Pro Lys Arg Asn Ser Asp Lys Leu Ile Ala Arg Lys
    1130                1135                1140
Lys Asp Trp Asp Pro Lys Lys Tyr Gly Gly Phe Asp Ser Pro Thr
    1145                1150                1155
Val Ala Tyr Ser Val Leu Val Val Ala Lys Val Glu Lys Gly Lys
    1160                1165                1170
Ser Lys Lys Leu Lys Ser Val Lys Glu Leu Leu Gly Ile Thr Ile
    1175                1180                1185
Met Glu Arg Ser Ser Phe Glu Lys Asn Pro Ile Asp Phe Leu Glu
    1190                1195                1200
Ala Lys Gly Tyr Lys Glu Val Lys Lys Asp Leu Ile Ile Lys Leu
    1205                1210                1215
Pro Lys Tyr Ser Leu Phe Glu Leu Glu Asn Gly Arg Lys Arg Met
    1220                1225                1230
Leu Ala Ser Ala Gly Glu Leu Gln Lys Gly Asn Glu Leu Ala Leu
    1235                1240                1245
Pro Ser Lys Tyr Val Asn Phe Leu Tyr Leu Ala Ser His Tyr Glu
    1250                1255                1260
Lys Leu Lys Gly Ser Pro Glu Asp Asn Glu Gln Lys Gln Leu Phe
    1265                1270                1275
Val Glu Gln His Lys His Tyr Leu Asp Glu Ile Ile Glu Gln Ile
    1280                1285                1290
Ser Glu Phe Ser Lys Arg Val Ile Leu Ala Asp Ala Asn Leu Asp
    1295                1300                1305
Lys Val Leu Ser Ala Tyr Asn Lys His Arg Asp Lys Pro Ile Arg
    1310                1315                1320
Glu Gln Ala Glu Asn Ile Ile His Leu Phe Thr Leu Thr Asn Leu
    1325                1330                1335
Gly Ala Pro Ala Ala Phe Lys Tyr Phe Asp Thr Thr Ile Asp Arg
    1340                1345                1350
Lys Arg Tyr Thr Ser Thr Lys Glu Val Leu Asp Ala Thr Leu Ile
    1355                1360                1365
His Gln Ser Ile Thr Gly Leu Tyr Glu Thr Arg Ile Asp Leu Ser
    1370                1375                1380
Gln Leu Gly Gly Asp Ser Pro Lys Lys Lys Arg Lys Val Glu Ala
    1385                1390                1395
Ser Gly Pro Ala Gly Ser Gly Arg Ala Asp Ala Leu Asp Asp Phe
    1400                1405                1410
Asp Leu Asp Met Leu Gly Ser Asp Ala Leu Asp Asp Phe Asp Leu
    1415                1420                1425
```

```
Asp Met Leu Gly Ser Asp Ala Leu Asp Asp Phe Asp Leu Asp Met
    1430                1435                1440

Leu Gly Ser Asp Ala Leu Asp Asp Phe Asp Leu Asp Met Leu Gly
    1445                1450                1455

Ser Asp Ala Leu Asp Asp Phe Asp Leu Asp Met Leu Gly Ser Asp
    1460                1465                1470

Ala Leu Asp Asp Phe Asp Leu Asp Met Leu Gly Ser Asp Ala Leu
    1475                1480                1485

Asp Asp Phe Asp Leu Asp Met Leu Gly Ser Asp Ala Leu Asp Asp
    1490                1495                1500

Phe Asp Leu Asp Met Leu Gly Ser Asp Ala Leu Asp Asp Phe Asp
    1505                1510                1515

Leu Asp Met Leu Gly Ser Asp Ala Leu Asp Asp Phe Asp Leu Asp
    1520                1525                1530

Met Leu Tyr Ile Asp
    1535

<210> SEQ ID NO 33
<211> LENGTH: 1388
<212> TYPE: PRT
<213> ORGANISM: Artificial sequence
<220> FEATURE:
<223> OTHER INFORMATION: Synthetic peptide

<400> SEQUENCE: 33

Met Tyr Pro Tyr Asp Val Pro Asp Tyr Ala Ser Pro Lys Lys Arg
1               5                   10                  15

Lys Val Glu Ala Ser Asp Lys Lys Tyr Ser Ile Gly Leu Ala Ile Gly
                20                  25                  30

Thr Asn Ser Val Gly Trp Ala Val Ile Thr Asp Glu Tyr Lys Val Pro
            35                  40                  45

Ser Lys Lys Phe Lys Val Leu Gly Asn Thr Asp Arg His Ser Ile Lys
        50                  55                  60

Lys Asn Leu Ile Gly Ala Leu Leu Phe Asp Ser Gly Glu Thr Ala Glu
65                  70                  75                  80

Ala Thr Arg Leu Lys Arg Thr Ala Arg Arg Arg Tyr Thr Arg Arg Lys
                85                  90                  95

Asn Arg Ile Cys Tyr Leu Gln Glu Ile Phe Ser Asn Glu Met Ala Lys
                100                 105                 110

Val Asp Asp Ser Phe Phe His Arg Leu Glu Glu Ser Phe Leu Val Glu
            115                 120                 125

Glu Asp Lys Lys His Glu Arg His Pro Ile Phe Gly Asn Ile Val Asp
        130                 135                 140

Glu Val Ala Tyr His Glu Lys Tyr Pro Thr Ile Tyr His Leu Arg Lys
145                 150                 155                 160

Lys Leu Val Asp Ser Thr Asp Lys Ala Asp Leu Arg Leu Ile Tyr Leu
                165                 170                 175

Ala Leu Ala His Met Ile Lys Phe Arg Gly His Phe Leu Ile Glu Gly
                180                 185                 190

Asp Leu Asn Pro Asp Asn Ser Asp Val Asp Lys Leu Phe Ile Gln Leu
            195                 200                 205

Val Gln Thr Tyr Asn Gln Leu Phe Glu Glu Asn Pro Ile Asn Ala Ser
        210                 215                 220

Gly Val Asp Ala Lys Ala Ile Leu Ser Ala Arg Leu Ser Lys Ser Arg
225                 230                 235                 240
```

```
Arg Leu Glu Asn Leu Ile Ala Gln Leu Pro Gly Glu Lys Lys Asn Gly
            245                 250                 255

Leu Phe Gly Asn Leu Ile Ala Leu Ser Leu Gly Leu Thr Pro Asn Phe
        260                 265                 270

Lys Ser Asn Phe Asp Leu Ala Glu Asp Ala Lys Leu Gln Leu Ser Lys
    275                 280                 285

Asp Thr Tyr Asp Asp Leu Asp Asn Leu Leu Ala Gln Ile Gly Asp
290                 295                 300

Gln Tyr Ala Asp Leu Phe Leu Ala Ala Lys Asn Leu Ser Asp Ala Ile
305                 310                 315                 320

Leu Leu Ser Asp Ile Leu Arg Val Asn Thr Glu Ile Thr Lys Ala Pro
                325                 330                 335

Leu Ser Ala Ser Met Ile Lys Arg Tyr Asp Glu His His Gln Asp Leu
            340                 345                 350

Thr Leu Leu Lys Ala Leu Val Arg Gln Gln Leu Pro Glu Lys Tyr Lys
        355                 360                 365

Glu Ile Phe Phe Asp Gln Ser Lys Asn Gly Tyr Ala Gly Tyr Ile Asp
    370                 375                 380

Gly Gly Ala Ser Gln Glu Glu Phe Tyr Lys Phe Ile Lys Pro Ile Leu
385                 390                 395                 400

Glu Lys Met Asp Gly Thr Glu Glu Leu Leu Val Lys Leu Asn Arg Glu
                405                 410                 415

Asp Leu Leu Arg Lys Gln Arg Thr Phe Asp Asn Gly Ser Ile Pro His
            420                 425                 430

Gln Ile His Leu Gly Glu Leu His Ala Ile Leu Arg Arg Gln Glu Asp
        435                 440                 445

Phe Tyr Pro Phe Leu Lys Asp Asn Arg Glu Lys Ile Glu Lys Ile Leu
    450                 455                 460

Thr Phe Arg Ile Pro Tyr Tyr Val Gly Pro Leu Ala Arg Gly Asn Ser
465                 470                 475                 480

Arg Phe Ala Trp Met Thr Arg Lys Ser Glu Glu Thr Ile Thr Pro Trp
                485                 490                 495

Asn Phe Glu Glu Val Val Asp Lys Gly Ala Ser Ala Gln Ser Phe Ile
            500                 505                 510

Glu Arg Met Thr Asn Phe Asp Lys Asn Leu Pro Asn Glu Lys Val Leu
        515                 520                 525

Pro Lys His Ser Leu Leu Tyr Glu Tyr Phe Thr Val Tyr Asn Glu Leu
    530                 535                 540

Thr Lys Val Lys Tyr Val Thr Glu Gly Met Arg Lys Pro Ala Phe Leu
545                 550                 555                 560

Ser Gly Glu Gln Lys Lys Ala Ile Val Asp Leu Leu Phe Lys Thr Asn
                565                 570                 575

Arg Lys Val Thr Val Lys Gln Leu Lys Glu Asp Tyr Phe Lys Lys Ile
            580                 585                 590

Glu Cys Phe Asp Ser Val Glu Ile Ser Gly Val Glu Asp Arg Phe Asn
        595                 600                 605

Ala Ser Leu Gly Thr Tyr His Asp Leu Leu Lys Ile Ile Lys Asp Lys
    610                 615                 620

Asp Phe Leu Asp Asn Glu Glu Asn Glu Asp Ile Leu Glu Asp Ile Val
625                 630                 635                 640

Leu Thr Leu Thr Leu Phe Glu Asp Arg Glu Met Ile Glu Glu Arg Leu
                645                 650                 655

Lys Thr Tyr Ala His Leu Phe Asp Asp Lys Val Met Lys Gln Leu Lys
```

-continued

```
            660             665             670
Arg Arg Arg Tyr Thr Gly Trp Gly Arg Leu Ser Arg Lys Leu Ile Asn
        675             680             685

Gly Ile Arg Asp Lys Gln Ser Gly Lys Thr Ile Leu Asp Phe Leu Lys
        690             695             700

Ser Asp Gly Phe Ala Asn Arg Asn Phe Met Gln Leu Ile His Asp Asp
705             710             715             720

Ser Leu Thr Phe Lys Glu Asp Ile Gln Lys Ala Gln Val Ser Gly Gln
                725             730             735

Gly Asp Ser Leu His Glu His Ile Ala Asn Leu Ala Gly Ser Pro Ala
        740             745             750

Ile Lys Lys Gly Ile Leu Gln Thr Val Lys Val Val Asp Glu Leu Val
        755             760             765

Lys Val Met Gly Arg His Lys Pro Glu Asn Ile Val Ile Glu Met Ala
        770             775             780

Arg Glu Asn Gln Thr Thr Gln Lys Gly Gln Lys Asn Ser Arg Glu Arg
785             790             795             800

Met Lys Arg Ile Glu Glu Gly Ile Lys Glu Leu Gly Ser Gln Ile Leu
                805             810             815

Lys Glu His Pro Val Glu Asn Thr Gln Leu Gln Asn Glu Lys Leu Tyr
                820             825             830

Leu Tyr Tyr Leu Gln Asn Gly Arg Asp Met Tyr Val Asp Gln Glu Leu
        835             840             845

Asp Ile Asn Arg Leu Ser Asp Tyr Asp Val Asp Ala Ile Val Pro Gln
        850             855             860

Ser Phe Leu Lys Asp Asp Ser Ile Asp Asn Lys Val Leu Thr Arg Ser
865             870             875             880

Asp Lys Asn Arg Gly Lys Ser Asp Asn Val Pro Ser Glu Glu Val Val
                885             890             895

Lys Lys Met Lys Asn Tyr Trp Arg Gln Leu Leu Asn Ala Lys Leu Ile
                900             905             910

Thr Gln Arg Lys Phe Asp Asn Leu Thr Lys Ala Glu Arg Gly Gly Leu
        915             920             925

Ser Glu Leu Asp Lys Ala Gly Phe Ile Lys Arg Gln Leu Val Glu Thr
        930             935             940

Arg Gln Ile Thr Lys His Val Ala Gln Ile Leu Asp Ser Arg Met Asn
945             950             955             960

Thr Lys Tyr Asp Glu Asn Asp Lys Leu Ile Arg Glu Val Lys Val Ile
                965             970             975

Thr Leu Lys Ser Lys Leu Val Ser Asp Phe Arg Lys Asp Phe Gln Phe
        980             985             990

Tyr Lys Val Arg Glu Ile Asn Asn Tyr His His Ala His Asp Ala Tyr
        995             1000            1005

Leu Asn Ala Val Val Gly Thr Ala Leu Ile Lys Lys Tyr Pro Lys
        1010            1015            1020

Leu Glu Ser Glu Phe Val Tyr Gly Asp Tyr Lys Val Tyr Asp Val
        1025            1030            1035

Arg Lys Met Ile Ala Lys Ser Glu Gln Glu Ile Gly Lys Ala Thr
        1040            1045            1050

Ala Lys Tyr Phe Phe Tyr Ser Asn Ile Met Asn Phe Phe Lys Thr
        1055            1060            1065

Glu Ile Thr Leu Ala Asn Gly Glu Ile Arg Lys Arg Pro Leu Ile
        1070            1075            1080
```

Glu Thr Asn Gly Glu Thr Gly Glu Ile Val Trp Asp Lys Gly Arg
    1085                1090                1095

Asp Phe Ala Thr Val Arg Lys Val Leu Ser Met Pro Gln Val Asn
    1100                1105                1110

Ile Val Lys Lys Thr Glu Val Gln Thr Gly Gly Phe Ser Lys Glu
    1115                1120                1125

Ser Ile Leu Pro Lys Arg Asn Ser Asp Lys Leu Ile Ala Arg Lys
    1130                1135                1140

Lys Asp Trp Asp Pro Lys Lys Tyr Gly Gly Phe Asp Ser Pro Thr
    1145                1150                1155

Val Ala Tyr Ser Val Leu Val Val Ala Lys Val Glu Lys Gly Lys
    1160                1165                1170

Ser Lys Lys Leu Lys Ser Val Lys Glu Leu Leu Gly Ile Thr Ile
    1175                1180                1185

Met Glu Arg Ser Ser Phe Glu Lys Asn Pro Ile Asp Phe Leu Glu
    1190                1195                1200

Ala Lys Gly Tyr Lys Glu Val Lys Lys Asp Leu Ile Ile Lys Leu
    1205                1210                1215

Pro Lys Tyr Ser Leu Phe Glu Leu Glu Asn Gly Arg Lys Arg Met
    1220                1225                1230

Leu Ala Ser Ala Gly Glu Leu Gln Lys Gly Asn Glu Leu Ala Leu
    1235                1240                1245

Pro Ser Lys Tyr Val Asn Phe Leu Tyr Leu Ala Ser His Tyr Glu
    1250                1255                1260

Lys Leu Lys Gly Ser Pro Glu Asp Asn Glu Gln Lys Gln Leu Phe
    1265                1270                1275

Val Glu Gln His Lys His Tyr Leu Asp Glu Ile Ile Glu Gln Ile
    1280                1285                1290

Ser Glu Phe Ser Lys Arg Val Ile Leu Ala Asp Ala Asn Leu Asp
    1295                1300                1305

Lys Val Leu Ser Ala Tyr Asn Lys His Arg Asp Lys Pro Ile Arg
    1310                1315                1320

Glu Gln Ala Glu Asn Ile Ile His Leu Phe Thr Leu Thr Asn Leu
    1325                1330                1335

Gly Ala Pro Ala Ala Phe Lys Tyr Phe Asp Thr Thr Ile Asp Arg
    1340                1345                1350

Lys Arg Tyr Thr Ser Thr Lys Glu Val Leu Asp Ala Thr Leu Ile
    1355                1360                1365

His Gln Ser Ile Thr Gly Leu Tyr Glu Thr Arg Ile Asp Leu Ser
    1370                1375                1380

Gln Leu Gly Gly Asp
    1385

<210> SEQ ID NO 34
<211> LENGTH: 1529
<212> TYPE: PRT
<213> ORGANISM: Artificial sequence
<220> FEATURE:
<223> OTHER INFORMATION: Synthetic peptide

<400> SEQUENCE: 34

Ala Ser Pro Lys Lys Lys Arg Lys Val Glu Ala Ser Asp Lys Lys Tyr
1               5                   10                  15

Ser Ile Gly Leu Ala Ile Gly Thr Asn Ser Val Gly Trp Ala Val Ile
            20                  25                  30

-continued

Thr Asp Glu Tyr Lys Val Pro Ser Lys Lys Phe Lys Val Leu Gly Asn
             35                  40                  45

Thr Asp Arg His Ser Ile Lys Lys Asn Leu Ile Gly Ala Leu Leu Phe
 50                  55                  60

Asp Ser Gly Glu Thr Ala Glu Ala Thr Arg Leu Lys Arg Thr Ala Arg
 65                  70                  75                  80

Arg Arg Tyr Thr Arg Arg Lys Asn Arg Ile Cys Tyr Leu Gln Glu Ile
             85                  90                  95

Phe Ser Asn Glu Met Ala Lys Val Asp Asp Ser Phe Phe His Arg Leu
            100                 105                 110

Glu Glu Ser Phe Leu Val Glu Asp Lys Lys His Glu Arg His Pro
            115                 120                 125

Ile Phe Gly Asn Ile Val Asp Glu Val Ala Tyr His Glu Lys Tyr Pro
            130                 135                 140

Thr Ile Tyr His Leu Arg Lys Lys Leu Val Asp Ser Thr Asp Lys Ala
145                 150                 155                 160

Asp Leu Arg Leu Ile Tyr Leu Ala Leu Ala His Met Ile Lys Phe Arg
                165                 170                 175

Gly His Phe Leu Ile Glu Gly Asp Leu Asn Pro Asp Asn Ser Asp Val
            180                 185                 190

Asp Lys Leu Phe Ile Gln Leu Val Gln Thr Tyr Asn Gln Leu Phe Glu
            195                 200                 205

Glu Asn Pro Ile Asn Ala Ser Gly Val Asp Ala Lys Ala Ile Leu Ser
210                 215                 220

Ala Arg Leu Ser Lys Ser Arg Arg Leu Glu Asn Leu Ile Ala Gln Leu
225                 230                 235                 240

Pro Gly Glu Lys Lys Asn Gly Leu Phe Gly Asn Leu Ile Ala Leu Ser
                245                 250                 255

Leu Gly Leu Thr Pro Asn Phe Lys Ser Asn Phe Asp Leu Ala Glu Asp
            260                 265                 270

Ala Lys Leu Gln Leu Ser Lys Asp Thr Tyr Asp Asp Asp Leu Asp Asn
            275                 280                 285

Leu Leu Ala Gln Ile Gly Asp Gln Tyr Ala Asp Leu Phe Leu Ala Ala
            290                 295                 300

Lys Asn Leu Ser Asp Ala Ile Leu Leu Ser Asp Ile Leu Arg Val Asn
305                 310                 315                 320

Thr Glu Ile Thr Lys Ala Pro Leu Ser Ala Ser Met Ile Lys Arg Tyr
                325                 330                 335

Asp Glu His His Gln Asp Leu Thr Leu Leu Lys Ala Leu Val Arg Gln
            340                 345                 350

Gln Leu Pro Glu Lys Tyr Lys Glu Ile Phe Phe Asp Gln Ser Lys Asn
            355                 360                 365

Gly Tyr Ala Gly Tyr Ile Asp Gly Gly Ala Ser Gln Glu Glu Phe Tyr
370                 375                 380

Lys Phe Ile Lys Pro Ile Leu Glu Lys Met Asp Gly Thr Glu Glu Leu
385                 390                 395                 400

Leu Val Lys Leu Asn Arg Glu Asp Leu Leu Arg Lys Gln Arg Thr Phe
                405                 410                 415

Asp Asn Gly Ser Ile Pro His Gln Ile His Leu Gly Glu Leu His Ala
            420                 425                 430

Ile Leu Arg Arg Gln Glu Asp Phe Tyr Pro Phe Leu Lys Asp Asn Arg
            435                 440                 445

```
Glu Lys Ile Glu Lys Ile Leu Thr Phe Arg Ile Pro Tyr Tyr Val Gly
    450                 455                 460

Pro Leu Ala Arg Gly Asn Ser Arg Phe Ala Trp Met Thr Arg Lys Ser
465                 470                 475                 480

Glu Glu Thr Ile Thr Pro Trp Asn Phe Glu Glu Val Val Asp Lys Gly
                485                 490                 495

Ala Ser Ala Gln Ser Phe Ile Glu Arg Met Thr Asn Phe Asp Lys Asn
            500                 505                 510

Leu Pro Asn Glu Lys Val Leu Pro Lys His Ser Leu Leu Tyr Glu Tyr
        515                 520                 525

Phe Thr Val Tyr Asn Glu Leu Thr Lys Val Lys Tyr Val Thr Glu Gly
    530                 535                 540

Met Arg Lys Pro Ala Phe Leu Ser Gly Glu Gln Lys Lys Ala Ile Val
545                 550                 555                 560

Asp Leu Leu Phe Lys Thr Asn Arg Lys Val Thr Val Lys Gln Leu Lys
                565                 570                 575

Glu Asp Tyr Phe Lys Lys Ile Glu Cys Phe Asp Ser Val Glu Ile Ser
            580                 585                 590

Gly Val Glu Asp Arg Phe Asn Ala Ser Leu Gly Thr Tyr His Asp Leu
        595                 600                 605

Leu Lys Ile Ile Lys Asp Lys Asp Phe Leu Asp Asn Glu Glu Asn Glu
    610                 615                 620

Asp Ile Leu Glu Asp Ile Val Leu Thr Leu Thr Leu Phe Glu Asp Arg
625                 630                 635                 640

Glu Met Ile Glu Glu Arg Leu Lys Thr Tyr Ala His Leu Phe Asp Asp
                645                 650                 655

Lys Val Met Lys Gln Leu Lys Arg Arg Arg Tyr Thr Gly Trp Gly Arg
            660                 665                 670

Leu Ser Arg Lys Leu Ile Asn Gly Ile Arg Asp Lys Gln Ser Gly Lys
        675                 680                 685

Thr Ile Leu Asp Phe Leu Lys Ser Asp Gly Phe Ala Asn Arg Asn Phe
    690                 695                 700

Met Gln Leu Ile His Asp Asp Ser Leu Thr Phe Lys Glu Asp Ile Gln
705                 710                 715                 720

Lys Ala Gln Val Ser Gly Gln Gly Asp Ser Leu His Glu His Ile Ala
                725                 730                 735

Asn Leu Ala Gly Ser Pro Ala Ile Lys Lys Gly Ile Leu Gln Thr Val
            740                 745                 750

Lys Val Val Asp Glu Leu Val Lys Val Met Gly Arg His Lys Pro Glu
        755                 760                 765

Asn Ile Val Ile Glu Met Ala Arg Glu Asn Gln Thr Thr Gln Lys Gly
    770                 775                 780

Gln Lys Asn Ser Arg Glu Arg Met Lys Arg Ile Glu Glu Gly Ile Lys
785                 790                 795                 800

Glu Leu Gly Ser Gln Ile Leu Lys Glu His Pro Val Glu Asn Thr Gln
                805                 810                 815

Leu Gln Asn Glu Lys Leu Tyr Leu Tyr Tyr Leu Gln Asn Gly Arg Asp
            820                 825                 830

Met Tyr Val Asp Gln Glu Leu Asp Ile Asn Arg Leu Ser Asp Tyr Asp
        835                 840                 845

Val Asp Ala Ile Val Pro Gln Ser Phe Leu Lys Asp Asp Ser Ile Asp
    850                 855                 860

Asn Lys Val Leu Thr Arg Ser Asp Lys Asn Arg Gly Lys Ser Asp Asn
```

```
865                 870                 875                 880
Val Pro Ser Glu Glu Val Val Lys Lys Met Lys Asn Tyr Trp Arg Gln
                    885                 890                 895
Leu Leu Asn Ala Lys Leu Ile Thr Gln Arg Lys Phe Asp Asn Leu Thr
                    900                 905                 910
Lys Ala Glu Arg Gly Gly Leu Ser Glu Leu Asp Lys Ala Gly Phe Ile
                    915                 920                 925
Lys Arg Gln Leu Val Glu Thr Arg Gln Ile Thr Lys His Val Ala Gln
                    930                 935                 940
Ile Leu Asp Ser Arg Met Asn Thr Lys Tyr Asp Glu Asn Asp Lys Leu
945                 950                 955                 960
Ile Arg Glu Val Lys Val Ile Thr Leu Lys Ser Lys Leu Val Ser Asp
                    965                 970                 975
Phe Arg Lys Asp Phe Gln Phe Tyr Lys Val Arg Glu Ile Asn Asn Tyr
                    980                 985                 990
His His Ala His Asp Ala Tyr Leu Asn Ala Val Val Gly Thr Ala Leu
                    995                 1000                1005
Ile Lys Lys Tyr Pro Lys Leu Glu Ser Glu Phe Val Tyr Gly Asp
                    1010                1015                1020
Tyr Lys Val Tyr Asp Val Arg Lys Met Ile Ala Lys Ser Glu Gln
                    1025                1030                1035
Glu Ile Gly Lys Ala Thr Ala Lys Tyr Phe Phe Tyr Ser Asn Ile
                    1040                1045                1050
Met Asn Phe Phe Lys Thr Glu Ile Thr Leu Ala Asn Gly Glu Ile
                    1055                1060                1065
Arg Lys Arg Pro Leu Ile Glu Thr Asn Gly Glu Thr Gly Glu Ile
                    1070                1075                1080
Val Trp Asp Lys Gly Arg Asp Phe Ala Thr Val Arg Lys Val Leu
                    1085                1090                1095
Ser Met Pro Gln Val Asn Ile Val Lys Lys Thr Glu Val Gln Thr
                    1100                1105                1110
Gly Gly Phe Ser Lys Glu Ser Ile Leu Pro Lys Arg Asn Ser Asp
                    1115                1120                1125
Lys Leu Ile Ala Arg Lys Lys Asp Trp Asp Pro Lys Lys Tyr Gly
                    1130                1135                1140
Gly Phe Asp Ser Pro Thr Val Ala Tyr Ser Val Leu Val Val Ala
                    1145                1150                1155
Lys Val Glu Lys Gly Lys Ser Lys Lys Leu Lys Ser Val Lys Glu
                    1160                1165                1170
Leu Leu Gly Ile Thr Ile Met Glu Arg Ser Ser Phe Glu Lys Asn
                    1175                1180                1185
Pro Ile Asp Phe Leu Glu Ala Lys Gly Tyr Lys Glu Val Lys Lys
                    1190                1195                1200
Asp Leu Ile Ile Lys Leu Pro Lys Tyr Ser Leu Phe Glu Leu Glu
                    1205                1210                1215
Asn Gly Arg Lys Arg Met Leu Ala Ser Ala Gly Glu Leu Gln Lys
                    1220                1225                1230
Gly Asn Glu Leu Ala Leu Pro Ser Lys Tyr Val Asn Phe Leu Tyr
                    1235                1240                1245
Leu Ala Ser His Tyr Glu Lys Leu Lys Gly Ser Pro Glu Asp Asn
                    1250                1255                1260
Glu Gln Lys Gln Leu Phe Val Glu Gln His Lys His Tyr Leu Asp
                    1265                1270                1275
```

```
Glu Ile Ile Glu Gln Ile Ser Glu Phe Ser Lys Arg Val Ile Leu
        1280                1285                1290

Ala Asp Ala Asn Leu Asp Lys Val Leu Ser Ala Tyr Asn Lys His
    1295                1300                1305

Arg Asp Lys Pro Ile Arg Glu Gln Ala Glu Asn Ile Ile His Leu
    1310                1315                1320

Phe Thr Leu Thr Asn Leu Gly Ala Pro Ala Ala Phe Lys Tyr Phe
    1325                1330                1335

Asp Thr Thr Ile Asp Arg Lys Arg Tyr Thr Ser Thr Lys Glu Val
    1340                1345                1350

Leu Asp Ala Thr Leu Ile His Gln Ser Ile Thr Gly Leu Tyr Glu
    1355                1360                1365

Thr Arg Ile Asp Leu Ser Gln Leu Gly Gly Asp Ser Pro Lys Lys
    1370                1375                1380

Lys Arg Lys Val Glu Ala Ser Gly Pro Ala Gly Ser Gly Arg Ala
    1385                1390                1395

Asp Ala Leu Asp Asp Phe Asp Leu Asp Met Leu Gly Ser Asp Ala
    1400                1405                1410

Leu Asp Asp Phe Asp Leu Asp Met Leu Gly Ser Asp Ala Leu Asp
    1415                1420                1425

Asp Phe Asp Leu Asp Met Leu Gly Ser Asp Ala Leu Asp Asp Phe
    1430                1435                1440

Asp Leu Asp Met Leu Gly Ser Asp Ala Leu Asp Asp Phe Asp Leu
    1445                1450                1455

Asp Met Leu Gly Ser Asp Ala Leu Asp Asp Phe Asp Leu Asp Met
    1460                1465                1470

Leu Gly Ser Asp Ala Leu Asp Asp Phe Asp Leu Asp Met Leu Gly
    1475                1480                1485

Ser Asp Ala Leu Asp Asp Phe Asp Leu Asp Met Leu Gly Ser Asp
    1490                1495                1500

Ala Leu Asp Asp Phe Asp Leu Asp Met Leu Gly Ser Asp Ala Leu
    1505                1510                1515

Asp Asp Phe Asp Leu Asp Met Leu Tyr Ile Asp
    1520                1525

<210> SEQ ID NO 35
<211> LENGTH: 1368
<212> TYPE: PRT
<213> ORGANISM: Streptococcus pyogenes

<400> SEQUENCE: 35

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
```

```
            100                 105                 110
His Glu Arg His Pro Ile Phe Gly Asn Ile Val Asp Glu Val Ala Tyr
            115                 120                 125
His Glu Lys Tyr Pro Thr Ile Tyr His Leu Arg Lys Lys Leu Val Asp
130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
            165                 170                 175
Asp Asn Ser Asp Val Asp Lys Leu Phe Ile Gln Leu Val Gln Thr Tyr
            180                 185                 190
Asn Gln Leu Phe Glu Glu Asn Pro Ile Asn Ala Ser Gly Val Asp Ala
            195                 200                 205
Lys Ala Ile Leu Ser Ala Arg Leu Ser Lys Ser Arg Arg Leu Glu Asn
            210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
            245                 250                 255
Asp Leu Ala Glu Asp Ala Lys Leu Gln Leu Ser Lys Asp Thr Tyr Asp
            260                 265                 270
Asp Asp Leu Asp Asn Leu Leu Ala Gln Ile Gly Asp Gln Tyr Ala Asp
            275                 280                 285
Leu Phe Leu Ala Ala Lys Asn Leu Ser Asp Ala Ile Leu Leu Ser Asp
            290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
            325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
            355                 360                 365
Gln Glu Glu Phe Tyr Lys Phe Ile Lys Pro Ile Leu Glu Lys Met Asp
            370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
            405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
            435                 440                 445
Pro Tyr Tyr Val Gly Pro Leu Ala Arg Gly Asn Ser Arg Phe Ala Trp
            450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
            485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
            515                 520                 525
```

```
Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
930                 935                 940
```

```
Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
```

```
                1340                1345                1350
Gly Leu Tyr Glu Thr Arg Ile Asp Leu Ser Gln Leu Gly Gly Asp
            1355                1360                1365
```

<210> SEQ ID NO 36
<211> LENGTH: 14
<212> TYPE: PRT
<213> ORGANISM: Artificial sequence
<220> FEATURE:
<223> OTHER INFORMATION: Synthetic peptide

<400> SEQUENCE: 36

```
Ser Gly Tyr Gly Arg Lys Lys Arg Arg Gln Arg Arg Cys
1               5                   10
```

<210> SEQ ID NO 37
<211> LENGTH: 11
<212> TYPE: PRT
<213> ORGANISM: Artificial sequence
<220> FEATURE:
<223> OTHER INFORMATION: Synthetic peptide

<400> SEQUENCE: 37

```
Tyr Gly Arg Lys Lys Arg Arg Gln Arg Arg
1               5                   10
```

<210> SEQ ID NO 38
<211> LENGTH: 12
<212> TYPE: PRT
<213> ORGANISM: Artificial sequence
<220> FEATURE:
<223> OTHER INFORMATION: Synthetic peptide

<400> SEQUENCE: 38

```
Arg Arg Gln Arg Arg Thr Ser Lys Leu Met Lys Arg
1               5                   10
```

<210> SEQ ID NO 39
<211> LENGTH: 27
<212> TYPE: PRT
<213> ORGANISM: Artificial sequence
<220> FEATURE:
<223> OTHER INFORMATION: Synthetic peptide

<400> SEQUENCE: 39

```
Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25
```

<210> SEQ ID NO 40
<211> LENGTH: 33
<212> TYPE: PRT
<213> ORGANISM: Artificial sequence
<220> FEATURE:
<223> OTHER INFORMATION: Synthetic peptide

<400> SEQUENCE: 40

```
Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala
```

-continued

```
<210> SEQ ID NO 41
<211> LENGTH: 16
<212> TYPE: PRT
<213> ORGANISM: Artificial sequence
<220> FEATURE:
<223> OTHER INFORMATION: Synthetic peptide

<400> SEQUENCE: 41

Arg Gln Ile Lys Ile Trp Phe Gln Asn Arg Arg Met Lys Trp Lys Lys
1               5                   10                  15

<210> SEQ ID NO 42
<211> LENGTH: 8
<212> TYPE: PRT
<213> ORGANISM: Artificial sequence
<220> FEATURE:
<223> OTHER INFORMATION: Synthetic peptide

<400> SEQUENCE: 42

Lys Lys Arg Arg Gln Arg Arg Arg
1               5

<210> SEQ ID NO 43
<211> LENGTH: 9
<212> TYPE: PRT
<213> ORGANISM: Artificial sequence
<220> FEATURE:
<223> OTHER INFORMATION: Synthetic peptide

<400> SEQUENCE: 43

Arg Lys Lys Arg Arg Gln Arg Arg Arg
1               5

<210> SEQ ID NO 44
<211> LENGTH: 189
<212> TYPE: PRT
<213> ORGANISM: Artificial sequence
<220> FEATURE:
<223> OTHER INFORMATION: Synthetic peptide

<400> SEQUENCE: 44

Val Gly Ser Ser Leu Ser Cys Ile Asn Leu Asp Trp Asp Val Ile Arg
1               5                   10                  15

Asp Lys Thr Lys Thr Lys Ile Glu Ser Leu Lys Glu His Gly Pro Ile
                20                  25                  30

Lys Asn Lys Met Ser Glu Ser Pro Asn Lys Thr Val Ser Glu Glu Lys
            35                  40                  45

Ala Lys Gln Tyr Leu Glu Glu Phe His Gln Thr Ala Leu Glu His Pro
        50                  55                  60

Glu Leu Ser Glu Leu Lys Thr Val Thr Gly Thr Asn Pro Val Phe Ala
65                  70                  75                  80

Gly Ala Asn Tyr Ala Ala Trp Ala Val Asn Val Ala Gln Val Ile Asp
                85                  90                  95

Ser Glu Thr Ala Asp Asn Leu Glu Lys Thr Thr Ala Ala Leu Ser Ile
            100                 105                 110

Leu Pro Gly Ile Gly Ser Val Met Gly Ile Ala Asp Gly Ala Val His
        115                 120                 125

His Asn Thr Glu Glu Ile Val Ala Gln Ser Ile Ala Leu Ser Ser Leu
    130                 135                 140

Met Val Ala Gln Ala Ile Pro Leu Val Gly Glu Leu Val Asp Ile Gly
145                 150                 155                 160

Phe Ala Ala Tyr Asn Phe Val Glu Ser Ile Ile Asn Leu Phe Gln Val
```

```
                    165                 170                 175

Val His Asn Ser Tyr Asn Arg Pro Ala Tyr Ser Pro Gly
            180                 185

<210> SEQ ID NO 45
<211> LENGTH: 30
<212> TYPE: PRT
<213> ORGANISM: Artificial sequence
<220> FEATURE:
<223> OTHER INFORMATION: Synthetic peptide

<400> SEQUENCE: 45

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30

<210> SEQ ID NO 46
<211> LENGTH: 115
<212> TYPE: PRT
<213> ORGANISM: Artificial sequence
<220> FEATURE:
<223> OTHER INFORMATION: Synthetic peptide

<400> SEQUENCE: 46

Val Leu Ala Gly Asn Pro Ala Lys His Asp Leu Asp Ile Lys Pro Thr
1               5                   10                  15

Val Ile Ser His Arg Leu His Phe Pro Glu Gly Gly Ser Leu Ala Ala
            20                  25                  30

Leu Thr Ala His Gln Ala Cys His Leu Pro Leu Glu Thr Phe Thr Arg
        35                  40                  45

His Arg Gln Pro Arg Gly Trp Glu Gln Leu Glu Gln Cys Gly Tyr Pro
    50                  55                  60

Val Gln Arg Leu Val Ala Leu Tyr Leu Ala Ala Arg Leu Ser Trp Asn
65                  70                  75                  80

Gln Val Asp Gln Val Ile Arg Asn Ala Leu Ala Ser Pro Gly Ser Gly
                85                  90                  95

Gly Asp Leu Gly Glu Ala Ile Arg Glu Gln Pro Glu Gln Ala Arg Leu
            100                 105                 110

Ala Leu Thr
        115

<210> SEQ ID NO 47
<211> LENGTH: 24
<212> TYPE: PRT
<213> ORGANISM: Artificial sequence
<220> FEATURE:
<223> OTHER INFORMATION: Synthetic peptide

<400> SEQUENCE: 47

Gly Leu Phe Glu Ala Ile Glu Gly Phe Ile Glu Asn Gly Trp Glu Gly
1               5                   10                  15

Met Ile Asp Gly Trp Tyr Gly Cys
            20

<210> SEQ ID NO 48
<211> LENGTH: 26
<212> TYPE: PRT
<213> ORGANISM: Artificial sequence
<220> FEATURE:
<223> OTHER INFORMATION: Synthetic peptide
```

```
<400> SEQUENCE: 48

Lys Lys Ala Leu Leu Ala Leu Ala Leu His His Leu Ala His Leu Ala
1               5                   10                  15

Leu His Leu Ala Leu Ala Leu Lys Lys Ala
            20                  25

<210> SEQ ID NO 49
<211> LENGTH: 18
<212> TYPE: PRT
<213> ORGANISM: Artificial sequence
<220> FEATURE:
<223> OTHER INFORMATION: Synthetic peptide

<400> SEQUENCE: 49

Lys Trp Lys Leu Phe Lys Lys Ile Gly Ala Val Leu Lys Val Leu Thr
1               5                   10                  15

Thr Gly

<210> SEQ ID NO 50
<211> LENGTH: 24
<212> TYPE: PRT
<213> ORGANISM: Artificial sequence
<220> FEATURE:
<223> OTHER INFORMATION: Synthetic peptide

<400> SEQUENCE: 50

Leu Leu Gly Arg Arg Gly Trp Glu Val Leu Lys Tyr Trp Trp Asn Leu
1               5                   10                  15

Leu Gln Tyr Trp Ser Gln Glu Leu
            20

<210> SEQ ID NO 51
<211> LENGTH: 23
<212> TYPE: PRT
<213> ORGANISM: Artificial sequence
<220> FEATURE:
<223> OTHER INFORMATION: Synthetic peptide

<400> SEQUENCE: 51

Gly Leu Phe His Ala Ile Ala His Phe Ile His Gly Gly Trp His Gly
1               5                   10                  15

Leu Ile His Gly Trp Tyr Gly
            20

<210> SEQ ID NO 52
<211> LENGTH: 23
<212> TYPE: PRT
<213> ORGANISM: Artificial sequence
<220> FEATURE:
<223> OTHER INFORMATION: Synthetic peptide

<400> SEQUENCE: 52

Gly Leu Phe Gly Ala Ile Ala Gly Phe Ile Glu Asn Gly Trp Glu Gly
1               5                   10                  15

Met Ile Asp Gly Trp Tyr Gly
            20

<210> SEQ ID NO 53
<211> LENGTH: 23
<212> TYPE: PRT
<213> ORGANISM: Artificial sequence
<220> FEATURE:
<223> OTHER INFORMATION: Synthetic peptide
```

<400> SEQUENCE: 53

Leu Ile Arg Leu Trp Ser His Leu Ile His Ile Trp Phe Gln Asn Arg
1               5                   10                  15

Arg Leu Lys Trp Lys Lys Lys
            20

<210> SEQ ID NO 54
<211> LENGTH: 21
<212> TYPE: PRT
<213> ORGANISM: Artificial sequence
<220> FEATURE:
<223> OTHER INFORMATION: Synthetic peptide

<400> SEQUENCE: 54

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 55
<211> LENGTH: 8861
<212> TYPE: DNA
<213> ORGANISM: Artificial sequence
<220> FEATURE:
<223> OTHER INFORMATION: Synthetic polynucleotide sequence

<400> SEQUENCE: 55

| | | | | | |
|---|---|---|---|---|---|
| gagggcctat | ttcccatgat | tccttcatat | ttgcatatac | gatacaaggc | tgttagagag | 60 |
| ataattggaa | ttaatttgac | tgtaaacaca | aagatattag | tacaaaatac | gtgacgtaga | 120 |
| aagtaataat | ttcttgggta | gtttgcagtt | ttaaaattat | gttttaaaat | ggactatcat | 180 |
| atgcttaccg | taacttgaaa | gtatttcgat | ttcttggctt | tatatatctt | gtggaaagga | 240 |
| cgaaacaccg | agctgggaag | ttcttcctgg | ttttagagct | agaaatagca | agttaaaata | 300 |
| aggctagtcc | gttatcaact | tgaaaaagtg | gcaccgagtc | ggtgcttttt | tgttttagag | 360 |
| ctagaaatag | caagttaaaa | taaggctagt | ccgttttag | cgcgtgcgcc | aattctgcag | 420 |
| acaaatggct | ctagaggtac | ccgttacata | acttacggta | aatggcccgc | ctggctgacc | 480 |
| gcccaacgac | ccccgcccat | tgacgtcaat | agtaacgcca | atagggactt | tccattgacg | 540 |
| tcaatgggtg | gagtatttac | ggtaaactgc | ccacttggca | gtacatcaag | tgtatcatat | 600 |
| gccaagtacg | ccccctattg | acgtcaatga | cggtaaatgg | cccgcctggc | attgtgccca | 660 |
| gtacatgacc | ttatgggact | ttcctacttg | gcagtacatc | tacgtattag | tcatcgctat | 720 |
| taccatggtc | gaggtgagcc | ccacgttctg | cttcactctc | cccatctccc | cccctcccc | 780 |
| accccccaatt | ttgtatttat | ttatttttta | attattttgt | gcagcgatgg | gggcgggggg | 840 |
| ggggggggg | cgcgcgccag | gcggggcggg | gcggggcgag | gggcggggcg | gggcgaggcg | 900 |
| gagaggtgcg | gcggcagcca | atcagagcgg | cgcgctccga | aagtttcctt | ttatggcgag | 960 |
| gcggcggcg | cggcggccct | ataaaaagcg | aagcgcgcgg | cgggcgggag | tcgctgcgac | 1020 |
| gctgccttcg | ccccgtgccc | cgctccgccg | ccgcctcgcg | ccgcccgccc | cggctctgac | 1080 |
| tgaccgcgtt | actcccacag | gtgagcgggc | gggacggccc | ttctcctccg | ggctgtaatt | 1140 |
| agctgagcaa | gaggtaaggg | tttaagggat | ggttggttgg | tggggtatta | atgtttaatt | 1200 |
| acctggagca | cctgcctgaa | atcacttttt | ttcaggttgg | accggtgcca | ccatgtaccc | 1260 |
| atacgatgtt | ccagattacg | cttcgccgaa | gaaaaagcgc | aaggtcgaag | cgtccgacaa | 1320 |
| gaagtacagc | atcggcctgg | ccatcggcac | caactctgtg | ggctgggccg | tgatcaccga | 1380 |

-continued

```
cgagtacaag gtgcccagca agaaattcaa ggtgctgggc aacaccgacc ggcacagcat    1440
caagaagaac ctgatcggag ccctgctgtt cgacagcggc gaaacagccg aggccacccg    1500
gctgaagaga accgccagaa gaagatacac cagacggaag aaccggatct gctatctgca    1560
agagatcttc agcaacgaga tggccaaggt ggacgacagc ttcttccaca gactggaaga    1620
gtccttcctg gtggaagagg ataagaagca cgagcggcac cccatcttcg caacatcgt     1680
ggacgaggtg gcctaccacg agaagtaccc caccatctac cacctgagaa agaaactggt    1740
ggacagcacc gacaaggccg acctgcggct gatctatctg gccctggccc acatgatcaa    1800
gttccggggc cacttcctga tcagggcga cctgaacccc gacaacagcg acgtggacaa     1860
gctgttcatc cagctggtgc agacctacaa ccagctgttc gaggaaaaac ccatcaacgc    1920
cagcggcgtg gacgccaagg ccatcctgtc tgccagactg agcaagagca gacggctgga    1980
aaatctgatc gcccagctgc ccggcgagaa gaagaatggc ctgttcggca acctgattgc    2040
cctgagcctg ggcctgaccc ccaacttcaa gagcaacttc gacctggccg aggatgccaa    2100
actgcagctg agcaaggaca cctacgacga cgacctggac aacctgctgg cccagatcgg    2160
cgaccagtac gccgacctgt ttctggccgc caagaacctg tccgacgcca tcctgctgag    2220
cgacatcctg agagtgaaca ccgagatcac caaggccccc ctgagcgcct ctatgatcaa    2280
gagatacgac gagcaccacc aggacctgac cctgctgaaa gctctcgtgc ggcagcagct    2340
gcctgagaag tacaaagaga ttttcttcga ccagagcaag aacggctacg ccggctacat    2400
tgacggcgga gccagccagg aagagttcta caagttcatc aagcccatcc tggaaaagat    2460
ggacggcacc gaggaactgc tcgtgaagct gaacagagag gacctgctgc ggaagcagcg    2520
gaccttcgac aacggcagca tcccccacca gatccacctg ggagagctgc acgccattct    2580
gcggcggcag gaagattttt acccattcct gaaggacaac cgggaaaaga tcgagaagat    2640
cctgaccttc cgcatcccct actacgtggg ccctctggcc aggggaaaca gcagattcgc    2700
ctggatgacc agaaagagcg aggaaaccat cacccctgg aacttcgagg aagtggtgga    2760
caagggcgct tccgcccaga gcttcatcga gcggatgacc aacttcgata agaacctgcc    2820
caacgagaag gtgctgccca gcacagcct gctgtacgag tacttcaccg tgtataacga    2880
gctgaccaaa gtgaaatacg tgaccgaggg aatgagaaag cccgccttcc tgagcggcga    2940
gcagaaaaag gccatcgtgg acctgctgtt caagaccaac cggaaagtga ccgtgaagca    3000
gctgaaagag gactacttca gaaaaatcga gtgcttcgac tccgtggaaa tctccggcgt    3060
ggaagatcgg ttcaacgcct ccctgggcac ataccacgat ctgctgaaaa ttatcaagga    3120
caaggacttc ctggacaatg aggaaaacga ggacattctg gaagatatcg tgctgaccct    3180
gacactgttt gaggacagag agatgatcga ggaacgctg aaaaacctatg cccacctgtt    3240
cgacgacaaa gtgatgaagc agctgaagcg gcggagatac accggctggg gcaggctgag    3300
ccggaagctg atcaacggca tccgggacaa gcagtccggc aagacaatcc tggatttcct    3360
gaagtccgac ggcttcgcca acagaaactt catgcagctg atccacgacg acagcctgac    3420
ctttaaagag gacatccaga aagcccaggt gtccggccag ggcgatagcc tgcacgagca    3480
cattgccaat ctggccggca gccccgccat taagaagggc atcctgcaga cagtgaaggt    3540
ggtggacgag ctcgtgaaag tgatgggccg gcacaagccc gagaacatcg tgatcgaaat    3600
ggccagagag aaccagacca cccagaaggg acagaagaac agccgcgaga gaatgaagcg    3660
gatcgaagag ggcatcaaag agctgggcag ccagatcctg aaagaacacc ccgtggaaaa    3720
```

```
cacccagctg cagaacgaga agctgtacct gtactacctg cagaatgggc gggatatgta   3780
cgtggaccag gaactggaca tcaaccggct gtccgactac gatgtggacg ccatcgtgcc   3840
tcagagcttt ctgaaggacg actccatcga caacaaggtg ctgaccagaa gcgacaagaa   3900
ccggggcaag agcgacaacg tgccctccga agaggtcgtg aagaagatga agaactactg   3960
gcggcagctg ctgaacgcca agctgattac ccagagaaag ttcgacaatc tgaccaaggc   4020
cgagagaggc ggcctgagcg aactggataa ggccggcttc atcaagagac agctggtgga   4080
aacccggcag atcacaaagc acgtggcaca gatcctggac tcccggatga cactaagta   4140
cgacgagaat gacaagctga tccgggaagt gaaagtgatc ccctgaagt ccaagctggt   4200
gtccgatttc cggaaggatt ccagttttta caaagtgcgc gagatcaaca actaccacca   4260
cgcccacgac gcctacctga acgcgtcgt gggaaccgcc ctgatcaaaa agtaccctaa   4320
gctggaaagc gagttcgtgt acggcgacta caaggtgtac gacgtgcgga gatgatcgc   4380
caagagcgag caggaaatcg gcaaggctac cgccaagtac ttcttctaca gcaacatcat   4440
gaactttttc aagaccgaga ttaccctggc caacggcgag atccggaagc ggcctctgat   4500
cgagacaaac ggcgaaaccg gggagatcgt gtgggataag ggccggggatt ttgccaccgt   4560
gcggaaagtg ctgagcatgc cccaagtgaa tatcgtgaaa aagaccgagg tgcagacagg   4620
cggcttcagc aaagagtcta tcctgcccaa gaggaacagc gataagctga tcgccagaaa   4680
gaaggactgg gaccctaaga agtacggcgg cttcgacagc cccaccgtgg cctattctgt   4740
gctggtggtg gccaaagtgg aaaagggcaa gtccaagaaa ctgaagagtg tgaaagagct   4800
gctgggggatc accatcatgg aaagaagcag cttcgagaag aatcccatcg actttctgga   4860
agccaagggc tacaaagaag tgaaaaagga cctgatcatc aagctgccta agtactccct   4920
gttcgagctg gaaaacggcc ggaagagaat gctggcctct gccggcgaac tgcagaaggg   4980
aaacgaactg gccctgcct ccaaatatgt gaacttcctg tacctggcca gccactatga   5040
gaagctgaag ggctccccg aggataatga gcagaaacag ctgtttgtgg aacagcacaa   5100
gcactacctg gacgagatca tcgagcagat cagcgagttc tccaagagag tgatcctggc   5160
cgacgctaat ctggacaaag tgctgtccgc ctacaacaag caccgggata gcccatcag   5220
agagcaggcc gagaatatca tccacctgtt taccctgacc aatctgggag cccctgccgc   5280
cttcaagtac tttgacacca ccatcgaccg gaagaggtac accagcacca agaggtgct   5340
ggacgccacc ctgatccacc agagcatcac cggcctgtac gagacacgga tcgacctgtc   5400
tcagctggga ggcgacagcc ccaagaagaa gagaaaggtg gaggcagcg ggccggccgg   5460
atccgggcgc gccgacgcgc tggacgattt cgatctcgac atgctgggtt ctgatgccct   5520
cgatgacttt gacctggata tgttgggaag cgacgcattg gatgactttg atctggacat   5580
gctcggctcc gatgctctgg acgattcga tctcgatatg ttagggtcag acgcactgga   5640
tgatttcgac cttgatatgt tgggaagcga tgcccttgat gatttcgacc tggacatgct   5700
cggcagcgac gccctggacg atttcgatct ggacatgctg ggtccgatg ccttggatga   5760
ttttgacttg gatatgctgg ggagtgatgc cctggacgac tttgacctgg acatgctggg   5820
ctccgatgcg ctcgatgact tcgatttgga tatgttgtat atcgattgat taattaagaa   5880
ttcctagagc tcgctgatca gcctcgactg tgccttctag ttgccagcca tctgttgttt   5940
gcccctcccc cgtgccttcc ttgacccctgg aaggtgccac tcccactgtc ctttcctaat   6000
aaaatgagga aattgcatcg cattgtctga gtaggtgtca ttctattctg ggggtgggg   6060
tggggcagga cagcaagggg gaggattggg aagagaatag caggcatgct ggggagcggc   6120
```

```
cgcaggaacc cctagtgatg gagttggcca ctccctctct gcgcgctcgc tcgctcactg    6180
aggccgggcg accaaaggtc gcccgacgcc cgggctttgc ccgggcggcc tcagtgagcg    6240
agcgagcgcg cagctgcctg caggggcgcc tgatgcggta ttttctcctt acgcatctgt    6300
gcggtatttc acaccgcata cgtcaaagca accatagtac gcgccctgta gcggcgcatt    6360
aagcgcggcg ggtgtggtgg ttacgcgcag cgtgaccgct acacttgcca gcgccctagc    6420
gcccgctcct ttcgctttct tcccttcctt tctcgccacg ttcgccggct ttccccgtca    6480
agctctaaat cggggggctcc ctttagggtt ccgatttagt gctttacggc acctcgaccc    6540
caaaaaactt gatttgggtg atggttcacg tagtgggcca tcgccctgat agacggtttt    6600
tcgccctttg acgttggagt ccacgttctt aatagtggga ctcttgttcc aaactggaac    6660
aacactcaac cctatctcgg gctattcttt tgatttataa gggattttgc cgatttcggc    6720
ctattggtta aaaaatgagc tgatttaaca aaaatttaac gcgaatttta acaaaatatt    6780
aacgtttaca attttatggt gcactctcag tacaatctgc tctgatgccg catagttaag    6840
ccagccccga cacccgccaa cacccgctga cgcgccctga cgggcttgtc tgctcccggc    6900
atccgcttac agacaagctg tgaccgtctc cgggagctgc atgtgtcaga gttttcacc    6960 gtcatcaccg aaacgcgcga gacgaaaggg cctcgtgata cgcctatttt tataggttaa    7020
tgtcatgata ataatggttt cttagacgtc aggtggcact tttcggggaa atgtgcgcgg    7080
aaccCctatt tgtttatttt tctaaataca ttcaaatatg tatccgctca tgagacaata    7140
accctgataa atgcttcaat aatattgaaa aggaagagt atgagtattc aacatttccg    7200
tgtcgccctt attcccttt ttgcggcatt ttgccttcct gttttgctc acccagaaac    7260 gctggtgaaa gtaaaagatg ctgaagatca gttgggtgca cgagtgggtt acatcgaact    7320
ggatctcaac agcggtaaga tccttgagag ttttcgcccc gaagaacgtt ttccaatgat    7380
gagcactttt aaagttctgc tatgtggcgc ggtattatcc cgtattgacg ccgggcaaga    7440
gcaactcggt cgccgcatac actattctca gaatgacttg gttgagtact caccagtcac    7500
agaaaagcat cttacggatg gcatgacagt aagagaatta tgcagtgctg ccataaccat    7560
gagtgataac actgcggcca acttacttct gacaacgatc ggaggaccga aggagctaac    7620
cgcttttttg cacaacatgg ggatcatgt aactcgcctt gatcgttggg aaccggagct    7680
gaatgaagcc ataccaaacg acgagcgtga ccacacgatg cctgtagcaa tggcaacaac    7740
gttgcgcaaa ctattaactg gcgaactact tactctagct tcccggcaac aattaataga    7800
ctggatggag gcggataaag ttgcaggacc acttctgcgc tcggcccttc cggctggctg    7860
gtttattgct gataaatctg gagccggtga gcgtggaagc cgcggtatca ttgcagcact    7920
ggggccagat ggtaagccct cccgtatcgt agttatctac acgacgggga gtcaggcaac    7980
tatggatgaa cgaaatagac agatcgctga gataggtgcc tcactgatta agcattggta    8040
actgtcagac caagtttact catatatact ttagattgat ttaaaacttc attttaatt    8100 taaaaggatc taggtgaaga tcctttttga taatctcatg accaaaatcc cttaacgtga    8160
gttttcgttc cactgagcgt cagacccgt agaaaagatc aaaggatctt cttgagatcc    8220 ttttttttctg cgcgtaatct gctgcttgca acaaaaaaa ccaccgctac cagcggtggt    8280
ttgtttgccg gatcaagagc taccaactct ttttccgaag gtaactggct tcagcagagc    8340
gcagatacca aatactgtcc ttctagtgta gccgtagtta ggccaccact tcaagaactc    8400
tgtagcaccg cctacatacc tcgctctgct aatcctgtta ccagtggctg ctgccagtgg    8460
```

```
cgataagtcg tgtcttaccg ggttggactc aagacgatag ttaccggata aggcgcagcg    8520
gtcgggctga acgggggtt cgtgcacaca gcccagcttg gagcgaacga cctacaccga     8580
actgagatac ctacagcgtg agctatgaga aagcgccacg cttcccgaag ggagaaaggc    8640
ggacaggtat ccggtaagcg gcagggtcgg aacaggagag cgcacgaggg agcttccagg    8700
gggaaacgcc tggtatcttt atagtcctgt cgggtttcgc cacctctgac ttgagcgtcg    8760 attttttgtga tgctcgtcag gggggcgag cctatggaaa aacgccagca acgcggcctt    8820
tttacggttc ctggccttt gctggccttt tgctcacatg t                         8861
```

<210> SEQ ID NO 56
<211> LENGTH: 5
<212> TYPE: PRT
<213> ORGANISM: Artificial sequence
<220> FEATURE:
<223> OTHER INFORMATION: Synthetic peptide

<400> SEQUENCE: 56

Gly Ser Gly Ser Gly
1               5

<210> SEQ ID NO 57
<211> LENGTH: 100
<212> TYPE: RNA
<213> ORGANISM: Artificial sequence
<220> FEATURE:
<223> OTHER INFORMATION: Synthetic polynucleotide

<400> SEQUENCE: 57

```
agcugggaag uucuuccugg uuuuagagcu agaaauagca aguuaaaaua aggcuagucc    60
guuaucaacu ugaaaaagug gcaccgaguc ggugcuuuuu                          100
```

<210> SEQ ID NO 58
<211> LENGTH: 100
<212> TYPE: RNA
<213> ORGANISM: Artificial sequence
<220> FEATURE:
<223> OTHER INFORMATION: Synthetic polynucleotide

<400> SEQUENCE: 58

```
ucccuugggu cagggguccg uuuuagagcu agaaauagca aguuaaaaua aggcuagucc    60
guuaucaacu ugaaaaagug gcaccgaguc ggugcuuuuu                          100
```

<210> SEQ ID NO 59
<211> LENGTH: 100
<212> TYPE: RNA
<213> ORGANISM: Artificial sequence
<220> FEATURE:
<223> OTHER INFORMATION: Synthetic polynucleotide

<400> SEQUENCE: 59

```
acacaaggca uccgucuccg uuuuagagcu agaaauagca aguuaaaaua aggcuagucc    60
guuaucaacu ugaaaaagug gcaccgaguc ggugcuuuuu                          100
```

<210> SEQ ID NO 60
<211> LENGTH: 100
<212> TYPE: RNA
<213> ORGANISM: Artificial sequence
<220> FEATURE:
<223> OTHER INFORMATION: Synthetic polynucleotide

<400> SEQUENCE: 60

```
uauuuauugu gcacuuaacg uuuuagagcu agaaauagca aguuaaaaua aggcuagucc    60
guuaucaacu ugaaaagug gcaccgaguc ggugcuuuuu                         100
```

```
<210> SEQ ID NO 61
<211> LENGTH: 100
<212> TYPE: RNA
<213> ORGANISM: Artificial sequence
<220> FEATURE:
<223> OTHER INFORMATION: Synthetic polynucleotide

<400> SEQUENCE: 61
```

```
gcuacuugga aggcugaaag uuuuagagcu agaaauagca aguuaaaaua aggcuagucc    60
guuaucaacu ugaaaaagug gcaccgaguc ggugcuuuuu                        100
```

```
<210> SEQ ID NO 62
<211> LENGTH: 160
<212> TYPE: RNA
<213> ORGANISM: Artificial sequence
<220> FEATURE:
<223> OTHER INFORMATION: Synthetic polynucleotide

<400> SEQUENCE: 62
```

```
agcugggaag uucuuccugg uuuuagagcu aggccaacau gaggaucacc caugucugca    60
gggccuagca aguuaaaaua aggcuagucc guuaucaacu uggccaacau gaggaucacc   120
caugucugca gggccaagug gcaccgaguc ggugcuuuuu                        160
```

```
<210> SEQ ID NO 63
<211> LENGTH: 160
<212> TYPE: RNA
<213> ORGANISM: Artificial sequence
<220> FEATURE:
<223> OTHER INFORMATION: Synthetic polynucleotide

<400> SEQUENCE: 63
```

```
ucccuugggu caggguccg uuuuagagcu aggccaacau gaggaucacc caugucugca     60
gggccuagca aguuaaaaua aggcuagucc guuaucaacu uggccaacau gaggaucacc   120
caugucugca gggccaagug gcaccgaguc ggugcuuuuu                        160
```

```
<210> SEQ ID NO 64
<211> LENGTH: 160
<212> TYPE: RNA
<213> ORGANISM: Artificial sequence
<220> FEATURE:
<223> OTHER INFORMATION: Synthetic polynucleotide

<400> SEQUENCE: 64
```

```
acacaaggca uccgucuccg uuuuagagcu aggccaacau gaggaucacc caugucugca    60
gggccuagca aguuaaaaua aggcuagucc guuaucaacu uggccaacau gaggaucacc   120
caugucugca gggccaagug gcaccgaguc ggugcuuuuu                        160
```

```
<210> SEQ ID NO 65
<211> LENGTH: 160
<212> TYPE: RNA
<213> ORGANISM: Artificial sequence
<220> FEATURE:
<223> OTHER INFORMATION: Synthetic polynucleotide

<400> SEQUENCE: 65
```

```
uauuuauugu gcacuuaacg uuuuagagcu aggccaacau gaggaucacc caugucugca    60
gggccuagca aguuaaaaua aggcuagucc guuaucaacu uggccaacau gaggaucacc   120
```

-continued

```
caugucugca gggccaagug gcaccgaguc ggugcuuuuu                          160
```

<210> SEQ ID NO 66
<211> LENGTH: 159
<212> TYPE: RNA
<213> ORGANISM: Artificial sequence
<220> FEATURE:
<223> OTHER INFORMATION: Synthetic polynucleotide

<400> SEQUENCE: 66

```
gcuacuugga aggcugaagu uuuagagcua ggccaacaug aggaucaccc augucugcag    60
ggccuagcaa guuaaaauaa ggcuaguccg uuaucaacuu ggccaacaug aggaucaccc   120
augucugcag ggccaaguggg caccgagucg gugcuuuuu                          159
```

<210> SEQ ID NO 67
<211> LENGTH: 81
<212> TYPE: RNA
<213> ORGANISM: Artificial sequence
<220> FEATURE:
<223> OTHER INFORMATION: Synthetic polynucleotide

<400> SEQUENCE: 67

```
guuuuagagc uagaaauagc aaguuaaaau aaggcuaguc cguuaucaac uugaaaaagu    60
ggcaccgagu cggugcuuuu u                                              81
```

<210> SEQ ID NO 68
<211> LENGTH: 26
<212> TYPE: RNA
<213> ORGANISM: Artificial sequence
<220> FEATURE:
<223> OTHER INFORMATION: Synthetic polynucleotide

<400> SEQUENCE: 68

```
aacaugagga ucacccaugu cugcag                                         26
```

<210> SEQ ID NO 69
<211> LENGTH: 19
<212> TYPE: RNA
<213> ORGANISM: Artificial sequence
<220> FEATURE:
<223> OTHER INFORMATION: Synthetic polynucleotide

<400> SEQUENCE: 69

```
agcugggaag uucuuccug                                                 19
```

<210> SEQ ID NO 70
<211> LENGTH: 19
<212> TYPE: RNA
<213> ORGANISM: Artificial sequence
<220> FEATURE:
<223> OTHER INFORMATION: Synthetic polynucleotide

<400> SEQUENCE: 70

```
ucccuugggu caggggucc                                                 19
```

<210> SEQ ID NO 71
<211> LENGTH: 19
<212> TYPE: RNA
<213> ORGANISM: Artificial sequence
<220> FEATURE:
<223> OTHER INFORMATION: Synthetic polynucleotide

<400> SEQUENCE: 71
acacaaggca uccgucucc								19

<210> SEQ ID NO 72
<211> LENGTH: 19
<212> TYPE: RNA
<213> ORGANISM: Artificial sequence
<220> FEATURE:
<223> OTHER INFORMATION: Synthetic polynucleotide

<400> SEQUENCE: 72
uauuuauugu gcacuuaac								19

<210> SEQ ID NO 73
<211> LENGTH: 19
<212> TYPE: RNA
<213> ORGANISM: Artificial sequence
<220> FEATURE:
<223> OTHER INFORMATION: Synthetic polynucleotide

<400> SEQUENCE: 73
gcuacuugga aggcugaaa								19

<210> SEQ ID NO 74
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 74
aatctatcaa caatagaggc aaggca							26

<210> SEQ ID NO 75
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 75
cagctcccag cgtagctaca								20

<210> SEQ ID NO 76
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 76
aagccataca cgtttgagga cta							23

<210> SEQ ID NO 77
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 77
ttggcgtctg cttgttgatc a								21

<210> SEQ ID NO 78
<211> LENGTH: 22
<212> TYPE: DNA
<213> ORGANISM: Artificial sequence

```
<220> FEATURE:
<223> OTHER INFORMATION: Synthetic oligonucleotide

<400> SEQUENCE: 78
ggctctccag aacatcatcc ct                                              22

<210> SEQ ID NO 79
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 79
acggaccaga gcgaaagcat t                                               21

<210> SEQ ID NO 80
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 80
tccgtcaatt cctttaagtt tcagct                                          26

<210> SEQ ID NO 81
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 81
caggactgaa agacttgctc gagat                                           25

<210> SEQ ID NO 82
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 82
cagcaggtca gcaaagaact tatagc                                          26

<210> SEQ ID NO 83
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 83
acgggaagct cactggcatg g                                               21

<210> SEQ ID NO 84
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 84
atgcctgctt caccaccttc ttg                                             23
```

```
<210> SEQ ID NO 85
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 85
tggataccgc agctaggaat aatg                                            24

<210> SEQ ID NO 86
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 86
tcacctctag cggcgcaata c                                               21

<210> SEQ ID NO 87
<211> LENGTH: 71616
<212> TYPE: DNA
<213> ORGANISM: Homosapiens

<400> SEQUENCE: 87
gagaggcctc tgcctgaagc tcccttaatc tgtcagatca cagatcaaaa gctatcacac     60
actgcccaag ggaccctaaa gggagccact ctcagaaaat aaatccaaac ctccttttt    120 ctggccactg aaacgttcaa taattagttc attatctaca tcattcacat gtttaatatt    180
tattgacttt ggaattattg attactttgc tgagtatctt atgaatttaa tctatattaa    240
tattaaggtg atgtatcaaa ttgcattcca gagtgtggat ttgactctag tgccataatc    300
agtctcctgg gacaaacagc tgtttctctt ccctcattat agaaaaaaat tgcccttggc    360
aaatgtcaaa gaacatcctt ttatcaatct ctcttaccaa tcaatccaag caaatgcagt    420
gggatttctt ttccccagag ttgaagtcac ctcctgacag gaagttaagt ctttaggcac    480
tgaatcatag cactgagctg aagcccagga ctaagcaaga atgagtgaga atttggagac    540
ttaaggtttg gtcatctgta gaggattggg ttttgtcttg ttttgttttt gttttggtgt    600
cctgcaaggt ttctcactgc ccttcatcag gtaaatgcc ctgtccctga actgccaat     660 tgtgttaccc cattccctta gcaacagtga ttgctactga agaaacagga ggccaacaaa    720
gaatatcact cattccaccag tagagtgtct atgtcagaga tattagataa acaggaaaac    780
taacaattac attgcaggct gtggaaacag agagaggtac ctaaggcaca cctgtgggaa    840
tatgaaagtt tggtttcata aaaggattct ggaggaagtc acctctgaca tttgagttga    900
gtcctacagg atatgaagaa agtagcccca tgttccggtt actatggctg tgtaataaat    960
tacctaaaac atactggatt aaagctatga aaacatcttt tctgcccaga gattctgtgg   1020
gcctgaaatt cacatggaac acataaggca taccttgttt ctgctccatg atgtctaagg   1080
attcagctgg aagactggga ggctgggggc tggaatttat ctgaagaatg actcatttac   1140
atgtctactg gttgaccctg gctgttggct gagggggcct cagctctctc tacattgttt   1200
ctctactttg gctagtttgg atttcctcaa aacatgatgg ctggtcctca gtgtcagcat   1260
cccaaaaaga gaatgccgga cacagtggct cacacctgta acctcagcaa tttgggaggc   1320
tgaggtggga ggttgcttga gttcaggagt tcaagaccag cctgggcaac atagtgagac   1380
tctgtctcta ccaaaaattt ttaaaatttt aaaaatcagc caggtgtggt tatgcacacc   1440
```

```
tatagtccca gttacttagg aggctgaggc aggaggatca cttgattcca ggaggtcaag    1500
gctgctgtga gctatgacca caccactgca tttcagcctg ggtaacagaa tgagactctg    1560
tttcaaacaa acaaaaaccc aaaaaaaaaa aaaagagaga gagagggagt tagaaggaag    1620
atgcatcatt tttatgacct ggacttggaa gtcaccaagc agcacttctg cagtaccctg    1680
ttggttggaa tagttgtagc ccaaacccga attcgaaggg aggagaatag ataacatccc    1740
tgggtgacag gaatgtcaaa gtcccaaaca gcatatgaca tgtgacaaat attggtgtgg    1800
ccttctttgg aagatccaat cttccatacc aggcaaaggg atggaagact aaggaacaac    1860
atgagggata gccagagagg gaaaaagcat cacttgttct aggaactaca aatagcttga    1920
agaagcaaag atgtctagat gcctcccaat atgcagagtg gggtgtacag aagagagtgg    1980
taagggcgct gggagagcta aggtgggcaa gagagcttcc tctgtcatgc taagaaagtt    2040
ggaatttatc ttgatggtgg tgaaagcaga gggctatggt tagattcaca tttgagattt    2100 agattttttag atttaaaatg atcaccctgg tgacactggc ttaactcaca attttgccca    2160
aggcctatgc taccacagtg cttctgaaac tttaaagcac attagaatca cctggaggtc    2220
ttgttaaacc atggattgct gggccttgaa accccagaga ttctgattca gtagatcgag    2280
aatagggcct gagaatttgt atttctaaca gtttccagg tgatgctgag gctgctggcc    2340
cagcgaccac atttgataat catagccctc tgataaatcc tatcaaaata tcctaatggc    2400
agagcaaggg aattctggtg atatcctccc ctacccataa cctgacagct attaggatct    2460
gcctacttga ggctaaaagc aaccaagaga ggaacagcta cagtgtacca cagagtccct    2520
caacatcttt gcccacgcca cggtgcccca gcttcttacc aagtgtgcct gattcctctt    2580
gactacctcc aaggaagtgg agaaagacaa gttcttgcga agccttcgtc ttctctgata    2640
tgctattcta tgtctatttc tttggccaaa aagatggggc aatgatatca actttgcagg    2700
gagctggagc atttgctagt gacctttcta tgccagaact tgctaagcat gctagctaat    2760
aatgatgtag cacagggtgc ggtggctcac gcctgtaatc tcagcacttt gggcggccga    2820
ggcgggcgga tcacctgagg tcaggagttc gagaccagcc tggccaacat gatgaaaccc    2880
catctctact aaaaatacaa aaattagcca ggcgtggtgg tgggcacctg caatcccagc    2940
tactctggag gctgagacag aatctcttga acccaggagg tggagattgc agtgagcaga    3000
gatggcacca ctgcattcca gcctgggcaa caaagcaaga ctctgtctca ataataata    3060 ataataataa ctaatgatgc agctttctct ctctgagtat ataatgcagt tctgatgatg    3120
tgaggaaggg cctcactgtt ggtgtggcag agtctgagac catggctggc aatgaaaaca    3180 ctacccttg atgcctatgg gctctcccctt tatggtttca aggagggctt ctcaatcttg    3240
gcagaatttt ggactggata gttctttgtt gcacaggtgg ggggctgtcc tgcacatcac    3300
aggatgtttc atccctggcc tctacctact agatgccagt agaacatacc caccccacag    3360
ctgcctgttg tgacaatcaa aagcatctcc agatactttg cagggggaaa atgatttctc    3420
caggcctggc atatacataa cagtatttaa gcagctgcct agaattaatt aaacacagaa    3480
ggatgtctct catccagaat gccctggacc acctctttga taggcaatca gatcccacct    3540
cctccaccct attttgaag gccctgtgcc aacaccactt cttccatgaa tacttccttg    3600
attcccccat ccctagctct atataaatct cccactcaac actcacacct gttagtttac    3660
attcctcttg acacttgtca tttagcatcc taagtatgta aacatgtctc tcttcacgat    3720
tcacaaagtg gctttggaag aactttagta ccttcccatc ttctctgcca tggaaagtgt    3780
```

```
acacaactga catttctttt tttttttaaga cagtatcttg ctatgatggc cgggctggaa   3840
tgctgtggct attcacaggc acaatcatag ctcactgcag ccttgagctc ccaggctcaa   3900
gtgatcctcc cgcctcagcc tcctgagtag ctgagatcac aggcatgcac taccacactc   3960
ggctcacatt tgacatcctc taaagcatat ataaaatgtg aagaaaactt tcacaatttg   4020
catcccttg taatatgtaa cagaaataaa attctctttt aaaatctatc aacaataggc    4080
aaggcacggt ggctcacgcc tgtcgtctca gcactttgtg aggcccaggc gggcagatcg   4140
tttgagccta aagttcaag accaccctgg gcaacatagc gaaaccccct ttctacaaaa    4200
aatacaaaaa ctagctgggt gtggtggtgc acacctgtag tcccagctac ttggaaggct   4260
gaaatgggaa gactgcttga gcccgggagg gagaagttgc agtaagccag gaccacacca   4320
ctgcactcca gcctgggcaa cagagtgaga ctctgtctca aacaaacaaa taaatgaggc   4380
gggtggatca cgaggtcagt agatcgagac catcctggct aacacggtga aacccgtctc   4440
tactaaaaaa aaaaaaaaat acaaaaaatt agccaggcat ggtggcgggc gcctgtagtc   4500
ccagttactc gggaggctga ggcaggagaa tggcgtgaaa ccgggaggca gagcttgcag   4560
tgagccgaga tcgcaccact gccctccagc ctgggcgaca gagcgagact ccgtctcaat   4620
caatcaatca atcaataaaa tctattaaca atatttattg tgcacttaac aggaacatgc   4680
cctgtccaaa aaaactttta cagggcttaa ctcattttat ccttaccaca atcctatgaa   4740
gtaggaactt ttataaaacg cattttataa acaaggcaca gagaggttaa ttaacttgcc   4800
ctctggtcac acagctagga agtgggcaga gtacagattt acacaaggca tccgtctcct   4860
ggccccacat acccaactgc tgtaaaccca taccggcggc caagcagcct caatttgtgc   4920
atgcacccac ttcccagcaa gacagcagct cccaagttcc tcctgtttag aatttttagaa  4980
gcggcgggcc accaggctgc agtctccctt gggtcagggg tcctggttgc actccgtgct   5040
ttgcacaaag caggctctcc attttttgtta aatgcacgaa tagtgctaag ctgggaagtt   5100
cttcctgagg tctaacctct agctgctccc ccacagaaga gtgcctgcgg ccagtggcca   5160
ccaggggtcg ccgcagcacc cagcgctgga gggcggagcg ggcggcagac ccggagcagc   5220
atgtggactc tcgggcgccg cgcagtagcc ggcctcctgg cgtcacccag cccagcccag   5280
gcccagaccc tcacccgggt cccgcggccg gcagagttgg ccccactctg cggccgccgt   5340
ggcctgcgca ccgacatcga tgcgacctgc acgccccgcc gcgcagtaag tatccgcgcc   5400
gggaacagcc gcgggccgca cgccgcgggc cgcacgccgc acgcctgcgc agggaggcgc   5460
cgcgcacgcc ggggtcgctc cgggtacgcg cgctggacta gctcaccccg ctccttctca   5520
gggcggcccg gcggaagcgg ccttgcaact cccttctctg gttctcccgg ttgcatttac   5580
actggcttct gctttccgaa ggaaaagggg acattttgtc ctgcggtgcg actgcgggtc   5640
aaggcacggg cgaaggcagg gcaggctggt ggaggggacc ggttccgagg ggtgtgcggc   5700
tgtctccatg cttgtcactt tctgcgata acttgtttca gtaatattaa tagatggtat    5760
ctgctagtat atacatacac ataatgtgtg tgtctgtgtg tatctgtata tagcgtgtgt   5820
gttgtgtgtg tgtgtttgcg cgcacgggcg cgcgcacacc taatatttc aaggctggat    5880
ttttttgaac gaaatgcttt cctggaacga ggtgaaactt tcagagctgc agaatagcta   5940
gagcagcagg ggccctggct tttggaaact gacccgacct ttattccaga ttctgcccca   6000
ctccgcagag ctgtgtgacc ttgggggatt cccctaacct ctctgagacg tggctttgtt   6060
ttctgtaggg agaagataaa ggtgacgccc atttgcgga cctggtgtga ggattaaatg     6120
ggaataacat agataaagtc ttcagaactt caaattagtt ccccttcctt cctttggggg   6180
```

```
gtacaaagaa atatctgacc cagttacgcc acggcttgaa aggaggaaac ccaaagaatg      6240
gctgtgggga tgaggaagat tcctcaaggg gaggacatgg tatttaatga gggtcttgaa      6300
gatgccaagg aagtggtaga gggtgtttca cgaggaggga accgtctggg caaaggccag      6360
gaaggcggaa ggggatccct tcagagtggc tggtacgccg catgtattag gggagatgaa      6420
agaggcaggc cacgtccaag ccatatttgt gttgctctcc ggagtttgta ctttaggctt      6480
gaacttccca cacgtgttat ttggcccaca ttgtgtttga agaaactttg ggattggttg      6540
ccagtgctta aaagttagga cttagaaaat ggatttcctg gcaggacgcg gtggctcatg      6600
cccataatct cagcactttg ggaggcctag gaaggtggat cacctgaggt ccggagttca      6660
agactaacct ggccaacatg gtgaaaccca gtatctacta aaaatacaa aaaaaaaaa       6720 aaagaagaa gaagaagaag aaaataaaga aaagttagcc gggcgtggtg tcgcgcgcct      6780
gtaatcccag ctactccaga ggctgcggca ggagaatcgc ttgagcccgg gaggcagagg      6840
ttgcattaag ccaagatcgc ccaatgcact ccggcctggg cgacagagca agactccgtc      6900
tcaaaaaata ataataataa ataaaaataa aaaataaaat ggatttccca gcatctctgg      6960
aaaaataggc aagtgtggcc atgatggtcc ttagatctcc tctaggaaag cagacattta      7020
ttacttggct tctgtgcact atctgagctg ccacgtattg ggcttccacc cctgcctgtg      7080
tggacagcat gggttgtcag cagagttgtg ttttgttttg ttttttgag acagagtttc      7140 cctcttgttg cccaggctgg agtgcagtgg ctcagtctca gctcactgca acctctgcct      7200
cctgggttca agtgattctc ctgcctcagc ctcccgagta gctgggatta tcggctaatt      7260
ttgtattttt agtagagaca gatttctcca tgttggtcag gctggtctcg aactcccaac      7320
ctcaggtgat ccgcccacct cgccctccca aagtgctgga attacaggcg tgagccaccg      7380
cgtctggcca tcagcagagt ttttaattta ggagaatgac aagaggtggt acagttttt       7440 agatggtacc tggtggctgt taagggctat tgactgacaa acacacccaa cttggcgctg      7500
ccgcccagga ggtggacact gggtttctgg atagatggtt agcaacctct gtcaccagct      7560
gggcctcttt ttttctatac tgaattaatc acatttgttt aacctgtctg ttccatagtt      7620
cccttgcaca tcttgggtat ttgaggagtt gggtgggtgg cagtggcaac tggggccacc      7680
atcctgttta attattttaa agccctgact gtcctggatt gaccctaagc tcccctggt       7740 ctccaaaatt catcagaaac tgagttcact tgaaggcctc ttccccaccc ttttctccac      7800
cccttgcatc tacttctaaa gcagctgttc aacagaaaca gaatgggagc cacacacata      7860
attctacatt ttctagttaa aaagaaaaaa aaatcatttt caacaatata tttattcaac      7920
ctagtacata caaaatatta tcattccaac atgtaatcag tattttaaaa atcagtaatg      7980
agaccaggca cggtggctca cgactgtaat cccaggactt gggaggccg aggcgagtgg       8040 atcatctgag atcaggagtt caagaccagc ctggccaaca tggtgaaacc ccatctctac      8100
taaaaactag ctcagcatgg tggtgggtgc ctgtagtccc agctactcgg gaggctgagg      8160
catgagaatc acttgagccc aggaggcaga ggttgcagtg agccaagatt tgggggatt       8220 ctgtgacata caaaaaaaat cagtaataag atatcttgca tactcttttc gtactcatat      8280
acttccagca tatctcaatt cacaatttct aagtaaatgc tctatctgta tttacttta       8340 taaaattcac aattaaaaat gaaggttcac atagtcaagt tgttccaaac acacttaaat      8400
gtctcctagg ctgggtgtgg ttgctcacac ctgtaatccc agcactttgg gaggctgaga      8460
tgggcggatc acctgaggtc aggagtttga gaccagcctg gccaacatgg tgaaaccccg      8520
```

```
tctctactaa aaatacaaaa attagctgga tgtggtggca ctcacctgta atcccagcta    8580
ctcaggaggc tgaggcagga taattgcttg aacccgggag gtggtggagg ttgcagtgag    8640
ccgagatcgc accactgcct tccaacctgg gcgacagagc gagactccgt ctcaaaaaaa    8700
aaaaaaaggc tcctaataac tttattactt tattatcacc tcaaataatt aaaattaaat    8760
gaagttgaaa atccaggtcc tcagtcccat tagccacatt tctagtgctc agtagccacg    8820
ggggctggtg accaccacat gggacagcat atttagtacc tgatcattgg ttctcagatc    8880
tggctactca gcagaaccaa gaatccacag aaacggcttt taaaagcaca gccccacagc    8940
ccccagcccc agccttacct acctggaggc tgggaaggac tctgattcca cgaggcagcc    9000
tatgttttt gatggaggga tgtgacaggg gctgcatctt taacgtttcc tcttaaatac     9060
tggagacagc ttcgaggagg agataactgg atgtgtctta gtccatttga tggagggatg    9120
tgacggggct gcgtctttaa cgtttcctct taaataccgg agacagcttc gagaaggaga    9180
taactggatg tttcttagtc cattttctgt tgcttgtgac agaatacctg aaactgggca    9240
atttatatgg taaaaaattt tcttcttact gctctggagg ctgagaagtc caagtcaag     9300
tcccttcttg ctggtgggga ctttgcagag tattgaggcg gcaccgggcg tcatatggta    9360
aggggctgag tgtgctacct caggtgtctt tttcttttct tataaagcct aactagtttc    9420
actcccatga taaccatta atctatgaat ggattaatcc attattgagg gaagaacctt     9480
catgacccag tcaccgctta aaggcccac ctctcaatac tgccacatcg ggaattaagt     9540
ttcaacatga gtttcggagg tgacaaacat tcaaaccata gcatgctgtc tcttaaatga    9600
ctcaataagc tcctgtggca tccacttctg catgccttgg gcagctttta gacatctgtc    9660
cattttccta gagggacaag accaccacct gtgatcctat gaccttttgg ctttaggcct    9720
aacaagcagg ttatacctc actcactttc aaatcatttt tattgtcttg cagacaattt     9780
acacaagttt acacatagaa aaggatatgt aaatatttat acgctgccgg gcgcggtggc    9840
tcacgcctgt aatcccagca ctttgggagg ccgaggcagg tggatcacga gttcaggaga    9900
tggagaccat cctggctaat acgatgaaac cccatctcta ctaaaaatac aaaaaattag    9960
ccgggcgtgg tgacgggtgc ctgtagtccc cactactcgg gacgctgagg caggagaatg    10020
gcgtgaaccc gggaggcaga gcttgcagtg atccgagatc gtgccactgc actccagcct    10080
gggtgacaga gcgagactgc atctcaaaga aaaaaataaa taataaata aatatttata     10140
ctgcttataa actaataata aatgctatgg tctgcatgtt tgtgtcaccc caccattcat    10200
atgttaaaac ctaatcacca aagtgatatt aggaggtggg gcccttggga ggtgatgagg    10260
tatgagggtg gagcccatat gattgggatt agtgcccttc taaaatagcc caacggagcc    10320
cagtgacaag gcatcatcta tgaaccagga aactggccct caccagacac caaagctgtt    10380
ggtgcattga tcttggattt cccaccctcc aggactctaa gaaacacatt tctattgttt    10440
ataagccacc cagtggctgg tattttgtta taacatccca gactaagaca aataacaaat    10500
acttgtatcc ctgacaccag gttaagagat agaatttgtt tgttcctctg gaggcccttg    10560
tcttcacccc atcactgccc tgtcctccct ggaggaatct gccagcccga attctgttca    10620
tcgtacccte ctttttcttag agtttgacct cctctgtatc tcccccaatc catgtattgc    10680
ttatatacaa ggtattctgc tgtatctgtt ctgctatggc ttgccccttt tgttcaacac    10740
tgtttttgtg cgtcatctgc attgatgcat gcagttgtcc tttatttgtt ctcactgctg    10800
gatagtatct ggttgggtaa atatatcaca ctgtaaatca cactatccag gttcctttag    10860
gtgacatttg gttgattgca gtgttctgtt gttacgatgg tgctgctgtg actgttcttg    10920
```

```
tgcatggaca gaagttcctt tcaggtgaat ttctcagaat ggaattgctg ggcaaagggg   10980
cagccaataa tcaactcatt tgatgccaaa agtggtggtg ccagttcatc ctcccctgcg   11040
aggtatgggt cctgattcac tcttcaagtg ctgtggtttg acagggccgg gggtgacaag   11100
gggacacctg ggaaggaaag ctgggctccc tgctggccat ccaggccagt ccttaccagg   11160
gggtaggcaa tgattgggtc aagtggttcc tgaccactgg gcctgagact tcaggcccag   11220
aaactatcta atatttcctc aaatgcatcc catgagcagg cactgtgtga gtgagcacac   11280
acatctgaag cctcaagcta ggcaagccta ccatgacttg tggtccaagg gctcacgggt   11340
gacctggagt tagagggaga catggctgcc aggtggcttt agaaagaaca ctcatcatgg   11400
ccaggtgcgg tggcttacgc ctgtaatccc agcactttgg gaggccaagg tgggtggatc   11460
atgaggtcag gagtgagacc agcctgacca acatgctgaa acctgtctct cctaaaaaca   11520
caaaaattag ctgggcatgg aggtgcacgc ctgtaatccc agctactcag gaggctgagg   11580
caggagaatc acttgaaccc gggaggcgga ggttgcaata agcctagatt gtgccactgc   11640
attccagcct gggcaacaga gcaagactcc gtctcagaaa aaaaaaaaa aaggaagaac   11700 actcatccta tgaccttgac ctccaagctt gcctccctc aagcagaaca gaatggagcc   11760
tcccttaggc agaggcggaa gtttgcctct cacctagttc tccattcttt tgttcagagc   11820
ctgaataccc tcaggctctg tacttgggt atttctgttc tcttgtttta tgctcacggt   11880
tgtgaggttt gttgtgagta ccacgatccc ttccttcaga ggagtaaact gaggttccaa   11940
aaggtttagc agttgcccga ggaatattaa attggcaaaa gcaggtagaa tataaagcaa   12000
ggagtatttg gcaacggttc ttttttatga ttaaaaacag ccgaagaaag acttctactt   12060
gtgcctttga aggagtaact gcatttgacc ttcccaccag taacaaccat caaatctcta   12120
ttaaattaaa cacacacaca cacaaacaaa aacagctatt gtgaaggtat cagcgactaa   12180
gacaactaag gtttgagggg ccaggatcct ggagagatgg aaacttccct gaggtgagcc   12240
ccacattctc agacactttt ccttggatgt tttgagcact gctttaattc ctgggaaaac   12300
aattccttcc actgtgcaca gactctgggg ccagacagct tgggttcaat cccagctctg   12360
ccacttaatg tctgtgtatc tgtgtaggca agttacccct tggtgcgtca gtttcctcat   12420
ctgtaaaaca caactatagt tgatcctcat tcgttaagag tctgtacttg ttaatttgct   12480
cacttgctaa aatttgttac cccaaaatca gtaccctag ccttttgggg tcgtttcaaa   12540
gatgtgtgca gagcggcaaa aaatgtgag ctcctccagg ctcatgttcc cagccaaggt   12600
ccaacaaagt gctgccctgc cttcttattt cagctgtcat agtgtaaact gtgtcctttt   12660
cacagtctga ttagtgccat gttttcaga ttttatgct ttttcttgg ttatttctct   12720 gttaaaattg tctccaagtg tagtgcaaag tttagcacga ggaggctgtg atgttcctta   12780
cagagaaaat gcatgtgtta gagaagcttt gtcaggcatg agttaaggtg ctgttgtcct   12840
gagatcaatt aatttgttgt tgttgttgtt tgagacaggg tctccctctg ttgcccaggc   12900
tgctggagtg caatggtgta atcatagctc actgcagcct ctacctctct ggctcaagca   12960
atcctcccac ctcggcctcc tgagtagctg ggactacagg tacacccac cacacccaga   13020 taatgttttt gatattttt taggtggaat tttgctcatc acccaggctg gagtgcaatg   13080
gtgcgatcct ggctcactgc aacctccacc tcccggattc aagcaattct tctgcctcag   13140
cctcctgagt agcacagatt acaggcacat gtcatcacgc cttgctaatt tttgtgtttt   13200
tagtagaggc ggggtttcac catgttggcc aggctagtct tgaactcctg acctcaggtg   13260
```

```
atccacccgc ctccgcctcc caaactgcag agattatagg cacgaaccac aatgcccggc    13320
ctcatgtttt ttattttca agttgaaatg aggtctctct atgttgccca ggttggtctc     13380
aaactcttga gctcaagtaa tcctcccacc ttggcctccc aaagtgcggg gattacaggt    13440
gtgagctacc atgcccagcc aagatcagtg ttaatgaatc aactatatat attacataag    13500
gtgtctttaa acagaaataa ggttatatat tgatcgattg gtaacaatgt tgtgaccagc    13560
agcttacagg gtacctagcc ttgtatttct cctataaata atttgctcgt tgagtgtttg    13620
tggcaacttt gtagcacata actaccaaga ataaggactg taataagagt acgtccctca    13680
caggattgta atgaagactg agtccattta cataaaggct gagagcagtg tcaagcagat    13740
ggagaacact gtagaatgtg cgatagctct aacagtggtt atcatggctg ccctctcact    13800
tcttcagaga catgtgtttc taaggtctgc actctgcccc accctcccca tccactgtcc    13860
cccagcccgt ttcctcctcc acttacttcc cagccctgtg ccttctgcct tctcttttct    13920
gagtttgcta agggcactgc tggctcaaga gcagtaacta acagtctctc gcctcttctc    13980
tccatggcaa ccagtgacct ttggagaatg taaaccttat caccaatctc ttaaagccct    14040
tcggtgcctt cccaggatga cgtccagctg aggtccttgg caagacccag ggcgccccct    14100
cctcgctcca tcacctcccc tgtcacctcc cctgcatctc cctactccag ctgcaccact    14160
cttgtgcccc agtggctctt gtctgattat ttccttcatc tccccagctg gtcagcagag    14220
ctggtggtaa tcaactcaga ccctgtcacc tggatgtcca gcagttaggg actaaaaaaa    14280
atcaacaggt cacattctgt cctgcagatc atgataataa gatctgtcag acagcagtca    14340
gcagtcagag ccaaatcttc tggacttcag caggattctg cctcttgcta tttcctgttg    14400
cctctcttag tgaccttta agagcattgt ggatgcctcc cagcctcctg ctaaccaccc    14460
tgtaacctga acagcctgca gcagccctgc ccagtagaac ttcctgatgt gatggaaatg    14520
ctgtgtctgc accactagcc acatgtggcc acaggattct cgaaactggt ggtgcagttg    14580
aggagctgac tttatatttt atctcattaa atttaaatgt aaatagctac gtgtggcttg    14640
ttggctagcc tattggaaaa cacgggctta gagagacaca gggagaatca ctgtaatgca    14700
ctaaaagaag gtaaaaaaaa aaaaatccta agaaatattc ctaaaatact ttaatatagg    14760
gctgggtgcg gtggctcaca tccagcattt tgggaagctg aggagggcag atcacttgag    14820
gccaggagtt caagaccagc ctggccaaca tggtgaaacc ccgtctctac taaaaataca    14880
aaaaatcggg tgcggtggcg ggtgcctgta atcccagcta cgcgggaggc tgaggcacga    14940
gaatcactcg aacccgggag gcggggggttg cagtgagccg agatcgtgcc actgcactcc    15000
agcctgggcg acagagcgag acttcatctc aaaaacaaaa aacaaaaacc aaaaaaaaaa    15060
acttcagcat gattatttaa ccaaaatgca ggttagttgt tcaccggatg cagagtccaa    15120
ttaacaagag caaggcctgg taccaaaaaa agtgaattta ctccgaaact agcttgggtg    15180
aggggtacaa agcatcctgc ctttctttaa aagtgctgct tcccttgga agtagaaagt     15240 ggacactttt ataaggtaag gggggaagtg tgcaagggca agtgggggg tccctctgct     15300 agttccgtgc atactctaca ggacagttga cttggcacct tcctggttag taataagctg    15360
tagcagtggc caagtgggca tgctttcagt atgcccccc agtgaatgaa agtcctgagg    15420
caacccccaa gggtggaagt gccaggccac cacccactgg aggtgaaagt tccgtgatgg    15480
gtttgctttg gtctgcgaat ctactgtcat gtggagagat ctgtgctctg gaagagcata    15540
cagttagaaa agcttgccct gaagggaatg tatggtgaag gggaggtgaa aggttatatt    15600
tgcatttctg aagggctaag taggaaaccg ggaaccaggg gagaggagaa gagaagagag    15660
```

```
gataatttttt tttaagaaaa gcaacatatt ccctttttct tagaaaaaat ggagcactcg   15720
gttacaggca ctcgaatgta gaagtagcaa tatataaatt atgcattaat gggttataat   15780
tcactgaaaa atagtaacgt acttcttaac tttggctttc agagttcgaa ccaacgtggc   15840
ctcaaccaga tttggaatgt caaaaagcag agtgtctatt tgatgaattt gaggaaatct   15900
ggaactttgg gccacccagg gtaagataaa acaccttcca cgtcataggt atcttcctct   15960
ctccttccct gcctctccca ttagaacctg gttttcttcc tgagcagcaa caatcttagg   16020
catctttcca tgtgactgag tatccaccac attattttta atgaaatagt attagattgc   16080
atggatgtga cataatccat ttaacccatc ccctactgtt ggacattcag gttgtttcca   16140
gagtttcaat attattttat ttaataccct aatagttaga gcaggccatg ctgctatcac   16200
aaatagaccc aaatatttaa tagctcaaac caataacgtt tgtgtcctcc tctctgggca   16260
gtacagggtt ggcatacctc ctgaagtgaa ttaggaacta cactcattcc agcttccagt   16320
ttggtcttta tctgtcagtg ccttactgtc ctctgcattg ttgagtctca gtcaccttgt   16380
ccaagttcca ttggccagaa agggctagaa gcacagaagg gctggaagtg gcatttgttc   16440
ctcactcaca ttctggtggg aagaacttag tggtgtggcc ttagctgact gtaagggagg   16500
ctgggaaata tagtctagcg agtgccctgg aaaaagccgg cacggcattc cccatggaaa   16560
gctgtcaggc acggctacag tctaccccct gccaaccagt atctgcatgg accctccttc   16620
cacactcaga tgcatttacc cccagcccca agagagccaa ccgatgccca tgtggtcacc   16680
acagccacct ccgagtccaa gattccagg tgacatgcag tctcctctct cccagcttta    16740
ggaatggctt cttctgatct acacacagac acagacacac acacacagac acacacacac   16800
acacacacac acacacacga tggagagggg caggataact gcaactgtaa ctccattcag   16860
aaaagaggca cagcactagc tgcccgcagc actggagccc tgctgggcag cactggatca   16920
acctctgccc tggcagagga gcatgttcct ccacaaatcc ctgcttcagc ctctcgagag   16980
gctcctcctt gtctgttatt ttccttggcc acaaggcagg caggcagtgg gaagtgtgcc   17040
ctcctccggg gcaaggagcc ttcacagccc acttcctgct aataacagtt tggggttcca   17100
cagggtgttt taagactcca gtcagctatt ttaggccaga ctcatttctc tctctctctc   17160 tcttttttt tcttttatga aatcacaccc tgagacccag gctggagtgc agtggtgcga   17220
tctcggctca ctgcagcctc cgcctccggg gttcaagcaa tcctcctgcc tcagcctcct   17280
gagtagctgg gactataggc gtgcagtgcc acacctagct aattttttgta tttttagtaa   17340 agacggggtt tcaccatgtt ggccaggctg gtcttgaact cctgacctca gatgatccgc   17400
ccgcctcggc ctcccaaagt gctgggatta ctggcatgag ccactgcgcc cagcccagac   17460
tcatttttct ttgagagtag gcttttccca aaagtaggct tctgagctat tcactttcag   17520
gcagtcccat gtgccaggaa ccacatccaa atttcctccg tggatgggag tctcaggctg   17580
ccttatctcc ttgcatgtcc ccatgcccag ctgtctcagc ctaagggcag gtaccttgaa   17640
gtcaagttaa acaataagat tggagaccag caatgccctc agcctggttt ttgcagcagg   17700
actgagtccc ttgttttggc tcaatgggaa gtctttgctg ttcaaagcct tagcttctct   17760
ggctgagtgc ggtggctcac gcctgtcatc ctagctcttt ggaggccga ggtgagcaga    17820 tcactgaggc caggagttca agaccagcct ggccaacatg gtgaaaccct gtctctacta   17880
aaaatacaaa aagttagcca ggcgtggtgg caggcacctg taatcccagc tactcgggag   17940
cctgaggcag gagaatcgct taaacccagg agatggaggc tgcagtgagc tgagatcatg   18000
```

```
ccattgcact ccagcctggg taacgagcga aattccatct ctaaaaaaaa gaaaaaaaaa    18060
aggccttaga ttctcccttt gactttccac gtttgtgcag ccttttatct ccaatgctcc    18120
atttcattcc atctcctggc ttattctttt cttgtcacat ctactaaaag caacaagaag    18180
ccaccggtat tcaggaacat tctacctgtc cccagagcta tatgctcagt aggcatacag    18240
ttggccctcc aggttatctg agactcagat ttccagaggg ctttgcatgg ctcacaaggt    18300
ctgaagaacc tctgagcctc ccgcctgcgg tgtctgttca ttgactttgc cacagtctca    18360
aagaggcact gcatgctgca tgtttgaggt ttttgctttg gtggcatcca tttccagcct    18420
cggcttccgg cattcctccc ccagcagact ctctgctgct ttccccttac tccttctggc    18480
agttctggga ggttgcatag ggcccttgca ggatgcccca agtccagctg cctctggcct    18540
ctgggaagca cacccttgac ctgccatgtg taggaagaca gcccgcttct gccagggccc    18600
aactctgccg gcaggtagca ccttccaacc tcttcacttt ggactttata actgtcaggt    18660
ataaagtcgg ttgtgtcctt acgtttctca aattcttcaa gacacgtcaa ccagcctctc    18720
ctacgcattc tctccagctc agtctcaaaa cacacccttt ctctccagct cactctcaaa    18780 acacaccta tcaggccaac cactcttttt aaaggacagc tcctcaccaa tccagtcagg    18840
tagccttccc cacattgtat cctggaagtg ggtgatggac tgggtgggga agagggtcat    18900
atggcaaatc tgtatgtctt acagtaattg tctagcagcc cctggtgtct tactttaggc    18960
cccctggaaa ctttcagata gtggagttgt ctgatacata tcttataacc tacagatatt    19020
aatatatcct cacaggggca caaaagctct tacaaggatg tttattataa taatatttt     19080 attgttataa tttacatgcc ataaaactaa ccatttaaa atgtataatg caagggtttt     19140
tagtatattc acaagattgt gcagctgtca ctactaattc cagaacattt tcattattcc    19200
agaaggaaac cctattcata ttagcaatca ctcccccatt ccgcctttcc ctaaaaccca    19260
gcaatcacta atctactttc tgtctctgtg gattttaaagt aattttaaat ttgaaaaata   19320
gtatctataa ggaaatgtat ctagtcacaa gcatacagct tgatgaattt gtaaaaattg    19380
aacagtccta tgaacatacc ctgtaagctc aagacataga atgttaccag ccctgcaag    19440 caagctgcct gctcacttct agtcattaac ccctccctct tttccttcta gtcattaacc    19500
cttcagagta actattctga ttaccaatag catagattag ttctgcctgt tgttttactt    19560
tatataaact gtctcattaa gtataaacat gtttgtgtat acttgtgtat ttctttctat    19620
cacaatgatg tttgtgagat tcatccatgc tgttcctata gacaattcta ttttgcagcg    19680
tagtattcca ttgcatgact ataccacaat ttatctgtga tattacaaag gaatacttgg    19740
gcagtttcca gtttggggct ataggatagt tgtgatacaa atattttagt atagtacatg    19800
tcttttggtg aacctgggta cacatttctg ttgtgtatac cccttaagag tggagctgat    19860
gatcctggct aacaaggtga aaccccgtct ctactaaaaa tacaaaaaat tagccgggcg    19920
tggtagcggg cgcctgtagt cccagctact cgggaggctg aggcaggaga atggcgtgaa    19980
cccgggaggc ggagcttgct tgcagtgagc cgagatcgcg ccactgcact ccagcctggg    20040
cgacagagcg agactccgtc tcaaaaaaaa aaaaaaaaaa agagtggagc tgatgggtca    20100
tagcatgtaa atgcattcaa ctttagtaga tactgtccaa cagttttcca aagtgattgt    20160
ccaacttact tgcctatcag cagtatctga aaagtctagt tgcttctttt cttggccaac    20220 tcttttttt tttttgagat ggagttttgc tcttgttgcc caggctggag cgcaatggca    20280
cgtcctctgc tcactgcaac ctccgcctcc tgggttcaag caattctcct gcctcagcct    20340
cccgagtagc tgggattaca ggcatgcgcc actatgcccg gctaatttg tatttttagt    20400
```

```
agagacaggg tttctccatg ttggtcaagc tggtctcgaa ctcctaacct caggtgatcc   20460
gcccgcctcg gcctcccgaa gtgctgggat tacaggcatg agccaccgcg ccaggccggc   20520
caactctttt ttatttatt ttatttact ttaaagacag ggtttcactt tgtcacccag    20580
gatggaatgc aatggcacga tcacagctca ctgcagcctt gacctccctg gctcgggtga   20640
tccctcccac ctcaggctcc tgaggagcta gaactacagg catgggccat gcccagctaa   20700 tttttaatt tttggtagag acggggtctc tgttgtctca gattcctggg ttcaagtgat    20760
ccttctccct tggcctccca aagttctggt attacaggca tgagccactg cacccagccc   20820
atggccagct cttgatacga tctgtctctt tcttttcttt ttttttttt aatttgagaa    20880 gtgttaaata atctttcttt gatattatac ataaaccaca ccaaaatgtc tttcagtaag   20940
taaaatgaac catttttagat acagaaaatt ctaattagat tggcatagtt aaggccaaaa  21000
atataaagtt gacattgcta ccttatcttc agcccttgcc tttaagaggc aaatgaacac   21060
aaaatacagg tgaatcttgc ttggttctga gacagtgaag gactttcccc cagtatttaa   21120
atatatttac ataaccagtt acataaatct aaatattaaa aaaatctcca atagatttta   21180
gatggcattc accatctttg tgaaaagttg aacattacta atgaaatctg atcatatctt   21240
tagaaggata aacagtgata gcatttactg aatcagaata actgtttttt ggggttttct   21300
ttgagacgga gttttgctct tgttgcccag gctggagtgc agtggtgcca ctcagctca   21360 ctgcaacctc cgcccctgg attcaagaga ttatcctgcc tcagcctccc gagtagctgg    21420
gattacaggc tcgccccacc atgcccagct aattttttgta ttttagtag aggcgaggtt   21480 tcaccatgtc agccaggctg gtcttgaact cctgacctca ggtgatccac ccgcctcagc   21540
ctcccaaaat gctaggatta caggcgtgag ccaccaggcc cagcctattt ttttttttt    21600 tcttttttg agacggagtc tcactctgtc acccaggctg gagtgcagtg gcacaatgtc    21660
agctcattgc aacctccacc tccggggttt cagtgattct cctgtctcag cctcccaagt   21720
agctgggaac tacaggcgtg caccacaagc ccagctaatt tttgtatttt tagtagagac   21780
agggttttgc catattggcc tggctagttt caaactcctg acctcaggtg agccacctac   21840
ctcggcctcc gaaagtcctg ggattacaga cgtgagccac tgcactgcct ggcccagaaa   21900
ggactattaa ttgtagttgc ctctgggaat ggggctgcc tgcttctttc tgtaacccct    21960
tctgtgctgt ttaaattttt ttttttttt tttttttga cacagagtct cgctctgtcg    22020
cccaggctgg agtgcagtgg cgcaatctcg gctcactgca agctccgcct cccaggttca   22080
cgccattctc ctgcctcagc ctcctgagta gctgggacta caggcacccg tcaccacgcc   22140
cggctaattt tttgtatttt cagtagagac ggggtttcac catgttagcc aggatggtct   22200
cgatcctctg accgtgttat ctgcctgcct cggcctccca gagtgctggg attacaggca   22260
tgagctacca cgcccggcct ttaaatttt actttgggcc gggcacggtg ccttacgcct    22320
gtaatcctaa catttcgaga agctgaggca cgtggtggat cacttgatgt cacgagttca   22380
gaccagccac tgcactccag cctgggtgac agagtgagac tctgtctcaa aaaaaaaaa    22440 aaaagaaaga aaacttttta ctttttacat gttattttca tcaatttaat gaatttaaat   22500
aacaaatgta taaatttgat attaataaaa tggaagcatt tggtaatcat gttttgggtt   22560
ttgtgcttcc tctgcagctc tctagatgag accacctatg aaagactagc agaggaaacg   22620
ctggactctt tagcagagtt ttttgaagac cttgcagaca agccatacac gtttgaggac   22680
tatgatgtct cctttgggt acctcttgac ttcttttatt tttctgtttc ccctctaag    22740
```

```
aattttagtt cactaaaatg aagaatttcc ctccagcaga gctaagcatc aagtagcatg   22800
tagttgtagg taggattaaa agactagggt tccgggaggt gaaggttgca gtgagccaaa   22860
atcacgccac tgcactccag cctgggtgac agagcgagac tctgtcatag atggatggat   22920
ggatggatgg atggatggat ggatggatag atagatagat agatagatag atagctggat   22980
agatagataa gatagataag acaagactag gcttcaagct gcagtccagc tctaccaggc   23040
ttgttgtgac tctgggcaag tcactcagcc tctctgagcc tcattttcca gcttcagtgg   23100
atacccatga aggcaaatca gagaggggcc tgagtgtgta tttgtccagc aggcagatgg   23160
agggaacaac aaactagacc cgtagttctt cagtagggat aagataactg cccaaaagtt   23220
atttagatta caaagacttg agccctgctc ctgtgagaca gtgatggggt aggtcgggtg   23280
cattcctggg aagcatattt ttgaaaagct cacctgggat tctaatgtgt atccctaggt   23340
cttattccta gagattttga ttacttggtc tggggtgtgg catgacctgg gcagggcact   23400
gggattttta agctccacag atgattccaa tatgcagcta gtatgagaac ttgtttttt   23460 ttgaaggagt ctcactctgt cacccaggct ggagtgcagt ggcgcaatct cggctcactg   23520
ctccgcttcc tgggttcaag cagttctcct gcctcagcct cccgagtagc tgggattata   23580
ggcatctgcc accatgccca gctaatttt gcattttagt aaagacgggg tttcaccatg   23640
ttggttaggc tggtctcgat ctcctgacct caaatggtcc accccatca gccttccaaa   23700 gttttgggat aacaggcgtg agccaccagg tccggcctgg tgtgagaact tctgagttgg   23760
atgaaacatt agccccagat cctagaagcc agggaagtgc tggtctttat cgactggcca   23820
ccaggtggca gatttgggca agggtctgcc tttgggttta gaattattgc ttaggcctta   23880
aagtagttct tttttgccag tgggagaaaa tccctcaaag atggttttct gggttggttg   23940
gtttgtttgt ctgtttgttt gttttttgag acagagtctc cctctgttat tcagcctgga   24000
gtgcagtggc atgatctcac tgcaacctct gcctctcggg ttcaagcagt tctcctgcct   24060
caacctccca gtagctgga attataggca cacgccccca cacccagcta attttgtat   24120 ttttagtaga cagtgtttt caccacgttg gccaggctgg ttttgaactc ctgaactcaa   24180
gtaatcctcc cacctcagcc tcccaaagtg ctaggattac aggtgtgagc caccgcgcct   24240
ggctcctcaa agatgttaat cctcttgatg gcaattgact aataccagaa aatgtcacga   24300
agcgtgcatt ttggattcaa tcatggaatt gttgaggaca atcagccatc agactaaagc   24360
gatagaaata gtattggaaa ttgcagcggg agcactgaat ggagaaggca ctccacataa   24420
tggaggaggc aaccaagtct tagagaaggt atcaagcctg actataagga cagtgaggga   24480
attgaaaaaa caaaaaagga gcaatggagc agggaaggat tgaatgcctt tcaagtagat   24540
tcagtaattg ctgttagcag caaaaaatgc agtagtgcct gggcagggct ttaaagtgct   24600
tgcacaggca gccctagagg gccgggctgc ttgggaactc ttacaaactg acctaccaac   24660
ttgagcatcc acagcctgat cagaggtggg ggagttaagg gccttctctc ccctagcctc   24720
tactagagcc tgtaactgca gggaaaccaa gttgcaggct aaactctgcc cacacatgca   24780
gacattgatt agcaagctac aaaaacagtc atgaaacctg tttttatagg attagtgaag   24840
ccccagtttg accagagtac tttgcatgaa tgtttgtta gaagcaaatg tgccaatatt   24900
ctagcagctg cgtttggttt acttcttctt cttcttttt tttttttg agttgaagcc   24960 tagctctgtc acccaggctg gagtgcagtt gtgtgatctc agctcactgc aacctctgcc   25020
tcccaggttc aagcgattct cccgcctcaa cctcctgagt agctgggatt acagacatgt   25080
accacaatac agggctaagt tttgtatttt tagtagaaat ggggtttcac catgttggcc   25140
```

```
aggctggtct caaactcctg atctcaagtg atccacccgc ctcagcctcc taaagtgctg    25200
ggttaacagg catgagccac ggcacctggc aaaagtcatc tttggttta cttctattga    25260 actgaaaaag tcacaaatat atttatattt aattaaatat atttatataa aaatatggta    25320
tttagtatta ttatttttag agacagggcc tcgctctgtc acccaggctg gagtgcagtg    25380
gcacaatcat agctcactgc agcctcaagc ttctgggctc aagtgatcgt tccacctcag    25440
cctccctagt agctgggact acaggcacat gccaccatac tcggctaatt attttatttt    25500
atttatgggt ctcgctatgt ttcccaggct ggtctcaaac tcctggcctc aagcgattct    25560
ctcacctcgg cctcccaaag caccgggatt acaggtgtgt gccagcacac ccagccacaa    25620
atctataaat ttagaaagga ggactatttc taaagagggt cccactacct gtaggcagga    25680
agcagagcct ctggccataa ctgaaaaaca agcacttcca agaaggggca aagggaacat    25740
gaatttatgc tgagaggcgt agctaagcat acatattcaa cagattatgg gaggatctat    25800
gaatattcac aaagggagga tctatgaata tgcacacatg tggagtaagc taacgtgtgc    25860
agcatgtctc ccatgttcac cttaggcaga aacttaacac taacatgtat tacagggcaa    25920
caaaatgaga ctgcatatct acataaccta gctatttggt aggctgaagc aggagcatca    25980
cttaagactg ggagttcgag gcagctgtga gccatgatcg caccactgtt ctccagccag    26040
gatgacaggg caagaccctg tcttagacca ctctgtggtc agtggttatc aggaaggaat    26100
gctagtcagt tgtgctgaaa ccactaaaaa ggaagggcag aattaggtga tgagttgata    26160
ccagtggtga agtgagtctt ttttttttt ttcttttga gatggagtct tgctctgttg    26220
cccaggctgg agtgtagtgg tgtgatctca gctcatcgca acctccacct cctgggttca    26280
agtgattctc ttgcctcagc ctcccgagta gctgggatta caggcgcctg ccaccacgcc    26340
tggctaattt ttttatattt ttagtagaga ctgggttttg ccatgttgtc aggctagtct    26400
tgaactcctg acctcaggta atccaactgc tttggcctcc caaagtgctg ggattacagg    26460
cagctccaaa gtgctgggat tacaggcatg agccaccatg catggcctga ataattttt    26520 ttgaaagggc tagtttctat ttagccctta ggggaaaaaa aactaatggc agttagggag    26580
ggaatagaac gagtcctgtt tgaactcctt tcccatcatg gccaaaactt aaaattttt    26640 ttagatatct ctgggctccc cttggccaaa agatagtttg ttgagtcagt tgggagctta    26700
gaattttgtt tttatttctc acatcattga atcaatttga accaggcgac aaaaccttct    26760
gctcccagta gtgggtcaga gaaccttcct gattcctgcc ctgagattgt ctctctgaag    26820
acaacattag gctagtaggc tttccagatt ctgtaaccca ttctttcaaa ggaagagatg    26880
cctatatttt tctagccaat tcatatacct tgagtatcac tcaagggcaa aattatttct    26940
aacaaatcat ttactaatta gcaaatgctt aagtgtagat ttagaaagct aaagctatac    27000
agtggctgcc atctatagtt tggacttgtg attaactaca ttgaaatgct aactctgtac    27060
cctagagtat gaattcctga ttagagtcct tcaggtgcta actaatttat gtatttcatg    27120
tttgataata ttattacttg agctttgtgg gagagcagtc ttttcctccc ctgagatata    27180
gctagaagtt acctcctttg tgaagccttc ctagatactc caagcagaca cggtccttcc    27240 tttctcccctt gcccagcact ctgaggttga ctctgtggag cactgatccc tctgtgttat    27300
aattgtctat ttacacgtca gctaccacct ataacacact gagttcctca acagcaggga    27360
cactgtccat tctttgatcc cagtgtctgg aacagtgcca agtacatagt agggacttaa    27420
taaatattga ttcatatgta aatgagactt ttccaaaaca tgctttcgtt gatgcctctc    27480
```

```
agcatttata caccttttac caactcgcta ctggccacat agacaaatga aagcagtaat    27540
ccagatacac ccaagaggac atctgttctt ttttctctct gtggagtggg agacttaagt    27600
ggcttcttaa ctggtgtgtc gtctgatcaa gtggtccagg taacaggtgg atgccaatgt    27660
ctggcccagg catcacccct tactggcact ggtcattaca gaagacactc taccagagct    27720
gaaaggacct cttgtcacta ggcagctgtg gagtccgctc tacttgacct agtaaaatct    27780
gcctggagac tgttagagtc accccactac ctgaagttac ctccaggctg acctcttttt    27840
tttcccaggt ggagtcctgg catcttagat attttaataa ggatttgctt gttgacatgt    27900
tctttattca ctaaggtgtc agcatattac tgtcttagaa ctgagggttc ttcatctttt    27960
ttggatcagg acctccctct aagaatctga tgactgctct ggtccctctc ccaataaaaa    28020
cttccatact cacctgttaa aaaaaaaaaa aactttaaac aaattaacag agttttattc    28080
agcaaagaat gattcataaa tcgggaaggc tgcaaccaga ataggttcag agagactcca    28140
cggtgtgcca cgtggttgga gaggatttag gatttatgca cagaaaaagg aaagtgacat    28200
gcagaaaatg aaagtgaggg cctggtgctg gtgcggtgcc tcacgcctgt aatcccagca    28260
ctttgggagg ccgaggcggg cagatcatga ggtcaggaga tcgagaccat cctggctaac    28320
acggtgaaac cctgtctcta ctaaaaatgc aaaaacttag ccgggcgtgg tggcaggcac    28380
ctgtagtccc agctacttgg gaggctgagg caggagaatg gtgtgaacct gggaggcgga    28440
gcttgcagtg agccaggatc cgccactgc actccagcct gggcgacaga gcgagacttc    28500
atcttaaaaa aaagaaaag aaaaaggaaa atgaaagtga ggtacagaaa cagccaggtt    28560
ggttacagct tggtgtttgc cttaaacttg gtttgaacag ttggccgcct ttgattagcc    28620
aaaactcggt gattggtaca agagtagatt gcagttcact atgtacagag aagcccttag    28680
atccgaactc aaaataggta aggaggcagt tttagctaca cttaagttaa catactcagg    28740
agtaccattc cagcttcaag ctggaagtgt ctgcagcccc ctgagaccac ttaatcccaa    28800
gttaaaaacc cctgctcaga ggcagcatct tttttttttt tttttttttt tttttgaga    28860 gagatctcac tctgtcaccc aggctggagt gcagtggcac gatctcagct cactgcaacc    28920
accacctcct gggctcaagg gattctcttg cctcagtctc ccgagtaact gggattacag    28980
gcgcgtgcca ctatgtccag ctaattttt tttttgtatt tttagtagag atggggtttc    29040
accatgttgg cctggctggt cttgaactct gacctcaag tgatccactg gcctcagcct    29100
cccaaagtgc tggcattaga ggtgtgagtc actgttcctg gcccagtgag gcaccatctc    29160
attggatatg gagacaaagg atctggctta gcatcctgga tttgtatttt ctttccaaga    29220
gtccttaagt gatatctaac ttttgcgagc tgcagtttcc tcagctatga gatgagtgac    29280
attaacctcc tctcttcaga tttataagag gatcaattaa aatggcatag gtaaaagtgc    29340
atcctagcaa gttggtatct actttagaaa tgaaggaggt catatgtatg tgaagtctcc    29400
agacccaaca tgccatctta tatgtgtcta tttctacaag tgagctagtg acaacagtaa    29460 ttgctattt tgctcctaca tgggtaggc tgatcttgac taggaggagt caataagact    29520
caccagccgg gcgtggtggc tcacgcctgt aatcccagca ctttgggagg ccaaggcggg    29580
cggatcacga ggtcaggaga tcgagaccat tctggctaac acggtgaaac cccgtctcta    29640
ctaaaaaaat acaaaaaaat tagctgggcg tggtggtggg cgcctgtagt cccagctact    29700
cgggaagctg aggcaggaga atggcgtgaa cccgggaggc agagcttgca gtgaaccaag    29760
atcgagccac tgcactctag cctgggtgac agagcgagac tccatctcaa aaaaaaaaa    29820 aagactcacc agctgtggcc actgtctgtg ctaattggct agtgcctgca tctcagaaac    29880
```

```
tgctacatat tttgactatt cccctgcac  ttaagggcat  gcacactccc  aaaatagact  29940
cagattgtct aaggaataat gatgatgatg  aagagaaagc  cctctttatc  tggtctattt  30000
gtagtcagtt ccaaaagcat taagaatttc  tgctgaacta  atgcagctag  tttctttcct  30060
gtcaccactt tccttccaaa atagtttcaa  gatctgtggg  ggaaaaaatc  tatttacagt  30120
gaacagactg gtgggaggaa gttgagcatt  ggggttttct  gccctgtgta  accttgccct  30180
aagttgggca gatggtatca cactacctgg  acatcatctg  ctcattcact  atttgaccag  30240
ttggtcattc attcacaaat gtccttttg   caggagggat  ggaggtgcta  gacctgcaga  30300
tgctagcatg aaaagacaga tctcctgctg  ctaaggtgct  taaagtagtg  gaggtcaggg  30360
gacaagcaag cagtcaggca gctctgaatg  cagaggcagg  aagcaccacg  aggcaatggg  30420
acccacagag gggtagcagg gtagaggtga  gtgggtctca  tgtggggagg  gaggaagttg  30480
actgcagaga aggtgccagg gggtgaaaat  agcttgagag  ctgtggagct  agaagggctc  30540
tcacatttgc ttattaatat gcccctttgaa aaagagtggc  ctgatacctg  gagtcactca  30600
aaagatttcc aattccgata ggaaaaagtc  aattttggct  tcagtggttg  catgtgcacc  30660
ccctgatttg ctgtatgctg aggcattgtg  gtgatggacg  caagtgcgga  gaccttgagc  30720
acgcatctgc ccctagttct tgccctgagt  cctcgaagga  ggcaggagag  acatcaaggc  30780
agacaggcgc cgctcatcag tgatgagacc  agacctggaa  ctcgcgtctt  atactcagtc  30840
ctctgccctt tctgctggat tgtggccccc  cagtataggg  tgcaacacac  aactggagca  30900
tttaagggcc acaaagagaa caaattacca  atgattgtgt  gttgattctt  tgagctcttt  30960
tttttattta ttatacttta agtgttaggg  tacatgtgca  caatgtgcag  gttagttaca  31020
tatgtataca tgtgccatgc tggtgtgctg  cacccattaa  ctcgtcattt  agcattaggt  31080
atagctccta aagctatccc tcccccttc   cccctccctc  accccacaa   cagtccccag  31140 agtgtgatgt tcccccttcct gtgaccatgt gttctcattg  ttcagttccc  acctatgagt  31200
gagaatatgc agtgtttgat tttttgttct  tgcgatagtt  tactgagaat  gatgatttcc  31260
agtttcatcc atgtccctac aaaggacatg  aactcatcat  tttttattgc  tgcatagtat  31320
tccatggtgt atatgtgcca catttttctta atccagtcta  tcattgttgg  atgagctctt  31380
tatctcatgg aaaaataatt tataaaactc  tgtatgagag  gagtgggaaa  tagtattaac  31440
gggtgcgggg tttcttttttg ggacaatgga  aatagctgga  attagatagt  ggtgatgttt  31500
gcacactttg tgaaatacta aaaactcctg  aattatacag  ttttaagaaa  cttttattta  31560 tttgttttttg agagaagttc tctgtgtcac  ccaggctgaa  gtgtggtggc  gtgatcaccg  31620
gttattgcag cctcaatctc tgaggctcaa  gcgattctcc  cacctcagcc  taccaagtag  31680
atgtgactat aggtgcgcac caccacaccc  agtgaatttg  taatttttg   taaaaacaag  31740 gttttaccat gttgcccagt ctggtcttga  actcctgggc  ccaagcgatc  ctccctcctt  31800
gggctcccga agtgccagga tacaagcatg  agtcaccaca  tgcagcctca  gttttaagaa  31860
acttttaaat aaatgaaata tagtcatacc  aaaacagtaa  aaatgggttt  caggaaaaaa  31920
aatgtttttt taaacaaact tacgtattgt  ataatcccag  ccctttttaaa aaatgctttc  31980 aaaaactggc agtcaactca taaaaggaca  atacttatg   attccactga  tgaagtagtc  32040 aaagtagtc aaaaatcaca gaaacaccac  cataaatgta  aattttttat  tttcaattaa  32100
aaaaacatct ttttttttagt caaaatcata  gaaatagaaa  gtagacaggt  ggttactaag  32160
ggctatggga tggggaaatt agtgtctaat  gggcatagag  tttcagtgtt  acaaggtgaa  32220
```

```
aagttctaga gttatgctgc ccagcagtgt gaatatactt tattgttctg tacacttaac    32280
atggttaata tggtaaattt agcgttatgt gcttttact  atagtaaaat taaaaaaaaa    32340
aaaaatgggg ccgagtgcag tagctcacac ctgtaacata atcccagcac tttgggaggc    32400
cgaggtagga ggatcacttg aggccagaag tttgaaacca gcctggtcaa tatagcgaga    32460
cctcatctct acaaaagaaa aatgttaaaa ttagacaggt gtggtgtctg tagtcccagc    32520
tctctggagg cagggactga gtcagaggat cacttgagca tagggggtttg aggctgcagt    32580 gagccatgat cctgccactg ctgcagcctg agcaacagag caagaccctg ttgtaaaaac    32640
aaacaaacaa aaactggcag ctgatacctg agagtgaata tcttttatcg ctggttaatg    32700
ggattgagag aatgcttcat cttatagaaa gaacagtgtc tttggaccca cagagacctg    32760
gatttaagat tagctctgcc aattactgag tactctttac tatgaacctc tgttttcctc    32820
atctgtgaaa ctggaataat gaatcctacc gccaacaatt gtagtcaagt tggaaacaat    32880
ttacacaaag tgccaaacac caagcctggc acagtaggaa ccgagtaaat agtggttaat    32940 attttatca  gtgtctgcat tgctgacgtc tccatcattt ctatacattt gttttgaat     33000 cagaaaaaga tgttatttta aaaaaataac ccagtagtgc cccttgtccc attcctatca    33060
gttatattat tattgttact accctctgga atttcaataa ctctttgttt tttgggtttt    33120
ttgttttgtt ttgctttgct tttgagacag atctctgtc  gcccagtctg gtgtgtagtg    33180
gtgtgatctc agctcactgc agcctcaacc tcctgggctc aggtgatcct cccacttcag    33240
cctcccaagt agctgggacc acaggcgcat gccaccacac ttggctaatt tttgcatttt    33300
tagtagagac agggttttgc catattgcct aggccggtct ggaacttctg ggctcaagcc    33360
atctgcctgc ctcggcctcc caaagtgctg gaatttcagg catgagccat gcctggccta    33420
aatagctctc tgtgtttgca aaagtgtgtt ataagaatca ttcagagcct ctcgattgga    33480
tggaggctct agaatgcaca gaaaaaggct gccaccgtgt atctctgcaa gtcatgcaca    33540
agatggggaa cagcaggctt cccctgctt  accagttcaa atacagagaa ctagccctgt    33600
agctgtttct ttcatatctc acccattcta aagagaccac aggccttaga agtaaaggac    33660
tcttttgttg aaagagtgtt ttcaaattta aatgagcatt tattggtcaa agatgcacca    33720
actagtcttt tgaagaattc aaggctcttt agagaaaaat aaagccttgg aggagtatct    33780
gagaagcttg ttagatgcgt gggaagagtc tggaaataaa aaacttcatc tggagtttct    33840
gccttctacc aacagagctg aagctaatgc tctcctaaga caagcaaagc agatggtttg    33900
catacttcct taccttcctt ttacttcctc tgtaatagac ttgtcatgtc tgatgtttga    33960
gttgacgtgg tactctaata gagttagagt ctgcattttt tttatgtcct ctagtatgtt    34020
ctggttgatg gttgagggca acaaaccagc agtcccagat gccagcacca agacctgaga    34080
caggtcactt aactctccga gcttcaccac cattctcacc ttgcagacct cacagggaac    34140
agggaaagct ctatgagata caacatcatt atgattaatc ctattctgat tctgaaagca    34200
aagctcttcc tacacaaact cctatttcta aatactaaaa gacatttctt tatggtgtat    34260
tttgtgtact tgtagaaatg gaaagtgttg agataaaaca tgaagcaatg atgacaaagt    34320
gctaactttt tcttgtttta atttctttat gcttttttc  cacctaatcc cctagagtgg    34380
tgtcttaact gtcaaactgg gtggagatct aggaacctat gtgatcaaca agcagacgcc    34440
aaacaagcaa atctggctat cttctccatc caggtatgta ggtatgttca gaagtcaaca    34500
tatgtaattc ttaaagactt ccgaaatgtg acattgtgga ccatttaaga aatgtcggct    34560
gagcacagtg gctgacacct gtaatcccaa cactttgaga ggctgaggta ggaggatcac    34620
```

```
ttgaggacag gagttcagaa ccatcctggg caacatagtg agtccctgtc tctgtaaaga   34680
aaataaaaat aaagtcacag ctgggtgcag gcttacacct gtaatcccag cactttggga   34740
ggccaaggcc tgtggatcac ttgagctcag gagtttgaga ccagcctggg caatgtcaca   34800
aagccccacc tctactaaaa atataaaaat tagccaggtg tggtggcaca cgcctatagt   34860
cccaactact tggaaggctg aggttgagcc tcagcctgag cccaggaggt ggaggttgca   34920
gtgagccaag atcgcgccac tgcactccag cctgggcaac agggccagac cctgtcccaa   34980
aaaaaaaaaa aaagtcatcg tcttatgtta gcatccttgt aagtgagcct ttcctgatat   35040
tttgcagcct gtctcattct cagtagaaaa gtttactcta gttacataac ttctccctgc   35100
tgacaatttg gatactgtaa gcaggcatca ggatattaag atctgaagtg agtagcttat   35160
aacttttcca aatccagcct agacagtttt cctctattaa attattgccc tgactttaaa   35220
agaagctact tttgaccttg tagcgtttga acaagttgca ctttgtcttc aaagcaagtt   35280
aaagtttgac ctctacttgt tttgagcctc tcaggtaaag ggttatttga attccctttg   35340
caggttgggg ttgtgtaccc tgtggaggtg gtagagtgtt atatattgct gctccagggc   35400
atttaatccc tcctgccttt tccattgatg tgctttcaat ctagaggaat aaagattgt   35460 gttggagaca caatgtggcc tgcatagcat ctgaaagcct gagaacatgc agggagagac   35520
atccctcatc cctcagcagc ctggctgctg ttgaagtgg tgtaagaaag taaagagaa    35580 atgcccacaa aacgttctca gatccagtca ttcattagca cttccaaaga gagcatgttg   35640
actgtgaatt gggaaagggc cagataaaac tagcatagaa ttctttgaaa gactaacggt   35700
atttgcattt tttaaaaatt ataaccttac tctaccccct aacattgaca tcattttag    35760 gtaattaata ttttcccatt tattattctg tgatctctaa tgctttgttc agaataaata   35820
gtgtgtttcc tttccccaca ctttcatcca agaagtgtgc tagagttcaa caaaaacagc   35880
actagaaatc actgtcattc taggaaggcc ctaattcaca gattgtattg gttttttagac  35940 ccagttagtg tgctggaggt tggaggattt taacctctgt gggccaacta gcctctgtgg   36000
cctcagtcat tcttcctgac cctggctgtg cttgagcctg tgtgttctta tccttcatct   36060 ccggggggaac gaagtggatc agctcggtcc agcgatcact tttggggatc agtggctttg   36120
tagatatcgg gcaggcactt accccaaaag aactttcccc atatctgaag actgaaaacg   36180
tccatatcgt atttggacac actgcccagc aatacgctct agctgtgttc agaagcatgg   36240
gaatttggaa agatctgctg agcatgccgt ttactgtcac agatactatc ttcctcaaaa   36300
aaaaaaaata tatatatata tatggggac ggggcaggtt gagactgggt gagactgaag    36360
aggtgccttg gccagagcag gccacaccca gagaccacag gctccccggt ccacctcagg   36420 cccctccct tcctgcgccg tttccggcag atccagagtg gccaccgccg gatgggagtc     36480
gggggaaggg aggcagagaa gcgggccctg aggacaagct ctcagtgctt ctgtgggaag   36540
tggcggcaag acggcagctc ccagcggggg atggaggccg agtcagtctg ctggtcactg   36600
gaggccagga tgctgcctaa cacagccgtc ccgctccggg cctcaccacc agggcggctc   36660
tccccactcc cggcctgctg cccacacaga ctgcggggtt ccgggggagc aggacccagg   36720
ccgttctgcg cctgtcttct tggaaggagc aggccggagc gcgggagcgc cgtgtagctg   36780
tacctgcgaa ggcacaggat tccgcgggaa gatcccgcag tttcgggccg tcgtcattgt   36840 ttttataccct gtggcaaatg gcatgaccag acacacggtt atgtctggag aaaccctgt    36900 agaggagcag gaggttgtgg acatgctgtg gcccggacag tggctgccga gcagttggag   36960
```

```
cctgcacccg cccaacttgg ctaaagaagt ccccatactc tctgtggaaa agatttccag   37020
aagctgttgt gtcaatatca aagcctcaaa acaacaacaa caacaacaaa acatgaaat    37080 tatcaacaat aaagatcatc cttgagtctg ctttgaaaag tagggtgaaa ttctgcagag   37140
gcattcaact ggcaagatac caccctcata gccagatctg caggtctcag ccatcatgcc   37200
agggaaaatg ctccattcac cactcctcag cttctgcttc tggtttcaga ggtctctgta   37260
ttggaggggc tttaaagcaa gaagggtctt tacccactta ctcttattca cagatgtgaa   37320
tatgcaggtc cagtggggaa agtgacatgt cctaagtcag aatagagtca acaagaaaac   37380
agggcccaaa atgacttagc ctctagtgta taatgggcat tgatgagcta ctggaaatac   37440
agagatgaag aaaacacagt cccatcttca aggagctcaa tctagcaagg agacagact    37500 ctttgtaggt gggaccgggc ttccctgcag cagaaggaag cttgaaattg gtaacgagcc   37560
tcagaaggga cagaggcagg ccaccatgct accctgagag gatcgcatgt ggacacgggg   37620
ctatgacctg gccctgcttt gacccactag ctgtgctgta gggccaggtg gagcctggag   37680
tggcctgtgc taagggcta ctatgagctc tttccactcc cccaaggcat tgcataaata    37740
atgtcacttt ctgtttgcac agcaaaatca gggacacaat tttctagaac atggggtgcc   37800
tccccctccc ccagcccaac agaagttcta caatgactga tgggcccttg tttttgtttg   37860
agacggaaca ccccacaggg ttccgagtgg tgatttgtgg cccacaggcc actggcaagt   37920
ggaggcagag ctgcagagcc ctcgggagcc acagagggcc tgctggccgc cacgacatgc   37980
caactcagct gctgctggcc ctcctgtggg cggcagtgct agtgatgtgc agaatcttag   38040
gactagtgcc aaggaaccta taaatacccc gggtgaccca ggcgtgcact gctgtggtgg   38100
ccttcacagt cagaagatga caagctgaga aggggagaat cggcccaagg tgagatccac   38160
agaaaggcca gggccaagat gcggccagca cctcaggctg gtggtggtct tacgttgacc   38220
atgccagagg ccagtccttg attgctccaa accctctgtt cgagggttcc aaatgaaatg   38280
agcaggtcct cgtgtcagga cctaggttag tttctgaaaa agcatgaaaa gcaggcctcc   38340
tgaacttccc cgagtgactg atgcaaagtg cgtcctgcat gcttcacagc accatggaga   38400
ggatcttcag gggcaaactg cagactatct gaatgacggc actgaccatc agcaaaccgc   38460
agagctgcct gaccaagaaa ttgcgagaca gaagcaatgc ttgcaggcga agaagaaggg   38520
gccagacaca gtggctcacg cctgtaatcc cagcactttg ggaggccaag gcaggcggat   38580
cacttgaggt caggagtttg agaccagcct gggcaacata gtgaaaccct gtctctacta   38640
aaaatacaaa aaattcgcca ggcatggtgg caggcacctg taatcccagc tgcttgggag   38700
actgagacag gagaattgct tgaacccagg aggcgaaggt tgtaacgaac tgaaatcgtg   38760
ccacagcact ccatcctggg cgacagagtg agactgtctc aaaaaaagga ggagaagaag   38820
gaaaggccaa ggcaggaatg aaacaggcca tgaatgttgg agtgaagcaa ctggcctcct   38880
cgtgctaagc ggctactgtg agttctttcc actcccccaa gacattgcat aaataatgtc   38940
actttctgac actcaccccg ctgaatgtcc tgcctctgct caagggtggt atgatgggga   39000
cttggcagtg gaggggaaca gggaaaccag acatggtggt ctcccgcctt cctggctaca   39060
agtccctctg aagaaatcca aaggagtaaa gagcttggag agtaggcctc tgtagggtgc   39120
aagggcacag ctggagacgg agctcctgag gctgcagctg atgctgcccg ctctgcctga   39180
actgcaccaa aaacgtgatg aggccatagc gggagtccac ggaggaggat gcctactgcc   39240
cgacctctag cagagactaa gcaaggtgca tgaaaacttg aacccatgt gtcacaccca    39300 tgaccactac atgaagatgg cccaaaacct ggcccaggaa ttgaagaaag actcttccaa   39360
```

```
tttgctgtaa gaaaatggcc caggggggcaa gcacggtagc tcacacctgt aatcctagca   39420
ctttgggaag ctgacgcagg cagatggctt gagctcagga gttccagacc agcctgggca   39480
acatggtgaa accccgtctc taccaaaaat acaaaaatta gccgggtgtg gtgatgcatg   39540
cctgtggtcc cagctactca ggaggctgag gtggaaggat tgcctgagtc tgtggggcag   39600
aggttgcagt gagctgagat cacaccactg cactccagcc tgggtgacac agtgagaccc   39660
catctcaaaa aaaaaaaaaa gaaagaaaac ggcccaggaa ggctggaggg ccgccgtgtc   39720
cattgagaga gtgctccagg cactccaaaa agaaaatgac cacaatggga agaaaccagc   39780
tgaccatgag accaagttcc aaccttttac aagtggcctg tggctcctgg cgccccgccc   39840
acagctgaca ggggctcaga agtgctaggg ggaccatggg ccaccagggc caccaggagg   39900
gaggcaggta acgatgcgag ggcttggatg cagaacacca gctggtttga ttctgttttc   39960
cctgtacctg ggtcctgaat gcccagaggc tcagggaaac accagccagt gctgctgcct   40020
ttaaagcact tttgactgat ctcttgttaa tttagcaact gttattggtt gatgctgcag   40080
ttgctcttat tgaagtttga ttgatagcat taggatggta aggcactatt tttcaaataa   40140
aggttgttta atataaaaaa aattttgttt ttttttctct cagcctttca cattggttca   40200
aaatatcttt catctggctg catttctgat ttttgttttg tttttttttt cttaatttta   40260
tttattttta attaaaaata atttttttg tcaacatggg gtctcacttt gttgcctagg   40320
ttggtctgaa actcgtggct tcaagcaatc ctcccacatc agcctcccaa agtgctgggg   40380
ttatgggtgt gagccactgc agcagcctgt ttttttttgtt tgtttgtttt ttttaatttg   40440
acaagttttc aggtcctgtg aaatcagcag tcttacctcc caccttgcgc accctgagga   40500
ggttgcagaa taaaggagaa ttctaggac acgtgggcat cagtgcctgt gctcagagca   40560
cctcaggcag tgtggagggg tctagaggtt actcaggctc tgcctggcaa cccgatagca   40620
gtatcagagt atagggccaa ggggacggtc cttgggcttg gtgtggttta ttagtccttt   40680
tcctgtgacc ctgatggttt ggttcactca tttttatctc catactggga acaggttcaa   40740
gccccagcat ttggttgata atgcaggaat ccttgatact tttattgccc aagcttccct   40800
tcctggtgac ctcatcctag cctcagtctt tggaaaagcc ctccttgagt gctcaggcag   40860
actcaggtgc cctttcttct gggctcccat gcactctgtt cttacctcca tcagggtgcc   40920
acatgcacta gtgttatctg ctgccgtggc caatcatcca tgaggccatg aggaagtgga   40980
atgtacatct ggtataagaa gacatggcag aagccagcct ccgatctgtc cacacgaata   41040
cagcattccc aaagcaacgt gcatgtgcca ttattcactg gatgagcttg aggtggatga   41100
actagcccac caggctctca atgtcatgaa tttaacactg aattaagaaa aatatgtttt   41160
aaaaataata gttaggtga ttgctggggt gctaggagag gaaggaatgg ggaataactg    41220
tttaatgggt atagttggcc ttgtgtatct gtgggttcca catctgattc aaccaaccgt   41280
ggatcaaaat atttgaaaat aaaaaacaaa acaaaaatga tacaaataaa accaatata   41340 acaactatta acagcattta cattgtacta ggcattataa gtaatctgga gatgacttaa   41400
agcatacaga aggatgtgcc taggttagat gcatgtatcg taccatttca tatcagggac   41460
ttgagtaccc acggattttg gtatctgcag atcctggaac cccttcccta tggataccaa   41520
ggaacaacag cactgggtct ccttttgggg tgatgcagat gttttgaagc taggcagagg   41580
tagtggttgc acaacattgt aaatgtacta aatgccacca aattattcat ttttaaatgg   41640
ttaatgtgtt atgtgaattt caccttaaca actaataata ttataggtaa ggcacaagtt   41700
```

```
acatctgtag cacaaaaatg gccctaattt ttaaaacact gctccagcat agcaggtatc   41760
acatgtgagg tagcaaaagc tggagatcaa agtgtgatac ctggagactt atcagtaagg   41820
gtcaaatgtt ttttcaggtt ttgagaatca ttcttggaat tgttccagaa gatatatcgt   41880
ataactcttc ttagatgcta agataagaag gcagatatac actagctcat tttgtgttat   41940
tttctagagc tttactccag tcaatttctt gggggcagca tttgtggaat cagtggttca   42000
tctgaagggc tgtgctgtgg aattactatg catttgtttt gtcttccagt ggacctaagc   42060
gttatgactg gactgggaaa aactgggtgt actcccacga cggcgtgtcc ctccatgagc   42120
tgctggccgc agagctcact aaagccttaa aaaccaaact ggacttgtct tccttggcct   42180
attccggaaa agatgcttga tgcccagccc cgttttaagg acattaaaag ctatcaggcc   42240
aagaccccag cttcattatg cagctgaggt ctgtttttg ttgttgttgt tgtttatttt   42300
ttttattcct gcttttgagg acagttgggc tatgtgtcac agctctgtag aaagaatgtg   42360
ttgcctccta ccttgccccc aagttctgat ttttaatttc tatggaagat tttttggatt   42420
gtcggatttc ctccctcaca tgatacccct tatcttttat aatgtcttat gcctatacct   42480
gaatataaca acctttaaaa aagcaaaata ataagaagga aaaattccag gagggaaaat   42540
gaattgtctt cactcttcat tctttgaagg atttactgca agaagtacat gaagagcagc   42600
tggtcaacct gctcactgtt ctatctccaa atgagacaca ttaaagggta gcctacaaat   42660
gttttcaggc ttcttttcaaa gtgtaagcac ttctgagctc tttagcattg aagtgtcgaa   42720
agcaactcac acgggaagat catttcttat ttgtgctctg tgactgccaa ggtgtggcct   42780
gcactgggtt gtccagggag acctagtgct gtttctccca catattcaca tacgtgtctg   42840
tgtgtatata tattttttca atttaaaggt tagtatggaa tcagctgcta caagaatgca   42900
aaaaatcttc caaagacaag aaaagaggaa aaaagccgt tttcatgagc tgagtgatgt   42960
agcgtaacaa acaaaatcat ggagctgagg aggtgccttg taaacatgaa ggggcagata   43020
aaggaaggag atactcatgt tgataaagag agccctggtc ctagacatag ttcagccaca   43080
aagtagttgt cccttttgtgg acaagtttcc caaattccct ggacctctgc ttccccatct   43140
gttaaatgag agaatagagt atggttgatt cccagcattc agtggtcctg tcaagcaacc   43200
taacaggcta gttctaattc cctattgggt agatgagggg atgacaaaga acagttttta   43260
agctatatag gaaacattgt tattggtgtt gccctatcgt gatttcagtt gaattcatgt   43320
gaaaataata gccatccttg gcctggcgcg gtggctcaca cctgtaatcc cagcactttt   43380
ggaggccaag gtgggtggat cacctgaggt caggagttca agaccagcct ggccaacatg   43440
atgaaacccc gtctctacta aaaatacaaa aaattagccg ggcatgatgg caggtgcctg   43500
taatcccagc tacttgggag gctgaagcgg aagaatcgct tgaacccaga ggtggaggtt   43560
gcagtgagcc gagatcgtgc cattgcactg taacctgggt gactgagcaa aactctgtct   43620
caaaataata ataacaatat aataataata atagccatcc tttattgtac ccttactggg   43680
ttaatcgtat tataccacat tacctcattt taatttttac tgacctgcac tttatacaaa   43740
gcaacaagcc tccaggacat taaaattcat gcaaagttat gctcatgtta tattattttc   43800
ttacttaaag aaggatttat tagtggctgg gcatggtggc gtgcacctgt aatcccaggt   43860
actcaggagg ctgagacggg agaattgctt gaccccaggc ggaggaggtt acagtgagtc   43920
gagatcgtac ctgagcgaca gagcgagact ccgtctcaaa aaaaaaaaaa aggagggttt   43980
attaatgaga agtttgtatt aatatgtagc aaaggctttt ccaatgggtg aataaaaaca   44040
cattccatta agtcaagctg ggagcagtgg catataccta tagtcccagc tgcacaggag   44100
```

```
gctgagacag gaggattgct tgaagccagg aattggagat cagcctgggc aacacagcaa   44160
gatcctatct cttaaaaaaa gaaaaaaaaa cctattaata ataaaacagt ataaacaaaa   44220
gctaaatagg taaatatttt tttctgaaat aaaattattt tttgagtctg atggaaatgt   44280
ttaagtgcag taggccagtg ccagtgagaa ataaataac atcatacatg tttgtatgtg    44340
tttgcatctt gcttctactg aaagtttcag tgcaccccac ttacttagaa ctcggtgaca   44400
tgatgtactc ctttatctgg gacacagcac aaaagaggta tgcagtgggg ctgctctgac   44460
atgaaagtgg aagttaagga atctgggctc ttatggggtc cttgtgggcc agcccttcag   44520
gcctatttta ctttcatttt acatatagct ctaattggtt tgattatctc gttcccaagg   44580
cagtgggaga tccccattta aggaaagaaa aggggcctgg cacagtggct catgcctgta   44640
atcccagcac tttgggaggc tgaggcaagt gtatcacctg aggtcaggag ttcaagacca   44700
gcctggccaa catggcaaaa tcccgtctct actaaaaata ttaaaaaatt ggctgggcgt   44760
ggtggttcgt gcctataatt tcagctactc aggaggctga ggcaggagaa tcgctgtaac   44820
ctgggggtg gaggttgcag tgagacgaga tcatgccact tcactccagc ctggccaaca    44880
gagccatact ccgtctcaaa taaataaata aataaataaa gggacttcaa acacatgaac   44940
agcagccagg ggaagaatca aaatcatatt ctgtcaagca aactggaaaa gtaccactgt   45000
gtgtaccaat agcctcccca ccacagaccc tgggagcatc gcctcattta tggtgtggtc   45060
cagtcatcca tgtgaaggat gagtttccag gaaaaggtta ttaaatattc actgtaacat   45120
actggaggag gtgaggaatt gcataataca atcttagaaa actttttttt cccctttcta   45180
tttttttgaga caggatctca ctttggcact caggctggag acagtggta caatcaaagc     45240
tcatggcagc ctcgacctcc ctgggcttgg gcaatcctcc cacaggtgtg cacctccata   45300
gctggctaat ttgtgtattt tttgtagaga tggggtttca ccatgttgcc caggctggtc   45360
tctaacactt aggctcaagt gatccacctg cctcgtcctc ccaagatgct gggattacag   45420
gtgtgtgcca caggtgttca tcagaaagct ttttctatta ttttttacctt cttgagtggg   45480
tagaacctca gccacataga aaataaaatg ttctggcatg acttatttag ctctctggaa   45540
ttacaaagaa ggaatgaggt gtgtaaaaga gaacctgggt ttttgaatca caaatttaga   45600
atttaatcga aactctgcct cttacttgtt tgtagacact gacagtggcc tcatgttttt   45660
ttttttttta atctataaaa tggagatatc taacatgttg agcctgggcc cacaggcaaa   45720
gcacaatcct gatgtgagaa gtactcagtt catgacaact gttgttctca catgcatagc   45780
ataatttcat attcacattg gaggacttct cccaaaatat ggatgacgtt ccctactcaa   45840
ccttgaactt aatcaaaata ctcagtttac ttaacttcgt attagattct gattccctgg   45900
aaccattat cgtgtgcctt accatgctta tattttactt gatcttttgc ataccttcta     45960
aaactatttt agccaattta aaatttgaca gtttgcatta aattataggt ttacaatatg   46020
ctttatccag ctatacctgc cccaaattct gacagatgct tttgccacct ctaaaggaag   46080
acccatgttc atagtgatgg agtttgtgtg gactaaccat gcaaggttgc caaggaaaaa   46140
tcgctttacg cttccaaggt acacactaag atgaaagtaa ttttagtccg tgtccagttg   46200
gattcttggc acatagttat cttctgctag aacaaactaa aacagctaca tgccagcaag   46260
ggagaaaggg gaaggagggg caaagttttg aaatttcatg taaatttatg ctgttcaaaa   46320
cgacgagttc atgactttgt gtatagagta agaaatgcct tttcttttttt gagacagagt   46380
cttgctctgt cacccaggct ggagtgcagt ggcacgatct gggctcacta caacctccgc   46440
```

```
ctcctgggtt caagcaattc tctgcctcag cctcccgagt agctgggatt acaggtgcct    46500
gccaccacac ccggctaatt tttgtatttt tagtagagac ggggtttcac catcatggcc    46560
aggctggtct tgaactcctg acctagtaat ccacctgcct ccgcctccca aagtgctggg    46620
attacaggcg tgagccactg cacccagcca gaaatgcctt ctaatctttg gtttatctta    46680
attagccagg acacttggag tgcatcccga agtacctgat cagtggcccc tttggaatgt    46740
gtaaaactca gctcacttat atccctgcat ccgctacaga gacagaatcc aagctcatat    46800
gttccatctt ctctggctgt atagtttaag gaatggaagg caccagaaca gatttattga    46860
aatgtttatt agctgaagat ttatttagac agttgaggaa aacatcagca cccagcagta    46920
aaattggctc tcaaagattt tcttctcctg tggaaagtca gacctctgag gccccatcca    46980
ggtagaagta ctagtgcaag aagggcctct gctgtccact tgtgtttctg tgatctgtgg    47040
gaacattgtt aacgccacat cttgacctca aattgtttag ctcctggcca gacacggtgg    47100
ctcacacctg taatcccagc actttgagag gctgaggcag gtggatcacc tgaggttagg    47160
agttcgaggc cagcctggtc aacatggtaa accccgcct ctactaaaaa tacaaaaatt    47220
agctggccgt agtggcgcac gcctgttatc ccagctactc gggaggctga ggcaggagaa    47280
ttgcttgaac ctgggtggtg gaggttgcag tgagccgaga ttacaccact gcactccagc    47340
ctgggtgaca agaggaaac tccattaaaa aaatgtaatt cccgtgtctg ccatcttaag    47400
tgtaaaggtg gctaaattat atagaaaaat aagacaatat catttcccaa ttacattcct    47460
ttcctaccgc actctatgat gctagctgag atttttccaa aagaaaatgg cttaaataaa    47520
accctaagag aaagaaaaac tttaaatccc tccaaagctc aaaagtaata gaaacagatg    47580
agtttggagt caggatttct ctgtaagatt gcctaggctg tgtactgcac atctccaggt    47640
gccactgttg acagagatta taactacaat gtgaagtgaa tggtgccact gacagttatg    47700
caaaccgtcc agagcatagc cacctgatcc tgctgggatt cctcttgcca gtccatcagc    47760
agttcccctt gaaagtttca ccaaacatcc cttaaatctg ccctctcctg cccgtcccca    47820
gtggaggtcc tcatcatttt tcacctgcat ttttgcagga gctttcttat atccaccttc    47880
ctccttttct ctcagcccat catctagcta cacagtctcc agggtaagct ttcagaaagg    47940
caatctcttg tctgtaaaac ctaagcagga ccaaggccaa gtttcttagc ctgaaaaatg    48000
tgcttttctg actgaactgt tcaggcactg actctacata taattatgct tttctacccc    48060
ctcacactca acactttgac tccagcaatc ccaaatcccc agatccctaa gtgtgctgtg    48120
ctattttcac gtggctctca gacttggcca gtgctgtttc cattttggtc tttattcccc    48180
acatctctgc ctgggggta gattctaccc tgaaaaatgt tcttggcaca gccttgcaaa    48240
ctcctcctcc actcagcctc tgcctggatg cccttgattg ttccatgtcc tcagcatacc    48300
atgtttgtct ttcccagcac tgacctacca tgtgtcaccc ctgcttggct gtaccttcca    48360
tgaggctagg actatgtgtc tccttttgttg actgctgttg ccctagcatc ttgcacagtt    48420
ccttgcacac aattagagct ctataaatgt caaataaatg tgttataatt atatgtttaa    48480
gatagttgtt caaataaact ctaataaccc ccaactccaa gagtgttagc aagaaatata    48540
aattttacag aagaatggtt ggaggtgggg agggtgtcca cggagtgagt tacctcacac    48600
aggcacggaa aaacttgaac ctcctaagga catttttaag ctctcttttcc catttttctct    48660 cctggattcc cattgcctgg tctcattttct ctcttctcca ccacaccact tcctcaaaaa    48720
ttcctttagg gtttgttctt aagcttagat aggtttccca ttctgaaata caaaggcctg    48780
ataattagcc aacttacctt gttggggatg tggaaggcaa gactctcaga ctccatgact    48840
```

```
caggtatatt gcaacaatta ggctgaaagt tccttgagag taagtgtcca aatcttttca   48900
tgtttggttc ccagggctca ctacagttgt tggtatatca taggcactct aatatcttct   48960
taaagaatca atatcattaa aatggccata actgcccata gcaatttaca gattcaatgc   49020
tatttctatc aaactatcaa ggtcattttt gttttatttt ttttctttga gatagaatct   49080
cgctattgtc acccaggctg gagtgcagtg gcgcgatctc gactcactgc aacctccgcc   49140
tcccgggttc aagtaattct cctgcctcag cctcccgagt agctgggatt acacgtgcct   49200
gccaccacac ctggctaatt tttgtatttt tagtagagac aaggcttcaa catgttggcc   49260
aggctggtct tgaactcctg acctcaggtg atccacctgc cttggcctcc caaagtgcag   49320
ggattacagc atgagccact gtgcccggcc catggtaatt tttcacagaa tcagaagaaa   49380
ctattctaaa attcatatag cggccaggcg aggtggctca cgcctgtaat cccagcactt   49440
tgggagacag aggcaggagg atcatctgag gtcaggagtt cgagaccagc ctgtccaaca   49500
tggtgaaacc ctgtctctac taaaaataca aaaatttgcc agtcgtgatg gcgggcacct   49560
gtagtcccag ctactcgaga ggctgaggca ggagaattgc ttgaacccgg gaggtggagg   49620
ttgcagtgag ccgagatcac gccactgcac tccagcctgg gcaacagagt gagactccat   49680
ctcaaaaaaa taaataaaat aaaataaaat aaaattcata tagaaccaaa aaagagccca   49740
aatagccaaa gtaatcctga gcaaaaagaa caaagctgga agcatcacat tacccaactt   49800
caaactctac tacaaggcta tagcaactaa aacagcatgg cactgctaca aaaacagaca   49860
ggtagactaa cggaacagaa tagacaactc agaaataaag ccacacacct acagccatct   49920
gaacttggac aaactcaaca atattaagta atggggaaag gactccctat tcaaaaagta   49980
gtgctgggat aactggctat ccatatacag aagaatgaaa ctagactgct acctatcccc   50040
atatacaaaa attaaatcaa gatggattaa agacttaaat gtaagatctc aaactaaaaa   50100
atcctagaag agccaggcgc ggtggctcat gcctgtaatc ccagcactct gggaggctga   50160
ggcggatgga tcacctgagg ataggagttc gaggccaggc tggccaacat ggtgaaaccc   50220
tgtctctact aaaaatacaa aaattagctg gcatggtag tgtgtgcctg taatctcagc   50280
tactcgggag gctgagacag gagaatcgct tgagcctggg aggcagagtg agcccagatc   50340
gcaccattac actccagcct gggtgacagg agcaagattc catctcaaaa aagaaaaag   50400 aaaaaaaaaa tcctagaaga aaacctagta aatgcccttc ttatatcagc cttgacaaag   50460
aagttatgac taaatcctag aaagcaattg caacaaaaac aaaaatttac aagtgggatc   50520
taattaaact aaagagattc tgcacagcaa gagaagctat caagggagta aacagacagc   50580
ctacagaatg ggagaaaata ttcacaaatt atgcatctga caaaggtcta atatccagaa   50640
tctataagga acttaaatca acaagcaaaa accaaataac cccattaaaa agtaggcaaa   50700
ggacacgaac agacatgtct caaaagaaga aatacaagtg accaacgaac atgaaaaaat   50760
cctcatcatc actaatcatg agagaaatgc aaatcaaaag cacagtgaga tatcatttca   50820
taccagcaag aatgactatt aaaaaagtca aaaaataaca gatgttgcaa gactgcagag   50880
aaaagagaac gtttatacac tgttggtagg aatgtaaata cattcaacca ctgtggagaa   50940
cagtttggag atttctcaaa gaactgaatt gaactaccag tcgacccagc aatgccatta   51000
ttgagtatat gcccaaagga aaataaattg ttctatcaaa aagacaaata cacccatgtg   51060
ttcatcacag cactattcac aatggcaaag acatgaaacc aaaccaggtg ctcatcaatg   51120
gtggattaga ttgtgtacat atataccacc atatggtaca tatacactgt ggaatactat   51180
```

```
gctgccataa aaaagaatgt aatcatgtat tttgcagcaa tatggatgta gctagaggcc    51240
attattctaa acaaactaac acagaaacag aaaccaaata atgcatgttc tgacttaaaa    51300
gtgggagcta acactgaat acacatgggc ataaagatgg gaacaataga cagtgggggc     51360
tattagagag gcaagggctg aaaaactacc tattcggtgc cctgctcact atctgggtga    51420
cagagtcatt agcactccaa agctcagcat cacacagtat acctttgtaa caaacctgca    51480 catgtaccc ctgattctaa aataaaagtc gaaggaaaac aacaaaaaca aaagaaata     51540 actcctgagt tggggtctcc atctcttagt tcagcctatt ggcagtcccc ttttcaagt    51600 tctaaggagc ctgtactaga ctactcttca tttagtccca taataatccc tctttcaatt    51660
attttgcctt caaacctata gggaagggat tggaaatgaa gtttcagtca ttccctaagt    51720
aaaatgtata tacatatttt aattgaaaca ggatttcact ctgttgccca ggctggagtg    51780
cagtggtgtg gtcatggctc actgcagcct caacctcctg ggctcaagca atgcttccat    51840
ctcatcctcc caagtagctg ggactacagg ctcgtaaatt ttttagagaa caaaacaca    51900 gtctttagat ttaaacatgt gaaagcagaa atttttaaaa tacaatgaaa gagttggaag    51960
acagagttga aattgttcag aaattacagt aaaaatacta agagatagga aatagtcaac    52020
ttccaaatga aagaatcac gaaagagaga acagaaaaga tagaaaaaaa attatcaaag    52080
aaataattca agaacatttc cttaaagtga agggcatgag attccaggta tattccacat    52140
atagaaaaat atcccataca aaatcacatt gttatgaatt tcataacat gagggacaaa     52200 aaaagataat ataagtaacc agagagggaa aaaataaata aacaaaacaa gacaaatagg    52260
tcatatacaa agtaatattc atcacaatag cttcatagtt ctcaataata acaaaaagcc    52320
tttaaaattc tggttgaagc agttcagaca atgccatcac ccaaaaatat gccattttgg    52380
catactgatt attattagct gaaagcactt gagaaacagc agactgtaca ggaagggctt    52440
tccaacctcc tcttttctac ctaaaaacag gctagaaaat ttcccatgat aaaggtgccc    52500
tccctctact agaaagagaa aaacatcctt atcaccagag atagggaatc aatgccaaaa    52560
tggatctgaa caaacttatt ggaataaccc ttgtcttcca ctacttatcc ccaatatagc    52620
tcttagtaat ttccccaagc cccttttgtct tgtcatttct tcacaaattt atcatttctt    52680
tgtctaaaac atatataaac ttgtctgcta tggtgacttc ttcgggtcta catttgcttg    52740
tgaggactcc caggtacatg taaaattgta ataagacttg cgtgcttttc tactgttaat    52800
ctttcctgtg tcagtttaat tcttaggcct agctggaaac ttaagagggt agaacagaaa    52860 ttttttccttt cctacatggt gaagggacat tctgtaataa aactagcctc aacattaaaa    52920
aaatgtgatg taataaaaaa caaaggaaaa agaaaacaaa acagaaaagc aattaataac    52980
actaggaaac acgaggcatt gtacaggata ggaaacgtcc tgttatgtta cacaatgcaa    53040
cagtgggtat tgttttcatc attattataa tgaaaatgct aaatagtgat ttgaccaaca    53100
atccagttta aaacatttgg aggaatgtga atgtttatgg ccagaaaatg gggagaaaaa    53160
tggttaagga aacaaaatct catcatctag agtgggaagg agactgataa ttcctaatat    53220
gaaccaaaaa ctcaaacttt ttttttttt tttgagatgg ggtctcgctc tgtcgcccag    53280
gctggagtac agtggcacga tctcagctca ctgcaacctc tgcctcccag gttcaagaga    53340
ttctcctgcc tcagcctctt cagtatttgg gactacagtt gcacactatg atgtctggct    53400 aattttttgta ttttttagtag agatgggggtt tcgccatgtt ggccaggctg gtctcgaact    53460
cctgacctca gatgatcagt ccgccttggc ccccaaagt gctgggatta cagacatgag    53520
ccattgcacc tggcctgaaa actcatttta tttagatatg ttaagggaaa tctcaaaata    53580
```

```
atcagctaga aaaattgaaa atggttgccc atgaggaggg gagaactgtt attatttatg    53640
tcaaataaaa tttgtaggaa gccattgatt tggactgtgc tcctgcacta ggccccaata    53700
gaccaaacca catggagtca ctcttgctaa agttccacgt caccaaacca aagctaagta    53760
gtttatctta ccttctggga aattagggga gagaaataat agacaaatcc ccaaacaggc    53820
cagttttagc tggcatataa ggaagtcctc tctgttttaa ccgtattagg agagtaactt    53880
tgaaaagacc gtccactttt tggtccctgt ttctgttttc ttctgccttt tctgcctata    53940
aagctaactt cctctgccca gctcactgga gtaccttctc tgaattttta gaagacaggc    54000
tgccctgatc catgaattgc aaatgaaagc caattagatc atttaactaa attcattgta    54060
attttgtctt ttgacatttg taaacaagcc ttgtagtact tgctaaacaa tgggctgggc    54120
gcagtagctc acacctgtaa tcctagcact tgggaggct gaggtgggtg gatcacctga    54180
ggtcaggagt tcgagaccag cctggtcaac atggtgaaac tccgtctcta ctaaaaattc    54240
aaaagttaga tgggcatggt agcatgtgcc tgtagtccca gctactcagg aagctgaggc    54300
aggagaattg cttgaatctg ggaggcagag gttgcagtga gctgagatag tgccactgta    54360
ctccagcctg ggcagcagag caacactctg tctcaaaaaa aaaaacaaaa acaaaaacaa    54420
aaaaacaact tgctaaacaa catatgttta ttatttggta aattataaac aataaattca    54480
aaactttaaa aagaaaacat tttattgata gctcactgaa tacaaattta taaaatatta    54540
tttatgcatt aagtttcagt tacacatttt cacccatcat tacagatgtc atatggagtt    54600
gctagagtat gagaagagct tcttcatccc aacagctttc aaagtgaaga ggcgactcat    54660
gcctgtaatc ccagcacttt gggaggctga ggcgggtggt tcacttgagg tcaggagttt    54720
gagaccagcc tggccaacat ggtgaaacct cgtctctact aaaaatacaa aaattagctg    54780
ggcgtggtgg cgcacacctg taatcccagc tactcaggag gctgaggcag gagaatcact    54840
tgagcccgtg aggtggaggt tgaagtgagc caagatcatg ccactgcact ccagcctggg    54900
taacaaagca agattctgtc tcaaaaaaaa aaaaaaaaa aaagtgaaca tctgggtccc    54960
ccagatctct tcagagatat gtaatgttct ccttttttcca actacataac tctttaagct    55020
gggttttctt catatactcc aatgaaaaca acatattgca acagatggaa tgaagaggca    55080
agtagaagaa tccagctgtt ttctattaag ccaaacatta caattgtcag ctgaagaatt    55140
ctgagattca taaatttgga aagaaaagct tcatttctca taaagattg cagcctgcag    55200 ggtggccatt ctgacaggct aagaaatgta gtctctggcc agaagccaaa aacagacact    55260
gagggtcaga agaataagat gggcatttat gctgaatagg atggccaaat atacatattc    55320
aataaactac agtcatgaat attcatgaaa ggagaaacat gcacatgctc aattgagctt    55380
catgcctctc catgggacgc gtgtgcaaaa aatggcagca ttagcatgat cagagggtgg    55440
agttttctgt cctctgatat caaaaggtga aacagaggac acagaaaccc tcactgcaca    55500
tcctctgtaa actggccaga accactccat tgtgggcagt ctgttatcag gaaggaatgc    55560
tggttagttg tgcagaaact gcaaaggaa ggggcagtgt cagaccattg gttgatatca    55620
gcggtgcagc tcgtctttcc aaagggctgg tttctgttta acctgtagga aggaaatcct    55680
aatggcgttt agcaatggag agggtataac aacacatcat ggcaagaact cagttttcaa    55740
ggtttctctg gggtccccctt ggccaagagg tggtgcatcc gtttagtcag ctggggggact    55800 taggatttca ttttttatttc tcagagtttt ataaaactct aaaataatta tttgacagcc    55860
aggtgggagg gggtccctgg agaaactcca accagcctgc ctactagggt ggagccttgg    55920
```

```
gagtttgcag cagggaggag cctggcgcct cctcttccta tgtgaacctg ggattctagc   55980
agcctggtgg gaagcactgt agcaggagac tctggccttg cagaggatcc ctgttcccct   56040
catcccttta tttccccttt tcacttaata aaccctgct  ttactcaccc tttaaaccat   56100
ctgcaagcct aaattttgt  ggctgtggga tagacaagaa ccttctcttt agctgaacta   56160
aggaaaagtc ctgcaatgat cccattcttc acaccaaata tgttttgttt caaaagtata   56220
gttatttatc ataaatatgt cattaatatt gttaaatcaa atttagccta aagctgcctc   56280
cttatatagt ttaagcttga cctaaaggtt tctctgtact tagtgaattg tagcctaccc   56340
agatgtgtaa acaagactgt gaactactct tgtgacaaac attggatttt ggccaatcaa   56400
aggaggtcaa ctcttgacac tgctttcaaa taaggcaaat attgagctgt aaacaatctg   56460
gctgttccta tacctcactt ctgttttctg tacgccactt ttctgtctct gtccataaat   56520
gttcttccac cacgtggctg tgctggagtc tctgaaccta ctctggctga ggaggctgcc   56580
caattctcaa actgttcaat taaactcggt taaatttaat ttgtctaagg ttttcttta   56640 accatataaa caagtgagtt tatgattgtt atgtcttttt tcttttcttt tttgagacaa   56700
ggtcccactc tgtcccccag ctggaatac  agtggcatga tcacggctca ctgtagtctc   56760
gcactcccag gctcaagcga tcctccatct cagcctcctg agtagttggg agtacaagtg   56820
catgcaacca tgcctggcta atttttttt  ttttgtatt  ttttgtagag atagggtttt   56880
gctacattgc ccaggttgat ctcgaactcc tgagctcaag tgatcctctt gcctcagcct   56940
tccaaagtgc tgggaccaca ggcatgagtc accacaccca gctattattt ctaaattaat   57000
gaacagatga acattttcaa aatttctcag ttttaatttt aaatatgatt aaaaggatag   57060
atataacaca caaacaaaag ctctatggag tcctctataa ctcaagaata taaagggtcc   57120
tgagattttt cttaaagag  aaccactgca ctctcctggc ctactagctc tccgcaatcc   57180
atcctgcttc tcccccttggc aggagagacc tgttctagac cctcaaggac ccctcataac   57240
atcacctagc tattatctaa ggaatctttc tccatttgga cttcccatt  ttttcttccc   57300 ccttttaaggt cccctattc ttttcatcta attttgtgtg ccacctgcag agtccttctt   57360
cttcttcttc tccttctcct tctccttctt cttctcagag tcttgttctg ttgcccaggc   57420
tggattgcag tggcacgatc tcggctcact tcagcctctg ccttctgggt tccagtgatt   57480
ctcctgcctc aggctcctgg gtagctggga ctacaggtac ccaccatcat gactggctaa   57540 ttttttttgta ttttttagtag agacggggtt tcacaatgtt agccaggatg gtctctatct   57600
cctgacctcg tgatccggcc gcctcggcct tccaaagtgc tgggattaca ggcatgagcc   57660
accgcacccg gcgactaatt tttttttttt tttttttttt tgagacggag tctcactctg   57720
tcgcccaggc cggactgcgg actgcagtgg cacaatctcg gctcactgca agctccgctt   57780
cccgggttca cgccattctc ctgcctcagc ctcccgagta gctgggacta caggcacccg   57840
ccaccgcgcc tggctaattt tttgtatttt tagtagagac ggggtttcac cttgttagcc   57900
aggatggtct cgatctcctg acctcatgat ccacccgcct cggcctccca aagtgctggg   57960
attacaggcg tgagccaccg cgccggccg  gcgactaatt tttatatttt tagtagagac   58020
ggggtttcgc catgttggct gggctggtct tgaactcctg acctcaggtg atccgcccgc   58080
cttggcctcc caaagtgttg ggattacagg catgagccaa cgcacccggc ctgagtcctg   58140
cttcttccag atctggtgcc cagtcctgac gccagaaagg gggtcttgtt ccagacccca   58200
agagtgttct tggatcttgc ctgggaaaga attcagggta agtcgcagag tataatgaag   58260
ttaagatagt taattagagg ctactcaatt acagagtagg gcatcctcag aaaacaagag   58320
```

```
gaggaaggcg ctaccttaaa tgtagtgctt gcttatgtag gttgtataag aattgtgtac    58380
tttattacaa aggcttgtga tcagcttgtg acaggctatt ggtactgtta ttttcctgtt    58440
actattgatt tcagcaagaa tttatgagta cactattata tttaaggcaa aacctattcc    58500
ttaagaatgc ttttgttct taaaatactg ggacatttcc ataagttctg agtctttagt     58560
tagcaacatt aactcattcc ctcaatcata aacatctcat gaccaagagt gcccagttcc    58620
tggggaatgt aacccagcag gtttggcttt attcggcctt tattcaagat ggagtcactc    58680
tggttaggac acctctgaca gtccctggaa atccaaagga acccttctgt gtggcacagg    58740
gaatggaaga aagaaagaga tgaggcagga aaatagggtc tggaggcaga aaacataagc    58800
cgattcacac ttcagctatg acaggaaata tcctctccat agggcgtatg cctgtaactt    58860
tacttcatcc tcttcattta cataggacgt atcctaagta accaatggaa tcgtctagag    58920
ggtatttaaa ctcccaaaaa ttctgtaaca gggcctttga gccctatgc tcgggcccgc     58980 tcccacactg tggagtgtac tttcattttc aataaatccc ttcattcctt ccttgctttc    59040
tttgtgcttt gtgcatttta tctaattctt tgttcaagac gccaggaacc tggacgccct    59100
cccctggtaa tagagagatg agcctttcaa atgacctgac tcctttatcc cagccaggtg    59160
tgtgcccgac cctgaaagga ggaatagga ggggacgtt caacccggcc tcccgctctg      59220
tgttagcagc gtctggatgg gtcagggtgg aggtggggt gttctaccct gctatttgct     59280
cctagagaag cttctctgct tcactagtct cacagttcta aaggcaagaa cagccctagt    59340
gggatcttcc aaggattta gaaagaatg aataagggaa aaattaaaat attgcagggt      59400
gccataaaaa catcccagta aaacaaacac ctttctagat gctcattgga acgtaaatgg    59460
agctcagccc ccatcccttc acaccagatc cagtcttcat ctttgtggtt cactgccccc    59520
tcaccactca ggaggaaaac cccagcttct gttctggctc cccttctctc acttagaatt    59580
tttcaccaga gtttcagaaa gatttgtcag gaccactcca tgcccaaggt aaaaagtgta    59640
agtggtacaa aaaggtagaa actcatcaga ccccccaaaga gtgtcattta accatacaaa   59700
gccctgataa actccagggc agaagaaaaa gctgcatcct tgactccact ggggcattct    59760
tatgtaaact aagatccaag aactgcatca ggagagaaat caagagccct ggggatgtta    59820
ggatgagccc tagaggtgct aagacaggtt atttgaaaaa ccaaaaagta gactgagatt    59880
cccttccttt tcagggaaga attgagacct ttcctttctt actgttcaga gtgggggctg    59940
ataagggtaa ttatttcctg gagccactgg ctactgccct gggaaggaaa tccgctgggt    60000
tgggggaggg aggaaggcag aaccaggcat taactctccc tccactacat ccctttcccg    60060
tacccctccc ctcctctcct tcccccact ccctgccccc gcctccgaa aatgacactt       60120 ggcctgagaa aggaggaagg tagaataggt ggacacttcc cttgtcctgc tccagggtg     60180 tctcagtgac aaggagatgt gaaaaagaa ggaatcccaa ggctcccctt ggaaagaagg      60240
gagatctcca ggggctttgg gaagtcaggt tagtactggg aaggctgaag actcccagta    60300
gatagcgttc agggctgcat ttggctgcaa tcctataaaa tacattcttc tctaaggttg    60360
gatacaagca tttagaagac tggccattaa aaaataaac agtattaata atattaataa      60420
tcatgagtgt cagtagtgtt gaatttttc tggaatcctt tcccaagttg cctaatgccc      60480
agagaaggaa aataacagtg tttagtagac ataaattata ggattagtgc aagtagctat    60540
tgagatgatg agccaaggct tgtaaattgg ttttgttttg gttttcctaa ttagatgttt    60600
gcgcctatct gtgtatgtgt gtgtgtgttt gtgcgtgtgc atgctcgcat gtggttaatt    60660
```

```
tcatgactttt tgcctctggc tcttcctgat taaaaaaaat acttaaaatg gtaggaagtg   60720
gcacacaccc ttgatggacc tgtgtttata ttaaagaatt ggcttagtaa atttaactgg   60780
gacaaggaaa ctgtgaagga ctgtattttt gccattattt aataattcat atattcaacc   60840
gttactgatt gcctattttg aaccaggcca cgtgctagga tacaatggtt aacaaacaca   60900
ttccctcccc tcaaggaatt catggtctag tgaaatacag agatagaaaa gaaatagaaa   60960
agtatatcaa taaaatgcat tgtggaaaga gttatggtca tagtgtgtac tatatgctta   61020
tagaggctgc ctttgtataa acatacataa gactgctttt taaattataa aaggcagtac   61080
ataggccagg cgtggtggct cacacctgta atcccagcac tttgggaggc cgaggcgggt   61140
ggatcatctg aggccacgag ttcgagacca gcctggccaa catggtgaaa ccccatttct   61200
actaaaaata caaaaaaaaa aaaaaaatta gccaggtgtg gtggtgggcg cctcatccca   61260
gctatcagga ggctgaggcg ggagaatcac ttaaacccag acggaggtta cagtgagctg   61320
aggtggagcc attgcactcc agcctaggca acaagagcaa aactccatct caaaaaaaaa   61380
aaaaaaaaaa aaaggcagt acatagtaca aactgcttgg gttttgttgt tgttgtttta   61440
ctgtaccata taggttggag atcattccac ctagtagctg aacattttaa gcagatcatc   61500
tggctacagg cagtgagtag gatgaactgg gagagtgatg agtgagttag agagttaggg   61560
agggagggtg ctgtcggagt gttaccggaa aggggtcccg atccacaccc taagagaggg   61620
ttcttggatc tcgcacaaga aagaattcag ggcgagtcca tacagtaaag tgaaagcaag   61680
tttattaaga aagtagagaa ataaaagaat ggctactcca tagacagagc agccccgagg   61740
gctgctgttg cccatttta tggttattcc ttgatgatat gctaaacaag gggtggatta   61800
ttcatgcctc ccttttaga ccatataggg taacttcctg acgttgccat ggcatttgta   61860
aactgtcatg gcgctggtgg gggcgtagta gtgaggatga ccagaggtca ctctcgtggc   61920
catcttagtg ttggtaggtt ttggccggct ccaacaccgg cttgttgttt tatcagcaag   61980
gtctttatga cccatattct atgcccacct cctgtctcat cctgtgactt agaatgcctt   62040
aactgtctgg gaatgcagcc cagtaggttt cagccttatt ttacccagct cctatttaag   62100
ataaagttgc tctggttcac acgcctctga caagaacatc ttcatgcctg tgcctggttg   62160
agagagggag gcctctgcgc tgctgctgga tctagtgaag attcactcag tctctcaaat   62220
tcctctacag tttctctaat ggaagagaaa agtggtgtta ttgctgctag ggagcaacct   62280
agaagttatt ttatttatgc catagatatg gtgggctaag cactgtgcca acgttcaata   62340
agtcactgca gattctccat aaattattgt gacaagtaca attgtttgta aggcttagat   62400
ctaggtgtgt aagtccaaag aagggtgtga agcatctgta tttctgttat gtagttatta   62460
ggaaaaagga tgttggggcc ttaaaatggc cattttttaac atttccaaac ttgtgttgaa   62520
ttctaagatt ttataattgt atgtttccag ttgagaagag ctttgatatt ggtagctcta   62580
aataaataaa taccgttgac ctggaagaga aggtaaagtt tagggagagg ccttttttta   62640
gctttatatt taaacatttt ttataaatgt gattcatggg ccaggcctgg tggctcacac   62700
ctgtaatccc agcacttttg gaggccaatg caggtggatc acttgaggct aggagttcga   62760
gagcagcctg gccaacatgg taaaaccca tctctactaa aaattagcca ggtgtggtag   62820
cacacacctg taatcccagc tactcaggag gctgaggcag gggaatcact tgaacccagg   62880
aggcgaaggt tgcagtgagc cgagattgtg ccactgcact ccagcctggg tgacagagtc   62940
agactccgtc tcaaaagcaa aacaaaacaa aatgttattc ataatgctcg ggttgtaact   63000
atagtactta tctagcaaaa gcttgctttt ttttttttgg cttgactaa ttgaaactgc   63060
```

```
aagagcttac tggcagagtg gtgtactggt caatatttaa ccaattctcc aaagggaaa    63120 aaccctgatt tgtatgtagg atttgtcagt ttccatggta taaatagtct tcccacagct    63180
ggtagggtga ccaacttgtt ctggtttgcc aggggctttc ccattttag gcctgaaagt    63240 cctgaatccc agaaaattcc tcattcccca ggaaatagct tgattggtca ccctaatggc    63300
tggttgcaag ctcccgatat gacagaactg gacgagaagt tgggcagaga tgtgcacatg    63360
gtaccagcct atgccaggag cagcggcctc cagcacccca ctgtcaggga gtccttggcc    63420
cagtagagga tggttagcag ggcccggctg ttgttcatat tagctctcaa atttaccacc    63480
aaccctgtat tagtttcctg gagctgctgt aacaaagttc cacaaacggg ggtcttaaac    63540
acagaaatct attatctcac agttctggag ggcagaaata gaaaattaag gtatgagcag    63600
gactctgctc ttttgatggc tctagataat ccgttgtatg tcttttcctc agcttctggt    63660
ttcacaggta atctttggcg atccttgact tgcatctgtg taactccagt ctctacctcc    63720
atcatcctgt ggcattcttc tttatttttc tttctttttt tcttttcgag acagagtttc    63780
gctctgttac ccaggctgga gtgcagtggc gtgatctcgg ctcactgcaa cctctgcctc    63840
ccaggttcaa gcgattctct tgcctctggc tcccgagtag ctgagattac aggtgtgcgc    63900
caccacaccc agctaatttt tgcattttta gtagaggcgg ggtttcacca tgctggccag    63960
gctggtctcg ggctcccgac ctcaggtcat ctccctgcct tggccttcta agtgctggg    64020 attacaagcg tgagccactg cactcggccc atggcattct tcttttggtg cctttgtctt    64080
cactgacttc ttgtaaggaa atcagtcgta ttggattaga ggcctacctt attccagtat    64140
gatctcattg tcttaattta actaaaacat ctgcaacaac cttatttcta aatgaggtca    64200
cattctgagg tattagggtt tagtacttca acatatcttt tttttttttt tgagacaggg    64260
tctcattctg tcactcaggc tggagtgcag tggtgcaatc acacagctca ctgtaacttt    64320
gaactcctgg gctcgagcag tcctcctatc tcagcctccc agataggtaa gattacaggt    64380
acatatcacc atgcctagct aattttttcaa attttttata ggggctgggc ccagtggctc    64440
acaccttgta atccctgtaa tcccaacact ttggtaggct gaggcgggcg gatcacttga    64500
ggtcaagagt ttgagaccag cctggccaac atggtaaaat cccatctcta ctaaaaaaaa    64560
tacaaaaatt agccggatgt ggtggtgggt acctatcata ccagctactc acaaggctga    64620
ggccggaaaa tccctggaac ccgaggggcg gagatcgcag tgaaccgaga tcacgccatg    64680
cactccagcc tgggtgacag agcaagacat aaccttaaaa aagaaaaaaa aaaatgtaga    64740
gatgaagtct tgctgtgttg cccaggctag tctcaaatgc ctgggctcaa gcaatccttc    64800
tgcctcagta tcccaaagtg ctaggattac aggcatgagg cactgcacca ggcctacatc    64860
ctcttttttt tttttttttt tttttttttt tgagatagag tcttgctctg tctcccaggc    64920
tggagtgcag tggcacgacc tcggctcact gcaacttcca cctcctgggt tcaagtgatt    64980
cttctgcctc agcctccaga gtagctaaga ctacaggcat aatatctctc ttagatatga    65040
caaataatat cacagagtgt acacccactg tgatgttagg agtaatacct ccctatgata    65100
ttacaagtaa tactgccttt agatactaca aataatatca cagggtgtac atctactgtg    65160
atattaggag taataccctcc cttagatatt acaaataata tcacagggta tacccacg    65220 gtgatattag gagtaatatc tctcttaagc gatcctccca tctcagcctc acagaattaa    65280
aggaattaca ggaagagctg ctatacctgg ctggatctat gttttaaaaa tataacccag    65340
ataaccctgt ggtcagtgtc taagatgaat tggattagac caagggagaa aaactaaaga    65400
```

| | | | | | |
|---|---|---|---|---|---|
| tgggaatact | agtttgggac | tttgcttgct | tgcttgctct | catttagaaa | acatttagta | 65460 |
| gttctacaat | gctcaggcac | tgttctggga | gtcacaaata | taggattgaa | taaagtaaat | 65520 |
| aaagcacttg | ctctcctgga | gctcactttt | cactggggga | atgcagatag | tagacacata | 65580 |
| catctatagt | atcagtaagt | gctaatagaa | aaatgaagca | ggtgagatgg | atcatgctga | 65640 |
| gtagaatgta | tcttctttc | cttccttcct | tccttccctc | cctccttcct | tctttccttc | 65700 |
| cttctttctt | tccttccttt | cttcttttct | ctttcttcct | ttctctctct | ttctttgctt | 65760 |
| tttattgtct | taaaatgtac | ataacataaa | atttaccctc | ttaaccattt | ttaagaatac | 65820 |
| aattcaaggc | cgggcatggt | ggctcacacc | tataatccca | gcatttggg | aggctgaggc | 65880 |
| aggcggatca | tgaggtcagg | agtttgaggc | cagtctggcc | aatatgatga | aaccccatct | 65940 |
| ctactaaaaa | atacaaaaat | tagccaggct | tggtggcaca | tgcctgtagt | cccagctacc | 66000 |
| cgggaggctg | aggcaggaga | atagctggaa | cctgggaggc | agaggttgca | gtgagctgag | 66060 |
| atcgcaccac | tgcactcctg | cctggacaag | agagcaagac | tctgtctcaa | aaataaataa | 66120 |
| ataaataaat | aataataata | ataataatac | aattcagtag | ccttaagtac | atttgcattg | 66180 |
| ttatgcagcc | atcaccacca | tccatctcca | gaattttttt | gagtggagct | ctttttaata | 66240 |
| gagtagttga | aggcctctgt | gacacagtag | catctgagca | gaagcttgaa | tgaagtgaga | 66300 |
| aaagaatcct | tttgcatagt | ttaggggaag | tatgttccat | tcctggtcct | ggaaatagtt | 66360 |
| aagactatca | caatagtgca | ggagaaagat | gatacaatac | agtttgtgta | gctgaaaccc | 66420 |
| cgtcttcaga | atgtaaagga | gaacagatgg | gaagtcatgt | tcctcccaga | agtaattcat | 66480 |
| gtagcagaga | agccaatgca | gatccacgag | acagacaatt | cagtgctctg | cacaagaact | 66540 |
| gtgctttaag | catggagagg | atttttgtat | ctgtcctggg | atcctacatc | aaacagcatg | 66600 |
| tggtgattgt | gaacacaaac | gtacaagact | gtgaaccta | ccaagtttcc | ttcttccatt | 66660 |
| agatatgaat | aaggagtcat | gagtttcctt | tggaatgtcc | tttagcctgt | tggtacatgt | 66720 |
| tttgcctgtg | acgaatgcag | ttactcataa | atcattgagc | acattgggta | cagagggcaa | 66780 |
| aagataaatt | cctgtatttc | ctctattcgg | tcaacagaaa | tacctctagg | ccataatcca | 66840 |
| ttcatccaat | ctaataattt | tgccatccat | aaaaccttca | ggtgttctga | attcaacatc | 66900 |
| tttttttttt | tttttttttt | tttttgagac | agagtcttgc | tctgtcaccc | aggctggagt | 66960 |
| gcaatggcag | gatctcggct | tactgcaacc | tccgcctccc | agattcaagc | gattctcctg | 67020 |
| cctcagcctc | ccgagtagct | gggattacag | gtgcccgcca | ccacgcccag | ctaattttt | 67080 |
| gtattttcag | tagagacggg | gtgtcaccat | gttggccagg | ctggtctcga | actcttgacc | 67140 |
| tcaggcaatc | cacccgcctc | agcctcccaa | agtgctggga | ttacaggcgt | gagccaccat | 67200 |
| gcctggctga | attcgacatc | ttgcacctaa | ttcctgttca | gttaaagacc | caaatcatga | 67260 |
| tctctgactt | acctggatat | tgaaagatt | aacttgctgt | ggtgatacca | tactagagtc | 67320 |
| acaaaatcaa | gccctacct | gccacagcca | cctaaaggaa | attaggtgat | atacaaaaga | 67380 |
| aattgaccat | attgttgtcc | ttttagtgac | tctcctaatt | ttcttcccct | gaaaacttac | 67440 |
| agagaaattt | gagtatgttt | gccttaggtg | gatgcttgtt | tttttattga | tatgaaaagc | 67500 |
| agtaagagga | aatggagttt | tttggcctgt | taaggaaggg | cagccactgt | aaacacagtt | 67560 |
| gagtgcaaat | tcacagtgtt | agaatgttga | agtgtatata | atgattttgc | aaaatttct | 67620 |
| acaaggctga | tacagtatcc | aatcaggact | aggattagat | atattgtcat | gtatgtttgc | 67680 |
| gcaggaaatg | cagagactct | aaggtgctac | aactgcaatt | tgacatgtgg | atagttcac | 67740 |
| tggtaactgt | tgatctccct | gaggtttaag | tttacagttc | cacagctctt | tatctgaaac | 67800 |

```
tcttgggcta tgtgttatgg aatttagaat ttttccgaa atacgttgca tatattgtat    67860
attatgacat gatacctcca agaaagactt ggagtcacat cctataaaca aacacatgaa    67920
tatatcccag tgaaatgtat gactatttt actaaaacaa atgagaatca taaatagact    67980
tacattactt caggtcagat tttgctgccg aattagtttg ggcatcgaac ttttggtttc    68040
agagacaaaa ctgtgaaatt ttagattata ttatggggtt gtggacccat gtaaccctcc    68100
tctccgtaat tcctaaaagc aagcaattgc atcaaccagt ctcatgagta gctgcgattc    68160
tagaaatcaa gaatccggat ctgaaattag ccgggcatgg tggcaggcac ttgtaatccc    68220
agctactggg gaggctgagg caggagaatc gcttgaaccc aggaggaaac tgcagtgagc    68280
tgagatcgtg ctgctgcact ccagcctggg caacagagtg agactctgtc tcaaaaaaaa    68340 aaaaaaaaa aaaaaagaa tccagatctg gcaggaccg aattgctgac atgccccgg    68400 tatagcagag acgttttgcc tacatgttac acacctgagt aatagttgtc agcagctgat    68460
gaagaagatg aatgtgctct taatgtccat ctttgatttc cagtcatttt gcttctgggt    68520
cttggcttcc tgaggaaaga agtctccagt aggtgaatgc agtgatatgg agaatacttt    68580
cttctggctg catgcagtaa ctcacacctg taatcccagc acattgggag gctgaggtgg    68640
gcagtgcact tgaggttggg agttcgagac cagcctggcc aacatggcaa aaccccgtct    68700
ctactgaaaa tacaaaaatt agctgggcgt ggtgacagac acctgtcatc ccagctactc    68760
ggtaggctga ggcatgagaa tcacttgaac ttgggaggta gaggttgcag tgagccgaga    68820
tcgtgcctct gcactccagc tgggcaacac agcgagactc tgtctcaaaa aaaaaaagt    68880 gtgtgagaga gagtactttc ttcctgtttc ctcataggcc agttctctct ggcatgtgag    68940
tttaacatca gtcacctcct tcacacacag cgggtgcatt cgtaataggg ggtccttagc    69000
tgggagtttt tatggcacat cagtggggcg tgaaaacacc acataggagc taatatatct    69060
ttgctggctg ctttctccgg ctccgcagca gacagaaacc ctatgaatca tatccagggg    69120
tcaggtgcag gcaacagaca actaatatct cccaagtgag ttgaaaagga tcttgttacc    69180
cagcatccta aggaggttgt agccttggga accacaggca agaataatta actcagctcc    69240
tcggttagtg cctcttcagt tcgagatgga atttatttgc aggcatggct ccttaatatg    69300
ccaaacccat gctcaagaca tactccttct cctggaaggt taacgtggct cctgtggctg    69360
ttccatccct gaggaaaagt gaggaccatg ctctccaaac aggccatgtg ctggactacc    69420
tctgtttctg tctcctggga ttccaatcag caagtgagca acgaagcaac ccagacagtg    69480
tggttcatag gatggctggg taagtggctg tttgttttt ccttactgtg gatatgtatc    69540
agtgaaggaa tctgtagaac attcttgatg ggaacattta gtcatatcaa gtcaataaat    69600
taatgtttag gctgggcgca gtggctcacg cctgtaatcc caacaccttg ggaggccaag    69660
gcgggcagat catctgaggt caggagttca agaccagcct ggccaacatg gtaaaatccc    69720
gtctctacta aaaatacaaa aattagctgg gtgtggtggt gcatacttgt agtcccagct    69780
actctggagg ctgaggcaag agaattgcct gaacctggga gatggaggtt gcagtgagct    69840
aagagtgcac cattgcactc tagcctgggc aacagagtga gactctgtca aaaaaaatt    69900 aaaaaaaag aaaaatcatt attttatttt tgacttatta ttaatataaa taattatatc    69960
ttggccgggc atagtgtctc atgcctataa tcccagcact ttgggaggcc agggcaggca    70020
gatcacttga gccaagaagt ttaagaccag cctgggcaac acggtgaaac cctgtctcta    70080
caaaaaatat aaaaaattag ctgggagtgg tcagcttgcc tgcagcccta gctacctggg    70140
```

```
aggctgaggt gggaggatca cctcggccca ggaggtagag gctgcagtga gccatgattg    70200
taccactgca ctccagcctg ggtgatagag tgatgagacc ctgtctcaaa aaaaaaaaaa    70260 aaaaaaaaa gaagaaaga aagaaaaaag aaaggaaaag aaatcatata ttggtgagga      70320
gacaattcaa cacatatttt ttattgaaca catactatgt gtcagggtac cagatataag    70380
ctctatctac aaggatttta ggagctggag tatgtgtatg gggggatgta tgagtgtgta    70440
taacaaagac gactcctggg gaagaagagg aagacaagcc ccagaggtat actgcatagg    70500
cataatacac aacaggctag caaagaagca aaccatgggt atggtagaga gaatcagagg    70560
atacattggg gaccatgtct agtgagtgag gtcaggagag acttcaataa tctgagtgaa    70620
tttagacatg ggccttgaaa agtggacaag gtttgttgtt gttgttgttg ttgttgttgt    70680
tgttgttgtt gttgttgttt ttgagatgga gtctcattct gtcgcccagg ctggagtgca    70740
gtggtgcgat ctcggctcac tgcaagctcc gcctcccagg ttcataacat tctcctgcct    70800
cagcttcccg agtagctggg actacaggcg cccgccacca cgcccagcta ctttttttata  70860 tttttagtag agacggggtt tcaccgtgtt agtctgatg gtctcgatct cctgaccttg     70920
tgatccaccc accttggcct cccaaagtgc tgggattaca ggcgtgaacc actgcggccg    70980
gcctaaattt gttttaaaag tacgcatagg aaggctgggg gctgtggctt atgcctgtaa    71040
tcacagcact ttgggaggcc aagacaggca gatcacgagg tcaggagatc gagaccatcc    71100
tggctaacac agtgaaaccc cgtctctcca aaaaacaaa aaattatcca ggcctagtgg     71160
cacacgcctg tagtcccagc tacttgggag gctgaggcag gagaatcgct tgaatctggg    71220
aggtggaggg tgcagtgagc cactgcactc cagcctgggt gacagagcaa actaggtctc    71280 aaaaaaaaa aaaaaaaaaa gtacatgtgg gggacaggtg cagtgtctca gcctgtaatc    71340
aatcccagca ctttgggagg ctgaggtggg tggatcactt gaggtcagga gttcaagacc    71400
agcctggcca acatggagaa accccatctc tactaaaaat acaaaaattc gctgggcgtg    71460
gtggcgcacg tctgtagtcc cagctactgg gaagactaaa gtgagagaac tgcttgagcc    71520
cagaggtcga ggctgtggtg agcggtgatt tcaccacttc agtctagcct gggtgacaga    71580
gagagaccct gtctcatata aacaaataaa taaaag                              71616
```

<210> SEQ ID NO 88
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 88
agctgggaag ttcttcctg                                                 19

<210> SEQ ID NO 89
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 89
tcccttgggt cagggtcc                                                  19

<210> SEQ ID NO 90
<211> LENGTH: 19
<212> TYPE: DNA
<213> ORGANISM: Artificial sequence

```
<220> FEATURE:
<223> OTHER INFORMATION: Synthetic polynucleotide

<400> SEQUENCE: 90
acacaaggca tccgtctcc                                                    19

<210> SEQ ID NO 91
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 91
tatttattgt gcacttaac                                                    19

<210> SEQ ID NO 92
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 92
gctacttgga aggctgaaa                                                    19

<210> SEQ ID NO 93
<211> LENGTH: 4154
<212> TYPE: DNA
<213> ORGANISM: Artificial sequence
<220> FEATURE:
<223> OTHER INFORMATION: Synthetic polynucleotide

<400> SEQUENCE: 93
ccgaagaaaa agcgcaaggt cgaagcgtcc gacaagaagt acagcatcgg cctggccatc        60
ggcaccaact ctgtgggctg ggccgtgatc accgacgagt acaaggtgcc cagcaagaaa       120
ttcaaggtgc tgggcaacac cgaccggcac agcatcaaga agaacctgat cggagccctg       180
ctgttcgaca cggcgaaac agccgaggcc acccggctga agagaaccgc agaagaaga        240 tacaccagac ggaagaaccg gatctgctat ctgcaagaga tcttcagcaa cgagatggcc       300
aaggtggacg acagcttctt ccacagactg gaagagtcct tcctggtgga agaggataag       360
aagcacgagc ggcaccccat cttcggcaac atcgtggacg aggtggccta ccacgagaag       420
taccccacca tctaccacct gagaaagaaa ctggtggaca gcaccgacaa ggccgacctg       480
cggctgatct atctggccct ggcccacatg atcaagttcc ggggccactt cctgatcgag       540
ggcgacctga accccgacaa cagcgacgtg gacaagctgt tcatccagct ggtgcagacc       600
tacaaccagc tgttcgagga aaaccccatc aacgccagcg gcgtggacgc caaggccatc       660
ctgtctgcca gactgagcaa gagcagacgg ctggaaaatc tgatcgccca gctgcccggc       720
gagaagaaga tggcctgtt cggcaacctg attgccctga gcctgggcct gacccccaac       780
ttcaagagca acttcgacct ggccgaggat gccaaactgc agctgagcaa ggacacctac       840
gacgacgacc tggacaacct gctggcccag atcggcgacc agtacgccga cctgtttctg       900
gccgccaaga cctgtccga cgccatcctg ctgagcgaca tcctgagagt gaacaccgag       960
atcaccaagg ccccccgag cgcctctatg atcaagagat acgacgagca ccaccaggac       1020
ctgaccctgc tgaaagctct cgtgcggcag cagctgcctg agaagtacaa agagattttc       1080
ttcgaccaga gcaagaacgg ctacgccggc tacattgacg gcggagccag ccaggaagag       1140
```

```
ttctacaagt tcatcaagcc catcctggaa aagatggacg gcaccgagga actgctcgtg    1200
aagctgaaca gagaggacct gctgcggaag cagcggacct tcgacaacgg cagcatcccc    1260
caccagatcc acctgggaga gctgcacgcc attctgcggc ggcaggaaga ttttacccca    1320
ttcctgaagg acaaccggga aaagatcgag aagatcctga ccttccgcat cccctactac    1380
gtgggccctc tggccagggg aaacagcaga ttcgcctgga tgaccagaaa gagcgaggaa    1440
accatcaccc cctggaactt cgaggaagtg gtggacaagg gcgcttccgc ccagagcttc    1500
atcgagcgga tgaccaactt cgataagaac ctgcccaacg agaaggtgct gcccaagcac    1560
agcctgctgt acgagtactt caccgtgtat aacgagctga ccaaagtgaa atacgtgacc    1620
gagggaatga gaaagcccgc cttcctgagc ggcgagcaga aaaaggccat cgtggacctg    1680
ctgttcaaga ccaaccggaa agtgaccgtg aagcagctga agaggacta cttcaagaaa    1740
atcgagtgct tcgactccgt ggaaatctcc ggcgtggaag atcggttcaa cgcctccctg    1800
ggcacatacc acgatctgct gaaaattatc aaggacaagg acttcctgga caatgaggaa    1860
aacgaggaca ttctggaaga tatcgtgctg accctgacac tgtttgagga cagagagatg    1920
atcgaggaac ggctgaaaac ctatgcccac ctgttcgacg acaaagtgat gaagcagctg    1980
aagcggcgga gatacaccgg ctggggcagg ctgagccgga agctgatcaa cggcatccgg    2040
gacaagcagt ccggcaagac aatcctggat ttcctgaagt ccgacggctt cgccaacaga    2100
aacttcatgc agctgatcca cgacgacagc ctgaccttta agaggacat ccagaaagcc    2160
caggtgtccg gccagggcga tagcctgcac gagcacattg ccaatctggc cggcagcccc    2220
gccattaaga agggcatcct gcagacagtg aaggtggtgg acgagctcgt gaaagtgatg    2280
ggccggcaca agcccgagaa catcgtgatc gaaatggcca gagagaacca gaccacccag    2340
aagggacaga agaacagccg cgagagaatg aagcggatcg aagagggcat caaagagctg    2400
ggcagccaga tcctgaaaga acaccccgtg gaaaacaccc agctgcagaa cgagaagctg    2460
tacctgtact acctgcagaa tgggcgggat atgtacgtgg accaggaact ggacatcaac    2520
cggctgtccg actacgatgt ggacgccatc gtgcctcaga gctttctgaa ggacgactcc    2580
atcgacaaca aggtgctgac cagaagcgac aagaaccggg gcaagagcga caacgtgccc    2640
tccgaagagg tcgtgaagaa gatgaagaac tactggcggc agctgctgaa cgccaagctg    2700
attacccaga gaaagttcga caatctgacc aaggccgaga aggcggcct gagcgaactg    2760
gataaggccg gcttcatcaa gagacagctg gtggaaaccc ggcagatcac aaagcacgtg    2820
gcacagatcc tggactcccg gatgaacact aagtacgacg agaatgacaa gctgatccgg    2880
gaagtgaaag tgatcacccct gaagtccaag ctggtgtccg atttccggaa ggatttccag    2940
tttttacaaag tgcgcgagat caacaactac caccacgccc acgacgccta cctgaacgcc    3000
gtcgtgggaa ccgccctgat caaaaagtac cctaagctgg aaagcgagtt cgtgtacggc    3060
gactacaagg tgtacgacgt gcggaagatg atcgccaaga gcgagcagga aatcggcaag    3120
gctaccgcca agtacttctt ctacagcaac atcatgaact ttttcaagac cgagattacc    3180
ctggccaacg gcgagatccg gaagcggcct ctgatcgaga caaacggcga aaccggggag    3240
atcgtgtggg ataagggccg ggattttgcc accgtgcgga agtgctgag catgccccaa    3300
gtgaatatcg tgaaaaagac cgaggtgcag acaggcggct tcagcaaaga gtctatcctg    3360
cccaagagga acagcgataa gctgatcgcc agaaagaagg actgggaccc taagaagtac    3420
ggcggcttcg acagccccac cgtggcctat tctgtgctgg tggtggccaa agtggaaaag    3480
ggcaagtcca gaaaactgaa gagtgtgaaa gagctgctgg ggatcaccat catggaaaga    3540
```

```
agcagcttcg agaagaatcc catcgacttt ctggaagcca agggctacaa agaagtgaaa    3600
aaggacctga tcatcaagct gcctaagtac tccctgttcg agctggaaaa cggccggaag    3660
agaatgctgg cctctgccgg cgaactgcag aagggaaacg aactggccct gccctccaaa    3720
tatgtgaact tcctgtacct ggccagccac tatgagaagc tgaagggctc ccccgaggat    3780
aatgagcaga aacagctgtt tgtggaacag cacaagcact acctggacga gatcatcgag    3840
cagatcagcg agttctccaa gagagtgatc ctggccgacg ctaatctgga caaagtgctg    3900
tccgcctaca acaagcaccg ggataagccc atcagagagc aggccgagaa tatcatccac    3960
ctgtttaccc tgaccaatct gggagcccct gccgccttca gtactttga  caccaccatc    4020 gaccggaaga ggtacaccag caccaaagag gtgctggacg ccaccctgat ccaccagagc    4080
atcaccggcc tgtacgagac acggatcgac ctgtctcagc tgggaggcga cagccccaag    4140
aagaagagaa aggt                                                     4154
```

<210> SEQ ID NO 94
<211> LENGTH: 33
<212> TYPE: DNA
<213> ORGANISM: Artificial sequence
<220> FEATURE:
<223> OTHER INFORMATION: Synthetic polynucleotide

<400> SEQUENCE: 94

```
gacgcgctgg acgatttcga tctcgacatg ctg                                 33
```

<210> SEQ ID NO 95
<211> LENGTH: 384
<212> TYPE: DNA
<213> ORGANISM: Artificial sequence
<220> FEATURE:
<223> OTHER INFORMATION: Synthetic polynucleotide

<400> SEQUENCE: 95

```
gacgcgctgg acgatttcga tctcgacatg ctgggttctg atgccctcga tgactttgac    60
ctggatatgt tgggaagcga cgcattggat gactttgatc tggacatgct cggctccgat   120
gctctggacg atttcgatct cgatatgtta gggtcagacg cactgaatga tttcgacctt   180
gatatgttgg gaagcgatgc ccttgatgat ttcgacctgg acatgctcgg cagcgacgcc   240
ctggacgatt tcgatctgga catgctgggg tccgatgcct ggatgatttt tgacttggat   300
atgctgggga gtgatgccct ggacgacttt gacctggaca tgctgggctc cgatgcgctc   360
gatgacttcg atttggatat gttg                                         384
```

<210> SEQ ID NO 96
<211> LENGTH: 72
<212> TYPE: DNA
<213> ORGANISM: Artificial sequence
<220> FEATURE:
<223> OTHER INFORMATION: Synthetic polynucleotide

<400> SEQUENCE: 96

```
gaagaacttt tgagcaagaa ttatcatctt gagaacgaag tggctcgtct taagaaaggt    60
tctggcagtg ga                                                       72
```

<210> SEQ ID NO 97
<211> LENGTH: 60
<212> TYPE: DNA
<213> ORGANISM: Artificial sequence
<220> FEATURE:

<223> OTHER INFORMATION: Synthetic polynucleotide

<400> SEQUENCE: 97

```
tggaggcgga ggttctgggg gaggaggtag tggcggtggt ggttcaggag gcggcggaag      60
```

<210> SEQ ID NO 98
<211> LENGTH: 390
<212> TYPE: DNA
<213> ORGANISM: Artificial sequence
<220> FEATURE:
<223> OTHER INFORMATION: Synthetic polynucleotide

<400> SEQUENCE: 98

```
atggcttcaa actttactca gttcgtgctc gtggacaatg gtgggacagg ggatgtgaca      60
gtggctcctt ctaatttcgc taatggggtg cagagtgga tcagctccaa ctcacggagc      120
caggcctaca aggtgacatg cagcgtcagg cagtctagtg cccagaagag aaagtatacc      180
atcaaggtgg aggtccccaa agtggctacc cagacagtgg gcggagtcga actgcctgtc      240
gccgcttgga ggtcctacct gaacatggag ctcactatcc caattttcgc taccaattct      300
gactgtgaac tcatcgtgaa ggcaatgcag gggctcctca agacggtaa tcctatccct      360
tccgccatcg ccgctaactc aggtatctac                                      390
```

<210> SEQ ID NO 99
<211> LENGTH: 552
<212> TYPE: DNA
<213> ORGANISM: Artificial sequence
<220> FEATURE:
<223> OTHER INFORMATION: Synthetic polynucleotide

<400> SEQUENCE: 99

```
ccttcagggc agatcagcaa ccaggccctg gctctggccc ctagctccgc tccagtgctg      60
gcccagacta tggtgccctc tagtgctatg gtgcctctgg cccagccacc tgctccagcc      120
cctgtgctga ccccaggacc accccagtca ctgagcgctc cagtgcccaa gtctacacag      180
gccggcgagg ggactctgag tgaagctctg ctgcacctgc agttcgacgc tgatgaggac      240
ctgggagctc tgctggggaa cagcaccgat cccggagtgt tcacagatct ggcctccgtg      300
gacaactctg agttttcagca gctgctgaat cagggcgtgt ccatgtctca gtacagcc      360
gaaccaatgc tgatggagta ccccgaagcc attacccggc tggtgaccgg cagccagcgg      420
ccccccgacc ccgctccaac tcccctggga accagcggcc tgcctaatgg gctgtccgga      480
gatgaagact tctcaagcat cgctgatatg gactttagtg ccctgctgtc acagatttcc      540
tctagtgggc ag                                                         552
```

<210> SEQ ID NO 100
<211> LENGTH: 372
<212> TYPE: DNA
<213> ORGANISM: Artificial sequence
<220> FEATURE:
<223> OTHER INFORMATION: Synthetic polynucleotide

<400> SEQUENCE: 100

```
ggcttcagcg tggacaccag tgccctgctg gacctgttca gcccctcggt gaccgtgccc      60
gacatgagcc tgcctgacct tgacagcagc ctggccagta tccaagagct cctgtctccc      120
caggagcccc ccaggcctcc cgaggcagag aacagcagcc cggattcagg aagcagctg      180
gtgcactaca cagcgcagcc gctgttcctg ctggaccccg ctccgtgga caccgggagc      240
aacgacctgc cggtgctgtt tgagctggga gagggctcct acttctccga aggggacggc      300
```

```
ttcgccgagg acccccaccat ctccctgctg acaggctcgg agcctcccaa agccaaggac    360
cccactgtct cc                                                         372
```

<210> SEQ ID NO 101
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 101

```
acgcctgctt caccaccttc tt                                              22
```

<210> SEQ ID NO 102
<211> LENGTH: 15
<212> TYPE: PRT
<213> ORGANISM: Artificial Sequence
<220> FEATURE:
<223> OTHER INFORMATION: Interaction domain

<400> SEQUENCE: 102

```
Leu Ser Pro Glu Glu Thr Phe Ser Asp Leu Trp Lys Leu Pro Glu
1               5                   10                  15
```

<210> SEQ ID NO 103
<211> LENGTH: 24
<212> TYPE: PRT
<213> ORGANISM: Artificial Sequence
<220> FEATURE:
<223> OTHER INFORMATION: Interaction domain

<400> SEQUENCE: 103

```
Gln Ala Met Asp Asp Leu Met Leu Ser Pro Asp Asp Ile Glu Gln Trp
1               5                   10                  15

Phe Thr Glu Asp Pro Gly Pro Asp
            20
```

<210> SEQ ID NO 104
<211> LENGTH: 19
<212> TYPE: PRT
<213> ORGANISM: Artificial Sequence
<220> FEATURE:
<223> OTHER INFORMATION: Interaction domain

<400> SEQUENCE: 104

```
Asp Cys Gly Asn Ile Leu Pro Ser Asp Ile Met Asp Phe Val Leu Lys
1               5                   10                  15

Asn Thr Pro
```

<210> SEQ ID NO 105
<211> LENGTH: 23
<212> TYPE: PRT
<213> ORGANISM: Artificial Sequence
<220> FEATURE:
<223> OTHER INFORMATION: Interaction domain

<400> SEQUENCE: 105

```
Pro Val Gly Thr Asp Lys Glu Leu Ser Asp Leu Leu Asp Phe Ser Met
1               5                   10                  15

Met Phe Pro Leu Pro Val Thr
            20
```

<210> SEQ ID NO 106

```
<211> LENGTH: 23
<212> TYPE: PRT
<213> ORGANISM: Artificial Sequence
<220> FEATURE:
<223> OTHER INFORMATION: Interaction domain

<400> SEQUENCE: 106

Arg Arg Glu Ile Leu Ser Arg Arg Pro Ser Tyr Arg Lys Ile Leu Asn
1               5                   10                  15

Asp Leu Ser Ser Asp Ala Pro
            20

<210> SEQ ID NO 107
<211> LENGTH: 9
<212> TYPE: PRT
<213> ORGANISM: Artificial Sequence
<220> FEATURE:
<223> OTHER INFORMATION: Interaction domain

<400> SEQUENCE: 107

Asp Leu Phe Asp Tyr Asp Phe Leu Val
1               5

<210> SEQ ID NO 108
<211> LENGTH: 12
<212> TYPE: PRT
<213> ORGANISM: Artificial Sequence
<220> FEATURE:
<223> OTHER INFORMATION: Interaction domain

<400> SEQUENCE: 108

Glu Asp Leu Tyr Ser Ile Leu Trp Ser Asp Trp Tyr
1               5                   10

<210> SEQ ID NO 109
<211> LENGTH: 5
<212> TYPE: PRT
<213> ORGANISM: Artificial sequence
<220> FEATURE:
<223> OTHER INFORMATION: Synthetic peptide

<400> SEQUENCE: 109

Lys Lys Lys Arg Lys
1               5

<210> SEQ ID NO 110
<211> LENGTH: 100
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(20)
<223> OTHER INFORMATION: n is a or g or c or u

<400> SEQUENCE: 110
gnnnnnnnnn nnnnnnnnnn guuuuagagc uagaaauagc aaguuaaaau aaggcuaguc    60
cguuaucaac uugaaaaagu ggcaccgagu cggugcuuuu                        100

<210> SEQ ID NO 111
<211> LENGTH: 55
<212> TYPE: DNA
<213> ORGANISM: Artificial Sequence
<220> FEATURE:
<223> OTHER INFORMATION: Synthetic oligonucleotide
<220> FEATURE:
```

```
<221> NAME/KEY: misc_feature
<222> LOCATION: (1)..(19)
<223> OTHER INFORMATION: n is a or g or c or t/u
<220> FEATURE:
<221> NAME/KEY: misc_feature
<222> LOCATION: (22)..(41)
<223> OTHER INFORMATION: n is a or g or c or t/u
<220> FEATURE:
<221> NAME/KEY: misc_feature
<222> LOCATION: (43)..(55)
<223> OTHER INFORMATION: n is a or g or c or t/u

<400> SEQUENCE: 111
nnnnnnnnnn nnnnnnnnnc cnnnnnnnnn nnnnnnnnnn ncnnnnnnnn nnnnn      55

<210> SEQ ID NO 112
<211> LENGTH: 55
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(13)
<223> OTHER INFORMATION: n is a or g or c or t/u
<220> FEATURE:
<221> NAME/KEY: misc_feature
<222> LOCATION: (15)..(34)
<223> OTHER INFORMATION: n is a or g or c or t/u
<220> FEATURE:
<221> NAME/KEY: misc_feature
<222> LOCATION: (37)..(55)
<223> OTHER INFORMATION: n is a or g or c or t/u

<400> SEQUENCE: 112
nnnnnnnnnn nnngnnnnnn nnnnnnnnnn nnnnggnnnn nnnnnnnnnn nnnnn      55

<210> SEQ ID NO 113
<211> LENGTH: 24
<212> TYPE: DNA
<213> ORGANISM: Artificial Sequence
<220> FEATURE:
<223> OTHER INFORMATION: Primer target sequence

<400> SEQUENCE: 113
aatctatcaa caataggcaa ggca                                         24

<210> SEQ ID NO 114
<211> LENGTH: 19
<212> TYPE: DNA
<213> ORGANISM: Artificial Sequence
<220> FEATURE:
<223> OTHER INFORMATION: Primer target sequence

<400> SEQUENCE: 114
acatcgatgc gacctgcac                                               19

<210> SEQ ID NO 115
<211> LENGTH: 540
<212> TYPE: DNA
<213> ORGANISM: Artificial Sequence
<220> FEATURE:
<223> OTHER INFORMATION: Recombinant nucleotide sequence

<400> SEQUENCE: 115
agctgggagg cgacagcccc aagaagaaga gaaaggtgga ggccagcggg ccggccggat   60
ccgggcgcgc cgacgcgctg gacgatttcg atctcgacat gctgggttct gatgccctcg  120
atgactttga cctggatatg ttgggaagcg acgcattgga tgactttgat ctggacatgc  180
```

```
tcggctccga tgctctggac gatttcgatc tcgatatgtt agggtcagac gcactggatg    240
atttcgacct tgatatgttg ggaagcgatg cccttgatga tttcgacctg gacatgctcg    300
gcagcgacgc cctggacgat tcgatctgg acatgctggg gtccgatgcc ttggatgatt    360
ttgacttgga tatgctgggg agtgatgccc tggacgactt tgacctggac atgctgggct    420
ccgatgcgct cgatgacttc gatttggata tgttgtatat cgattgatta attaagaatt    480
cctagagctc gctgatcagc ctcgactgtg ccttctagtt gccagccatc tgttgtttgc    540
```

<210> SEQ ID NO 116
<211> LENGTH: 540
<212> TYPE: DNA
<213> ORGANISM: Artificial Sequence
<220> FEATURE:
<223> OTHER INFORMATION: Recombinant nucleotide sequence

<400> SEQUENCE: 116

```
gcaaacaaca gatggctggc aactagaagg cacagtcgag gctgatcagc gagctctagg     60
aattcttaat taatcaatcg atatacaaca tatccaaatc gaagtcatcg agcgcatcgg    120
agcccagcat gtccaggtca agtcgtcca gggcatcact ccccagcata tccaagtcaa    180
aatcatccaa ggcatcggac ccagcatgt ccagatcgaa atcgtccagg gcgtcgctgc    240
cgagcatgtc caggtcgaaa tcatcaaggg catcgcttcc aacatatca aggtcgaaat    300 catccagtgc gtctgaccct aacatatcga gatcgaaatc gtccagagca tcggagccga    360
gcatgtccag atcaaagtca tccaatgcgt cgcttcccaa catatccagg tcaaagtcat    420
cgagggcatc agaacccagc atgtcgagat cgaaatcgtc cagcgcgtcg gcgcgcccgg    480
atccggccgg cccgctggcc tccacctttc tcttcttctt ggggctgtcg cctcccagct    540
```

<210> SEQ ID NO 117
<211> LENGTH: 154
<212> TYPE: PRT
<213> ORGANISM: Artificial Sequence
<220> FEATURE:
<223> OTHER INFORMATION: Recombinant polypeptide

<400> SEQUENCE: 117

```
Leu Gly Gly Asp Ser Pro Lys Lys Arg Lys Val Glu Ala Ser Gly
1               5                   10                  15

Pro Ala Gly Ser Gly Arg Ala Asp Ala Leu Asp Asp Phe Asp Leu Asp
            20                  25                  30

Met Leu Gly Ser Asp Ala Leu Asp Asp Phe Asp Leu Asp Met Leu Gly
        35                  40                  45

Ser Asp Ala Leu Asp Asp Phe Asp Leu Asp Met Leu Gly Ser Asp Ala
    50                  55                  60

Leu Asp Asp Phe Asp Leu Asp Met Leu Gly Ser Asp Ala Leu Asp Asp
65                  70                  75                  80

Phe Asp Leu Asp Met Leu Gly Ser Asp Ala Leu Asp Asp Phe Asp Leu
                85                  90                  95

Asp Met Leu Gly Ser Asp Ala Leu Asp Asp Phe Asp Leu Asp Met Leu
            100                 105                 110

Gly Ser Asp Ala Leu Asp Asp Phe Asp Leu Asp Met Leu Gly Ser Asp
        115                 120                 125
```

```
Ala Leu Asp Asp Phe Asp Leu Asp Met Leu Gly Ser Asp Ala Leu Asp
    130                 135                 140

Asp Phe Asp Leu Asp Met Leu Tyr Ile Asp
145                 150
```

CRISPR-BASED METHODS AND PRODUCTS FOR INCREASING FRATAXIN LEVELS AND USES THEREOF

CROSS REFERENCE TO RELATED APPLICATIONS

The present application is a National Stage Application of PCT Application No. PCT/CA2015/050213 filed on Mar. 20, 2015, and published in English under PCT Article 21(2), which claims the benefit of U.S. Provisional Application Ser. No. 61/955,882 filed on Mar. 20, 2014. All documents above are incorporated herein by reference in their entirety.

SEQUENCE LISTING

Pursuant to 37 C.F.R. 1.821(c), a sequence listing is submitted herewith as an ASCII compliant text file named "11229_355_SeqList_v2.txt", created Nov. 21, 2018 and having a size of about 209 KB, which is incorporated herein by reference.

FIELD OF THE INVENTION

The present invention relates to increasing frataxin expression and/or levels and uses thereof, for example for the treatment of Friedreich ataxia.

BACKGROUND OF THE INVENTION

Frataxin

Frataxin is a small protein (Isoform 1: NCBI NM_000144.4, NP_000135 (210 aa), SEQ ID NO: 1; Isoform 2: NM_181425, NP_852090 (196 aa), SEQ ID NO: 2; Isoform 3: NM_001161706, NP_001155178, (171 aa), SEQ ID NO: 3; Uniprot Q16595; ENTREZ 2395; Ensembl ENSG00000165060; OMIM: 606829) found in cells throughout the body, with the highest levels in tissues with a high metabolic rate including heart, neurons, spinal cord, liver, pancreas (Langerhans cells), and muscles used for voluntary movement (skeletal muscles). Within cells, frataxin is found in mitochondria. It promotes the biosynthesis of heme as well as the assembly and repair of iron-sulfur clusters by delivering Fe2+ to proteins involved in these pathways. It also plays a primary role in the protection against oxidative stress through its ability to catalyze the oxidation of Fe2+ to Fe3+ and to store large amounts of the metal in the form of a ferrihydrite mineral. It is processed in two steps by mitochondrial processing peptidase (MPP). MPP first cleaves the precursor to intermediate form and subsequently converts the intermediate to a mature protein. Thus, in cells, 3 forms exist. For isoform 1, these forms are frataxin (56-210); frataxin (78-210) and frataxin (81-210), which is the main form of mature frataxin (Schoenfeld et al. 2005).

Friedreich Ataxia

Friedreich ataxia (FRDA), an autosomal recessive neurodegenerative and cardiac disease, is caused by a trinucleotide repeat expansion mutation in the first intron of the frataxin gene (FXN), which is located on the long arm of chromosome 9 (Location UCSC: 71,650,175 to 71715094 (64,920 bp; 9q21.11)). The mutation leads to a reduced expression of the frataxin mRNA and protein. Frataxin is essential for proper functioning of mitochondria. As noted above, it is involved in the removal of iron and when frataxin is reduced, iron builds up and causes free radical damage. Nerve and muscle cells are particularly sensitive to these deleterious effects. FRDA occurs in 1 in 50,000 persons in European populations but is much more frequent in the province of Quebec in Canada, because of founder effects. Males and females are affected equally. In the classic form, FRDA symptoms appear during or before the second decade of life. It is characterized by ataxia, areflexia, loss of vibratory sense and proprioception and dysarthria (Pandolfo 2012). Moreover, FRDA patients often have systemic involvement, with cardiomyopathy, diabetes mellitus and scoliosis. Early death can result from cardiomyopathy or associated arrhythmias. Degeneration of the dorsal root ganglion cells, their ascending dorsal spinal columns and the spinocerebellar tracts results in a progressive sensory ataxia. Many patients are wheelchair bound by their third decade. Associated oculomotor problems include optic atrophy, square-wave jerks and difficulty with fixation. Importantly, cognitive abilities are relatively spared. However, many patients suffer from depression.

The mutation responsible for FRDA is an unstable hyperexpansion of a GAA triplet repeat located in the first intron of the frataxin gene (Campuzano et al. 1996). In normal subjects, there are 6-34 repeats, whereas in FRDA patients there are 150 or more repeats. Patients with fewer repeats (150-200) have milder symptoms than those with longer sections with more triplet repeats (350 to 650). In some severely affected patients there are up to 1700 repeats. Since the frataxin gene mutation is located in an intron, it does not alter the amino acid sequence of the frataxin protein. There are 2-3% of FRDA patients who have a point mutation, either a missense or a non-sense. Some patients with a missense mutation have less severe symptoms because the mutated protein in still functional.

Pathological Mechanism

The pathological mechanisms have been reviewed by Pandolfo et al. (Pandolfo 2012). The repeated GAA triplets cause modifications in DNA methylation and the formation of triplex in the DNA, i.e., unusual non-B DNA conformations, which decrease transcription and subsequently reduce levels of the encoded protein, frataxin (level of expression is 5 to 35% of normal; (Coppola et al. 2006, Coppola et al. 2009)). Iron accumulation in mitochondria is mainly observed in the cardiac cells of patients and in the dentate nucleus of the brain. It is associated with oxidative damage. The reduction of frataxin leads to changes in gene expression of 185 different genes (Coppola et al. 2006, Coppola et al. 2009). Thus the reduction of frataxin has profound effects on several metabolic pathways and the correction of only one of these pathways by a drug may not be ideal.

Several strategies have been developed for treating Friedreich ataxia. These fall generally into the following 5 categories: 1) use of antioxidants to reduce the oxidative stress caused by iron accumulation in the mitochondria; 2) use of iron chelators to remove iron from the mitochondria; 3) use of Histone Deacetylase Inhibitors (HDACIs) to prevent DNA condensation and permit higher expression of frataxin; 4) use of molecules such as cisplatin, 3-nitroproprionnic acid (3-NP), Pentamidine or erythropoietin (EPO) to boost frataxin expression; and 5) gene therapy The present description refers to a number of documents, the content of which is herein incorporated by reference in their entirety.

SUMMARY OF THE INVENTION

The present inventors have shown for the first time that frataxin expression can be directly and efficiently increased in cells from Friedreich Ataxia patients comprising a mutated frataxin gene using a modified CRISPR system. The method comprises delivering a protein comprising a transcription activation domain (TAD) to the endogenous frataxin promoter. Surprisingly, frataxin expression could be substantially increased without correcting the endogenous gene (i.e, removing excess trinucleotide repeats) or its methylation level.

Thus, the present invention relates to inducing or increasing frataxin expression/levels in a cell using a modified Clustered Regularly Interspaced Short Palindromic Repeats (CRISPR) system/frataxin targeting system, and uses thereof. In an aspect, a "guide RNA" (gRNA) may be designed and used to specifically target the frataxin promoter to increase frataxin expression.

In a particular aspect, the present invention provides a modified CRISPR/Cas9-based system/frataxin targeting system comprising (or consisting of) a dCas9 fusion protein comprising two heterologous polypeptide domains and at least one gRNA to target the frataxin promoter. The first polypeptide domain comprises an inactive CRISPR-associated nuclease protein (dCas, such as dCas9) and the second polypeptide domain has transcription activation activity. This mutated inactive Cas nuclease (dCas, such as dCas9) fused with at least one transcription activation domain (TAD) is used to make a complex with the frataxin promoter and the gRNA targeting a nucleotide sequence within that promoter thereby enabling an increase in frataxin expression.

In a further aspect, the present invention provides a modified CRISPR/Cas9-based system/frataxin targeting system comprising (or consisting of) a first fusion protein comprising two heterologous polypeptide domains and at least one gRNA to target the frataxin promoter. The first polypeptide domain comprises a mutated inactive CRISPR-associated nuclease protein (dCas, such as dCas9) and the second polypeptide domain comprises a polypeptide sequence (i.e, a TAG) comprising a peptide epitope (in an embodiment, at least two peptide epitopes). The system further comprises a second fusion protein also comprising two heterologous polypeptide domains. The first polypeptide domain of the second fusion protein comprises an antigen binding domain (e.g., comprising an antigen-binding domain of an antibody, such as antibody scFv fragment) which is capable of binding to the peptide epitope of the first fusion protein (dCas/TAG), and the second polypeptide domain of the second fusion protein has transcription activation activity (e.g., it comprises at least one TAD). In this system, the first fusion protein may in embodiments comprise multiple repetitions of a peptide epitope (e.g., GCN4 peptide, SEQ ID NO: 4) fused to dCas9. This peptide epitope is recognized by the binding domain of the second fusion protein (such as an antibody/antibody fragment), which is fused to a transcription activation domain (e.g., VP64). The presence of multiple repetitions of the peptide epitopes on the first fusion protein comprising dCas (e.g., dCas9) allows recruitment of multiple second fusion proteins comprising transcription activators (comprising TADs) at a single target site on the frataxin promoter, thereby further increasing its expression. (see FIG. 13, from Tanenbaum et al., Cell, 2014);

In another aspect, the present invention provides a modified CRISPR/Cas9-based system/frataxin targeting system comprising (or consisting of) an MS2-fusion protein to be used in conjunction with a modified gRNA (comprising one or more (e.g., two) MS2 sequences which bind the MS2 polypeptide) and a dCas9-comprising fusion protein having transcription activating activity (comprising one or more TADS). The MS2 fusion protein comprises an MS2 domain (e.g., SEQ ID NO: 7, which recognizes specific MS2 sequences in the modified gRNA) and at least one (in an embodiment at least two) TAD (see for example FIG. 15). The MS2 fusion protein may comprises an MS2 polypeptide (SEQ ID NO: 7; FIG. 15B), the p65 polypeptide (SEQ ID NO: 8, FIG. 15C) and the HSF1 (human Heat-shock factor 1) polypeptide (SEQ ID NO: 9, FIG. 15D).

Accordingly, in an aspect, the present invention also provides at least one guide RNA (gRNA) comprising i) a gRNA guide sequence of at least 10 contiguous nucleotides corresponding to a target sequence in a frataxin promoter polynucleotide sequence; and ii) a Cas9 recognition sequence, wherein the target sequence is contiguous to a protospacer adjacent motif (PAM) recognized by a ribonucleoprotein complex comprising a Cas9 protein and/or an inactive Cas9 (dCas9) protein lacking nuclease activity.

In an further aspect, the present invention provides a frataxin targeting system comprising: a. a1) at least one gRNA (in a further embodiment, one) as; or a2) a vector comprising a nucleic acid sequence corresponding to the at least one gRNA and for expressing the at least one gRNA; and b. b1) a dCas9 fusion protein comprising an inactive Cas9 (dCas9) polypeptide domain lacking nuclease activity, wherein the dCas9 fusion protein further comprises i) at least one nuclear localization signal (in a further embodiment, one); and/or ii) (a) at least one transcription activation domain and/or (b) a polypeptide domain comprising at least one peptide epitope (in a further embodiment, one); or b2) a vector comprising a nucleic acid sequence encoding the fusion protein, for expression of the fusion protein.

In embodiments, the dCas9 protein or dCas9 polypeptide domain is derived from *Streptococcus pyogenes*, *Streptococcus thermophilus* or *Neisseria meningitides*. In an embodiment, the dCas9 protein or the dCas9 polypeptide domain is derived from *Streptococcus pyogenes*.

In an embodiment, the PAM is a NGG trinucleotide-sequence.

In an embodiment the dCas9 protein or dCas9 polypeptide domain comprises a mutation at an aspartic acid corresponding to position 10 of a Cas9 amino acid sequence as set forth in SEQ ID NO: 35 and/or at a histidine corresponding to position 840 of a Cas9 amino acid sequence as set forth in SEQ ID NO: 35. In an embodiment, the dCas9 protein or dCas9 polypeptide domain comprises mutations corresponding to D10A and H840A.

In an embodiment, the gRNA guide sequence consists of 12-22 (in embodiments, 10-20, 10-19, 10-18, 18-22, 18-20, 18-19, 19-22, or 20-22) and preferably 18, 19 or 20 nucleotides targeting a particular target region. In embodiments, the gRNA guide sequence is perfectly identical to a target region. The at least one gRNA may target the promoter region of the frataxin gene or an enhancer region of the frataxin gene.

In an embodiment the 3' end of the target sequence of the gRNA in the frataxin promoter ends at nucleotide position i) 4264; ii) 4670, iii) 4859; iv) 5023; or v) 5107, wherein the nucleotide position corresponds to that of the frataxin polynucleotide gene sequence having NCBI reference number NG_008845 (SEQ ID NO: 87).

In an embodiment the 3' end of the target sequence of the gRNA in the frataxin promoter ends at nucleotide position i) 4670; ii) 4701; iii) 4742; ii) 4859; or iii) 5107, wherein the nucleotide position corresponds to that of the frataxin polynucleotide gene sequence having NCBI reference number NG_008845 (SEQ ID NO: 87).

In an embodiment the target sequence of the gRNA in the frataxin promoter ends at wherein the 3' end of the target sequence ends at nucleotide position ii) 4670, ii) 4859; or iii) 5107, wherein the nucleotide positions corresponds to that of the frataxin polynucleotide gene sequence having NCBI reference number NG_008845 (SEQ ID NO: 87).

In an embodiment the target sequence of the gRNA in the frataxin promoter is comprised within a nucleotide sequence corresponding to i) nucleotides 3961-4258; ii) nucleotides 4268-49513; iii) nucleotides 4268-4996; iv) nucleotides 5027-5150; v) nucleotides 4268-4595; vi) nucleotides 4621-4996; vii) nucleotides 4561-4996; or viii) nucleotides 4280-5000; iv) the complement of anyone of i) to viii), wherein the nucleotide positions corresponds to that of the frataxin polynucleotide gene sequence having NCBI reference number NG_008845 (SEQ ID NO: 87).

In an embodiment, the RNA guide sequence and the target sequence do not comprise more than one NGG sequence. In an embodiment the RNA guide sequence and the target sequence do not comprise an NGG sequence.

In an embodiment, the target sequence of the gRNA in the frataxin promoter comprises or consist of:

In an embodiment, the target sequence of the gRNA in the frataxin promoter comprises or consists of the nucleotide sequence of:
  i) Positions 4246-4264;
  ii) Positions 4652-4670;
  iii) Positions 4841-4859;
  iv) Positions 5005-5023; or
  v) Positions 5089-5107,
    of the frataxin polynucleotide gene sequence having NCBI reference number NG_008845 (SEQ ID NO: 87, see also FIG. 2).

In an embodiment, the Cas9 recognition sequence comprises or consists of the sequence as set forth in SEQ ID NO: 67. In an embodiment, the gRNA comprises or consists of a sequence as set forth in any one of SEQ ID NOs: 57-61.

In an embodiment, the above dCas9 fusion protein comprises a polypeptide domain comprising at least one peptide epitope, and the system further comprises a fusion protein comprising i) an antigen-binding region which binds to the at least one peptide epitope and ii) at least one transcription activation domain. In an embodiment, the antigen-binding region comprises a single chain variable fragment which binds to the at least one peptide epitope. In an embodiment the dCas9 fusion protein comprises a polypeptide domain comprising at least two peptide epitopes.

In an embodiment the present invention further provides i) an MS2 fusion protein comprising a) at least one nuclear localization signal and/or b. b1) an MS2 polypeptide and b2) at least one transcription activation domain, or ii) a vector comprising a nucleic acid sequence encoding the MS2 fusion protein. In an aspect, the MS2 fusion protein is used with a gRNA which comprises an MS2 nucleic acid sequence in a tetraloop and an MS2 nucleic acid sequence in a stem loop of the gRNA which is capable of binding to the MS2 polypeptide.

Accordingly, the above gRNA may further comprise at least one MS2 nucleic acid sequence. In an embodiment, the gRNA comprises two MS2 sequences, one in a tetraloop one in a stem loop of the gRNA. In an embodiment, the MS2 nucleic acid sequence comprises or consists of the sequence set forth in SEQ ID NO: 68. In an embodiment, the gRNA comprises or consists of a sequence as set forth in any one of SEQ ID NOs: 62-66.

In an embodiment, the above transcription activation domain comprise a VP16 (SEQ ID NO: 17), VP64 or VP160 (SEQ ID NO: 18) transcription activation domain. In another embodiment, transcription activation domain comprises one or multiple copies of a VP16 TAD (SEQ ID NO: 17). In embodiments, the transcription activation domain may comprise a HSF1 (SEQ ID NO: 9) or a p65 activation (SEQ ID NO: 8) domain. The fusion protein may further comprise a linker connecting the various heterologous domains of the fusion protein (e.g., between the dCas9 polypeptide domain and the TAD or peptide epitope; between the MS2 polypeptide and the TAD; between peptide epitopes or between twoTADs). The fusion proteins of the present invention preferably comprise at least one nuclear localization signal. In an embodiment, the fusion proteins of the present invention comprise two NLSs. In an embodiment, the NLS is a mammalian nuclear localization signal derived from the simian virus 40 large T antigen. In a particular embodiment, the NLS comprises the sequence PKKKRKV (SEQ ID NO: 12). In a particular embodiment, the transcription activation domain comprises 10 copies of a VP16 TAD (VP160) (SEQ ID NO: 18).

In an embodiment, the above inactive dCas9 fusion protein has an amino acid sequence at least 95% (in embodiments at least 96,%, 97%, 98% or 99%) identical to the sequence set forth in FIG. 3 (SEQ ID NO: 33).

In embodiments the dCas9 fusion protein comprises between 2 and 24 (in an embodiment 10) GCN4 peptide epitopes. In an embodiment, the dCas9 fusion protein comprises a sunTAG polypeptide sequence as set forth in SEQ ID NO: 5 or 6.

In another embodiment, the amino acid sequence of the dCAs/TAD protein of the present invention comprises an amino acid sequence at least 95% identical to amino acids 10 to 1538 of the sequence set forth in FIG. 3 (SEQ ID NO: 34). In another embodiment, the amino acid sequence of the dCAs/TAD protein of the present invention comprises an amino acid sequence at least 95% identical to amino acids 10 to 1535 of the sequence set forth in FIG. 3 (amino acid 1-1526 of SEQ ID NO: 34). In particular embodiments, the dCas/TAD protein of the present invention comprises or consists of a sequence at least 95% (i.e. 95%, 96%, 97%, 98%, 99%, 99.5% or 100%) identical to the above-mentioned amino acid sequences of FIG. 3 (SEQ ID NOs:32 and 34).

In a further embodiment, the above-mentioned inactive fusion protein further comprises a protein transduction domain (PTD) to target the protein into a cell. In a particular embodiment, the PTD is TAT or Pep-1. In an embodiment, the TAT-PTD comprises the sequence SGYGRKKRRQRRRC (SEQ ID NO: 36).

In a further aspect, the fusion proteins and/or gRNAs of the present invention may be complexed with liposomes to facilitate their entry into target cells. Liposomes may be used alone or in combination with a PTD domain.

The present invention also provides an isolated polynucleotide encoding one or more of the above-mentioned gRNAs alone or in combination with the above-mentioned inactive fusion protein of the present invention. Vectors comprising one or more of such polynucleotides are also provided. A vector may encode for several gRNAs or fusion proteins. In a particular embodiment, the vector comprises a polynucleotide sequence at least 95% (i.e., 95%, 96%, 97%, 98%, or 99%) identical to the polynucleotide sequence as set forth in FIG. 4 (SEQ ID NO: 55), or to any one of SEQ ID NOs: 93-100.

In a particular embodiment, the vector of the present invention is a viral vector. In a particular embodiment, the viral vector is derived from a retrovirus, a lentivirus, an adeno associated virus, an adenovirus or a Herpes virus. In an embodiment, the vector is a viral vector. In an embodiment, the vector is an AAVDJ-8 or AAV2DJ9 adeno-associated virus vector.

In another aspect, the present invention also concerns a composition or combination comprising at least one of:
  i) the above-mentioned vectors; or
  ii) one or more gRNAs of the present invention;
  iii) the above frataxin targeting system; and
  iv) a cells comprising any one of i) to iii)
  The composition may further comprise a physiologically acceptable (e.g., a pharmaceutically acceptable) carrier.

In a further aspect, the present invention also concerns a kit comprising at least one of:
  i) the above-mentioned vectors; or
  ii) one or more of the above gRNAs;
  iii) the above frataxin targeting system; and
  iv) a cell comprising any one of i) to iii)

The present invention also provides a cell comprising one or more of the above-mentioned gRNAs, fusion proteins, frataxin targeting system, combinations, isolated polynucleotides and/or vectors of the present invention.

The present invention further relates to one or more of the above-mentioned gRNAs, frataxin targeting system, isolated polynucleotides, vectors, cells, compositions, combinations or kit for increasing frataxin expression in a cell.

In a related aspect, the present invention relates to a use of one or more of the above-mentioned gRNAs, frataxin targeting system, isolated polynucleotides, vectors, cells, compositions, combinations or kit for increasing frataxin expression in a cell.

In embodiments, the cell does not express frataxin or the cell expresses a low level of frataxin as compared to a normal cell. In an embodiment, the cell has an abnormal number of GAA trinucleotide repeats in intron 1 of the frataxin gene. In a particular embodiment the cell comprises at least 35, preferably at least 80, more preferably at least 150 and even more preferably at least 250 or more GAA trinucleotide repeats. In an embodiment, the cell is from a subject suffering from FRDA.

The present invention further relates to one or more of the above-mentioned gRNAs, frataxin targeting system, isolated polynucleotides, vectors, cells, compositions, combinations or kit for the treatment of Friedreich ataxia.

The present invention also relates to a use of one or more the above-mentioned gRNAs, frataxin targeting system, isolated polynucleotides, vectors, cells, compositions, combinations or kit for treating Friedreich ataxia.

The present invention relates to one or more the above-mentioned gRNAs, frataxin targeting system, isolated polynucleotides, vectors, cells, compositions, kits or combination for the preparation of a medicament for treating Friedreich ataxia.

In a related aspect, the present invention relates to a use of one or more the above-mentioned gRNAs, frataxin targeting system, isolated polynucleotides, vectors, cells, compositions, kits or combinations for the preparation of a medicament for treating Friedreich ataxia.

The present invention also relates to a method of increasing frataxin expression in a cell comprising expressing at least one of the above-mentioned gRNAs, or frataxin targeting systems, or administering at least one of the above-mentioned frataxin targeting systems, vectors, cells, compositions or combinations.

The present invention further concerns a method for treating Friedreich ataxia in a subject comprising expressing at least one the above-mentioned gRNAs, polynucleotides, vectors or frataxin targeting systems in a cell of the subject.

The present invention further concerns a method for treating Friedreich ataxia in a subject comprising administering to the subject one or more of the above-mentioned gRNAs frataxin targeting systems, vectors cells, compositions, or combinations.

In an embodiment, the above-mentioned method comprises transducing one or more viral vectors for expressing a gRNA and/or a Cas/TAD protein of the present invention in the cell.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

FIG. 2 shows the partial sequence of the human frataxin promoter (SEQ ID NO: 11, LOCUSNG_00884571616bpDNAlinearPRI02-JUL-2013, human frataxin gene ACCESSION NG_008845 VERSION NG_008845.2G1:254826725). Potential protospacer adjacent motifs (PAM) along the shown portion of the frataxin promoter are shaded (ngg sequences). The first positions of the transcriptional start sites (agt and cac) positioned at 5001 and 5159 are boxed. Start codon (ATG) of the protein coding sequence at position 5221-5223 is in bold capital letters. Primers used to amplify the frataxin promoter are shaded (4063-4086 [SEQ ID NO: 113] and 5454-5362 [SEQ ID NO: 114]). Exemplary target sequences (4246-4264 [SEQ ID NO: 92]; 4652-4670 [SEQ ID NO: 91]; 4841-4859 [SEQ ID NO: 90]; 5005-5023 [SEQ ID NO: 89]; 5089-5107 [SEQ ID NO: 88]) on the frataxin promoter, according to an embodiment of the present invention, are in bold and underlined and are also presented in Table 4 in Example 1;

FIG. 3 shows the amino acid sequence of dCas9-VP160 (SEQ ID NO: 32) comprising two Nuclear Localization Signal (NLS) (underlined and bold—PKKKRKV, SEQ ID NO: 12) at the N-Terminal and C-Terminal ends of dCas9-VP160. The sequence of the ten VP16 Transcription Activation Domain TAD (VP160) at the C-terminal of dCas9-VP160 are underlined (VP160, SEQ ID NO: 18; VP16, SEQ ID NO: 17). The theoretical isoelectric point of the dCas9 protein is 5.89 and its molecular weight is 176880.44 Daltons;

FIG. 4 shows the nucleic acid sequence of the pAC154-dual-dCas9-VP160 plasmid (SEQ ID NO: 55) for expression of the gRNA A and of the dCas9-VP160. Underlined and in bold is the sequence targeted in the promoter of the human frataxin gene by an exemplary gRNA (gRNA A) of the present invention (SEQ ID NO: 88);

FIG. 5 shows a partial sequence of the pAC154 plasmid (sense strand, SEQ ID NO: 115; antisense strand, SEQ ID NO: 116; full amino acid sequence, SEQ ID NO: 117) with the corresponding amino acid sequences coding for VP160 (SEQ ID NO: 18), composed of ten VP16 sequences. Each VP16 sequence (SEQ ID NO: 17) is shaded;

FIG. 15 shows the amino acid sequence of the MS2-p65-HSF1 fusion protein of the present invention. A. Amino acid sequence of the MS2-p65-HSF1 (SEQ ID NO: 10) fusion protein including a nuclear localization signal (PKKKRKV, bold (SEQ ID NO: 12)); shaded sequence corresponds to the p65 polypeptide (SEQ ID NO: 8). B. Amino acid sequence of the MS2 peptide (SEQ ID NO: 7). C. Amino acid sequence of the p65 transcription activation domain (SEQ ID NO: 8). D. Amino acid sequence of the HSF1 transcription activation domain (SEQ ID NO: 9);

FIG. 16 shows the amino acid sequence of a Cas9 protein lacking nuclease activity (dCas9, SEQ ID NO: 33) used in an embodiment of the present invention. The protein comprises an NLS (PKKKRKV [SEQ ID NO: 12]). This protein comprises the mutations known as D10A (corresponding to position 30 in this sequence) and H840A (corresponding to position 860 in this sequence) (in bold) which inactivate its nuclease activity;

FIG. 17 shows the amino acid sequence of the TAG peptide sequence (suntag) which may be fused to a dCas9 protein to enhance transcription of the frataxin gene. A. GCN4 peptide motif (SEQ ID NO: 4) which is repeated 10 times in the TAG peptide sequence. B. Nuclear localization signal (NLS, SEQ ID NO: 12) present in the TAG peptide sequence. C. Complete TAG amino acid sequence (SEQ ID NO: 6) including the NLS followed by 10 GCN4 peptide sequence interspaced with a linker sequence (GSGSG; (SEQ ID NO: 56));

FIG. 18 shows the nucleic acid sequences of exemplary gRNA sequences of the present invention. A. Nucleic acid sequences of gRNAs tested in Examples 1 and 2. DNA sequences encoding the gRNAs were cloned in an expression vector and expressed under the control of the U6 promoter. CrispA to CrispE gRNA sequences correspond to SEQ ID NOs: 57 to 61, respectively. The gRNA guide sequence is underlined (Crisp A to Crisp E gRNA guide sequences correspond to SEQ ID NOs: 69 to 73, respectively). B. Nucleic acid sequences of gRNAs which comprises 2 nucleic acid sequences recognized by the MS2 polypeptide (in bold in MS-2 CrispA, SEQ ID NO: 62). MS2-CrispA to MS2-CrispE gRNA sequences correspond to SEQ ID NOs: 62 to 66. The gRNA guide sequence is underlined (MS2-Crisp A to MS2-Crisp E gRNA guide sequences correspond to SEQ ID NOs: 69 to 73, respectively);

FIG. 19 shows the amino acid sequence of the Cas9 nuclease from *Streptococcus pyogenes* (SEQ ID NO: 35; Uniprot Q99ZW2); and FIG. 20 shows a list of mutations in Cas9 and their effect on protein function. Mutation(s) may be selected do design and prepare an inactive Cas9 nuclease which lacks nuclease activity but still binds the target frataxin DNA sequence in the present of a gRNA.

DESCRIPTION OF ILLUSTRATIVE EMBODIMENTS

Figure 1:
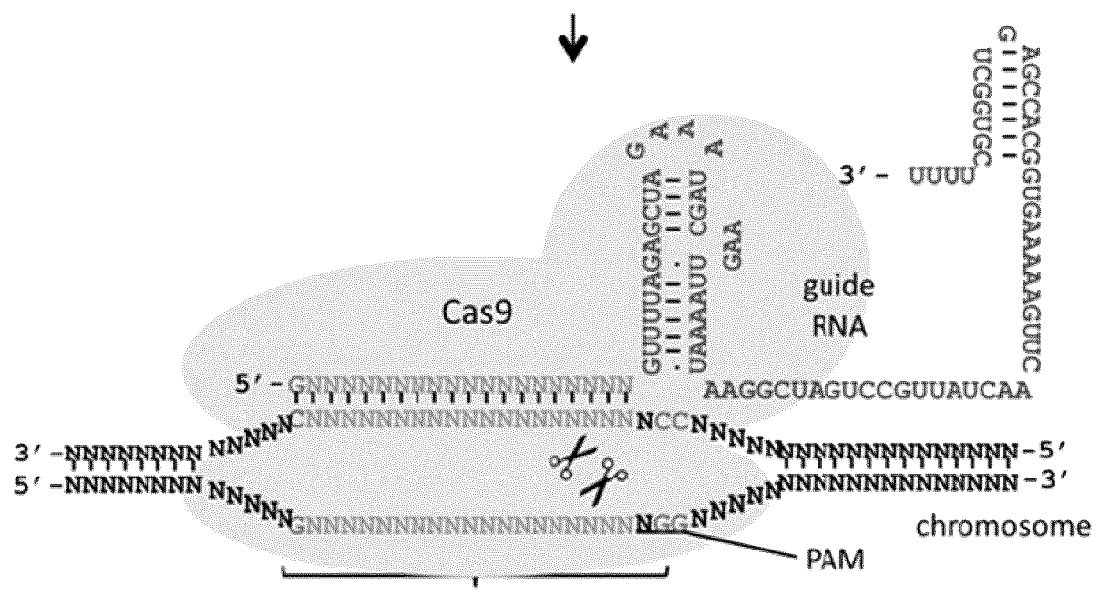
FIG. 1 is a schematic representation of the single-guide RNA (gRNA; SEQ ID NO: 110) and Cas9 nuclease protein targeting a sequence (sense, SEQ ID NO: 112; antisense, SEQ ID NO: 111) on a chromosome (Mali et al. 2013b)

Recent discoveries in the field of bacterial immunity have led to the development of a new system for controlling gene expression in cells. Bacterial and archaea have developed adaptive immune defenses termed clustered regularly interspaced short palindromic repeats (CRISPR) systems, which use crRNA and Cas proteins to degrade complementary sequences present in invading viral and plasmid DNA (Mali et al. 2013b). Jinek et al. (Jinek et al. 2012) and Mali et al. (Mali et al. 2013b) have engineered a type II bacterial CRISPR system using custom guide RNA (gRNA) to induce a double strand break in DNA (see FIG. 1). Cong et al. (Gong et al. 2013) and Cho et al. (Cho et al. 2013) have used this system to mutate several genes in mouse and human cells. This CRISPR system has been used to induce mutations in *C. elegans*, Zebrafish and in hiPSCs (human induced pluripotent stem cells) and to generated transgenic mice. However the original Cas9 nuclease combined with a gRNA produced frequent off-target mutagenesis (Fu et al. 2013). This problem has been resolved by mutating the Cas9 nuclease into a nickase and using two gRNA to cut both DNA strands (Mali et al. 2013a). The CRISPR system with an inactive Cas9 nuclease coupled or not with the VP64 transcription activation domain has also been used to reduce or enhance gene expression (Perez-Pinera et al. 2013).

Applicant shows herein for the first time that the CRISPR system may be used to efficiently increase frataxin protein expression in cells. Various gRNAs targeting the frataxin promoter were shown to increase frataxin expression in cells expressing a mutated (inactive) Cas (e.g., dCas9) nuclease, fused with at least one transcription activation domain (TAD). Frataxin expression was increased not only in normal cells but also in cells from Friedreich Ataxia patients bearing hyper-expansion of a GAA triplet repeat associated with low expression of frataxin. Targeting of the frataxin promoter and increased frataxin expression in these cells was possible without correcting the endogenous defect or modifying the DNA topology and/or its methylation level (e.g., using reagents modifying DNA methylation levels or the like).

The present invention relates to inducing or increasing frataxin expression/levels in a cell, and uses thereof. In an aspect, the present invention relates to the design of one or more gRNAs for inducing the expression of frataxin. In a particular aspect, a recombinant fusion protein comprising (a) an inactive Cas nuclease (e.g., dCas9) fused with (b) at least one transcription activation domain (TAD) domain (e.g., VP16, VP64 and VP160), is designed, prepared and introduced into/expressed in a cell together with a gRNA targeting the frataxin promoter, to induce frataxin expression or increase the level of frataxin protein within the cell. In a particular embodiment, the gRNA is modified to include nucleic acid sequences (e.g., two MS2 sequences) to which the MS2 peptide binds and a recombinant fusion protein comprising (a) the MS2 polypeptide fused with (b) at least one transcription activation domain (TAD) domain (e.g., p65 and/or HSF1) are designed and prepared. The fusion proteins are introduced/expressed into a cell together with at least one gRNA targeting the frataxin promoter, to induce frataxin expression or increase the level of frataxin protein within the cell.

In another aspect, a recombinant fusion protein comprising (a) an inactive Cas nuclease (e.g., dCas9) polypeptide fused with (b) a polypeptide (TAG) comprising one or more (in an embodiment, at least two) peptide epitopes (e.g., GCN4), is designed and prepared. A further fusion protein which binds to the peptide epitope (antigen binding protein) and which is fused to at least one transcription activation domain (TAD) is also designed and prepared. The fusion proteins are introduced/expressed into a cell together with a gRNA targeting the frataxin promoter, to induce frataxin expression or increase the level of frataxin protein within the cell.

The present invention further relates to uses of such induction or increasing frataxin expression/levels in a cell, such as for inducing/increasing expression of the frataxin protein in cells from a subject in need thereof, such as for the treatment of Friedreich ataxia.

Section headings as used in this section and the entire disclosure herein are merely for organizational purposes and are not intended to be limiting.

Definitions

In order to provide clear and consistent understanding of the terms in the instant application, the following definitions are provided.

Unless otherwise defined, all technical and scientific terms used herein have the same meaning as commonly understood by one of ordinary skill in the art. In case of conflict, the present document, including definitions, will control. Preferred methods and materials are described, but methods and materials similar or equivalent to those described herein can be used in practice or testing of the present invention. All publications, patent applications, patents, references to sequence database entries, and other references mentioned herein are incorporated by reference in their entirety.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps and are used interchangeably with, the phrases "including but not limited to" and "comprising but not limited to".

For the recitation of numeric ranges herein, each intervening number there between with the same degree of precision is explicitly contemplated. For example, for the range of 18-20, the numbers 18, 19 and 20 are explicitly contemplated, and for the range 6.0-7.0, the number 6.0, 6.1, 6.2, 6.3, 6.4, 6.5, 6.6, 6.7, 6.8, 6.9, and 7.0 are explicitly contemplated.

"Adeno-associated virus" or "AAV" as used interchangeably herein refers to a small virus belonging to the genus Dependovirus of the Parvoviridae family that infects humans and some other primate species. AAV is not currently known to cause disease and consequently the virus causes a very mild immune response.

"Binding region" as used herein refers to the region within a nuclease target region that is recognized and bound by the nuclease.

"Coding sequence" or "encoding nucleic acid" as used herein means the nucleic acids (RNA or DNA molecule) that comprise a nucleotide sequence which encodes a protein or gRNA. The coding sequence can further include initiation and termination signals operably linked to regulatory elements including a promoter and polyadenylation signal capable of directing expression in the cells of an individual or mammal to which the nucleic acid is administered. The coding sequence may be codon optimized.

"Complement" or "complementary" as used herein refers to Watson-Crick (e.g., A-T/U and C-G) or Hoogsteen base pairing between nucleotides or nucleotide analogs of nucleic acid molecules. "Complementarity" refers to a property shared between two nucleic acid sequences, such that when they are aligned antiparallel to each other, the nucleotide bases at each position will be complementary.

"Frataxin" as used herein refers to a protein found in mitochondria (Isoform 1: NCBI NM_000144.4, NP_000135 (210 aa), SEQ ID NO: 1; Isoform 2: NM_181425, NP_852090 (196 aa), SEQ ID NO: 2; Isoform 3: NM_001161706, NP_001155178, (171 aa), SEQ ID NO: 3; Uniprot Q16595; ENTREZ 2395; Ensembl ENSG00000165060; OMIM: 606829). The Frataxin gene or "FRX gene" (NCBI reference number NG_008845; NCBI Gene ID 2395) as used interchangeably herein is at locus 9q21.1.

"Fusion protein" as used herein refers to a chimeric protein created through the joining of two or more nucleic acid/genes that each originally coded for separate proteins or polypeptides. The translation of the fusion nucleic acid/gene results in a single polypeptide with functional properties derived from each of the original proteins.

A "TAG" in the context of the present invention is a polypeptide sequence comprising at least one peptide epitope (in embodiments at least 3, 4, 5, 6, 7, 10, 20, 24, or more peptide epitopes) which bind to a protein having antigen binding activity (e.g., an antibody or single chain variable fragment).

"Mutant gene" or "mutated gene" as used interchangeably herein refers to a gene (e.g., frataxin gene) that has undergone a detectable mutation. A mutant frataxin gene in the context of FRDA comprises an abnormal amount of GAA trinucleotide repeats (about 150 to more than 1700 repeats) in the first intron of the frataxin gene. The presence of these repeats affects the normal transmission and expression of the gene, thereby leading to reduced expression of functional frataxin protein.

"Normal frataxin gene" as used herein refers to a frataxin gene (e.g., NCBI reference number; NG_008845; NCBI Gene ID 2395, SEQ ID NO: 87) that has not undergone a change, such as a loss, gain, or exchange of genetic material. The normal gene undergoes normal gene transmission and gene expression. A "normal" frataxin gene in the context of the present invention is a frataxin gene which encodes a wild-type, functional frataxin protein and which expresses a level of frataxin protein which substantially corresponds to the level of frataxin protein normally found in healthy subjects (e.g., subjects not suffering from FRADA). Healthy subjects comprise less than 35 GAA repeats in intron 1 of the frataxin gene and the average amount of repeats in healthy subjects is between about 6-34 repeats.

"Promoter" as used herein means a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter. The "frataxin promoter" enables the expression of the frataxin protein in cells (see for example FIG. 2 (SEQ ID NO: 11) for a partial sequence of the human frataxin promoter and the frataxin gene sequence (SEQ ID NO: 87; NG_00845) for the complete promoter sequence). In an embodiment, the U6 promoter is used to express one or more gRNAs in a cell.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human. In an embodiment, the subject or patient may suffer from FRDA and has a mutated frataxin gene having an abnormal hyper-expansion of trinucleotide repeats in intron 1 of the frataxin gene. The subject or patient may be undergoing other forms of treatment.

"Target gene" as used herein refers to any nucleotide sequence encoding a known or putative gene product. The target gene may be a mutated gene involved in a genetic disease.

"Vector" as used herein means a nucleic acid sequence containing an origin of replication. A vector may be a viral vector, bacteriophage, bacterial artificial chromosome or yeast artificial chromosome. A vector may be a DNA or RNA vector. A vector may be a self-replicating extrachromosomal vector, and preferably, is a DNA plasmid. For example, the vector may comprise nucleic acid sequence(s) that/which encode(s) a fusion protein of the present invention such as a dCas9-TAD (e.g., dCas9-VP64 or dCas9-VP160) a dCas9-polyGCN4 (suntag), a MS2-TAD (e.g., MS2-p65-HFS1), or an antigen-binding protein-TAD (e.g., scFV-VP64 or scFV-VP160) fusion protein or that encodes at least one gRNA (e.g. SEQ ID NOs: 57-66). Alternatively, the vector may comprise nucleic acid sequence(s) that/which encode(s) one or more of the above fusion protein and at least one gRNA nucleotide sequence of the present invention (e.g., a gRNA A, C and/or D or a gRNA comprising SEQ ID NOs:57-66). A vector for expressing one or more gRNA will comprise a "DNA" sequence of the gRNA.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

CRISPR System

"Clustered Regularly Interspaced Short Palindromic Repeats" and "CRISPRs", as used interchangeably herein refers to loci containing multiple short direct repeats that are found in the genomes of approximately 40% of sequenced bacteria and 90% of sequenced archaea. The CRISPR system is a microbial nuclease system involved in defense against invading phages and plasmids that provides a form of acquired immunity. This defensive pathway has three steps. First a copy of the invading nucleic acid is integrated into the CRISPR locus. Short segments of foreign DNA, called spacers, are incorporated into the genome between CRISPR repeats, and serve as a 'memory' of past exposures. Next, CRISPR RNAs (i.e., crRNAs, the endogenous bacterial RNA that confers target specificity) are transcribed from this CRISPR locus. The crRNAs are then incorporated into effector complexes, where the crRNA guides the complex to the invading nucleic acid and the Cas proteins degrade this nucleic acid. There are several pathways of CRISPR activation, one of which requires a tracrRNA which plays a role in the maturation of crRNA. TracrRNA is complementary to and base pairs with a pre-crRNA forming an RNA duplex. This is cleaved by RNase III, an RNA-specific ribonuclease, to form a crRNA/tracrRNA hybrid (gRNA). This hybrid acts as a guide for the endonuclease Cas9, which cleaves the invading nucleic acid.

Cas9 forms a complex with the 3' end of the gRNA, and the protein-RNA pair recognizes its genomic target by complementary base pairing between the 5' end of the gRNA sequence and a predefined 20 bp DNA sequence, known as the protospacer. This complex is directed to homologous loci of pathogen DNA via regions encoded within the crRNA, i.e., the protospacers, and protospacer-adjacent motifs (PAMs) within the pathogen genome. The non-coding CRISPR array is transcribed and cleaved within direct repeats into short crRNAs containing individual spacer sequences, which direct Cas nucleases to the target site (protospacer). By simply exchanging the 20 bp recognition sequence of the expressed gRNA, the Cas9 nuclease can be directed to new genomic targets. CRISPR spacers are used to recognize and silence exogenous genetic elements in a manner analogous to RNAi in eukaryotic organisms.

Three classes of CRISPR systems (Types I, II and III effector systems) are known. The Type II effector system carries out targeted DNA double-strand break in four sequential steps, using a single effector enzyme, Cas9, to cleave dsDNA. Compared to the Type I and Type III effector systems, which require multiple distinct effectors acting as a complex, the Type II effector system may function in alternative contexts such as eukaryotic cells. The Type II effector system consists of a long pre-crRNA, which is transcribed from the spacer-containing CRISPR locus, the Cas9 protein, and a tracrRNA, which is involved in pre-crRNA processing. The tracrRNAs hybridize to the repeat regions separating the spacers of the pre-crRNA, thus initiating dsRNA cleavage by endogenous RNase III. This cleavage is followed by a second cleavage event within each spacer by Cas9, producing mature crRNAs that remain associated with the tracrRNA and Cas9, forming a Cas9: crRNA-tracrRNA complex.

The Cas9:crRNA-tracrRNA complex unwinds the DNA duplex and searches for sequences matching the crRNA to cleave. Target recognition occurs upon detection of complementarity between a "protospacer" sequence in the target DNA and the remaining spacer sequence in the crRNA. Cas9 mediates cleavage of target DNA if a correct protospacer-adjacent motif (PAM) is also present at the 3' end of the protospacer. For protospacer targeting, the sequence must be immediately followed by the protospacer-adjacent motif (PAM), a short sequence recognized by the Cas9 nuclease that is required for DNA cleavage. Members of the Cas9 family require different protospacer adjacent motifs (PAM) (Hou et al. 2013). As noted above, the PAM is the sequence of nucleotides which must follow the nucleotide sequence targeted by the gRNA. Different Type II systems have differing PAM requirements. Accordingly, selection of a specific polynucleotide target sequence (e.g., on the frataxin promoter) by a gRNA will be based on the recombinant dCas protein used.

The *S. pyogenes* CRISPR system may have the PAM sequence for this Cas9 (SpCas9) as 5'-NRG-3', where R is either A or G, and characterized the specificity of this system in human cells. A unique capability of the CRISPR/Cas9 system is the straightforward ability to simultaneously target multiple distinct genomic loci by co-expressing a single Cas9 protein with two or more sgRNAs (at least one, two, three, four, five, six seven, eight, nine or ten gRNAs). For example, the *Streptococcus pyogenes* Type II system naturally prefers to use an "NGG" sequence, where "N" can be any nucleotide, but also accepts other PAM sequences, such as "NAG" in engineered systems. Similarly, the Cas9 derived from *Neisseria meningitidis* (NmCas9) normally has a native PAM of NNNNGATT, but has activity across a variety of PAMs, including a highly degenerate NNNNGNNN PAM.

CRISPR/Cas9-Based Systems

An engineered form of the Type II effector system of *Streptococcus pyogenes* was shown to function in human cells for genome engineering. In this system, the Cas9 protein was directed to genomic target sites by a synthetically reconstituted "guide RNA" ("gRNA", also used interchangeably herein as a chimeric single guide RNA ("sgRNA")), which is a crRNA-tracrRNA fusion that obviates the need for RNase III and crRNA processing in general. It comprises a "gRNA guide sequence" or "gRNA target sequence" and a Cas9 recognition sequence, which is necessary for Cas (e.g., Cas9) binding to the targeted gene. The gRNA guide sequence is the sequence which confers specificity. It hybridizes with (i.e., it is complementary to) the opposite strand of a target sequence (i.e., it corresponds to the RNA sequence of a DNA target sequence).

Provided herein are CRISPR/Cas9-based engineered systems for use in increasing frataxin expression in cells. The CRISPR/Cas9-based engineered systems of the present invention are designed to target the frataxin promoter to increase frataxin gene transcription and ultimately to increase the level of frataxin protein in cells, such as cells from subjects suffering from FRDA or having an hyper trinucleotide expansion in the first intron of the frataxin gene (which reduces frataxin expression compared to subjects not having the hyper-expansion in intro 1). The CRISPR/Cas (e.g. CRISPR/Cas9)-based systems of the present invention include an inactive Cas (e.g. Cas9) fusion protein (lacking nuclease activity, dCas (e.g., dCas9)) and at least one gRNA.

In an embodiment, the inactive Cas9 (dCas9) fusion protein comprises an inactive Cas 9 (dCas9) polypeptide domain lacking nuclease activity and a polypeptide domain that has a different activity that which is endogenous to Cas9.

In a first aspect, the polypeptide domain that has a different activity that which is endogenous to Cas9 has transcription activation activity (the dCas9 polypeptide domain is fused to a transcriptional activator). In an embodiment, the dCas9 fusion protein comprises a polypeptide domain comprising one or more (at least one) transcriptional activation domains (TAD) (dCas9/TAD). The fact that the dCas9/TAD has transcription activation activity allows increasing frataxin expression when used in combination with a gRNA targeting the frataxin promoter sequence.

Figure 14:
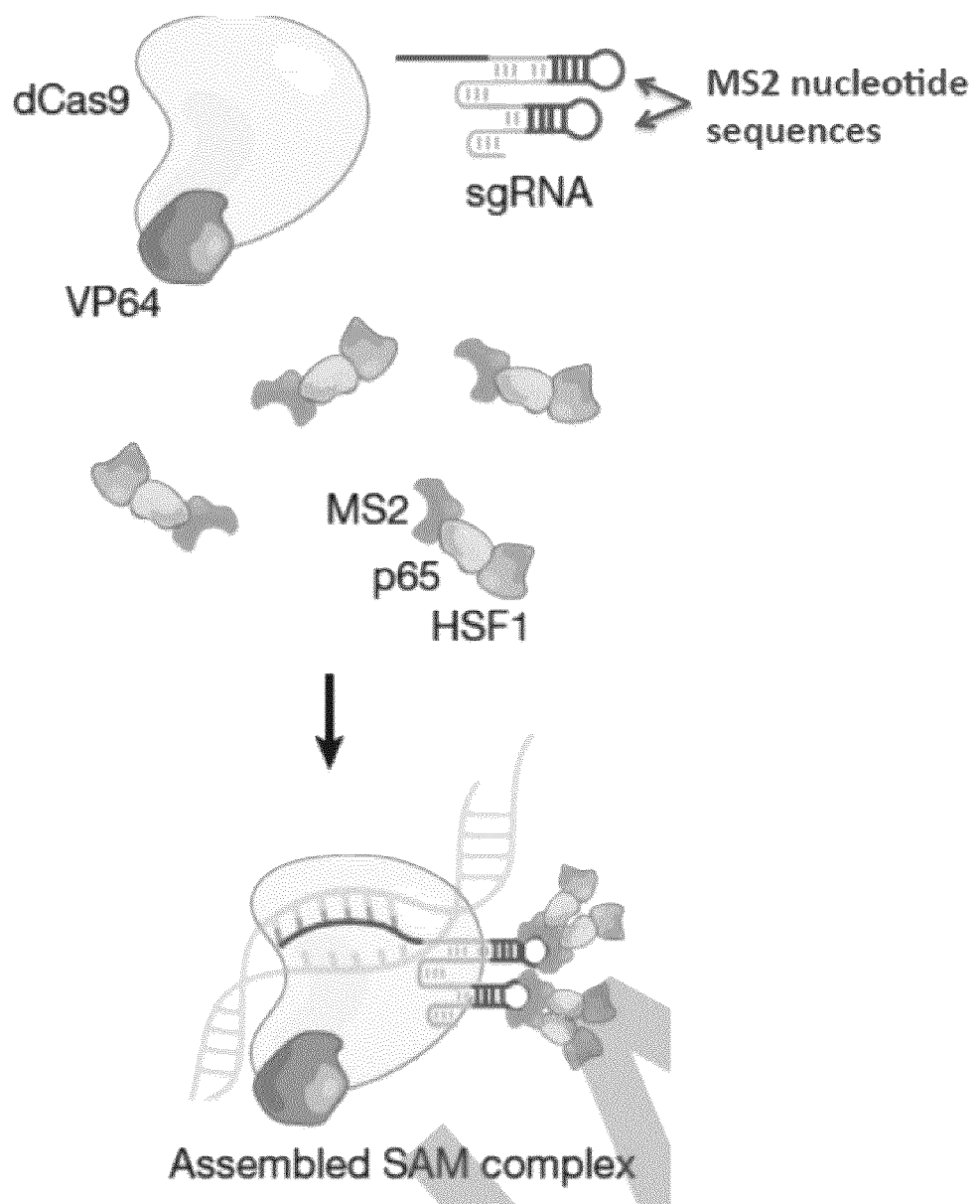
FIG. 14 shows an alternative embodiment of the methods of the present invention using a 3-component system i.e., a modified gRNA, a dCas9-TAD fusion protein and a MS2-p65-HSF1 fusion protein (SEQ ID NO: 10). Two MS2 nucleotide sequences were added: one on the tetraloop and one on the stem loop of the gRNA. A fusion protein comprising the MS2 peptide (SEQ ID NO: 7) and two TADs (e.g., the p65 (SEQ ID NO: 8) and HSF1 (SEQ ID NO: 9) transcription activation domains (TADs)) binds to each of the MS2 nucleotide sequences included in the gRNAs. The presence of 3 TADs (e.g., VP64 on the dCas9 protein and p65 and HSF1) produces a strong synergistic effect on the transcription of the gene (frataxin) targeted by the gRNA. (Figure from Konermann et al., Nature, 2014)

In a second aspect, the CRSPR/dCas9 system of the present invention is a 3-component modified CRISPR system. It comprises a gRNA; a dCas9 fusion protein and a fusion protein having antigen-binding activity (e.g., an antibody or a scFv fragment), which comprises transcription activation domain (e.g., VP16, VP64, VP160). In this system, the dCas9 fusion protein comprises an inactive Cas 9 (dCas9) polypeptide domain lacking nuclease activity and a polypeptide domain comprising at least one epitope. Preferably, multiple repetitions of a peptide epitope (e.g., GCN4 peptide, SEQ ID NO: 4) are fused to dCas9. This peptide epitope is recognized by a fusion protein having antigen-binding activity. The presence of multiple repetitions of the peptide epitopes on the dCas9 fusion protein allows to recruit multiple transcription activation domains (TADs) at a single target site on the frataxin promoter, thereby further increasing its expression. (Tanenbaum et al., Cell, 2014 and FIG. 13);

In a third aspect, the CRISPR/Cas9-based system of the present invention is also a 3-component system. It may comprise a modified gRNA (MS2-gRNA), a dCas9-TAD fusion protein and a MS2-TAD fusion protein. The MS2/TAD fusion protein comprises an MS2 polypeptide (SEQ ID NO: 7) and at least one transcription activation domain. The MS2-gRNA comprises at least one MS2 nucleotide sequence (SEQ ID NO: 68, FIG. 18). In an embodiment, two MS2 nucleotide sequences are included in the gRNA: one on the tetraloop and one on the stem loop of the gRNA. In an embodiment, a fusion protein comprising the MS2 peptide and two TADs (e.g., the p65 and HSF1 transcription activation domains (TADs)) binds to each of the MS2 nucleotide sequences included in the gRNA. The presence of multiple TADs (e.g., the VP64/VP160 on the dCas9/TAD protein and the p65 and HSF1 on the MS2/TAD fusion protein) produces a strong synergistic effect on the transcription of the gene (frataxin) targeted by the gRNA. (Konermann et al., Nature, 2014; see FIG. 14).

In accordance with the present invention, the target frataxin gene may or may not have a hyper-expansion of GAA triplets in intron 1. In an embodiment, the target frataxin gene is a mutated gene comprising at least 50, at least 75, at least 100, at least 150, at least 200, at least 250, at least 300, at least 500 or more GAA triplets in intron 1. In an embodiment, the target frataxin gene is from a subject suffering from FRDA. In an embodiment, the target gene is a normal gene from a healthy subject not suffering from FRDA.

a. Inactive Cas9 (dCas)

The wild type Cas9 protein is an endonuclease that cleaves nucleic acid and is encoded by the CRISPR loci and is involved in the Type II CRISPR system. Cas9 proteins are produced by numerous species of bacteria including *Streptococcus pyogene* (Deltcheva et al. 2011), *Streptococcus thermophiles* (Sapranauskas et al. 2011) and *Neisseria meningitides* (Hou et al. 2013). The CRISPR/Cas9-based system of the present invention uses an inactive Cas9 protein (dCas9) or a dCas9 fusion protein with no endonuclease activity. As used herein, "iCas9" and "dCas9" both refer to a Cas9 protein that has its nuclease activity inactivated. The inactive Cas9 protein used in accordance with the present invention may be derived from a Cas9 from any bacterial or archaea species. The dCas9 fusion protein (i.e., dCas9 polypeptide domain in the dCas9 fusion protein) of the present invention is thus i) derived from any naturally occurring Cas, and ii) lacks a nuclease activity normally associated with such protein. The dCas9 fusion protein comprises at least one amino acid mutation which knocks out nuclease activity of Cas9 (FIG. 19, SEQ ID NO: 35).

In an embodiment, the amino acid sequence of the dCas9 fusion protein of the present invention comprises an amino acid sequence at least 95% (in embodiments at least 96%, 97%, 98% or 99%) identical to the Cas9 sequence set forth in FIG. 19 (SEQ ID NO: 35) and comprises at least one amino acid mutation which knocks out nuclease activity of Cas9.

Several mutations are known to cause inactivation of Cas9 nuclease activity (see for example FIG. 20). The dCas9 fusion protein of the present invention may comprise any mutation or combination of mutations (such as those listed in FIG. 20) as long as it lacks nuclease activity but still provides acceptable target DNA binding activity. In embodiments, the at least one amino acid mutation may be at amino acid position 10 and/or 840, for example the at least one amino acid mutation may be at least one of D10A and H840A with respect to the amino acid numbering of the Cas9 sequence shown in FIG. 19. In other embodiments, the at least one mutation is selected from those listed in FIG. 20. In an embodiment, the at least one mutation is at amino acid position 10, 15, 66, 70, 74, 78, 840 or any combination thereof with respect to the amino acid numbering of the Cas9 amino acid sequence set forth in FIG. 19 (SEQ ID NO: 35). In an embodiment, the amino acid sequence of the dCas9 protein of the present invention comprises an amino acid sequence at least 95% (in embodiments at least 96%, 97%, 98% or 99%) identical to the dCas9 sequence set forth in FIG. 16 (SEQ ID NO: 33). In another embodiment, the amino acid sequence of the dCas9 protein of the present invention comprises an amino acid sequence at least 95% identical to amino acids 10 to 1407 of the sequence set forth in FIG. 3 (SEQ ID NO: 32)

In a particular embodiment, the dCas9 polypeptide domain in the dCas9 fusion protein is derived from *Streptococcus pyogenes* Cas9 (SEQ ID NO: 35) and comprises mutations at amino acid positions 10 and/or 840 (e.g., the mutations D10A and/or H840A). An example of a dCas9 protein is shown in FIG. 16 (SEQ ID NO: 33)).

dCas9 Fusion Proteins and MS2 Fusion Proteins

The CRISPR/Cas9-based system/Frataxin targeting system of the present invention includes one or more (at least one) fusion proteins. The fusion protein may comprise two heterologous polypeptide domains, wherein the first polypeptide domain comprises an inactive Cas9 polypeptide lacking nuclease activity (dCas9) and the second polypeptide domain has an activity heterologous to the dCas9 polypeptide, such as transcription activation activity, or comprises at least one peptide epitope interacting with a second fusion protein having antigen binding activity (antigen-binding protein).

In a first aspect, the fusion protein is a dCas9/TAD fusion protein which comprises a dCas9 polypeptide domain, as described above, fused to a second polypeptide domain that has transcription activation activity, such as a transcription activation domain (TAD), to induce the transcription of the frataxin gene and expression of the frataxin protein when in presence of an appropriate gRNA targeting the frataxin promoter. Thus, in an embodiment, the dCas9/TAD fusion protein of the present invention comprises one or more (i.e., at least one) of a "transcription activation domain" or "trans-activating domain" (TAD), which contains binding sites for other proteins (e.g., transcription co-regulators) and functions for activating transcription of the target frataxin gene and expression of the frataxin protein.

For example, gene expression of endogenous mammalian genes, such as human frataxin gene, may be achieved by targeting a dCas9/TAD fusion protein to the frataxin promoter via one or more gRNAs. The transactivation domain may include a VP16 protein, multiple VP16 proteins, such as a VP48 domain, VP64 domain, VP160 domain or the like. For example, the fusion protein may be dCas9-VP64 or dCas9-VP160 (e.g., SEQ ID NO: 32 or SEQ ID NO: 33) or a functional variant thereof enabling the transcription of the frataxin promoter when in the presence of at least one suitable gRNA.

In another aspect the fusion protein is a dCas9/TAG fusion protein comprising an inactive Cas9 (dCas9) polypeptide domain and a TAG polypeptide domain, comprising at least one polypeptide epitope, e.g., GCN4 polypeptide (SEQ ID NO: 4)) recognized by a second fusion protein or polypeptide having antigen binding activity and transcription activation activity. In an embodiment, the dCas/TAG fusion protein comprises 10 peptide epitopes. In an embodiment, the TAG polypeptide domain of the dCas9 fusion protein comprises at least 2, at least 3, at least 4, at least 5, at least 6, at least 7, at least, 8, at least 9, at least 10, at least 12, at least 16, at least 20 or at least 24 peptide epitopes. In an embodiment, the dCas9/TAD fusion protein comprises 10 GCN4 epitopes. In an embodiment, the TAG polypeptide domain of the dCas9/TAG fusion protein comprises the sequence as set forth in SEQ ID NO: 5 or 6).

Figure 13:
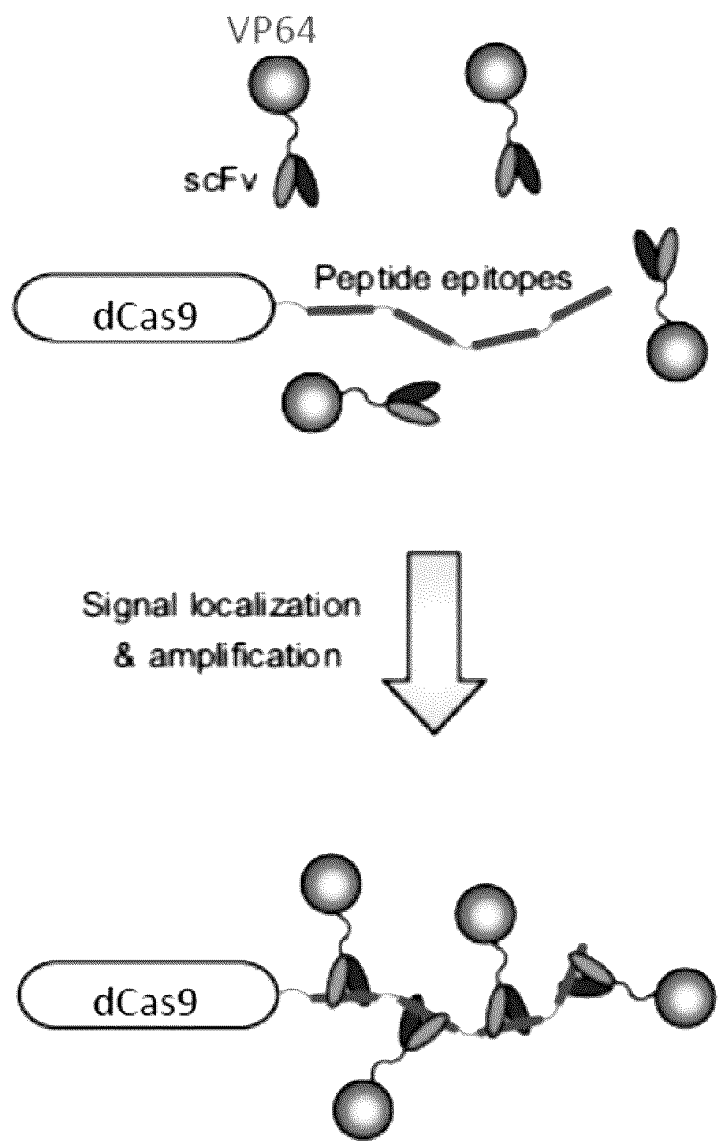
FIG. 13 shows an alternative embodiment of the methods of the present invention using a 3-component modified CRISPR system i.e., a gRNA; a modified dCas9 and a protein having antigen-binding activity (scFv fragment) coupled to a transcription activation domain. In this method, multiple repetitions of a peptide epitope (e.g., GCN4 peptide, SEQ ID NO: 4) are fused to dCas9. This peptide epitope is recognized by an antibody/antibody fragment coupled to a transcription activation domain (e.g., VP64). The presence of multiple repetitions of the peptide epitopes on the dCas9 fusion protein allows recruitment of multiple transcription activation domains (TADs) at a single target site on the frataxin promoter, thereby further increasing its expression. (Figure from Tanenbaum et al., Cell, 2014)

In an embodiment, the second fusion protein (antigen binding fusion protein) has transcription activation activity and is able to bind to the dCas9/TAG fusion protein comprising the at least one peptide epitope. In an embodiment, the antigen-binding fusion protein is an antibody or antigen-binding protein or polypeptide coupled to one or more (at least one) TAD (FIG. 13). In an embodiment, the antigen-binding protein is a single chain variable fragment (ScFv), which is coupled with VP64 or VP160 (Tanenbaum et al., 2014). The one or more transactivation domains allow recruitment of transcriptional activators and effectors at the target site on the frataxin promoter to increase frataxin expression.

In an embodiment, the dCas9/TAG comprises a dCas9 polypeptide fused to multiple repetitions of the peptide epitope (e.g., GCN4 peptide epitope EELLSKNYHLENE-VARLKK, SEQ ID NO: 4, see FIG. 17), interspaced with a linker (e.g., GSGSG, SEQ ID NO: 56).

In a third aspect, the present invention provides a MS2/TAD-fusion protein to be used in conjunction with a modified gRNA and a dCas9/TAD fusion protein having transcription activating activity (comprising one or more TADS). The MS2/TAD fusion protein comprises an MS2 domain (e.g., SEQ ID NO: 7, which recognizes specific nucleotide sequences on a modified gRNA) and at least two TADs (see for example FIG. 15). In an embodiment, the MS2/TAD fusion protein comprises the MS2 polypeptide, the p65 polypeptide (SEQ ID NO: 8, FIG. 15C) and HSF1 polypeptide (SEQ ID NO: 9, FIG. 15D). In an embodiment, the MS2 fusion protein comprises the sequence set forth in FIG. 15A (SEQ ID NO: 10), or a variant thereof which has transcription activation activity and which binds to a modified gRNA comprising the MS2 nucleotide sequence (FIG. 18 and SEQ ID NO: 68). Preferably, the MS2 fusion protein comprises a linker between the MS2 domain and the TADs. FIG. 15 shows the amino acid sequence of the MS2-p65-HSF1 fusion protein according to an embodiment of the present invention.

gRNAs

The gRNA provides the targeting specificity of the present invention. The gRNA provides both targeting specificity and scaffolding/binding ability for of the CRISPR/dCas9-based system. The gRNA of the present invention does not exist in nature, i.e., is a non naturally-occurring nucleic acid.

The gRNA of the present invention generally comprises (or consists of) a "gRNA guide sequence" or "gRNA target sequence" and a Cas (e.g., Cas9) recognition sequence", which is necessary for Cas/dCas (e.g., Cas9/dCas9) binding to the targeted frataxin gene. In a particular embodiment, the Cas9 recognition sequence comprises (or consists of) the sequence (SEQ ID NO: 67). The gRNA of the present invention may comprise any variant of this sequence, provided that it allows for the binding of the dCas9 fusion protein of the present invention on the frataxin target promoter sequence.

A "gRNA target sequence", or "gRNA guide sequence" is the nucleic acid sequence that binds to the target frataxin gene. This sequence immediately precedes (i.e., is 5' to) the PAM sequence in the genomic frataxin DNA. It is what gets put into a gRNA expression construct (e.g., vector/plasmid/AVV), it does NOT include the PAM sequence. The "PAM" (Protospacer Adjacent Motif) is the nucleic acid sequence, that immediately follows (is contiguous) to the target sequence on the frataxin gene but is not in the gRNA.

A "target region", "target sequence" or "protospacer" as used interchangeably herein refers to the region of the target gene which is targeted by the CRISPR/dCas9-based system, without the PAM. The CRISPR/dCas9-based system may include at least one gRNA, wherein the gRNAs target different DNA sequences on the frataxin promoter. The target DNA sequences may be overlapping. The target sequence or protospacer is followed by (e.g., (is contiguous to) a PAM sequence at the 3' end of the protospacer. In an embodiment, the target sequence is immediately adjacent to the PAM sequence and is located on the 5' end of the PAM.

The gRNA comprises a "gRNA guide sequence" or "gRNA target sequence", which corresponds to the target sequence on the frataxin DNA promoter that is followed by a PAM sequence. The gRNA may comprise a "G" at the 5' end of the polynucleotide sequence. The CRISPR/dCas9 system of the present invention may use gRNA of varying lengths. The gRNA may comprise at least a 10 nts, at least 11 nts, at least a 12 nts, at least a 13 nts, at least a 14 nts, at least a 15 nts, at least a 16 nts, at least a 17 nts, at least a 18 nts, at least a 19 nts, at least a 20 nts, at least a 21 nts, at least a 22 nts, at least a 23 nts, at least a 24 nts, at least a 25 nts, at least a 30 nts, or at least a 35 nts of the target frataxin promoter DNA sequence which is followed by a PAM sequence. The "gRNA guide sequence" or "gRNA target sequence" may be least 17 nucleotides (17, 18, 19, 20, 21, 22, 23), preferably between 17 and 30 nts long, more preferably between 18-22 nucleotides long. In an embodiment, gRNA guide sequence is between 10-40, 10-30, 12-30, 15-30, 18-30, or 10-22 nucleotides long. The PAM sequence may be "NGG", where "N" can be any nucleotide. gRNA may target any region of the frataxin promoter, which is immediately upstream (contiguous, adjoining, in 5') to a PAM (e.g., NGG) sequence including an enhancer region of the frataxin gene (Ensembl ENSG00000165060; OMIM: 606829, see also partial frataxin promoter sequence on FIG. 2). In an embodiment, the gRNA may target any region, which is followed by a PAM identified on the frataxin promoter sequence of FIG. 2 (SEQ ID NO: 11)).

Although a perfect match between the "gRNA guide sequence" and the DNA strand to which it binds on the frataxin promoter is preferred, a mismatch between a gRNA guide sequence and a target base on the frataxin promoter sequence is also permitted as along as it still allows for an increase in frataxin expression. A "seed" sequence of between 8-12 consecutive nucleotides on the gRNA perfectly complementary to the target gene sequence is preferred for proper recognition of the target sequence on the frataxin promoter. The remainder of the guide sequence may comprise one or more mismatch.

In general, gRNA activity is inversely correlated with the number of mismatches. Preferably, the gRNA of the present invention comprises 7 mismatches, 6 mismatches, 5 mismatches, 4 mismatches, 3 mismatches, more preferably 2 mismatches, or less, and even more preferably no mismatch, with the corresponding target frataxin promoter sequence. The smaller the number of nucleotides in the gRNA the smaller the number of mismatches tolerated. The binding affinity is thought to depend on the sum of matching gRNA-DNA combinations.

Non-limiting examples of gRNAs guide sequences are presented in FIG. 18. In a particular embodiment, the "gRNA guide sequence" comprises or consists of a nucleic acid sequence as set forth in SEQ ID NOs: 69-73. In an embodiment, the gRNA comprises the target sequence of nucleotides positions 4246-4264; positions 4652-4670; Positions 4841-4859; positions 5005-5023; or positions 5089-5107; of the frataxin promoter polynucleotide sequence having NCBI reference number NG_008845 (see also FIG. 2 and SEQ ID NO: 87).

In an embodiment, the gRNA target sequence on the frataxin promoter ends at position 5107 (or comprises a sequence including position 5107 and upstream) with respect to the nucleotide sequence shown in FIG. 2 (i.e., is adjacent to the NGG sequence beginning at position 5108). In an embodiment, the gRNA target sequence on the frataxin promoter ends at position 4859 (or comprises a sequence including position 4859 and upstream) with respect to the nucleotide sequence shown in FIG. 2 (i.e., is adjacent to the NGG sequence beginning at position 4860). In an embodiment, the gRNA target sequence on the frataxin promoter ends at position 4670 (or comprises a sequence including position 4670 and upstream) with respect to the nucleotide sequence shown in FIG. 2 (i.e., is adjacent to the NGG sequence beginning at position 4671). In an embodiment, the gRNA target sequence on the frataxin promoter ends at position 4701 (or comprises a sequence including position 4701 and upstream) with respect to the nucleotide sequence shown in FIG. 2 (i.e., is adjacent to the NGG sequence beginning at position 4702. In an embodiment, the gRNA target sequence on the frataxin promoter ends at position 44742 (or comprises a sequence including position 4742 and upstream) with respect to the nucleotide sequence shown in FIG. 2 (i.e., is adjacent to the NGG sequence beginning at position 4743).

In an embodiment, the gRNA target sequence on the frataxin promoter is not rich in polyG or polyC. In an embodiment, the gRNA target sequence on the frataxin promoter does not comprise more than one PAM (e.g., NGG sequence). In an embodiment, the gRNA target sequence on the frataxin promoter does not include an NGG (although it is adjacent to a PAM). In an embodiment, the gRNA target sequence comprises between 10-22 consecutive nucleotides, preferably 18-22 consecutive nucleotides upstream of and adjacent to a PAM (NGG sequence) located between:
  nucleotides 3961-4258;
  nucleotides 4268-49513;
  nucleotides 4268-4996
  nucleotides 5027-5150;
  nucleotides 4268-4595;
  nucleotides 4621-4996;
  nucleotides 4561-4996; or
  nucleotides 4280-5000;
of the frataxin promoter sequence shown in FIG. 2 (NG_008845; SEQ ID NO: 87).

The number of gRNAs administered to or expressed in a cell or subject in accordance with the methods of the present invention may be at least 1 gRNA, at least 2 gRNAs, at least 3 gRNAs at least 4 gRNAs, at least 5 gRNAs, at least 6 gRNAs, at least 7 gRNAs, at least 8 gRNAs, at least 9 gRNAs, at least 10 gRNAs, at least 11 gRNAs, at least 12 gRNAs, at least 13 gRNAs, at least 14 gRNAs, at least 15 gRNAs, at least 16 gRNAs, at least 17 gRNAs, or at least 18 gRNAs. The number of gRNAs administered to or expressed in a cell may be between at least 1 gRNA and at least 15 gRNAs, at least 1 gRNA to and least 10 gRNAs, at least 1 gRNA and at least 8 gRNAs, at least 1 gRNA and at least 6 gRNAs, at least 1 gRNA and at least 4 gRNAs, at least 1 gRNA to and least 3 gRNAs, at least 2 gRNA and at least 5 gRNAs, at least 2 gRNA and at least 3 gRNAs.

In a particular embodiment a combination of at least two gRNAs comprising a gRNA guide sequence as shown in FIG. 18 (SEQ ID NOs: 69-73) are used together to increase frataxin expression. In a particular embodiment, a combination of at least two gRNAs comprising a gRNA guide sequence comprising (or consisting of) the sequence i) AGCUGGGAAGUUCUUCCUG (CRISP A, SEQ ID NO: 69); ii) ACACAAGGCAUCCGUCUCC (CRISP C, SEQ ID NO: 71); or iii) UAUUUAUUGUGCACUUAAC (CRISP D, SEQ ID NO: 72) are used together to increase frataxin expression in a cell.

Trans-Activating Domains (TADs)

"Trans-activating domain(s)" or "transcription activation domain(s)" (TAD(s)) used in the context of the present invention refers to a polypeptide which has transcriptional activity (is able to activate or enhance transcription of a target nucleic acid). TADs are typically named after their amino acid composition. These amino acids are either essential for the activity or simply the most abundant in the TAD. Transactivation by the Gal4 transcription factor is mediated by acidic amino acids, whereas hydrophobic residues in Gcn4 play a similar role. Hence, the TADs in Gal4 and Gcn4 are referred to as acidic or hydrophobic activation domains, respectively.

Nine-amino-acid transactivation domain (9 aaTAD) defines a novel domain common to a large superfamily of eukaryotic transcription factors represented by Gal4, Oaf1, Leu3, Rtg3, Pho4, Gln3, Gcn4 in yeast and by p53, NFAT, NF-κB and VP16 in mammals. Prediction for 9 aa TADs (for both acidic and hydrophilic transactivation domains) is available online from ExPASy™ and EMBnet™ databases.

KIX domain of general coactivators Med15(Gal11) interacts with 9 aa TAD transcription factors Gal4, Pdr1, Oaf1, Gcn4, VP16, Pho4, Msn2, Ino2 and P201. 9aaTAD is a common transactivation domain which recruits multiple general coactivators (e.g., TAF9, MED15, CBP/p300 and GCN5). Accordingly, non-limiting examples of TAD that may be used in accordance with the present invention include TAD from Gal4, Pdr1, Oaf1, Gcn4, Pho4, Msn2, Ino2, P201, p53, Gli3, Pdr3, CREB, Rtg3, VP16, MLL, E2A, HSF1, NF-IL6, NFAT1 and NF-κβ. Other non-limiting examples of TAD include TAD from the SRF, TFAP2 or SP1 transcription factor, for which target sequences have been identified in the frataxin promoter (Li et al., 2010). Of course, the choice of a TAD will depend on numerous factors including the specific type of cells in which the gene will be expressed as well as the nature of the gene. Furthermore, one can appreciate that more than one TAD may be included in a fusion protein of the present invention (e.g., dCas9/TAD construct; MS2/TAD peptide construct or antigen-binding protein/TAD construct) of the present invention. Similarly, Also, a plurality of TADs having the same or different peptide sequences can be used in accordance with the present invention. In an embodiment, the TAD fused to the dCas9 protein/MS2 fusion or antibody/fragment thereof of the present invention is VP160 which corresponds to 10 times the sequence of the VP16 TAD (see FIGS. 4 and 5). In an embodiment, the TAD has the sequence DALDD-FDLDML (SEQ ID NO: 17) repeated 1-15 times, preferably 5 to 12 times, more preferably 10 times. Each TAD repeat is normally insterspaced by small linker sequences (e.g., two amino acid linker GS).

(NLS). Accordingly, as used herein the expression "nuclear localization signal" or "NLS" refers to an amino acid sequence, which 'directs' a protein for import into the cell nucleus by nuclear transport. Typically, this signal consists of one or more short sequences of positively charged lysines or arginines exposed on the protein surface. Different nuclear localized proteins may share the same NLS. An NLS has the opposite function of a nuclear export signal, which targets proteins out of the nucleus. Classical NLSs can be further classified as either monopartite or bipartite. The first NLS to be discovered was the sequence PKKKRKV (SEQ ID NO: 12) in the SV40 Large T-antigen (a monopartite NLS). The NLS of nucleoplasmin, KR[PAATKKAGQA]KKKK (SEQ ID NO: 13), is the prototype of the ubiquitous bipartite signal: two clusters of basic amino acids, separated by a spacer of about 10 amino acids.

There are many other types of NLS, which are the to be "non-classical", such as the acidic M9 domain of hnRNP A1, the sequence KIPIK in yeast transcription repressor Mata2, the complex signals of U snRNPs as well as a recently identified class of NLSs known as PY-NLSs. Thus, any type of NLS (classical or non-classical) may be used in accordance with the present invention as long as it targets the protein of interest into the nucleus of a target cell. Preferably, the NLS is derived from the simian virus 40 large T antigen. In an embodiment, the NLS of the dCas9 fusion proteins of the present invention comprises the following amino acid sequence: SPKKKRKVEAS (SEQ ID NO: 14). In an embodiment the NLS comprises the sequence KKKRKV (SEQ ID NO: 15). In an embodiment, the NLS comprises the sequence SPKKKRKVEASPKKKRKV (SEQ ID NO: 16). In another embodiment, the NLS comprises the sequence KKKRK (SEQ ID NO: 109).

TABLE 1

Examples of TADs from transcription factors.

| Transcription factor | 9aaTAD | Peptide-KIX interaction (NMR data) |
|---|---|---|
| P53 TAD1 | E TFSD LWKL (SEQ ID NO: 19) | LSPEETFSD LWKLPE (SEQ ID NO: 102) |
| P53 TAD2 | D DIEQ WFTE (SEQ ID NO: 20) | QAMDDLMLSPD DIEQ WFTEDPGPD (SEQ ID NO: 103) |
| MLL | S DIMD FVLK (SEQ ID NO: 21) | DCGNILPS DIMD FVLKNTP (SEQ ID NO: 104) |
| EA2 | D LLDF SMMF (SEQ ID NO: 22) | PVGTDKELSDLLDF SMMFPLPVT (SEQ ID NO: 105) |
| Rtg3 | E TLDF SLVT (SEQ ID NO: 23) | E2A Homolog |
| CREB | RKILNDLSS (SEQ ID NO: 24) | RREILSRRPSYRKILNDLSSDAP (SEQ ID NO: 106) |
| CREBαB6 | E AILAELKK (SEQ ID NO: 25) | CREB-mutant binding to KIX |
| Gli3 | DDVVQYLNS (SEQ ID NO: 26) | TAD homology to CREB/KIX |
| Gal4 | DDVYNYLFD (SEQ ID NO: 27) | Pdr1 and Oaf1 homolog |
| Oaf1 | DLFDYDFLV (SEQ ID NO: 28) | DLFDYDFLV (SEQ ID NO: 107) |
| Pip2 | DFFDYDLLF (SEQ ID NO: 29) | Oaf1 homolog |
| Pdr1 | EDLYSILWS (SEQ ID NO: 30) | EDLYSILWSDWY (SEQ ID NO: 108) |
| Pdr3 | TDLYHTLWN (SEQ ID NO: 31) | Pdr1 homolog |

Nuclear Localization Signal

The fusion recombinant proteins of the present invention may also comprises at least one Nuclear Localization Signal Protein Transduction Domains The fusion recombinant proteins of the present invention (e.g., dCas9/TAD, dCas9/TAG or MS2/TAD) of the present invention may also be coupled to a protein transduction domain to ensure entry of the protein into the target cells. Alternatively the gene coding for the gRNA and for the fusion proteins of the present invention may be delivered to the cells using various vectors, e.g., viral vectors.

Protein transduction domains (PTD) may be of various origins and allow intracellular delivery of a given therapeutic by facilitating the translocation of the protein/polypeptide into a cell membrane, organelle membrane, or vesicle membrane. PTD refers to a polypeptide, polynucleotide, carbohydrate, or organic or inorganic compound that facilitates traversing a lipid bilayer, micelle, cell membrane, organelle membrane, or vesicle membrane. A PTD attached to another molecule facilitates the molecule traversing a membrane, for example going from extracellular space to intracellular space, or cytosol to within an organelle including the mitochondria. In an embodiment, a PTD is covalently linked to the amino terminus of a recombinant protein of the present invention. In another embodiment, a PTD is covalently linked to the carboxyl terminus of a recombinant protein of the present invention. Exemplary protein transduction domains include but are not limited to a minimal undecapeptide protein transduction domain (corresponding to residues 47-57 of HIV-1 TAT comprising YGRKKRRQRRR (SEQ ID NO: 37); a polyarginine sequence comprising a number of arginines sufficient to direct entry into a cell (e.g., 3, 4, 5, 6, 7, 8, 9, 10, or 10-50 arginines); a VP22 domain (Zender et al. 2002); an Drosophila Antennapedia protein transduction domain (Noguchi et al. 2003); a truncated human calcitonin peptide (Trehin et al. 2004); RRQR-RTSKLMKR (SEQ ID NO: 38); Transportan GWTLN-SAGYLLGKINLKALAALAKKIL (SEQ ID NO: 39); KALAWEAKLAKALAKALAKHLAKALAKALKCEA (SEQ ID NO: 40); and RQIKIWFQNRRMKWKK (SEQ ID NO: 41). Further exemplary PTDs include but are not limited to, KKRRQRRR (SEQ ID NO: 42), RKKRRQRRR (SEQ ID NO: 43); or an arginine homopolymer of from 3 arginine residues to 50 arginine residues.

Other non-limiting examples of PTD include an endosomal escape peptide. Non-limiting examples of such endosomal escape peptides are listed in the Table 2 below.

TABLE 2

Endosomal escape peptides

| Peptide | Primary sequence | Mechanism | References |
|---|---|---|---|
| DT | VGSSLSCINLDWDVIRDKTKTKIE SLKEHGPIKNKMSESPNKTVSEE KAKQYLEEFHQTALEHPELSELKT VTGTNPVFAGANYAAWAVNVAQ VIDSETADNLEKTTAALSILPGIGS VMGIADGAVHHNTEEIVAQSIALS SLMVAQAIPLVGELVDIGFAAYNF VESIINLFQVVHNSYNRPAYSPG | Fusion | (Kakimoto et al. 2009) (SEQ ID NO: 44) |
| GALA | WEAALAEALAEALAEHLAEALAE ALEALAA | Membrane destabilization, pore formation and flip-flop of membrane lipids | (Kakudo et al. 2004) (SEQ ID NO: 45) |
| PEA | VLAGNPAKHDLDIKPTVISHRLHF PEGGSLAALTAHQACHLPLETFT RHRQPRGWEQLEQCGYPVQRLV ALYLAARLSWNQVDQVIRNALAS PGSGGDLGEAIREQPEQARLALT | Pore formation | (Fominaya, Uherek and Wels 1998) (SEQ ID NO: 46) |
| INF-7 | GLFEAIEGFIENGWEGMIDGWYG C | Membrane fusion and destabilization | (El-Sayed, Futaki and Harashima 2009) (SEQ ID NO: 47) |
| LAH4 | KKALLALALHHLAHLALHLALALK KA | Membrane destabilization | (Kichler et al. 2003) (SEQ ID NO: 48) |
| CM18 | KWKLFKKIGAVLKVLTTG | Membrane destabilization | (Salomone et al. 2012) (SEQ ID NO: 49) |
| HGP | LLGRRGWEVLKYWWNLLQYWS QEL | Pore formation and fusion | (Kwon, Bergen and Pun 2008) (SEQ ID NO: 50) |
| H5WYG | GLFHAIAHFIHGGWH GLIHGWYG | Membrane destabilization | (Midoux et al. 1998) (SEQ ID NO: 51) |
| HA2 | GLFGAIAGFIENGWEGMIDGWYG | Membrane fusion and destabilization | (Lorieau, Louis and Bax 2010) (SEQ ID NO: 52) |
| EB1 | LIRLWSHLIHIWFQNRRLKWKKK | Membrane destabilization | (Lundberg et al. 2007) (SEQ ID NO: 53) |

In an embodiment, the protein transduction domain is TAT or Pep-1. In an embodiment, the protein transduction domain is TAT and comprises the sequence SGYGRK-KRRQRRRC (SEQ ID NO: 36). In another embodiment, the protein transduction domain is TAT and comprises the sequence YGRKKRRQRRR (SEQ ID NO: 37). In another embodiment, the protein transduction domain is TAT and comprises the sequence KKRRQRRR (SEQ ID NO: 42). In another embodiment, the protein transduction domain is Pep-1 and comprises the sequence KETWWETWWTEWS-QPKKKRKV (SEQ ID NO: 54). In addition or alternatively to the above-mentioned protein transduction domains, the fusion recombinant protein of the present invention may be coupled to liposomes to further facilitate translocation into the cell and mitochondria.

Genetic constructs encoding a dCas/TAD protein in accordance with the present invention can be made using either conventional gene synthesis or modular assembly. A humanized Cas9 nucleic acid is available at the public, not-for-profit repository by AddGene (for example AddGene plasmid pAC154).

In an aspect, the gRNAs; dCas/TAD; dCas/TAG and/or MS2/TAD recombinant fusion proteins of the present invention may be used to increase/induce expression of the frataxin nucleic acid and the frataxin protein in cells. As used herein, the expression "increasing" in "increasing the expression of frataxin in a cell" is meant to include circumstances where, in the absence of a gRNA and of a Cas9 recombinant protein of the present invention, the frataxin protein is not expressed at all in the cell and where the cell already expresses a certain amount (baseline amount) of frataxin protein. It comprises increasing/enhancing expression of frataxin in cells expressing no frataxin, a normal level of frataxin or an abnormal/lower level of frataxin (as compared to normal conditions).

In an embodiment, the gRNA and recombinant fusion proteins of the present invention may be used to increase transcription of the frataxin promoter and expression of the frataxin protein in cells from a subject in need thereof.

As used herein, "a subject in need thereof" is a subject, which may benefit from an increased expression of the frataxin protein or of increased levels of the frataxin protein. Non-limiting examples of a subject in need thereof include a subject having cells showing a reduced level of frataxin expression or activity as compared to cells from a normal subject. In an embodiment, the subject in need thereof is a subject having an abnormal number of trinucleotide repeats in intron 1 of the frataxin gene. In an embodiment, the number of trinucleotide repeats is 35 or more, 65 or more, 75 or more, 85 or more, 100 or more, 110 or more, 125 or more, 150 or more, 175 or more, 200 or more, 225 or more, 250 or more, 300 or more, 350 or more, 500 or more or 1000 or more. In an embodiment, the subject in need thereof suffers from Friedreich ataxia. In an embodiment, the subject is a mammal, preferably, a human.

In an embodiment, the present invention relates to a method of increasing frataxin expression in a subject in need thereof comprising administering to the subject an effective amount of at least one gRNA and at least one (in embodiments at least two) recombinant fusion protein of the present invention (e.g., dCas/TAD; dCas/TAG; antigen-binding protein/TAD and/or MS2/TAD). In an embodiment, the recombinant protein is specifically formulated for crossing the plasma membrane and reaching the nucleus. In an embodiment, the present invention provides a composition comprising at least one (in embodiments at least two) recombinant fusion protein (e.g., (e.g., dCas/TAD; dCas/TAG; antigen-binding protein/TAD and/or MS2/TAD) of the present invention together with a pharmaceutically or physiologically acceptable carrier.

In an embodiment, the present invention relates to a method of increasing frataxin levels in a subject in need thereof, comprising administering to the subject an effective amount of at least one of the fusion proteins of the present invention ((e.g., dCas/TAD; dCas/TAG; antigen-binding protein/TAD and/or MS2/TAD) together with at least one gRNA targeting the frataxin promoter. In an embodiment, the present invention provides a composition comprising a recombinant fusion protein of the present invention together with a pharmaceutically or physiologically acceptable carrier.

Optimization of Codon Degeneracy

Because Cas nuclease proteins are normally expressed in bacteria, it may be advantageous to modify their nucleic acid sequences for optimal expression in eukaryotic cells (e.g., mammalian cells) when designing and preparing Cas recombinant proteins. This has already been done for the embodiment of the dCas9/TAD protein of the present invention described herein.

Accordingly, the following codon chart (Table 3) may be used, in a site-directed mutagenic scheme, to produce nucleic acids encoding the same or slightly different amino acid sequences of a given nucleic acid:

TABLE 3

Codons encoding the same amino acid

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

Sequence Similarity

"Homology" and "homologous" refers to sequence similarity between two peptides or two nucleic acid molecules. Homology can be determined by comparing each position in the aligned sequences. A degree of homology between nucleic acid or between amino acid sequences is a function of the number of identical or matching nucleotides or amino acids at positions shared by the sequences. As the term is used herein, a nucleic acid sequence is "substantially homologous" to another sequence if the two sequences are substantially identical and the functional activity of the sequences is conserved (as used herein, the term "homologous" does not infer evolutionary relatedness, but rather refers to substantial sequence identity, and thus is interchangeable with the terms "identity"/"identical"). Two nucleic acid sequences are considered substantially identical if, when optimally aligned (with gaps permitted), they share at least about 50% sequence similarity or identity, or if the sequences share defined functional motifs. In alternative embodiments, sequence similarity in optimally aligned substantially identical sequences may be at least 60%, 70%, 75%, 80%, 85%, 90% or 95%. For the sake of brevity, the units (e.g., 66, 67 . . . 81, 82, . . . 91, 92% . . . ) have not systematically been recited but are considered, nevertheless, within the scope of the present invention.

Substantially complementary nucleic acids are nucleic acids in which the complement of one molecule is substantially identical to the other molecule. Two nucleic acid or protein sequences are considered substantially identical if, when optimally aligned, they share at least about 70% sequence identity. In alternative embodiments, sequence identity may for example be at least 75%, at least 80%, at least 85%, at least 90%, at least 95%, at least 96%, at least 98% or at least 99%. Optimal alignment of sequences for comparisons of identity may be conducted using a variety of algorithms, such as the local homology algorithm of Smith and Waterman, 1981, Adv. Appl. Math 2: 482, the homology alignment algorithm of Needleman and Wunsch, 1970, J. Mol. Biol. 48:443, the search for similarity method of Pearson and Lipman (Pearson and Lipman 1988), and the computerized implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al. (Altschul et al. 1990) 1990 (using the published default settings). Software for performing BLAST analysis may be available through the National Center for Biotechnology Information (through the internet at http://www.ncbi.nlm.nih.gov/). The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold. Initial neighborhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, conditions. Hybridization to filter-bound sequences under moderately stringent conditions may, for example, be performed in 0.5 M NaHPO4, 7% sodium dodecyl sulfate (SDS), 1 mM EDTA at 65° C., and washing in 0.2×SSC/0.1% SDS at 42° C. (Ausubel 2010). Alternatively, hybridization to filter-bound sequences under stringent conditions may, for example, be performed in 0.5 M NaHPO4, 7% SDS, 1 mM EDTA at 65° C., and washing in 0.1×SSC/0.1% SDS at 68° C. (Ausubel 2010). Hybridization conditions may be modified in accordance with known methods depending on the sequence of interest (Tijssen 1993). Generally, stringent conditions are selected to be about 5° C. lower than the thermal melting point for the specific sequence at a defined ionic strength and pH.

In another aspect, the invention further provides a nucleic acid encoding the above-mentioned fusion proteins ((e.g., dCas/TAD; dCas/TAG; antigen-binding protein/TAD and/or MS2/TAD) and gRNAs. In an embodiment, the nucleic acid encoding dCas9 is as set forth in SEQ ID NO: 93. In an embodiment, the nucleic acid encoding for VP16 is as set forth in SEQ ID NO: 94. In an embodiment, the nucleic acid encoding VP160 is as set forth in SEQ ID NO: 95. In an embodiment, the nucleic acid encoding a GCN4 epitope with the linker is as set forth in SEQ ID NO: 96. In an embodiment, the nucleic acid encoding a GCN4 epitope epitope is as set forth in SEQ ID NO: 97. In an embodiment, the nucleic acid encoding a MS2 polypeptide is as set forth in SEQ ID NO: 98. In an embodiment, the nucleic acid encoding a p65 TAD is as set forth in SEQ ID NO: 99. In an embodiment, the nucleic acid encoding a HSF1 polypeptide is as set forth in SEQ ID NO: 100. The invention also provides a vector comprising the above-mentioned nucleic acid. In an embodiment, the vector further comprises a transcriptional regulatory element operably-linked to the above-mentioned nucleic acid. A first nucleic acid sequence is "operably-linked" with a second nucleic acid sequence when the first nucleic acid sequence is placed in a functional relationship with the second nucleic acid sequence. For instance, a promoter is operably-linked to a coding sequence if the promoter affects the transcription or expression of the coding sequences. Generally, "operably-linked" DNA sequences are contiguous and, where necessary to join two protein coding regions, in reading frame. However, since, for example, enhancers generally function when separated from the promoters by several kilobases and intronic sequences may be of variable lengths, some polynucleotide elements may be operably-linked but not contiguous. "Transcriptional regulatory element" is a generic term that refers to DNA sequences, such as initiation and termination signals, enhancers, and promoters, splicing signals, polyadenylation signals, which induce or control transcription of protein coding sequences with which they are operably-linked.

As indicated above, gRNAs and fusion proteins of the present invention (e.g., dCas/TAD, dCas9/TAG, MS2/TAD and antigen binding protein/TAD) of the present invention may be delivered into cells using one or more various viral vectors. Accordingly, preferably, the above-mentioned vector is a viral vector for introducing the gRNA and/or fusion protein of the present invention in a target cell. Non-limiting examples of viral vectors include retrovirus, lentivirus, Herpes virus, adenovirus or Adeno Associated Virus, as well known in the art.

The modified MV vector preferably targets one or more cell types expressing frataxin and affected in FRDA subjects. Accordingly, the modified AAV vector may have enhanced cardiac (e.g., cardiomyocytes), skeletal muscle, neuronal, liver, and/or pancreatic (e.g., Langerhans cells) tissue tropism. The modified AAV vector may be capable of delivering and expressing the at least one gRNA and fusion proteins of the present invention in the cell of a mammal. For example, the modified AAV vector may be an AAV-SASTG vector (Piacentino et al. (2012) Human Gene Therapy 23:635-646). The modified AAV vector may preferably deliver gRNAs and fusion proteins to neuronal, skeletal, pancreatic (e.g., Langherans cells) and cardiac (e.g., cardiomyocytes) muscle in vivo. The modified AAV vector may be based on one or more of several capsid types, including AAVI, AAV2, AAV5, AAV6, AAV8, and AAV9. The modified AAV vector may be based on AAV2 pseudotype with alternative muscle-tropic AAV capsids, such as AAV2/1, AAV2/6, AAV2/7, AAV2/8, AAV2/9, AAV2.5 and AAV/SASTG vectors that efficiently transduce skeletal muscle or cardiac muscle by systemic and local delivery. In an embodiment, the modified AAV vector is a AAV-DJ. In an embodiment, the modified AAV vector is a AAV-DJ8 vector. In an embodiment, the modified AAV vector is a AAV2-DJ8 vector.

In yet another aspect, the present invention provides a cell (e.g., a host cell) comprising the above-mentioned nucleic acid and/or vector. The invention further provides a recombinant expression system, vectors and host cells, such as those described above, for the expression/production of a recombinant protein, using for example culture media, production, isolation and purification methods well known in the art.

In another aspect, the present invention provides a composition (e.g., a pharmaceutical composition) comprising the above-mentioned gRNA and dCas9/TAD recombinant protein. In an embodiment, the composition further comprises one or more pharmaceutically acceptable carriers, excipients, and/or diluents.

As used herein, "pharmaceutically acceptable" (or "biologically acceptable") refers to materials characterized by the absence of (or limited) toxic or adverse biological effects in vivo. It refers to those compounds, compositions, and/or dosage forms which are, within the scope of sound medical judgment, suitable for use in contact with the biological fluids and/or tissues and/or organs of a subject (e.g., human, animal) without excessive toxicity, irritation, allergic response, or other problem or complication, commensurate with a reasonable benefit/risk ratio.

The present invention further provides a kit or package comprising at least one container means having disposed therein at least one of the above-mentioned gRNAs, fusion proteins; vectors, cells, frataxin targeting systems, combinations or compositions, together with instructions for increasing frataxin expression or levels in a cell or for treatment of Friedreich ataxia in a subject.

The present invention is illustrated in further details by the following non-limiting examples.

EXAMPLE 1 gRNA Efficiently Promotes Frataxin Expression in 293T Cells

Expression plasmids containing a gene coding for one of the gRNA under the U6 promoter and the dCas9 nuclease under the CAG promoter have been produced (see table 4 below and FIGS. 4 and 18). The original plasmid was obtained from Addgene (pAC154-dual-dCas9VP160-sgExpression-plasmid no. 48240). The resulting dCas9 protein comprises two NLS, one HA tag and a VP160 transactivation domain (See FIG. 3, (SEQ ID NO: 32)). The gRNAs produced target different nucleotide sequences in the promoter of the human frataxin gene (ACCESSION NG_008845, see Table 4 below and FIGS. 2 and 18).

TABLE 4 gRNAs targeting the human frataxin promoter

| gRNA name | Position of targeted nucleotides with reference to the sequence shown in FIG. 2 | Targeted nucleotide sequence in the frataxin promoter | SEQ ID NO: (RNA/DNA) |
|---|---|---|---|
| A | 5089-5107 | AGCTGGGAAGTTCTTCCTG | 69/88 |
| B | 5005-5023 | TCCCTTGGGTCAGGGGTCC | 70/89 |
| C | 4841-4859 | ACACAAGGCATCCGTCTCC | 71/90 |
| D | 4652-4670 | TATTTATTGTGCACTTAAC | 72/91 |
| E | 4246-4264 | GCTACTTGGAAGGCTGAAA | 73/92 |

Figure 6:
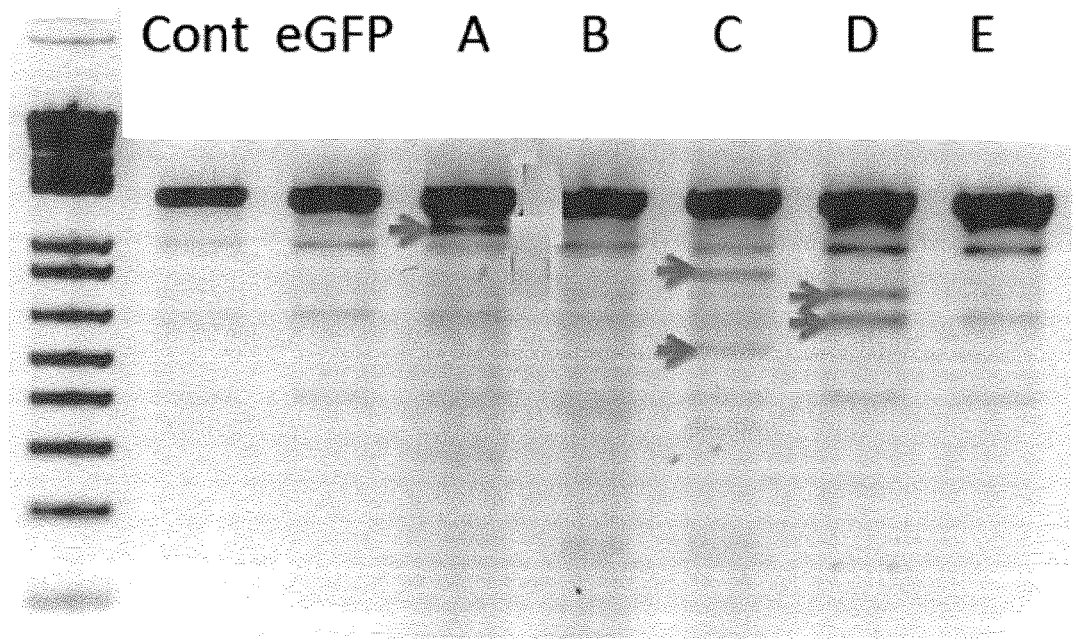
FIG. 6 shows that gRNAs of the present invention can efficiently bind to their target sequence on the frataxin promoter. Results are from a surveyor enzyme test for lysates obtained from 293T cells transfected with an active Cas9 nuclease and each of the exemplary gRNAs (named A, B, C, D and E) targeting the promoter of the human Frataxin gene (see FIG. 2 and SEQ ID NO: 11). The control lane corresponds to untransfected cells. When the gRNA binds to its target, the Cas9 nuclease forms a complex that cuts the DNA. This DNA break is spontaneously repaired by Non Homologous End Joining, which results in micro-insertions or micro-deletion (INDELs) in the DNA. These INDELs are detected by PCR amplification followed by digestion with the Surveyor enzyme that cuts the mismatched DNA double strands. Results show that gRNAs A, C and D can bind to their respective target sequence in the frataxin promoter. However, gRNAs B and E did not effectively bind to their respective target sequence and thus no additional DNA band was detected following the Surveyor enzyme test.

The efficient targeting of the promoter of the human frataxin gene by these gRNAs was initially tested in 293T cells. These cells were transfected with a plasmid coding for i) an active Cas9 nuclease from *Streptococcus pyogenes* and ii) a gRNA. When a gRNA binds correctly to its target sequence in the promoter, it forms a complex with the Cas9 nuclease. This results in a double strand break (DSB) in the promoter (FIG. 1). This DSB is spontaneously repaired by Non-Homologous End Joining (NHEJ), an imperfect repair process that results in micro-insertion or micro-deletions (INDELs) of some base pairs. The presence or absence such INDELs was detected by amplifying by PCR (oligos: aatctatcaacaatagaggcaaggca (forward, SEQ ID NO: 74) and cagctcccagcgtagctaca (reverse, SEQ ID NO: 75) part of the frataxin promoter. The amplicons were heated at 95° C. to separate the 2 DNA strands and slowly cooled at RT to favor the formation of heterodimers if INDELs were present in some of the amplicons. These amplicons were then exposed to the Surveyor enzyme that cuts double strands DNA, which have mismatches resulting in additional bands visualized on agarose gel stained with RedSafe™. The Surveyor enzyme results are illustrated in FIG. 6. These results indicate that gRNA A, C and D were able to bind effectively with their targeted sequence on the frataxin promoter.

Figure 7:
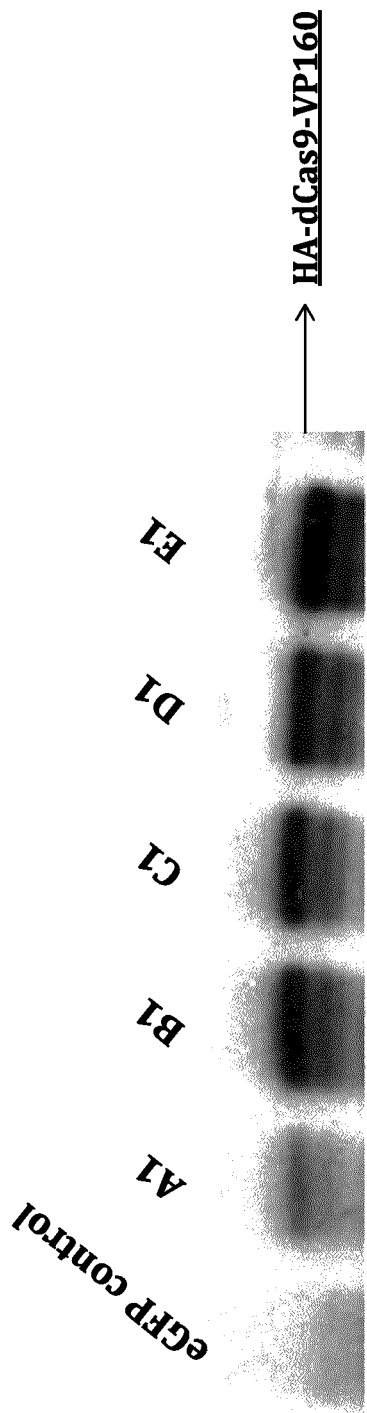
FIG. 7 shows that HA-dCas9-VP160 protein is efficiently expressed in cells. Results shown are from a Western blot using an HA antibody on lysates of 293T cells transfected with the HA-dcas9-VP160 gene and gRNAs A, B, C, D and E.
Figure 8:
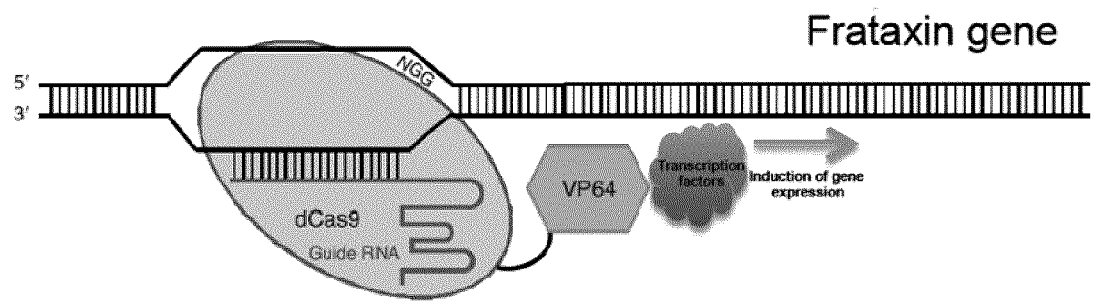
FIG. 8 shows a schematic representation of a single guide RNA (gRNA) that attaches to the promoter of the frataxin gene and forms a complex with the inactivated Cas9 (dCas9) coupled with VP160. This complex recruits transcription factors leading to the activation of frataxin gene transcription.

The induction of frataxin gene expression was initially tested by transfecting 293T cells with one or several plasmids pAC154 each coding for a different gRNAs and for the same HA-dCas9-VP160, an inactive Cas9 nuclease (dCas9) coupled with 10 VP16 sequences that act as transcription activation domains (see for Example FIG. 4 for pAC154 sequence coding for gRNA A and VP160 TAD and FIG. 8 for a schematic representation of the complex). The 293T cells were seeded into 6 plates the day before transfection at densities of 3.5×10$^5$ cells/well. 72 hours after transfection, total proteins were extracted from cells. The expression of the HA-dCas9-VP160 was initially confirmed by Western blot using an anti-HA antibody (FIG. 7).

Figure 9:
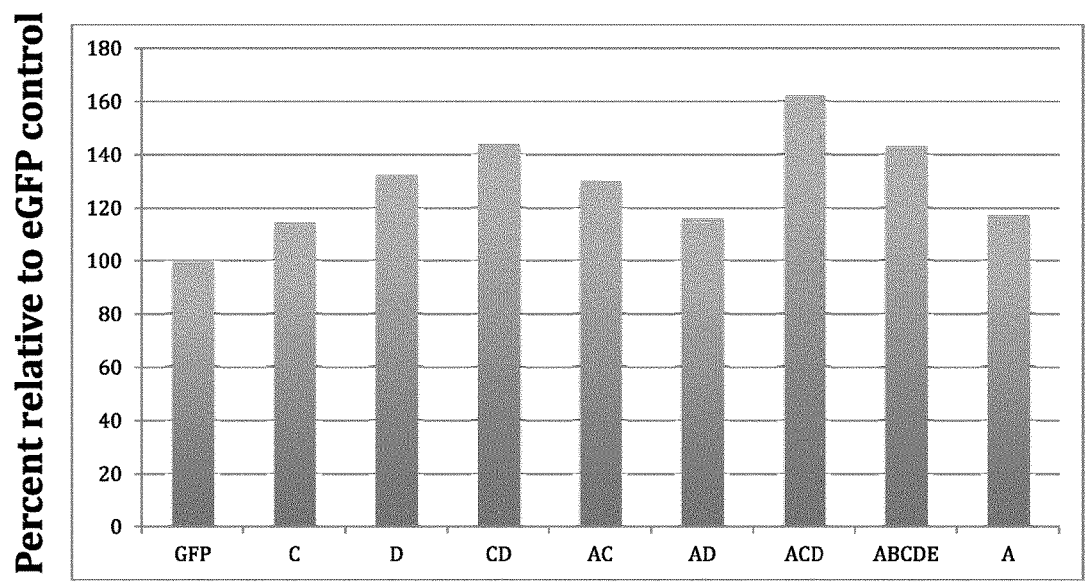
FIG. 9 shows that gRNAs of the present invention increase the expression of the frataxin gene in cells. Quantitative frataxin expression levels were determined by qRT-PCR on mRNA of 293T cells transfected with a plasmid coding for dCas9-VP160 and for one (or several) gRNA(s) targeting the promoter of the human frataxin gene. gRNAs A, C and D and various combinations of gRNAs increased the expression of the frataxin mRNA.

If the gRNAs and the HA-dCas9-VP160 proteins are able to attach to the frataxin promoter, this complex should drive the expression of the frataxin gene. The increased expression of the frataxin gene was first investigated by qRT-PCR amplification of the frataxin mRNA. FIG. 9 illustrates that gRNAs increased the expression of frataxin at the mRNA level (results normalized with the 18S RNA). The results were also normalized relative to cells transfected with a plasmid coding for eGFP rather than for the HA-dCas9-VP160 protein. Primers used for amplification are shown in Table 5 below.

Figure 11:
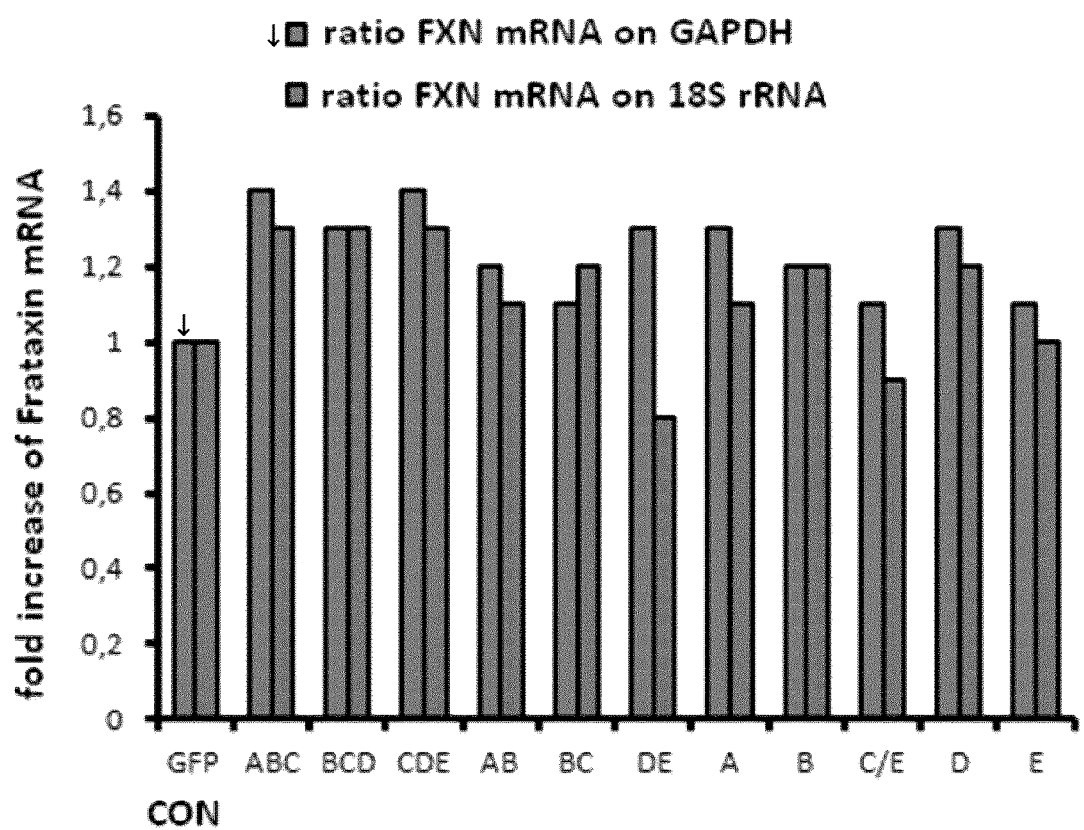
FIG. 11 shows that gRNAs targeting the frataxin promoter can increase the expression of frataxin mRNA in Friedreich cells. Results are from GFPqRT-PCR for the Frataxin mRNA from lysate of Friedreich cells 60 hours after nucleofection of a plasmid coding for dCas9-VP64 and one or several gRNA targeting the promoter of the human frataxin gene. Results were normalized with cells transfected with GFP and also normalized relative to 2 different control RNAs (left columns: ↓GAPDH; right columns: 18S rRNA)

EXAMPLE 2 gRNAs and dCas9-VP160 Significantly Increase the Expression of the Human Frataxin Gene in Fibroblasts of Friedreich Patients The ability of gRNAs and dCas9-VP160 to increase frataxin expression was next evaluated in cells of Friedreich Ataxia patients which normally express low levels of frataxin. Various combinations of gRNAs A, B, C, D and E also increased by 30 to 40% the frataxin mRNA in fibroblasts from a patient suffering from Friedreich ataxia Indeed, nucleofection of plasmids coding for dCas9-VP160 and for gRNA A, B and C increased the frataxin mRNA compared with a control nucleofected with a plasmid coding for eGFP (FIG. 11). The frataxin mRNA was amplified by PCR (using primers defined in Table 5 and normalized with 18S rRNA or GAPDH). The Friedreich fibroblasts used for this experiment were obtained from Coriell Institute for Medical Research (GM 04078) and have 541 and 420 trinucleotide repeats in intron 1 of each allele of the gene respectively.

TABLE 5

Primers used

| Gene Symbol | Description | GenBank | Size (bp) | T annealing (° C.) | Primer sequences 5'→3' Forward/Reverse | SEQ ID NOs |
|---|---|---|---|---|---|---|
| Hs FXN | Homo sapiens frataxin (FXN), region targeted common to isoforms 1, 2 and 3 | NM_000144 | 106 | 57 | AAGCCATACACGTTTGAGGACT A/ TTGGCGTCTGCTTGTTGATCA | SEQ ID NO: 76 SEQ ID NO: 77 |
| Hs GAPDH | Homo sapiens glyceraldehyde-3-phosphate dehydrogenase | NM_002046 | 194 | 57 | GGCTCTCCAGAACATCATCCCT/ ACGCCTGCTTCACCACCTTCTT | SEQ ID NO: 78/ SEQ ID NO: 101 |
| Hs 18S | Homo sapiens 18S ribosomal RNA (Rn18s) | NR_003286 | 119 | 57 | ACGGACCAGAGCGAAAGCATT/ TCCGTCAATTCCTTTAAGTTTCA GCT | SEQ ID NO: 79/ SEQ ID NO: 80 |
| Mm Hprt1 | Mus musculus hypoxanthine guanine phosphoribosyl transferase 1 | NM_013556 | 106 | 57 | CAGGACTGAAAGACTTGCTCGA GAT/ CAGCAGGTCAGCAAAGAACTTA TAGC | SEQ ID NO: 81/ SEQ ID NO: 82 |
| Mm GAPDH | Mus musculus glyceraldehyde-3-phosphate dehydrogenase | NM_008084 | 123 | 57 | ACGGGAAGCTCACTGGCATGG/ ATGCCTGCTTCACCACCTTCTT G | SEQ ID NO: 83/ SEQ ID NO: 84 |
| Mm 18S | 18S ribosomal RNA (Rn18s) | NR_003278 | 119 | 57 | TGGATACCGCAGCTAGGAATAA TG/ TCACCTCTAGCGGCGCAATAC | SEQ ID NO: 85/ SEQ ID NO: 86 |

Figure 10:
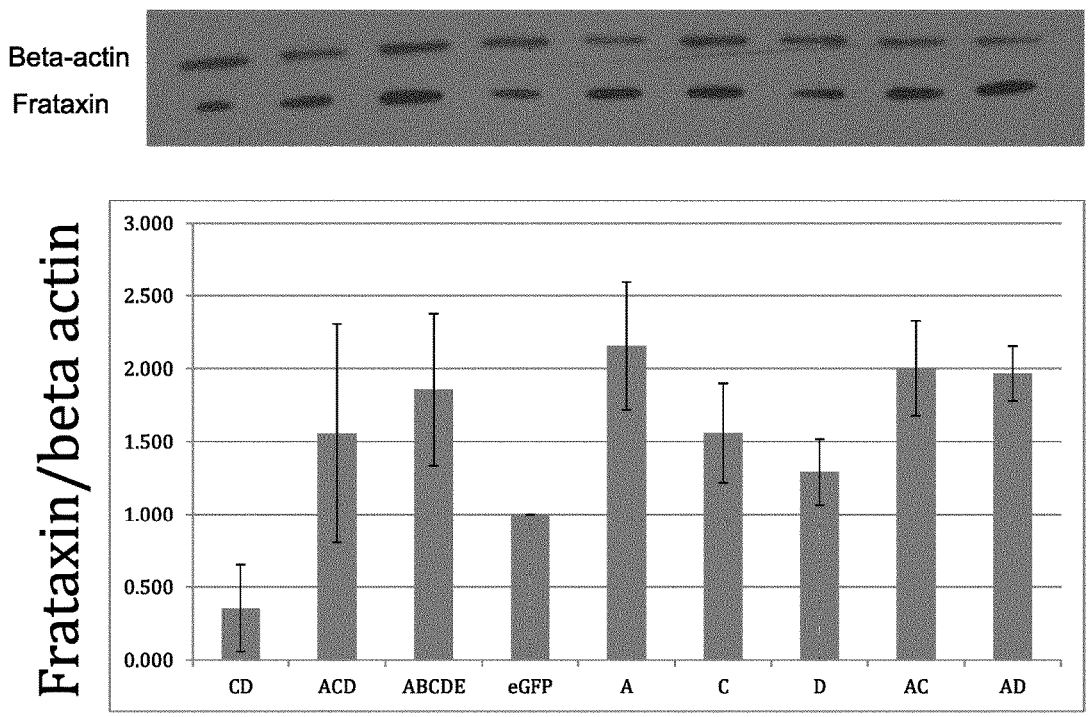
FIG. 10 shows that frataxin protein expression is increased by the presence of gRNAs. The top panel shows a Western blot for the frataxin and the beta-actin proteins using a lysate from 293T cells treated with dCas9-VP160 and one or combinations of several gRNAs targeting the promoter of the human frataxin gene. The intensity of the frataxin band was normalized with the intensity of the beta-actin band from the same sample. The bottom panel shows the average results for 3 Western blots. The normalized intensity of the frataxin protein was increased by the presence of the gRNAs used alone or in various combinations.

The gRNAs and the HA-dCas9-VP160 proteins were also able to increase the expression of the frataxin protein (FIG. 10) in the 293T cells transfected with one or several plasmids pAC154. Frataxin protein expression was normalized using β-actin as an internal standard. The mAb used to detect frataxin was #18A5DB1 from Mitosciences.

Figure 12:
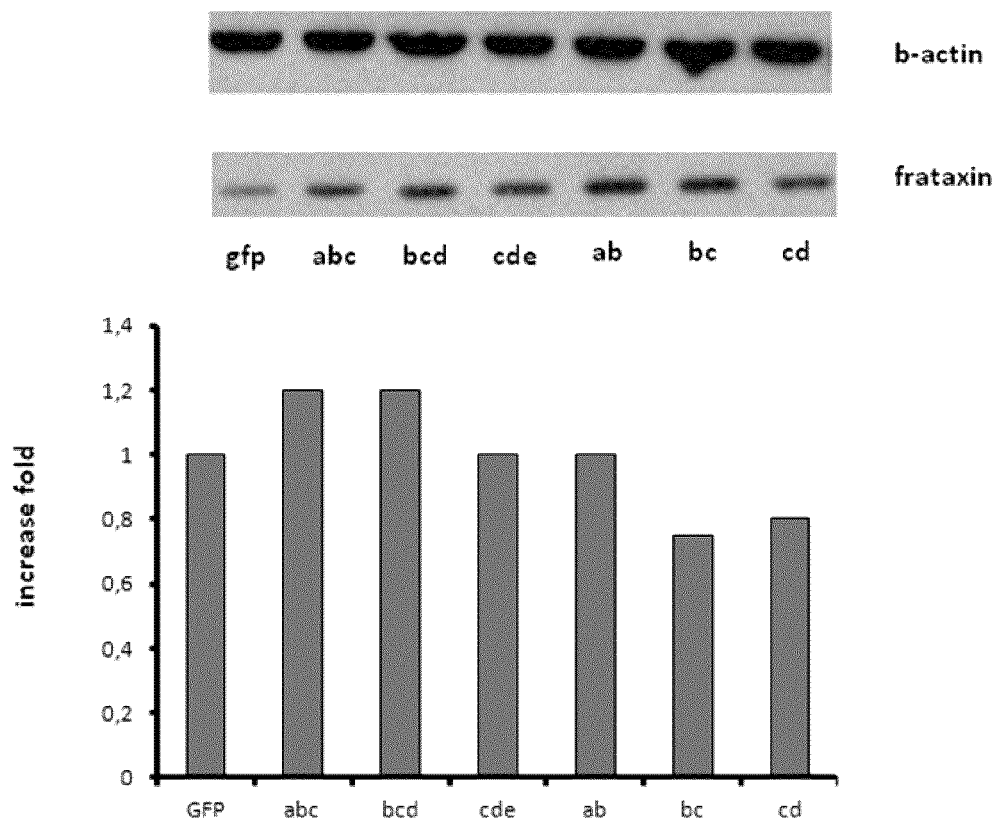
FIG. 12 shows that gRNAs targeting the frataxin promoter can increase the expression of frataxin protein in Friedreich cells. Top panel: Western blot of frataxin protein expression 60 hours following nucleofection of the plasmid coding for gRNA and the dCas9-VP64 in Friedreich fibroblasts. Bottom panel: Frataxin expression was quantified and normalized with β-actin expression (the frataxin antibody was from Mitosciences and the β-actin antibody was purchased from Sigma Aldrich)

Results obtained at the mRNA level were also confirmed at the protein level. The combination of gRNAs A, B and C also increased by almost 20% the frataxin protein in fibroblasts from the same Friedreich patient (FIG. 12). Co-nucleofection of pAC154 plasmid coding for gRNAs A, B and C, or co-nucleofection of B, C and D increased frataxin protein expression compared to control cells nucleofected with a plasmid coding for GFP from Amaxa inc. Frataxin protein expression was normalized using β-actin as an internal standard. The mAb used to detect frataxin was #18A5DB1 from Mitosciences.

Such an increase of frataxin protein in the subject cells may be used to reduce or prevent the symptoms associated with Friedreich ataxia.

EXAMPLE 3

Production and In Vivo Testing of AAV Vectors Coding for at Least One gRNA and Fusion Proteins dCAs9/TAD; dCas9/TAG, MS2-TAD and Antigen-Binding Protein/TAD AAV constructs such as AAV-DJ (or AAV-DJ8) for the gRNAs (alone or in combination) and fusion proteins to increase frataxin expression may be prepared. These AAV are produced at the Molecular Tools Platform of the Centre de Recherche Institut Universitaire en Santé Mentale de Québec. The plasmid to produce the DJ serotype AAV form is available from Cell Biolabs inc. One or multiple AAV vectors can be used to deliver the gRNAFrat and the TAD. For example, the dCas9-VP64, dCas9-VP160 or dCas9-SunTag may be separated in two parts sharing an overlapping sequence. This permits a recombination of the 2 parts following infection of a cell. Several articles describing these dual AAVs have been published by Duan and colleagues (Bostwick et al., Gosh et al., 2007, Gosh et al., 2008 and Gosh et al., 2011). Further AAV-DJ containing one or several gRNAFrat (or gRNAFrat-MS2) under the U6 and/or other promoter(s) can also be prepared. The AAV vectors may be delivered via the superficial temporal vein at different doses (1 to 10 E10 vector genomes per mouse for initial testing) to groups of ten 5 days old YG8sR mice (Pook et al., (2001); Al-Mandawi et al., (2004) and Al-Mandawi et al., (2006) and Virmouni et al., (2015); e.g., stock #024097). Control mice are injected with a AAV vector (e.g., AAV-DJ) coding for an irrelevant gRNA. Since the dCas9-VP64, dCas9-VP160 or dCas9-SunTag may be immunogenic, the YG8sR mouse is immunosuppressed with Tacrolimus for this experiment. The mice are sacrificed 1 month later. The RNA and the proteins are extracted from the brain, spinal cord, spinal ganglions, heart, liver and muscles for quantification of the frataxin mRNA and protein. This method allows to confirm induction of frataxin expression in vivo.

EXAMPLE 4

Specificity of Gene Expression Induced by the CRISPR System

The RNA-Seq technique permits to investigate the expression of the whole human or mouse genome (Wang et al., Pepke et al., Sultan et al., and Citrulli et al.). Briefly, this technique converts the mRNA into cDNA. These cDNAs are then fragmented and oligonucleotides are attached to allow sequencing of 100 bp of each DNA fragment with the Illumina sequencer. For each sample, about 50 million 100 bp sequences should be obtained. Thus RNA-Seq provides a precise quantitative evaluation of the expression of all genes. Even the mRNA expressed only once per cell and alternative splicings are identified by this method.

Three groups may be used for this experiment: 1) normal mice, 2) YG8sR mice and 3) YG8sR mice (Pook et al., (2001); Al-Mandawi et al., (2004) and Al-Mandawi et al., (2006) and Virmouni et al., (2015)) treated with the AAV vectors. The RNA-Seq technique is used to compare the expression of all genes in specific tissue such as the brain, spinal ganglia and the heart. This allows to verify whether frataxin expression is restored and to what level of the normal control. This technique also permits to detect whether the treatment induced any abnormal gene expression in the various tissues, which could be due to off-target effects and potential toxicity of the CRISPR system. This will thus permit to assess the specificity of the treatment and identify the metabolic consequence of restoring the frataxin expression.

EXAMPLE 5

Investigating the Possible Immune Response Against dCas9-VP64, dCas9-VP160, dCas9-SunTag or MS2-p65-HSF1

Fusions proteins of the present invention (e.g., dCas9-VP64, dCas9-VP160, dCas9-SunTag and MS2-p65-HSF1) are foreign protein for the mice (and human subjects). The newborn mice may not develop an immune response because their immune system is immature. However, this is not the case of adult mice and of FRDA patients. To investigate the potential immune response against these proteins, the AAV vectors can be administered i.v. to 6 months old YG8sR mice (Pook et al., (2001); Al-Mandawi et al., (2004) and Al-Mandawi et al., (2006) and Virmouni et al., (2015)). One month after the systemic delivery of an AAV derived vector (AAV-DJ), the presence of a humoral and cellular immune response against the proteins coded by the viral vector is investigated.

To detect the humoral response, the serum is obtained from the mice one month after the CRISPR treatment. The presence of antibodies in those sera, against the proteins extracted from the heart of mice treated or not with the CRISPR, is determined by for example western blot using as the primary antibody the mouse serum and a second anti-mouse IgG coupled to HRP.

To detect a potential cellular immune response, a muscle biopsy is obtained from mice treated or not with the CRISPR. Myoblasts, which are good antigen presenting cells, are grown from the satellite cells present in these muscle biopsies. These myoblasts are infected in vitro with the same AAV used in the CRISPR treatment. The presence of a cellular immune response against the myoblasts expressing one of the foreign proteins is determined by using a IFNγ ELISPOT assay with the T lymphocytes derived from the spleen of mice that received or not the CRISPR treatment.

EXAMPLE 6

Long-Term In Vivo Study in the YG8sR Mouse Model of FRDA

The CRISPR/dCas9 systems based treatments of the present invention can also be investigated in the YG8sR mice (Pook et al., (2001); Al-Mandawi et al., 2004 and Al-Mandawi et al., 2006) for a longer time period (i.e., 1 year). For these experiments, ten YG8sR mice are injected at 5 days of age with the AAV vectors of the CRISPR/dCas9 systems of the present invention. Ten control YG8sR mice receive a saline injection. The expression of frataxin is quantified in the white blood cells every month. At every 2 months during the one-year follow-up, the mouse activity is investigated. The heart function of treated mice (stroke volume, cardiac output, systolic and diastolic diameters) is investigated echography, as done in (Gerard et al., 2014).

Following the mouse sacrifice, the weight of the heart is measured to heart hypertrophy and treatment success. Absence of iron accumulation in the heart and brain is also investigated. Mitochondrial enzyme activity, aconitase activity, oxidative stress etc. in heart and brain using methods previously described may also be determined. The organs of mice of each group is sent to Jackson laboratory for examination to detect any potential toxicity from the treatment.

Although the present invention has been described hereinabove by way of specific embodiments thereof, it can be modified, without departing from the spirit and nature of the invention as defined in the appended claims.

REFERENCES

Al-Mandawi, S. et al. GAA repeat instability in Friedreich ataxia YAC transgenic mice. Genomics 84, 301-310 (2004).

Al-Mandawi, S. et al. GAA repeat expansion mutation mouse models of Friedreich ataxia exhibit oxidative stress leading to progressive neuronal and cardiac pathology. Genomics 88, 580-590 (2006).

Altschul, S. F., W. Gish, W. Miller, E. W. Myers & D. J. Lipman (1990) Basic local alignment search tool. *J Mol Biol*, 215, 403-10.

Annoni, A., Goudy, K., Akbarpour, M., Naldini, L. & Roncarolo, M. G. Immune responses in liver-directed lentiviral gene therapy. Translational research: the journal of laboratory and clinical medicine 161, 230-240, doi: 10.1016/j.trsl.2012.12.018 (2013).

Ausubel. 2010. *Current Protocols in Molecular Biology*. Green Publishing Associates, Inc., and John Wiley & Sons, Inc., Bostick, B., Ghosh, A., Yue, Y., Long, C. & Duan, D. Systemic AAV-9 transduction in mice is influenced by animal age but not by the route of administration. *Gene Ther* 14, 1605-1609, (2007).

Campuzano, V., L. Montermini, M. D. Motto, L. Pianese, M. Cossee, F. Cavalcanti, E. Monros, F. Rodius, F. Duclos, A. Monticelli, F. Zara, J. Canizares, H. Koutnikova, S. I. Bidichandani, C. Gellera, A. Brice, P. Trouillas, G. De Michele, A. Filla, R. De Frutos, F. Palau, P. I. Patel, S. Di Donato, J. L. Mandel, S. Cocozza, M. Koenig & M. Pandolfo (1996) Friedreich's ataxia: autosomal recessive disease caused by an intronic GAA triplet repeat expansion. *Science*, 271, 1423-7.

Cho, S. W., S. Kim, J. M. Kim & J. S. Kim (2013) Targeted genome engineering in human cells with the Cas9 RNA-guided endonuclease. *Nat Biotechnol*, 31, 230-2.

Cirulli, E. T. et al. Screening the human exome: a comparison of whole genome and whole transcriptome sequencing. *Genome Biol* 11, R57, doi:gb-2010-11-5-r57 [pii] 10.1186/gb-2010-11-5-r57.

Cong, L., F. A. Ran, D. Cox, S. Lin, R. Barretto, N. Habib, P. D. Hsu, X. Wu, W. Jiang, L. A. Marraffini & F. Zhang (2013) Multiplex genome engineering using CRISPR/Cas systems. *Science*, 339, 819-23.

Coppola, G., S. H. Choi, M. M. Santos, C. J. Miranda, D. Tentler, E. M. Wexler, M. Pandolfo & D. H. Geschwind (2006) Gene expression profiling in frataxin deficient mice: microarray evidence for significant expression changes without detectable neurodegeneration. *Neurobiol Dis*, 22, 302-11.

Coppola, G., D. Marmolino, D. Lu, Q. Wang, M. Cnop, M. Rai, F. Acquaviva, S. Cocozza, M. Pandolfo & D. H. Geschwind (2009) Functional genomic analysis of frataxin deficiency reveals tissue-specific alterations and identifies the PPARgamma pathway as a therapeutic target in Friedreich's ataxia. *Hum Mol Genet*, 18, 2452-61.

Deltcheva, E., K. Chylinski, C. M. Sharma, K. Gonzales, Y. Chao, Z. A. Pirzada, M. R. Eckert, J. Vogel & E. Charpentier (2011) CRISPR RNA maturation by trans-encoded small RNA and host factor RNase III. *Nature*, 471, 602-7.

El-Sayed, A., S. Futaki & H. Harashima (2009) Delivery of macromolecules using arginine-rich cell-penetrating peptides: ways to overcome endosomal entrapment. *AAPS J*, 11, 13-22.

Fominaya, J., C. Uherek & W. Wels (1998) A chimeric fusion protein containing transforming growth factor-alpha mediates gene transfer via binding to the EGF receptor. *Gene Ther*, 5, 521-30.

Fonfara et al., Phylogeny of Cas9 determines functional exchangeability of dual-RNA and Cas9 among orthologous, Nucleic Acids Res. 42:2577-2590(2014).

Fu, Y., J. A. Foden, C. Khayter, M. L. Maeder, D. Reyon, J. K. Joung & J. D. Sander (2013) High-frequency off-target mutagenesis induced by CRISPR-Cas nucleases in human cells. *Nat Biotechnol*, 31, 822-6.

Gerard, C. et al. An AAV9 coding for frataxin clearly improved the symptoms and prolonged the life of Friedreich ataxia mouse models. *Molecular Therapy Methods and Clinical Development* 1, 1-11 (2014).

Ghosh, A. & Duan, D. Expanding adeno-associated viral vector capacity: a tale of two vectors. Biotechnology & genetic engineering reviews 24, 165-177 (2007).

Ghosh, A., Yue, Y. & Duan, D. Efficient transgene reconstitution with hybrid dual AAV vectors carrying the minimized bridging sequences. Hum Gene Ther 22, 77-83 (2011).

Ghosh, A., Yue, Y., Lai, Y. & Duan, D. A hybrid vector system expands adeno-associated viral vector packaging capacity in a transgene-independent manner. Mol Ther 16, 124-130, (2008).

Hou, Z., Y. Zhang, N. E. Propson, S. E. Howden, L. F. Chu, E. J. Sontheimer & J. A. Thomson (2013) Efficient genome engineering in human pluripotent stem cells using Cas9 from *Neisseria meningitidis*. *Proc Natl Acad Sci USA*, 110, 15644-9.

Jiang et al., RNA-guided editing of bacterial genomes using CRISPR-Cas sytems, Nat. Biotechnol. 31:233-239(2013)

Jinek, M., K. Chylinski, I. Fonfara, M. Hauer, J. A. Doudna & E. Charpentier (2012) A programmable dual-RNA-guided DNA endonuclease in adaptive bacterial immunity. *Science*, 337, 816-21.

Jinek et al., Structures of Cas9 endonucleases reveal RNA-mediated conformational activation, Science 343: 1247997-1247997(2014)

Kakimoto, S., T. Hamada, Y. Komatsu, M. Takagi, T. Tanabe, H. Azuma, S. Shinkai & T. Nagasaki (2009) The conjugation of diphtheria toxin T domain to poly(ethylenimine) based vectors for enhanced endosomal escape during gene transfection. *Biomaterials*, 30, 402-8.

Kakudo, T., S. Chaki, S. Futaki, I. Nakase, K. Akaji, T. Kawakami, K. Maruyama, H. Kamiya & H. Harashima (2004) Transferrin-modified liposomes equipped with a pH-sensitive fusogenic peptide: an artificial viral-like delivery system. Biochemistry, 43, 5618-28.

Kichler, A., C. Leborgne, J. Marz, O. Danos & B. Bechinger (2003) Histidine-rich amphipathic peptide antibiotics promote efficient delivery of DNA into mammalian cells. *Proc Natl Acad Sci USA,* 100, 1564-8.

Konermann, S. et al. Genome-scale transcriptional activation by an engineered CRISPR-Cas9 complex. *Nature* 517, 583-588, doi:10.1038/nature14136 (2015).

Kwon, E. J., J. M. Bergen & S. H. Pun (2008) Application of an HIV gp41-derived peptide for enhanced intracellular trafficking of synthetic gene and siRNA delivery vehicles. *Bioconjug Chem,* 19, 920-7.

Li, K., A. Singh, D. R. Crooks, X. Dai, Z. Cong, L. Pan, D. Ha & T. A. Rouault (2010) Expression of human frataxin is regulated by transcription factors SRF and TFAP2. *PLoS One,* 5, e12286.

Lorieau, J. L., J. M. Louis & A. Bax (2010) The complete influenza hemagglutinin fusion domain adopts a tight helical hairpin arrangement at the lipid:water interface. *Proc Natl Acad Sci USA,* 107, 11341-6.

Lundberg, P., S. El-Andaloussi, T. Sutlu, H. Johansson & U. Langel (2007) Delivery of short interfering RNA using endosomolytic cell-penetrating peptides. *FASEB J,* 21, 2664-71.

Mali, P., J. Aach, P. B. Stranges, K. M. Esvelt, M. Moosburner, S. Kosuri, L. Yang & G. M. Church (2013a) CAS9 transcriptional activators for target specificity screening and paired nickases for cooperative genome engineering. *Nat Biotechnol,* 31, 833-8.

Mali, P., L. Yang, K. M. Esvelt, J. Aach, M. Guell, J. E. DiCarlo, J. E. Norville & G. M. Church (2013b) RNA-guided human genome engineering via Cas9. *Science,* 339, 823-6.

Markusic, D. M. & Herzog, R. W. Liver-Directed Adeno-Associated Viral Gene Therapy for Hemophilia. Journal of genetic syndrome & gene therapy 1, 1-9, doi:10.4172/2157-7412.S1-009 (2012).

Matrai, J. et al. Hepatocyte-targeted expression by integrase-defective lentiviral vectors induces antigen-specific tolerance in mice with low genotoxic risk. *Hepatology* 53, 1696-1707, doi:10.1002/hep.24230 (2011).

Midoux, P., A. Kichler, V. Boutin, J. C. Maurizot & M. Monsigny (1998) Membrane permeabilization and efficient gene transfer by a peptide containing several histidines. *Bioconjug Chem,* 9, 260-7.

Nietupski, J. B. et al. Systemic administration of AAV8-alpha-galactosidase A induces humoral tolerance in non-human primates despite low hepatic expression. *Mol Ther* 19, 1999-2011, doi:10.1038/mt.2011.119 (2011). Nishimasu et al., Crystal structure of Cas9 in complex with guide RNA and target DNA, *Cell* 156:935-494(2014)

Noguchi, H., H. Kaneto, G. C. Weir & S. Bonner-Weir (2003) PDX-1 protein containing its own antennapedia-like protein transduction domain can transduce pancreatic duct and islet cells. *Diabetes,* 52, 1732-7.

Pandolfo, M. (2012) Friedreich ataxia. *Handbook of Clinical Neurology,* 103, 275-294.

Pearson, W. R. & D. J. Lipman (1988) Improved tools for biological sequence comparison. *Proc Natl Acad Sci USA,* 85, 2444-8.

Pepke, S., Wold, B. & Mortazavi, A. Computation for ChIP-seq and RNA-seq studies. *Nat Methods* 6, S22-32, (2009).

Perez-Pinera, P., D. D. Kocak, C. M. Vockley, A. F. Adler, A. M. Kabadi, L. R. Polstein, P. I. Thakore, K. A. Glass, D. G. Ousterout, K. W. Leong, F. Guilak, G. E. Crawford, T. E. Reddy & C. A. Gersbach (2013) RNA-guided gene activation by CRISPR-Cas9-based transcription factors. *Nat Methods.*

Pook, M. A. et al. Rescue of the Friedreich's ataxia knockout mouse by human YAC transgenesis. *Neurogenetics* 3, 185-193 (2001).

Qi, L. S., M. H. Larson, L. A. Gilbert, J. A. Doudna, J. S. Weissman, A. P. Arkin & W. A. Lim (2013) Repurposing CRISPR as an RNA-guided platform for sequence-specific control of gene expression. *Cell,* 152, 1173-83.

Salomone, F., F. Cardarelli, M. Di Luca, C. Boccardi, R. Nifosi, G. Bardi, L. Di Bari, M. Serresi & F. Beltram (2012) A novel chimeric cell-penetrating peptide with membrane-disruptive properties for efficient endosomal escape. *J Control Release,* 163, 293-303.

Sapranauskas, R., G. Gasiunas, C. Fremaux, R. Barrangou, P. Horvath & V. Siksnys (2011) The *Streptococcus thermophilus* CRISPR/Cas system provides immunity in *Escherichia coli. Nucleic Acids Res,* 39, 9275-82.

Schoenfeld, R. A., E. Napoli, A. Wong, S. Zhan, L. Reutenauer, D. Morin, A. R. Buckpitt, F. Taroni, B. Lonnerdal, M. Ristow, H. Puccio & G. A. Cortopassi (2005) Frataxin deficiency alters heme pathway transcripts and decreases mitochondrial heme metabolites in mammalian cells. *Hum Mol Genet,* 14, 3787-99.

Sultan, M. et al. A global view of gene activity and alternative splicing by deep sequencing of the human transcriptome. *Science* 321, 956-960, doi: 1160342 [pii] 10.1126/science.1160342 (2008).

Tijssen. 1993. *Laboratory Techniques in Biochemistry and Molecular Biology*—Hybridization with Nucleic Acid Probes, Part I, Chapter 2 *"Overview of principles of hybridization and the strategy of nucleic acid probe assays",* Elsevier, New York.

Trehin, R., U. Krauss, A. G. Beck-Sickinger, H. P. Merkle & H. M. Nielsen (2004) Cellular uptake but low permeation of human calcitonin-derived cell penetrating peptides and Tat(47-57) through well-differentiated epithelial models. *Pharm Res,* 21, 1248-56.

Virmouni, S. A. et al. A novel GAA repeat expansion-based mouse model of Friedreich ataxia. *Disease Models & amp; Mechanisms* in press (2015).

Wang, Z., Gerstein, M. & Snyder, M. RNA-Seq: a revolutionary tool for transcriptomics. *Nat Rev Genet* 10, 57-63, doi:nrg2484 [pii] 10.1038/nrg2484 (2009).

Zhang, P. et al. Immunodominant liver-specific expression suppresses transgene-directed immune responses in murine pompe disease. *Hum Gene Ther* 23, 460-472, doi:10.1089/hum.2011.063 (2012).

Zender, L., F. Kuhnel, R. Kock, M. Manns & S. Kubicka (2002) VP22-mediated intercellular transport of p53 in hepatoma cells in vitro and in vivo. *Cancer Gene Ther,* 9, 489-96.

The invention claimed is:

1. A guide RNA (gRNA) comprising i) a gRNA guide sequence of at least 10 contiguous nucleotides corresponding to a target sequence in a frataxin promoter polynucleotide sequence; and ii) a Cas9 recognition sequence, wherein the target sequence is contiguous to a protospacer adjacent motif (PAM) recognized by a ribonucleoprotein complex comprising a Cas9 protein and/or an inactive Cas9 (dCas9) protein lacking nuclease activity, and wherein the 3' end of the target sequence ends at nucleotide position i) 4264, ii) 4670, iii) 4701, iv) 4742, v) 4859, vi) 5023, or vii) 5107, wherein the nucleotide position corresponds to that of the frataxin polynucleotide gene sequence set forth in SEQ ID NO: 87.

2. The gRNA of claim 1, wherein the target sequence comprises the nucleotide sequence of:
   i) positions 4246-4264;
   ii) positions 4652-4670;
   iii) positions 4841-4859;
   iv) positions 5005-5023; or
   v) positions 5089-5107;
of the frataxin polynucleotide gene sequence set forth in SEQ ID NO: 87.

3. The gRNA of claim 1, wherein the Cas9 recognition sequence comprises the sequence as set forth in SEQ ID NO: 67.

4. The gRNA of claim 1, comprising a sequence as set forth in any one of SEQ ID NOs: 57-61.

5. A frataxin targeting system comprising:
   I. a. a1) at least one gRNA as defined in claim 1; or
         a2) at least one vector comprising at least one nucleic acid sequence corresponding to the at least one gRNA for expressing the at least one gRNA; and
      b. b1) a dCas9 fusion protein comprising (i) an inactive Cas9 (dCas9) polypeptide domain lacking nuclease activity, (ii) at least one nuclear localization signal (NLS) and (iii) at least one transcription activation domain; or
         b2) a vector comprising a nucleic acid sequence encoding the dCas9 fusion protein, for expression of the dCas9 fusion protein; or
   II c. c1) at least one gRNA as defined in claim 1; or
         c2) at least one vector comprising at least one nucleic acid sequence corresponding to the at least one gRNA for expressing the at least one gRNA;
      d. d1) a first fusion protein comprising (i) an inactive Cas9 (dCas9) polypeptide domain lacking nuclease activity, (ii) at least one nuclear localization signal (NLS) and (iii) a polypeptide domain comprising at least one peptide epitope; or
         d2) a vector comprising a nucleic acid sequence encoding the first fusion protein, for expression of the first fusion protein; and
      e. e1) a second fusion protein comprising (i) an antigen-binding domain capable of binding to the at least one epitope and (ii) at least one transcription activation domain; or
         e2) a vector comprising a nucleic acid sequence encoding the second fusion protein, for expression of the second fusion protein.

6. The frataxin targeting system of claim 5, wherein the target sequence of said at least one gRNA comprises the nucleotide sequence of:
   i) positions 4246-4264;
   ii) positions 4652-4670;
   iii) positions 4841-4859;
   iv) positions 5005-5023; or
   v) positions 5089-5107;
of the frataxin polynucleotide gene sequence set forth in SEQ ID NO: 87.

7. The frataxin targeting system of claim 5, wherein the at least one gRNA is at least two gRNAs.

8. An isolated polynucleotide encoding the gRNA of claim 1.

9. A vector comprising the isolated polynucleotide of claim 8.

10. An isolated cell comprising the isolated polynucleotide of claim 8 or a vector comprising the isolated polynucleotide of claim 8.

11. A composition comprising a physiologically acceptable carrier and:
   (i) at least one gRNA as defined in claim 1,
   (ii) at least one vector encoding the at least one gRNA of (i) and/or
   (iii) an isolated cell comprising the at least one gRNA of (i) or the at least one vector of (ii); and optionally:
   (A). a dCas9 fusion protein comprising an inactive Cas9 (dCas9) polypeptide domain lacking nuclease activity, wherein the dCas9 fusion protein further comprises (I) at least one nuclear localization signal (NLS); and/or (II) (a) at least one transcription activation domain and/or (b) a polypeptide domain comprising at least one peptide epitope;
   (B). a vector for expressing the dCas9 fusion protein defined in (A); and/or
   (C). an isolated cell expressing the dCas9 fusion protein of (A) or comprising the vector of (B).

12. A combination comprising:
   (i) at least one gRNA as defined in claim 1;
   (ii) at least one vector encoding the at least one gRNA of (i) or
   (iii) an isolated cell comprising the at least one gRNA of (i) or the at least one vector of (ii); and:
   (A). a dCas9 fusion protein comprising an inactive Cas9 (dCas9) polypeptide domain lacking nuclease activity, wherein the dCas9 fusion protein further comprises (I) at least one nuclear localization signal (NLS); and/or (II) (a) at least one transcription activation domain and/or (b) a polypeptide domain comprising at least one peptide epitope;
   (B). a vector for expressing the dCas9 fusion protein defined in (A); and/or
   (C). an isolated cell expressing the dCas9 fusion protein of (A) or comprising the vector of (B).

13. The combination of claim 12, wherein the target sequence of said at least one gRNA comprises the nucleotide sequence of:
  i) positions 4246-4264;
  ii) positions 4652-4670;
  iii) positions 4841-4859;
  iv) positions 5005-5023; or
  v) positions 5089-5107;
of the frataxin polynucleotide gene sequence set forth in SEQ ID NO: 87.

14. The combination of claim 12, wherein the at least one g RNA is at least two gRNAs.

15. A kit comprising the frataxin targeting system of claim 5.

16. A method for treating Friedreich ataxia in a subject comprising administering to the subject the frataxin targeting system of claim 5.

17. A method for increasing frataxin expression in a cell comprising introducing or expressing in the cell the frataxin targeting system of claim 5.

* * * * *